US010352942B2

(12) United States Patent
Grote et al.

(10) Patent No.: US 10,352,942 B2
(45) Date of Patent: Jul. 16, 2019

(54) CORRELATED PEPTIDES FOR QUANTITATIVE MASS SPECTROMETRY

(71) Applicants: Cedars-Sinai Medical Center, Los Angeles, CA (US); The John Hopkins University, Baltimore, MD (US)

(72) Inventors: Eric Grote, Beverly Hills, CA (US); Qin Fu, Beverly Hills, CA (US); Jennifer Van Eyk, Los Angeles, CA (US); Vidya Venkatraman, Los Angeles, CA (US)

(73) Assignees: Cedars-Sinai Medical Center, Los Angeles, CA (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/571,243

(22) PCT Filed: May 31, 2016

(86) PCT No.: PCT/US2016/035117
§ 371 (c)(1),
(2) Date: Nov. 1, 2017

(87) PCT Pub. No.: WO2016/196522
PCT Pub. Date: Dec. 8, 2016

(65) Prior Publication Data
US 2018/0136220 A1 May 17, 2018

Related U.S. Application Data

(60) Provisional application No. 62/168,671, filed on May 29, 2015.

(51) Int. Cl.
C12Q 1/68 (2018.01)
G01N 33/53 (2006.01)
G01N 33/68 (2006.01)
G16B 30/00 (2019.01)
G16B 40/00 (2019.01)
G16B 99/00 (2019.01)

(52) U.S. Cl.
CPC .......... *G01N 33/6848* (2013.01); *C12Q 1/68* (2013.01); *G01N 33/53* (2013.01); *G01N 33/6827* (2013.01); *G16B 30/00* (2019.02); *G16B 40/00* (2019.02); *G16B 99/00* (2019.02)

(58) Field of Classification Search
CPC ...... C12Q 1/68; G01N 33/53; G01N 33/6827; G01N 33/6848; G06F 19/10; G06F 19/22; G06F 19/24; G16B 30/00; G16B 40/00; G16B 99/00
See application file for complete search history.

(56) References Cited

U.S. PATENT DOCUMENTS

| 5,585,089 A | 12/1996 | Queen et al. |
| 6,864,099 B2 | 3/2005 | Regnier |
| 7,794,947 B2 | 9/2010 | Aebersold et al. |
| 9,274,124 B2 | 3/2016 | Anderson |
| 9,435,778 B2 | 9/2016 | Escher et al. |
| 2002/0037532 A1 | 3/2002 | Regnier et al. |
| 2002/0115056 A1* | 8/2002 | Goodlett ............ G01N 33/6803 435/4 |
| 2004/0181351 A1 | 9/2004 | Thompson et al. |
| 2005/0095649 A1 | 5/2005 | Aebersold et al. |
| 2006/0029977 A1 | 2/2006 | Everett et al. |
| 2007/0218505 A1 | 9/2007 | Kearney |
| 2013/0010274 A1 | 11/2013 | Meng et al. |
| 2014/0236497 A1 | 8/2014 | Escher et al. |

FOREIGN PATENT DOCUMENTS

| EP | 3304090 A1 | 4/2018 |
| WO | WO 2014/195783 A1 | 12/2014 |
| WO | WO 2015/008453 A1 | 1/2015 |
| WO | 2016/196522 A1 | 12/2016 |
| WO | WO2017/162888 * | 9/2017 ............... C07K 7/08 |

OTHER PUBLICATIONS

Li et al. Tandem 18O Stable Isotope Labeling for Quantification of N-Glycoproteome. J Proteome Res. 2010, vol. 9, pp. 227-236. (Year: 2010).*
Ting et al., Pecan: Peptide Detection Directly from Data-Independent Acquisition (DIA) MS/MS Data. In: American Society for Mass Spectrometry, Baltimore, MD, 2014.
Pathobiological Determinants of Atherosclerosis in Youth (PDAY) Research Group, Natural history of aortic and coronary atherosclerotic lesions in youth. Findings from the PDAY study. Arterioscler Thromb. Sep. 1993; 13(9): 1291-8.
Rampoldi, et al., The rediscovery of uromodulin (tamm-horsfall protein): From tubulointerstitial nephropathy to chronic kidney disease. Kidney Int 2011, 80, pp. 338-347.
Kottgen, et al., Multiple loci associated with indices of renal function and chronic kidney disease. Nat Genet, 2009, 41, pp. 712-717.
Gudbjartsson, et al., Association of variants at umod with chronic kidney disease and kidney stones-role of age and comorbid diseases. PLoS Genetics, 2010, 6:e1001039.
Padmanabhan, et al., Genome-wide association study of blood pressure extremes identifies variant near umod associated with hypertension. PLoS Genetics, 2010, 6:e1001177.
Trudu, et al., Common noncoding umod gene variants induce salt-sensitive hypertension and kidney damage by increasing uromodulin expression. Nature Medicine, 2013, 19, pp. 1655-1660.

(Continued)

*Primary Examiner* — Marcela M Cordero Garcia
(74) *Attorney, Agent, or Firm* — Nixon Peabody LLP

(57) ABSTRACT

Described herein are methods for identifying signature peptides for quantifying a polypeptide of interest in a sample. The methods include cleaving the polypeptide into peptides; detecting a multiplicity of the peptides with a quantitative analytical instrument; comparing the linearity of signals attributable to pairs of the peptides in a multiplicity of samples; and selecting signature peptides from a group of peptides with more highly correlated signals.

20 Claims, 18 Drawing Sheets

Specification includes a Sequence Listing.

(56) References Cited

OTHER PUBLICATIONS

Thongboonkerg, Practical points in urinary proteomics. Journal of proteome research, 2007, 6, pp. 3881-3890.
Liebler, et al., Targeted quantitation of proteins by mass spectrometry. Biochemistry, 2013, 52, pp. 3797-3806.
Kusebauch, et al., Using peptideatlas, srmatlas, and passel: Comprehensive resources for discovery and targeted proteomics. Current protocols in bioinformatics / editoral board, Andreas D Baxevanis [et al] 2014, 46, pp. 13.25.1-13.25.8.
Chang, et al., Protein significance analysis in selected reaction monitoring (srm) measurements. Molecular & cellular proteomics : MCP 2012;11, pp. M111.014662-1 to M111.014662-13.
PCT/US2016/035117 International Preliminary Report on Patentability dated Dec. 14, 2017, 13 pages.
International Search Report and Written Opinion for PCT/US2016/035117, dated Sep. 16, 2016, 15 pages.
Bark et al., Linear and Accurate Quantitation of Proenkephalin-Derived Peptides by Isotopic Labeling with Internal Standards and Mass Spectrometry, Anal Biochem., 2009, vol. 389(1), pp. 18-26.
Eng et al., A Face in the Crowd: Recognizing Peptides Through Database Search, Molecular & Cellular Proteomics, 2011, vol. 10(11), 9 pages.
Parnas et al., Highly Sensitive ELISA-Based Assay for Quanitifying Protein Levels in Neuronal Cultrues, Brain Research Protocols, 1998, vol. 2, 333-338.
Worboys et al., Systematic Evaluation of Quantotypic Peptides for Targeted Analysis of the Human Kinome., Nat. Methods, 2014, vol. 11(10), pp. 1041-1044.
Kohler, et al., Derivation of specific antibody-producing tissue culture and tumor lines by cell fusion. Eur. J. Immunol., 1976, 6, pp. 511-519.
Riechmann, et al., Reshaping human antibodies for therapy. Nature, 1988, 332, pp. 323-327.
MacLean, et al., Skyline: an open source document editor for creating and analyzing targeted proteomics experiments. Bioinformatics, 2010, 26, pp. 966-968.
Rost, et al., OpenSWATH™ enables automated, targeted analysis of dataindependent acquisition MS data. Nature Biotechnology, 2014, 32(3), pp. 219-223.
Schubert, et al., Building high-quality assay libraries for targeted analysis of SWATH™ MS data. Nature Protocols, 2015, 10(3), pp. 426-441.
Venable, et al., Automated approach for quantitative analysis of complex peptide mixtures from tandem mass spectra. Nature methods, 2004, 1(1), pp. 39-45.
Dong, et al., Quantitative mass spectrometry identifies insulin signaling targets in C. elegans. Science, 2007, 317 (5838), pp. 660-663.
Gillet, et al., Targeted data extraction of the MS/MS spectra generated by data-independent acquisition: a new concept for consistent and accurate proteome analysis. Molecular & cellular proteomics, 2012, MCP 11 (6), pp. O111016717-1 to O111016717-17.
Wang, et al., Peptide identification from mixture tandem mass spectra. Molecular & cellular proteomics, 2010, MCP 9 (7), pp. 1476-1485.
Parker, et al., Identification of a Set of Conserved Eukaryotic Internal Retention Time Standards for Data-Independent Acquisition Mass Spectrometry. Mol Cell Proteomics, 2015, 14, pp. 2800-2813.
Bereman, Tools for monitoring system suitability in LC MS/MS centric proteomic experiments. Proteomics, 2015, 15 (5-6), pp. 891-902.
Bereman, et al., Implementation of statistical process control for proteomic experiments via LC MS/MS. J Am Soc Mass Spectrom, 2014, 25 (4), pp. 581-587.
Tsou, et al., DIA-Umpire: comprehensive computational framework for data-independent acquisition proteomics. Nature Methods, 2015, 12 (3), pp. 258-264.

Toprak, et al., Conserved peptide fragmentation as a benchmarking tool for mass spectrometers and a discriminating feature for targeted proteomics. Molecular & Cellular Proteomics, 2014, MCP 13 (8), pp. 2056-2071.
Kirk, et al., Cardiac resynchronization sensitizes the sarcomere to calcium by reactivating GSK-3beta. The Journal of Clinical Investigation, 2014, 124 (1), pp. 129-139.
Escher, et al., Using iRT, a normalized retention time for more targeted measurement of peptides. Proteomics, 2012, 12(8), pp. 1111-1121.
Wang, et al., Reversedphase chromatography with multiple fraction concatenation strategy for proteome profiling of human MCF10A cells. Proteomics, 2011, 11(10), pp. 2019-2026.
Han, et al., Large-scale phosphoproteome analysis of human liver tissue by enrichment and fractionation of phosphopeptides with strong anion exchange chromatography. Proteomics, 2008, 8 (7), pp. 1346.
Dephoure, et al., A solid phase extraction-based platform for rapid phosphoproteomic analysis. Methods, 2011, 54 (4), pp. 379-386.
Purvine, et al., Shotgun collision-induced dissociation of peptides using a time of flight mass analyzer. Proteomics, 2003, 3, pp. 847-850.
Panchaud, et al., Precursor acquisition independent from ion count: how to dive deeper into the proteomics ocean. Anal Chem, 2009, 81, pp. 6481-6488.
Geiger, et al., Proteomics on an Orbitrap benchtop mass spectrometer using all-ion fragmentation. Mol Cell Proteomics, 2010, 9, pp. 2252-2261.
Carvalho, et al., Metabolomics of *Mycobacterium tuberculosis* reveals compartmentalized co-catabolism of carbon substrates. Chem Biol, 2010, 17, pp. 1122-1131.
Weisbrod, et al., Accurate Peptide Fragment Mass Analysis: Multiplexed Peptide Identification and Quantification. J Proteome Res, 2012, 11, pp. 1621-1632.
Chapman, et al., Multiplexed and data-independent tandem mass spectrometry for global proteome profiling. Mass Spectrom Rev, 2014, 33, pp. 452-470.
Anderson, et al., Mass spectrometric quantitation of peptides and proteins using Stable Isotope Standards and Capture by Anti-Peptide Antibodies (SISCAPA). J Proteome Res, 2004, 3, pp. 235-244.
The ARIC Investigators, the Atherosclerosis Risk in Communities (ARIC) Study: Design and Objectives. Am J Epidemiology, 1989, 129, pp. 687-702.
Kottgen, et al., Uromodulin levels associate with a common UMOD variant and risk for incident ckd. J Am Soc Nephrol, 2010, 21, pp. 337-344.
Webb-Robertson, et al., A support vector machine model for the prediction of proteotypic peptides for accurate mass and time proteomics, Bioinformatics, 2008, 26(13), pp. 1503-1509.
Grant, et al., From lost in translation to paradise found: Enabling protein biomarker method transfer by mass spectrometry. Clin Chem, 2014, 60, pp. 941-944.
Lee, et al., Fit-for-purpose method development and validation for successful biomarker measurement. Pharmaceutical Research, 2006, 23, pp. 312-328.
Kessner, et al., ProteoWizard: open source software for rapid proteomics tools development. Bioinformatics, 2008, 24, pp. 2534-2536.
Elias, et al., Target-decoy search strategy for increased confidence in large-scale protein identifications by mass spectrometry. Nat Methods, 2007, 4, pp. 207-214.
Craig, et al., TANDEM: matching proteins with tandem mass spectra. Bioinformatics, 2004, 20, pp. 1466-1467.
Eng, et al., Comet: An open-source MS/MS sequence database search tool. Proteomics, 2013, 13, pp. 22-24.
Keller, et al., A uniform proteomics MS/MS analysis platform utilizing open XML file formats. Molecular Systems Biology, 2005, 1:2005.0017, pp. 1-8.
Shteynberg, et al., iProphet: multi-level integrative analysis of shotgun proteomic data improves peptide and protein identification rates and error estimates. Mol Cell Proteomics, 2011, 10, pp. M111.007690-1 to M111.007690-16.

(56) References Cited

OTHER PUBLICATIONS

Lam, et al., Development and validation of a spectral library searching method for peptide identification from MS/MS. Proteomics, 2007, 7, pp. 655-667.
Weisser, et al., an automated pipeline for high-throughput label-free quantitative proteomics. J Proteome Res, 2013, 12, pp. 1628-1644.
Mallick, et al., Computational prediction of proteotypic peptides for quantitative proteomics. Nat Biotechnol, 2007, 25, pp. 125-231.
Agger, et al., Simultaneous quantification of apolipoprotein A-I and apolipoprotein B by liquid-chromatography-multiple-reactionmonitoring mass spectrometry. Clin Chem, 2010, 56(12), pp. 1804-1813.
Keller, et al., Empirical statistical model to estimate the accuracy of peptide identifications made by MS/MS and database search. Anal. Chem., 2002, 74, pp. 5383-5392.
Collins, et al., Quantifying protein interaction dynamics by SWATH mass spectrometry: application to the 14-3-3 system. Nat Methods, 2013, 10, pp. 1246-1253.
Beasley-Green, et al., Multiplexed LC-MS/MS assay for urine albumin, J Proteome Res, 2014, 13(9), pp. 3930-3939.
Silva, et al., Absolute Quantification of Proteins by LCMSE: A Virtue of Parallel ms Acquisition *S. Mollecular Cellular Proteomics, 2005, 5, pp. 144-156.
Ramos, et al., Tandem parallel fragmentation of peptides for mass spectrometry. Anal Chem, 2006, 78, pp. 6391-6397.
Liu, et al., Constrained selected reaction monitoring: Quantification of selected post-translational modifications and protein isoforms. Methods, 2013, 61, pp. 304-312.
Rampoldi, et al., The effect of common uromodulin variants on urinary protein level and gene transcription. Kidney Int, 2013, 84, pp. 410-411.
Graham, et al., Validation of uromodulin as a candidate gene for human essential hypertension. Hypertension, 2014, 63, pp. 551-558.
Bleyer, et al., Medullary cystic kidney disease type 2. Am J Kidney Dis 2004, 43, pp. 1142-1144; author reply.
Anderson et al., Quantitative mass spectrometric multiple reaction monitoring assays for major plasma proteins. Molecular & Cellular Proteomics, 2006, 5, pp. 573-588.
Bereman et al., The development of selected reaction monitoring methods for targeted proteomics via empirical refinement. Proteomics, 2012, 12, pp. 1134-1141.
Farrah et al., Passel: The peptideatlas srm experiment library. Proteomics, 2012, 12, pp. 1170-1175.
Fu et al., Multiplex assays for biomarker research and clinical application: Translations science coming of age. Proteomics Clin Appl, 2010, 4, pp. 271-284.
Fu et al., Developing a Robust Urine UMOD and Albumin Assay by Liquid Chromatography-Targeted Mass Spectrometry, Poster Presentation (MP569) Jun. 1, 2015, 63th American Society for Mass Spectrometry (ASMS) Conference on Mass Spectrometry and Allied Topics, May 31-Jun. 4, 2015, St. Louis, Missouri.
Fu et al., Developing a Robust Urine UMOD and Albumin Assay by Liquid Chromatography-Targeted Mass Spectrometry, Abstract, 63th American Society for Mass Spectrometry (ASMS) Conference on Mass Spectrometry and Allied Topics, May 31-Jun. 4, 2015, St. Louis, Missouri.
Fu et al., A Robust SRM Assay for UMOD and Albumin in Urine, Poster Presentation (P04.31), 14th Human Proteome Organization (HUPO) World Congress, Sep. 27-30, 2015, Vancouver, Canada.
Fu et al., A Robust SRM Assay for UMOD and Albumin in Urine, Abstract Book, 14th Human Proteome Organization (HUPO) World Congress, Sep. 27-30, 2015, Vancouver, Canada.
Fu et al., A Robust SRM Assay for UMOD and Albumin in Urine, Abstract, 14th Human Proteome Organization (HUPO) World Congress, Sep. 27-30, 2015, Vancouver, Canada.
Fu et al., An Empirical Approach to Signature Peptide Choice for Selected Reaction Monitoring: Quantification of Uromodulin in Urine, Clinical Chemistry, 2016, 62(1), pp. 198-207.
Grote et al., Using pure protein to build a multiple reaction monitoring mass spectrometry assay for targeted detection and quantitation, Methods in molecular biology, 2013, 1005, pp. 199-213.
Holewinski et al., Methods for SwathTM: Data Independent Acquisition of TripleTOF Mass Spectrometers, Methods in Molecular Biology 1410, Quantitative Proteomics by Mass Spectrometry, Second Edition, Edited by Salvatore Sechi, Humana Press, 2016, pp. 265-279.
Kuzyk et al., Development of mrm-based assays for the absolute quantitation of plasma proteins. Methods in molecular biology, 2013, 1023, pp. 53-82.
Percy et al., Absolute quantitation of proteins in human blood by multiplexed multiple reaction monitoring mass spectrometry. Methods in molecular biology, 2013, 1000, pp. 167-189.
Prabakaran et al., Development of epitope-blocking elisa for universal detection of antibodies to human h5n1 influenza viruses. PLoS One, 2009, 4, e4566, pp. 1-10.
Schiess et al., Targeted proteomic strategy for clinical biomarker discovery. Mol. Oncol., 2009, 3, pp. 33-44.
Shuford et al., Peptide production and decay reates affect the quantitative accuracy of protein cleavage isotope dilution mass spectrometry (pc-idms). Molecular & Cellular Proteomics, 2012, 11, pp. 814-823.
Yassine et al., The application of multiple reaction monitoring and multi-analyte profiling to hdl proteins. Lipids health dis, 2014, 13(8), pp. 1-11.
Methods in Molecular Biology 1410, Quantitative Proteomics by Mass Spectrometry, Second Edition, Edited by Salvatore Sechi, Humana Press, 2016.
63th American Society for Mass Spectrometry (ASMS) Conference on Mass Spectrometry and Allied Topics, Program, May 31-Jun. 4, 2015, St. Louis, Missouri, pp. 1-236.

* cited by examiner

FIG. 1A

```
  1  MGQPSLTWMLMVVVASWFITTAATDTSEARWCSECHSNATCTEDEAVTTCTCQEGFTGDG   60
     ●━━━━━━━━━━●
        Signal peptide 61  LTCVDLDECAIPGAHNCSANSSCVNTPGSFSCVCPEGFRLSPGLGCTDVDECAEPGLSHC  120
                              ━━━━━━━━━━━━━━━━━━━━━━━━━━━━━━━━━━━━
                                           ΔUMOD-2

121  HALATCVNVVGSYLCVCPAGYRGDGWHCECSPGSCGPGLDCVPEGDALYCADPCQAHR TI  180
     ━━━━━━━━━━━━━━━━━━━━━━━━━━━━━━━━━━━━━━━━━━━━━━━━━━━━━●
                                                        ΔUMOD-2

181  DEYWR STEYGEYACDTDLR GWYR FVGQGGAR MAETCVPVLR CNTAAPMWLNGTHPSSDE  240
     ━━━━━━━━━━━━━━━━━━━━━━━━━●        ━━━━━━━━━━━━━━━━━━━━━━━━━━━
              ΔUMOD-4                              ΔUMOD-3

241  GIVSRK ACAHWSGH CCLWDASVQVK ACAGGYYVYN LTAPPECHLAYCTDPSSVEGTCEEC  300

301  SIDEDCKSNNGRWHCQCK QDFN ITDISLLEHRLECGANDMKVSLGKCQLKSLGFDK VFMY  360

361  LSDSR CSGFNDRDNR DWVSVVTPARD GPCGTVLTR NETHATYSNTLYLADEIIRDLNIK  420

421  INFACSYPLDMKVSLK ITALQPMV SALNIRVGGTGMFTVRMALFQTPSYTQPYQGSSVTLS  480

481  TEAFLYVGTMLDGGDLSREALLMTNCYATPSSNATDPLK YFIIQDR CPHTR DSTIQVVEN  540

541  GESSQGR FSVQMFR FAGNYDLVYLHCEVYLCDTMNEKCKPTCSGTRFR SGSVIDQSR VLN  600
                   ↑ Putative cleavage site                    ↑ Putative cleavage site 601  LGPITRKGVQATVSRAFSSLGLLKVWLPLLLSATLLTFQ  640
     ━━━━━━━━●━━━━━━━━━━━━━━━━━━━━━━━━━━━
           ↑ Propeptide         (SEQ ID NO: 82)
        GPI-anchor
```

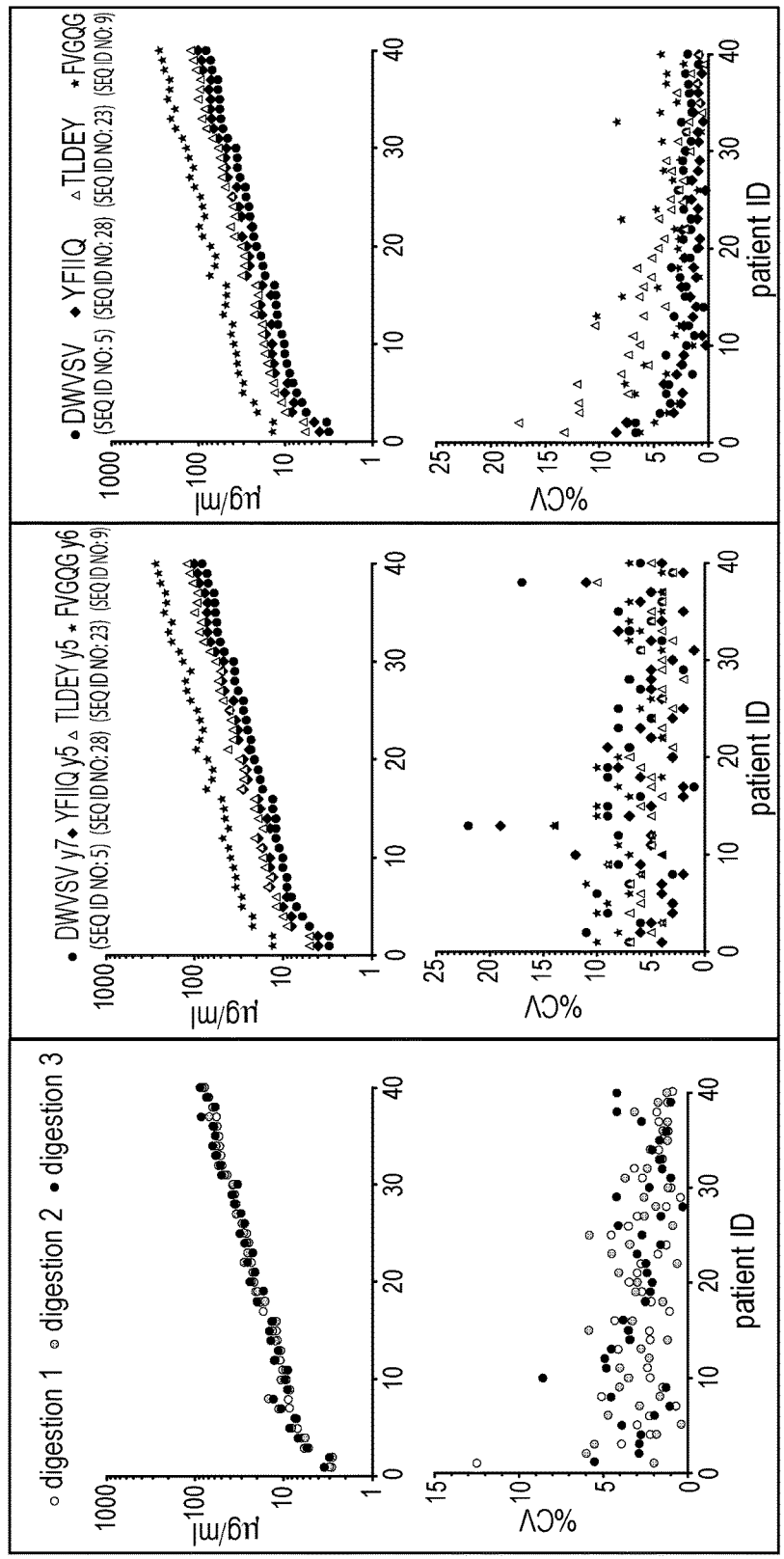
FIG. 2A LC-MS Injections
FIG. 2B Trypsin Digests
FIG. 2C SRM Transitions

Processing Settings

Peptide Filter:
- Number of Peptides per Protein: 5
- Number of Transitions per Peptide: 5
- Peptide Confidence Threshold % (0-99): 95
- False Discovery Rate Threshold % (0-100): 1.0
- ☑ Exclude Modified Peptides
- ☑ Exclude Shared Peptides
- ☐ Fix Rank XIC Options
- XIC Extraction Window (min): 5.0
- ○ XIC width (ppm): 75
- ● XIC width (Da): 0.050

☐ Clear Manual Selections

[OK] [Cancel]

SEQUENCE LISTING

<160> NUMBER OF SEQ ID NOS: 341

<210> SEQ ID NO 1
<211> LENGTH: 5
<212> TYPE: PRT
<213> ORGANISM: Artificial Sequence
<220> FEATURE:
<223> OTHER INFORMATION: synthetic construct

<400> SEQUENCE: 1

Ala Cys Ala His Trp
1               5

<210> SEQ ID NO 2
<211> LENGTH: 5

```
<212> TYPE: PRT
<213> ORGANISM: Artificial Sequence
<220> FEATURE:
<223> OTHER INFORMATION: synthetic construct

<400> SEQUENCE: 2

Ala Phe Ser Ser Leu
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic construct

<400> SEQUENCE: 3

Asp Gly Pro Cys Gly
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic construct

<400> SEQUENCE: 4

Asp Ser Thr Ile Gln
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct

<400> SEQUENCE: 5

Asp Trp Val Ser Val
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct

<400> SEQUENCE: 6

Phe Ala Gly Asn Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic construct

<400> SEQUENCE: 7

Phe Ala Leu Leu Met
1               5

<210> SEQ ID NO 8
<211> LENGTH: 5
<212> TYPE: PRT
```

```
<213> ORGANISM: Artificial Sequence
<220> FEATURE:
<223> OTHER INFORMATION: synthetic construct

<400> SEQUENCE: 8

Phe Ser Val Gln Met
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic construct

<400> SEQUENCE: 9

Phe Val Gly Gln Gly
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic construct

<400> SEQUENCE: 10

Gly Asp Gly Trp His
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic construct

<400> SEQUENCE: 11

Gly Val Gln Ala Thr
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic construct

<400> SEQUENCE: 12

Ile Asn Phe Ala Cys
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic construct

<400> SEQUENCE: 13

Lys Ala Cys Ala His
1               5

<210> SEQ ID NO 14
<211> LENGTH: 5
<212> TYPE: PRT
<213> ORGANISM: Artificial Sequence
```

```
<220> FEATURE:
<223> OTHER INFORMATION: synthetic construct

<400> SEQUENCE: 14

Lys Gly Val Gln Ala
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic construct

<400> SEQUENCE: 15

Leu Glu Cys Gly Ala
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic construct

<400> SEQUENCE: 16

Met Ala Glu Thr Cys
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic construct

<400> SEQUENCE: 17

Asn Glu Thr His Ala
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic construct

<400> SEQUENCE: 18

Gln Asp Phe Asn Ile
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic construct

<400> SEQUENCE: 19

Ser Gly Ser Val Ile
1               5

<210> SEQ ID NO 20
<211> LENGTH: 5
<212> TYPE: PRT
<213> ORGANISM: Artificial Sequence
<220> FEATURE:
```

```
<223> OTHER INFORMATION: synthetic construct

<400> SEQUENCE: 20

Ser Leu Gly Phe Asp
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic construct

<400> SEQUENCE: 21

Ser Thr Glu Tyr Gly
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic construct

<400> SEQUENCE: 22

Thr Ala Leu Gln Pro
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic construct

<400> SEQUENCE: 23

Thr Leu Asp Glu Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: synthetic construct

<400> SEQUENCE: 24

Val Phe Met Tyr Leu
1               5

<210> SEQ ID NO 25
<211> LENGTH: 5
<212> TYPE: PRT
<213> ORGANISM: Artificial Sequence
<220> FEATURE:
<223> OTHER INFORMATION: synthetic construct

<400> SEQUENCE: 25

Val Gly Gly Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic construct
```

<400> SEQUENCE: 26

Val Leu Asn Leu Gly
1               5

<210> SEQ ID NO 27
<211> LENGTH: 5
<212> TYPE: PRT
<213> ORGANISM: Artificial Sequence
<220> FEATURE:
<223> OTHER INFORMATION: synthetic construct

<400> SEQUENCE: 27

Val Trp Leu Pro Leu
1               5

<210> SEQ ID NO 28
<211> LENGTH: 5
<212> TYPE: PRT
<213> ORGANISM: Artificial Sequence
<220> FEATURE:
<223> OTHER INFORMATION: synthetic construct

<400> SEQUENCE: 28

Tyr Phe Ile Ile Gln
1               5

<210> SEQ ID NO 29
<211> LENGTH: 5
<212> TYPE: PRT
<213> ORGANISM: Artificial Sequence
<220> FEATURE:
<223> OTHER INFORMATION: synthetic construct

<400> SEQUENCE: 29

Trp His Cys Gln Cys
1               5

<210> SEQ ID NO 30
<211> LENGTH: 5
<212> TYPE: PRT
<213> ORGANISM: Artificial Sequence
<220> FEATURE:
<223> OTHER INFORMATION: synthetic construct

<400> SEQUENCE: 30

Cys Ser Gly Phe Asn
1               5

<210> SEQ ID NO 31
<211> LENGTH: 5
<212> TYPE: PRT
<213> ORGANISM: Artificial Sequence
<220> FEATURE:
<223> OTHER INFORMATION: synthetic construct

<400> SEQUENCE: 31

Cys Lys Pro Thr Cys
1               5

<210> SEQ ID NO 32
<211> LENGTH: 9
<212> TYPE: PRT
<213> ORGANISM: Artificial Sequence
<220> FEATURE:
<223> OTHER INFORMATION: synthetic construct

```
<400> SEQUENCE: 32

Arg Thr Leu Asp Glu Tyr Trp Arg Ser
1               5

<210> SEQ ID NO 33
<211> LENGTH: 17
<212> TYPE: PRT
<213> ORGANISM: Artificial Sequence
<220> FEATURE:
<223> OTHER INFORMATION: synthetic construct

<400> SEQUENCE: 33

Arg Ser Thr Glu Tyr Gly Glu Gly Tyr Ala Cys Asp Thr Asp Leu Arg
1               5                   10                  15

Gly

<210> SEQ ID NO 34
<211> LENGTH: 10
<212> TYPE: PRT
<213> ORGANISM: Artificial Sequence
<220> FEATURE:
<223> OTHER INFORMATION: synthetic construct

<400> SEQUENCE: 34

Arg Phe Val Gly Gln Gly Gly Ala Arg Met
1               5                   10

<210> SEQ ID NO 35
<211> LENGTH: 12
<212> TYPE: PRT
<213> ORGANISM: Artificial Sequence
<220> FEATURE:
<223> OTHER INFORMATION: synthetic construct

<400> SEQUENCE: 35

Arg Met Ala Glu Thr Cys Val Pro Val Leu Arg Cys
1               5                   10

<210> SEQ ID NO 36
<211> LENGTH: 21
<212> TYPE: PRT
<213> ORGANISM: Artificial Sequence
<220> FEATURE:
<223> OTHER INFORMATION: synthetic construct

<400> SEQUENCE: 36

Lys Ala Cys Ala His Trp Ser Gly His Cys Cys Leu Trp Asp Ala Ser
1               5                   10                  15

Val Gln Val Lys Ala
            20

<210> SEQ ID NO 37
<211> LENGTH: 8
<212> TYPE: PRT
<213> ORGANISM: Artificial Sequence
<220> FEATURE:
<223> OTHER INFORMATION: synthetic construct

<400> SEQUENCE: 37

Arg Trp His Cys Gln Cys Lys Gln
1               5

<210> SEQ ID NO 38
<211> LENGTH: 16
<212> TYPE: PRT
```

```
<213> ORGANISM: Artificial Sequence
<220> FEATURE:
<223> OTHER INFORMATION: synthetic construct

<400> SEQUENCE: 38

Lys Gln Asp Phe Asn Ile Thr Asp Ile Ser Leu Leu Glu His Arg Leu
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: synthetic construct

<400> SEQUENCE: 39

Arg Leu Glu Cys Gly Ala Asn Asp Met Lys Val
1               5                   10

<210> SEQ ID NO 40
<211> LENGTH: 8
<212> TYPE: PRT
<213> ORGANISM: Artificial Sequence
<220> FEATURE:
<223> OTHER INFORMATION: synthetic construct

<400> SEQUENCE: 40

Lys Ser Leu Gly Phe Asp Lys Val
1               5

<210> SEQ ID NO 41
<211> LENGTH: 11
<212> TYPE: PRT
<213> ORGANISM: Artificial Sequence
<220> FEATURE:
<223> OTHER INFORMATION: synthetic construct

<400> SEQUENCE: 41

Lys Val Phe Met Tyr Leu Ser Asp Ser Arg Cys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: synthetic construct

<400> SEQUENCE: 42

Arg Cys Ser Gly Phe Asn Asp Arg Asp
1               5

<210> SEQ ID NO 43
<211> LENGTH: 12
<212> TYPE: PRT
<213> ORGANISM: Artificial Sequence
<220> FEATURE:
<223> OTHER INFORMATION: synthetic construct

<400> SEQUENCE: 43

Arg Asp Trp Val Ser Val Val Thr Pro Ala Arg Asp
1               5                   10

<210> SEQ ID NO 44
<211> LENGTH: 12
<212> TYPE: PRT
<213> ORGANISM: Artificial Sequence
```

```
<220> FEATURE:
<223> OTHER INFORMATION: synthetic construct

<400> SEQUENCE: 44

Arg Asp Gly Pro Cys Gly Thr Val Leu Thr Arg Asn
1               5                   10

<210> SEQ ID NO 45
<211> LENGTH: 22
<212> TYPE: PRT
<213> ORGANISM: Artificial Sequence
<220> FEATURE:
<223> OTHER INFORMATION: synthetic construct

<400> SEQUENCE: 45

Arg Asn Glu Thr His Ala Thr Tyr Ser Asn Thr Leu Tyr Leu Ala Asp
1               5                   10                  15

Glu Ile Ile Ile Arg Asp
            20

<210> SEQ ID NO 46
<211> LENGTH: 14
<212> TYPE: PRT
<213> ORGANISM: Artificial Sequence
<220> FEATURE:
<223> OTHER INFORMATION: synthetic construct

<400> SEQUENCE: 46

Lys Ile Asn Phe Ala Cys Ser Tyr Pro Leu Asp Met Lys Val
1               5                   10

<210> SEQ ID NO 47
<211> LENGTH: 15
<212> TYPE: PRT
<213> ORGANISM: Artificial Sequence
<220> FEATURE:
<223> OTHER INFORMATION: synthetic construct

<400> SEQUENCE: 47

Lys Thr Ala Leu Gln Pro Met Val Ser Ala Leu Asn Ile Arg Val
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: synthetic construct

<400> SEQUENCE: 48

Arg Val Gly Gly Thr Gly Met Phe Thr Val Arg Met
1               5                   10

<210> SEQ ID NO 49
<211> LENGTH: 23
<212> TYPE: PRT
<213> ORGANISM: Artificial Sequence
<220> FEATURE:
<223> OTHER INFORMATION: synthetic construct

<400> SEQUENCE: 49

Arg Phe Ala Leu Leu Met Thr Asn Cys Tyr Ala Thr Pro Ser Ser Asn
1               5                   10                  15

Ala Thr Asp Pro Leu Lys Tyr
            20
```

<210> SEQ ID NO 50
<211> LENGTH: 9
<212> TYPE: PRT
<213> ORGANISM: Artificial Sequence
<220> FEATURE:
<223> OTHER INFORMATION: synthetic construct

<400> SEQUENCE: 50

Lys Tyr Phe Ile Ile Gln Asp Arg Cys
1               5

<210> SEQ ID NO 51
<211> LENGTH: 18
<212> TYPE: PRT
<213> ORGANISM: Artificial Sequence
<220> FEATURE:
<223> OTHER INFORMATION: synthetic construct

<400> SEQUENCE: 51

Arg Asp Ser Thr Ile Gln Val Val Glu Asn Gly Glu Ser Ser Gln Gly
1               5                   10                  15

Arg Phe

<210> SEQ ID NO 52
<211> LENGTH: 9
<212> TYPE: PRT
<213> ORGANISM: Artificial Sequence
<220> FEATURE:
<223> OTHER INFORMATION: synthetic construct

<400> SEQUENCE: 52

Arg Phe Ser Val Gln Met Phe Arg Phe
1               5

<210> SEQ ID NO 53
<211> LENGTH: 11
<212> TYPE: PRT
<213> ORGANISM: Artificial Sequence
<220> FEATURE:
<223> OTHER INFORMATION: synthetic construct

<400> SEQUENCE: 53

Lys Cys Lys Pro Thr Cys Ser Gly Thr Arg Phe
1               5                   10

<210> SEQ ID NO 54
<211> LENGTH: 11
<212> TYPE: PRT
<213> ORGANISM: Artificial Sequence
<220> FEATURE:
<223> OTHER INFORMATION: synthetic construct

<400> SEQUENCE: 54

Arg Ser Gly Ser Val Ile Asp Gln Ser Arg Val
1               5                   10

<210> SEQ ID NO 55
<211> LENGTH: 11
<212> TYPE: PRT
<213> ORGANISM: Artificial Sequence
<220> FEATURE:
<223> OTHER INFORMATION: synthetic construct

<400> SEQUENCE: 55

Arg Val Leu Asn Leu Gly Pro Ile Thr Arg Lys
1               5                   10

```
<210> SEQ ID NO 56
<211> LENGTH: 10
<212> TYPE: PRT
<213> ORGANISM: Artificial Sequence
<220> FEATURE:
<223> OTHER INFORMATION: synthetic construct

<400> SEQUENCE: 56

Lys Gly Val Gln Ala Thr Val Ser Arg Ala
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic construct

<400> SEQUENCE: 57

Arg Ala Phe Ser Ser Leu Gly Leu Leu Lys Val
1               5                   10

<210> SEQ ID NO 58
<211> LENGTH: 17
<212> TYPE: PRT
<213> ORGANISM: Artificial Sequence
<220> FEATURE:
<223> OTHER INFORMATION: synthetic construct

<400> SEQUENCE: 58

Lys Val Trp Leu Pro Leu Leu Leu Ser Ala Thr Leu Thr Leu Thr Phe
1               5                   10                  15

Gln

<210> SEQ ID NO 59
<211> LENGTH: 7
<212> TYPE: PRT
<213> ORGANISM: Artificial Sequence
<220> FEATURE:
<223> OTHER INFORMATION: synthetic construct

<400> SEQUENCE: 59

Thr Leu Asp Glu Tyr Trp Arg
1               5

<210> SEQ ID NO 60
<211> LENGTH: 10
<212> TYPE: PRT
<213> ORGANISM: Artificial Sequence
<220> FEATURE:
<223> OTHER INFORMATION: synthetic construct

<400> SEQUENCE: 60

Asp Gly Pro Cys Gly Thr Val Leu Thr Arg
1               5                   10

<210> SEQ ID NO 61
<211> LENGTH: 7
<212> TYPE: PRT
<213> ORGANISM: Artificial Sequence
<220> FEATURE:
<223> OTHER INFORMATION: synthetic construct

<400> SEQUENCE: 61

Tyr Phe Ile Ile Gln Asp Arg
```

```
<210> SEQ ID NO 62
<211> LENGTH: 8
<212> TYPE: PRT
<213> ORGANISM: Artificial Sequence
<220> FEATURE:
<223> OTHER INFORMATION: synthetic construct

<400> SEQUENCE: 62

Phe Val Gly Gln Gly Gly Ala Arg
1               5

<210> SEQ ID NO 63
<211> LENGTH: 10
<212> TYPE: PRT
<213> ORGANISM: Artificial Sequence
<220> FEATURE:
<223> OTHER INFORMATION: synthetic construct

<400> SEQUENCE: 63

Asp Trp Val Ser Val Val Thr Pro Ala Arg
1               5                   10

<210> SEQ ID NO 64
<211> LENGTH: 9
<212> TYPE: PRT
<213> ORGANISM: Artificial Sequence
<220> FEATURE:
<223> OTHER INFORMATION: synthetic construct

<400> SEQUENCE: 64

Ser Gly Ser Val Ile Asp Gln Ser Arg
1               5

<210> SEQ ID NO 65
<211> LENGTH: 7
<212> TYPE: PRT
<213> ORGANISM: Artificial Sequence
<220> FEATURE:
<223> OTHER INFORMATION: synthetic construct

<400> SEQUENCE: 65

Phe Ser Val Gln Met Phe Arg
1               5

<210> SEQ ID NO 66
<211> LENGTH: 15
<212> TYPE: PRT
<213> ORGANISM: Artificial Sequence
<220> FEATURE:
<223> OTHER INFORMATION: synthetic construct

<400> SEQUENCE: 66

Ser Thr Glu Tyr Gly Glu Gly Tyr Ala Cys Asp Thr Asp Leu Arg
1               5                   10                  15

<210> SEQ ID NO 67
<211> LENGTH: 9
<212> TYPE: PRT
<213> ORGANISM: Artificial Sequence
<220> FEATURE:
<223> OTHER INFORMATION: synthetic construct

<400> SEQUENCE: 67

Val Phe Met Tyr Leu Ser Asp Ser Arg
1               5
```

<210> SEQ ID NO 68
<211> LENGTH: 10
<212> TYPE: PRT
<213> ORGANISM: Artificial Sequence
<220> FEATURE:
<223> OTHER INFORMATION: synthetic construct

<400> SEQUENCE: 68

Met Ala Glu Thr Cys Val Pro Val Leu Arg
1               5                   10

<210> SEQ ID NO 69
<211> LENGTH: 16
<212> TYPE: PRT
<213> ORGANISM: Artificial Sequence
<220> FEATURE:
<223> OTHER INFORMATION: synthetic construct

<400> SEQUENCE: 69

Asp Ser Thr Ile Gln Val Val Glu Asn Gly Glu Ser Ser Gln Gly Arg
1               5                   10                  15

<210> SEQ ID NO 70
<211> LENGTH: 13
<212> TYPE: PRT
<213> ORGANISM: Artificial Sequence
<220> FEATURE:
<223> OTHER INFORMATION: synthetic construct

<400> SEQUENCE: 70

Thr Ala Leu Gln Pro Met Val Ser Ala Leu Asn Ile Arg
1               5                   10

<210> SEQ ID NO 71
<211> LENGTH: 12
<212> TYPE: PRT
<213> ORGANISM: Artificial Sequence
<220> FEATURE:
<223> OTHER INFORMATION: synthetic construct

<400> SEQUENCE: 71

Tyr Ser Gln Gln Gln Leu Met Glu Thr Ser His Arg
1               5                   10

<210> SEQ ID NO 72
<211> LENGTH: 13
<212> TYPE: PRT
<213> ORGANISM: Artificial Sequence
<220> FEATURE:
<223> OTHER INFORMATION: synthetic construct

<400> SEQUENCE: 72

Arg Asp Trp Glu Asn Pro Gly Val Thr Gln Leu Asn Arg
1               5                   10

<210> SEQ ID NO 73
<211> LENGTH: 9
<212> TYPE: PRT
<213> ORGANISM: Artificial Sequence
<220> FEATURE:
<223> OTHER INFORMATION: synthetic construct

<400> SEQUENCE: 73

Gly Asp Phe Gln Phe Asn Ile Ser Arg
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic construct

<400> SEQUENCE: 74

Ile Asp Pro Asn Ala Trp Val Glu Arg
1               5

<210> SEQ ID NO 75
<211> LENGTH: 20
<212> TYPE: PRT
<213> ORGANISM: Artificial Sequence
<220> FEATURE:
<223> OTHER INFORMATION: synthetic construct

<400> SEQUENCE: 75

Asp Val Ser Leu Leu His Lys Pro Thr Thr Gln Ile Ser Asp Phe His
1               5                   10                  15

Val Ala Thr Arg
            20

<210> SEQ ID NO 76
<211> LENGTH: 12
<212> TYPE: PRT
<213> ORGANISM: Artificial Sequence
<220> FEATURE:
<223> OTHER INFORMATION: synthetic construct

<400> SEQUENCE: 76

Val Asp Glu Asp Gln Pro Phe Pro Ala Val Pro Lys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: synthetic construct

<400> SEQUENCE: 77

Asp Trp Glu Asn Pro Gly Val Thr Gln Leu Asn Arg
1               5                   10

<210> SEQ ID NO 78
<211> LENGTH: 14
<212> TYPE: PRT
<213> ORGANISM: Artificial Sequence
<220> FEATURE:
<223> OTHER INFORMATION: synthetic construct

<400> SEQUENCE: 78

Ala Pro Leu Asp Asn Asp Ile Gly Val Ser Glu Ala Thr Arg
1               5                   10

<210> SEQ ID NO 79
<211> LENGTH: 9
<212> TYPE: PRT
<213> ORGANISM: Artificial Sequence
<220> FEATURE:
<223> OTHER INFORMATION: synthetic construct

<400> SEQUENCE: 79

Trp Val Gly Tyr Gly Gln Asp Ser Arg

```
1               5
```

<210> SEQ ID NO 80
<211> LENGTH: 8
<212> TYPE: PRT
<213> ORGANISM: Artificial Sequence
<220> FEATURE:
<223> OTHER INFORMATION: synthetic construct

<400> SEQUENCE: 80

```
Gly Asp Phe Gln Phe Asn Ile Ser
1               5
```

<210> SEQ ID NO 81
<211> LENGTH: 134
<212> TYPE: PRT
<213> ORGANISM: Artificial Sequence
<220> FEATURE:
<223> OTHER INFORMATION: synthetic construct

<400> SEQUENCE: 81

```
Ala Gly Gly Ser Ser Glu Pro Val Thr Gly Leu Ala Asp Lys Val Glu
1               5                   10                  15

Ala Thr Phe Gly Val Asp Glu Ser Ala Asn Lys Tyr Ile Leu Ala Gly
            20                  25                  30

Val Glu Ser Asn Lys Asp Ala Val Thr Pro Ala Asp Phe Ser Glu Trp
        35                  40                  45

Ser Lys Phe Leu Leu Gln Phe Gly Ala Gln Gly Ser Pro Leu Phe Lys
    50                  55                  60

Leu Gly Gly Asn Glu Thr Gln Val Arg Thr Pro Val Ile Ser Gly Gly
65                  70                  75                  80

Pro Tyr Tyr Glu Arg Thr Pro Val Ile Thr Gly Ala Pro Tyr Tyr Glu
                85                  90                  95

Arg Gly Asp Leu Asp Ala Ala Ser Tyr Tyr Ala Pro Val Arg Thr Gly
            100                 105                 110

Phe Ile Ile Asp Pro Gly Gly Val Ile Arg Gly Thr Phe Ile Ile Asp
        115                 120                 125

Pro Ala Ala Ile Val Arg
        130
```

<210> SEQ ID NO 82
<211> LENGTH: 640
<212> TYPE: PRT
<213> ORGANISM: Homo sapiens

<400> SEQUENCE: 82

```
Met Gly Gln Pro Ser Leu Thr Trp Met Leu Met Val Val Val Ala Ser
1               5                   10                  15

Trp Phe Ile Thr Thr Ala Ala Thr Asp Thr Ser Glu Ala Arg Trp Cys
            20                  25                  30

Ser Glu Cys His Ser Asn Ala Thr Cys Thr Asp Glu Ala Val Thr
        35                  40                  45

Thr Cys Thr Cys Gln Glu Gly Phe Thr Gly Asp Gly Leu Thr Cys Val
    50                  55                  60

Asp Leu Asp Glu Cys Ala Ile Pro Gly Ala His Asn Cys Ser Ala Asn
65                  70                  75                  80

Ser Ser Cys Val Asn Thr Pro Gly Ser Phe Ser Cys Val Cys Pro Glu
                85                  90                  95

Gly Phe Arg Leu Ser Pro Gly Leu Gly Cys Thr Asp Val Asp Glu Cys
```

```
                100             105              110
Ala Glu Pro Gly Leu Ser His Cys His Ala Leu Ala Thr Cys Val Asn
            115             120             125
Val Val Gly Ser Tyr Leu Cys Val Cys Pro Ala Gly Tyr Arg Gly Asp
            130             135             140
Gly Trp His Cys Glu Cys Ser Pro Gly Ser Cys Gly Pro Gly Leu Asp
145             150             155             160
Cys Val Pro Glu Gly Asp Ala Leu Val Cys Ala Asp Pro Cys Gln Ala
            165             170             175
His Arg Thr Leu Asp Glu Tyr Trp Arg Ser Thr Glu Tyr Gly Glu Gly
            180             185             190
Tyr Ala Cys Asp Thr Asp Leu Arg Gly Trp Tyr Arg Phe Val Gly Gln
            195             200             205
Gly Gly Ala Arg Met Ala Glu Thr Cys Val Pro Val Leu Arg Cys Asn
            210             215             220
Thr Ala Ala Pro Met Trp Leu Asn Gly Thr His Pro Ser Ser Asp Glu
225             230             235             240
Gly Ile Val Ser Arg Lys Ala Cys Ala His Trp Ser Gly His Cys Cys
                245             250             255
Leu Trp Asp Ala Ser Val Gln Val Lys Ala Cys Ala Gly Gly Tyr Tyr
            260             265             270
Val Tyr Asn Leu Thr Ala Pro Pro Glu Cys His Leu Ala Tyr Cys Thr
            275             280             285
Asp Pro Ser Ser Val Glu Gly Thr Cys Glu Glu Cys Ser Ile Asp Glu
            290             295             300
Asp Cys Lys Ser Asn Asn Gly Arg Trp His Cys Gln Cys Lys Gln Asp
305             310             315             320
Phe Asn Ile Thr Asp Ile Ser Leu Leu Glu His Arg Leu Glu Cys Gly
                325             330             335
Ala Asn Asp Met Lys Val Ser Leu Gly Lys Cys Gln Leu Lys Ser Leu
                340             345             350
Gly Phe Asp Lys Val Phe Met Tyr Leu Ser Asp Ser Arg Cys Ser Gly
            355             360             365
Phe Asn Asp Arg Asp Asn Arg Asp Trp Val Ser Val Val Thr Pro Ala
370             375             380
Arg Asp Gly Pro Cys Gly Thr Val Leu Thr Arg Asn Glu Thr His Ala
385             390             395             400
Thr Tyr Ser Asn Thr Leu Tyr Leu Ala Asp Glu Ile Ile Ile Arg Asp
                405             410             415
Leu Asn Ile Lys Ile Asn Phe Ala Cys Ser Tyr Pro Leu Asp Met Lys
                420             425             430
Val Ser Leu Lys Thr Ala Leu Gln Pro Met Val Ser Ala Leu Asn Ile
            435             440             445
Arg Val Gly Gly Thr Gly Met Phe Thr Val Arg Met Ala Leu Phe Gln
            450             455             460
Thr Pro Ser Tyr Thr Gln Pro Tyr Gln Gly Ser Ser Val Thr Leu Ser
465             470             475             480
Thr Glu Ala Phe Leu Tyr Val Gly Thr Met Leu Asp Gly Gly Asp Leu
                485             490             495
Ser Arg Phe Ala Leu Leu Met Thr Asn Cys Tyr Ala Thr Pro Ser Ser
            500             505             510
Asn Ala Thr Asp Pro Leu Lys Tyr Phe Ile Ile Gln Asp Arg Cys Pro
            515             520             525
```

```
His Thr Arg Asp Ser Thr Ile Gln Val Val Glu Asn Gly Glu Ser Ser
    530                 535                 540

Gln Gly Arg Phe Ser Val Gln Met Phe Arg Phe Ala Gly Asn Tyr Asp
545                 550                 555                 560

Leu Val Tyr Leu His Cys Glu Val Tyr Leu Cys Asp Thr Met Asn Glu
                565                 570                 575

Lys Cys Lys Pro Thr Cys Ser Gly Thr Arg Phe Arg Ser Gly Ser Val
                580                 585                 590

Ile Asp Gln Ser Arg Val Leu Asn Leu Gly Pro Ile Thr Arg Lys Gly
            595                 600                 605

Val Gln Ala Thr Val Ser Arg Ala Phe Ser Ser Leu Gly Leu Leu Lys
    610                 615                 620

Val Trp Leu Pro Leu Leu Leu Ser Ala Thr Leu Thr Leu Thr Phe Gln
625                 630                 635                 640

<210> SEQ ID NO 83
<211> LENGTH: 9
<212> TYPE: PRT
<213> ORGANISM: Artificial Sequence
<220> FEATURE:
<223> OTHER INFORMATION: synthetic construct

<400> SEQUENCE: 83

Gln Thr Ala Leu Val Glu Leu Val Lys
1               5

<210> SEQ ID NO 84
<211> LENGTH: 27
<212> TYPE: PRT
<213> ORGANISM: Artificial Sequence
<220> FEATURE:
<223> OTHER INFORMATION: synthetic construct

<400> SEQUENCE: 84

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25

<210> SEQ ID NO 85
<211> LENGTH: 10
<212> TYPE: PRT
<213> ORGANISM: Artificial Sequence
<220> FEATURE:
<223> OTHER INFORMATION: synthetic construct

<400> SEQUENCE: 85

Leu Val Asn Glu Val Thr Glu Phe Ala Lys
1               5                   10

<210> SEQ ID NO 86
<211> LENGTH: 16
<212> TYPE: PRT
<213> ORGANISM: Artificial Sequence
<220> FEATURE:
<223> OTHER INFORMATION: synthetic construct

<400> SEQUENCE: 86

Arg Pro Cys Phe Ser Ala Leu Glu Val Asp Glu Thr Tyr Val Pro Lys
1               5                   10                  15

<210> SEQ ID NO 87
```

```
<211> LENGTH: 17
<212> TYPE: PRT
<213> ORGANISM: Artificial Sequence
<220> FEATURE:
<223> OTHER INFORMATION: synthetic construct

<400> SEQUENCE: 87

Val Phe Asp Glu Phe Lys Pro Leu Val Glu Glu Pro Gln Asn Leu Ile
1               5                   10                  15

Lys

<210> SEQ ID NO 88
<211> LENGTH: 13
<212> TYPE: PRT
<213> ORGANISM: Artificial Sequence
<220> FEATURE:
<223> OTHER INFORMATION: synthetic construct

<400> SEQUENCE: 88

Gln Asn Cys Glu Leu Phe Glu Gln Leu Gly Glu Tyr Lys
1               5                   10

<210> SEQ ID NO 89
<211> LENGTH: 12
<212> TYPE: PRT
<213> ORGANISM: Artificial Sequence
<220> FEATURE:
<223> OTHER INFORMATION: synthetic construct

<400> SEQUENCE: 89

Ala Val Met Asp Asp Phe Ala Ala Phe Val Glu Lys
1               5                   10

<210> SEQ ID NO 90
<211> LENGTH: 22
<212> TYPE: PRT
<213> ORGANISM: Artificial Sequence
<220> FEATURE:
<223> OTHER INFORMATION: synthetic construct

<400> SEQUENCE: 90

Arg Met Pro Cys Ala Glu Asp Tyr Leu Ser Val Val Leu Asn Gln Leu
1               5                   10                  15

Cys Val Leu His Glu Lys
            20

<210> SEQ ID NO 91
<211> LENGTH: 10
<212> TYPE: PRT
<213> ORGANISM: Artificial Sequence
<220> FEATURE:
<223> OTHER INFORMATION: synthetic construct

<400> SEQUENCE: 91

Lys Gln Thr Ala Leu Val Glu Leu Val Lys
1               5                   10

<210> SEQ ID NO 92
<211> LENGTH: 17
<212> TYPE: PRT
<213> ORGANISM: Artificial Sequence
<220> FEATURE:
<223> OTHER INFORMATION: synthetic construct

<400> SEQUENCE: 92

Val His Thr Glu Cys Cys His Gly Asp Leu Leu Glu Cys Ala Asp Asp
```

```
1               5                   10                  15
Arg

<210> SEQ ID NO 93
<211> LENGTH: 8
<212> TYPE: PRT
<213> ORGANISM: Artificial Sequence
<220> FEATURE:
<223> OTHER INFORMATION: synthetic construct

<400> SEQUENCE: 93

Leu Cys Thr Val Ala Thr Leu Arg
1               5

<210> SEQ ID NO 94
<211> LENGTH: 23
<212> TYPE: PRT
<213> ORGANISM: Artificial Sequence
<220> FEATURE:
<223> OTHER INFORMATION: synthetic construct

<400> SEQUENCE: 94

Leu Val Arg Pro Glu Val Asp Val Met Cys Thr Ala Phe His Asp Asn
1               5                   10                  15

Glu Glu Thr Phe Leu Lys Lys
            20

<210> SEQ ID NO 95
<211> LENGTH: 10
<212> TYPE: PRT
<213> ORGANISM: Artificial Sequence
<220> FEATURE:
<223> OTHER INFORMATION: synthetic construct

<400> SEQUENCE: 95

Glu Cys Cys Glu Lys Pro Leu Leu Glu Lys
1               5                   10

<210> SEQ ID NO 96
<211> LENGTH: 11
<212> TYPE: PRT
<213> ORGANISM: Artificial Sequence
<220> FEATURE:
<223> OTHER INFORMATION: synthetic construct

<400> SEQUENCE: 96

Leu Val Ala Ala Ser Gln Ala Ala Leu Gly Leu
1               5                   10

<210> SEQ ID NO 97
<211> LENGTH: 8
<212> TYPE: PRT
<213> ORGANISM: Artificial Sequence
<220> FEATURE:
<223> OTHER INFORMATION: synthetic construct

<400> SEQUENCE: 97

Asp Asp Asn Pro Asn Leu Pro Arg
1               5

<210> SEQ ID NO 98
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 98

Phe Gln Asn Ala Leu Leu Val Arg
1               5

<210> SEQ ID NO 99
<211> LENGTH: 14
<212> TYPE: PRT
<213> ORGANISM: Artificial Sequence
<220> FEATURE:
<223> OTHER INFORMATION: synthetic construct

<400> SEQUENCE: 99

Val Pro Gln Val Ser Thr Pro Thr Leu Val Glu Val Ser Arg
1               5                   10

<210> SEQ ID NO 100
<211> LENGTH: 15
<212> TYPE: PRT
<213> ORGANISM: Artificial Sequence
<220> FEATURE:
<223> OTHER INFORMATION: synthetic construct

<400> SEQUENCE: 100

Arg His Pro Tyr Phe Tyr Ala Pro Glu Leu Leu Phe Phe Ala Lys
1               5                   10                  15

<210> SEQ ID NO 101
<211> LENGTH: 8
<212> TYPE: PRT
<213> ORGANISM: Artificial Sequence
<220> FEATURE:
<223> OTHER INFORMATION: synthetic construct

<400> SEQUENCE: 101

Ala Glu Phe Ala Glu Val Ser Lys
1               5

<210> SEQ ID NO 102
<211> LENGTH: 9
<212> TYPE: PRT
<213> ORGANISM: Artificial Sequence
<220> FEATURE:
<223> OTHER INFORMATION: synthetic construct

<400> SEQUENCE: 102

Ser Leu His Thr Leu Phe Gly Asp Lys
1               5

<210> SEQ ID NO 103
<211> LENGTH: 15
<212> TYPE: PRT
<213> ORGANISM: Artificial Sequence
<220> FEATURE:
<223> OTHER INFORMATION: synthetic construct

<400> SEQUENCE: 103

Lys Val Pro Gln Val Ser Thr Pro Thr Leu Val Glu Val Ser Arg
1               5                   10                  15

<210> SEQ ID NO 104
<211> LENGTH: 8
<212> TYPE: PRT
<213> ORGANISM: Artificial Sequence
<220> FEATURE:
<223> OTHER INFORMATION: synthetic construct
```

```
<400> SEQUENCE: 104

Lys Tyr Leu Tyr Glu Ile Ala Arg
1               5

<210> SEQ ID NO 105
<211> LENGTH: 8
<212> TYPE: PRT
<213> ORGANISM: Artificial Sequence
<220> FEATURE:
<223> OTHER INFORMATION: synthetic construct

<400> SEQUENCE: 105

Thr Tyr Glu Thr Thr Leu Glu Lys
1               5

<210> SEQ ID NO 106
<211> LENGTH: 12
<212> TYPE: PRT
<213> ORGANISM: Artificial Sequence
<220> FEATURE:
<223> OTHER INFORMATION: synthetic construct

<400> SEQUENCE: 106

Arg His Pro Asp Tyr Ser Val Val Leu Leu Leu Arg
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic construct

<400> SEQUENCE: 107

His Pro Asp Tyr Ser Val Val Leu Leu Leu Arg
1               5                   10

<210> SEQ ID NO 108
<211> LENGTH: 12
<212> TYPE: PRT
<213> ORGANISM: Artificial Sequence
<220> FEATURE:
<223> OTHER INFORMATION: synthetic construct

<400> SEQUENCE: 108

Lys Leu Val Ala Ala Ser Gln Ala Ala Leu Gly Leu
1               5                   10

<210> SEQ ID NO 109
<211> LENGTH: 22
<212> TYPE: PRT
<213> ORGANISM: Artificial Sequence
<220> FEATURE:
<223> OTHER INFORMATION: synthetic construct

<400> SEQUENCE: 109

Leu Val Arg Pro Glu Val Asp Val Met Cys Thr Ala Phe His Asp Asn
1               5                   10                  15

Glu Glu Thr Phe Leu Lys
            20

<210> SEQ ID NO 110
<211> LENGTH: 10
<212> TYPE: PRT
<213> ORGANISM: Artificial Sequence
<220> FEATURE:
```

<223> OTHER INFORMATION: synthetic construct

<400> SEQUENCE: 110

Phe Lys Asp Leu Gly Glu Glu Asn Phe Lys
1               5                   10

<210> SEQ ID NO 111
<211> LENGTH: 7
<212> TYPE: PRT
<213> ORGANISM: Artificial Sequence
<220> FEATURE:
<223> OTHER INFORMATION: synthetic construct

<400> SEQUENCE: 111

Tyr Leu Tyr Glu Ile Ala Arg
1               5

<210> SEQ ID NO 112
<211> LENGTH: 22
<212> TYPE: PRT
<213> ORGANISM: Artificial Sequence
<220> FEATURE:
<223> OTHER INFORMATION: synthetic construct

<400> SEQUENCE: 112

Val His Thr Glu Cys Cys His Gly Asp Leu Leu Glu Cys Ala Asp Asp
1               5                   10                  15

Arg Ala Asp Leu Ala Lys
            20

<210> SEQ ID NO 113
<211> LENGTH: 16
<212> TYPE: PRT
<213> ORGANISM: Artificial Sequence
<220> FEATURE:
<223> OTHER INFORMATION: synthetic construct

<400> SEQUENCE: 113

Asn Glu Cys Phe Leu Gln His Lys Asp Asp Asn Pro Asn Leu Pro Arg
1               5                   10                  15

<210> SEQ ID NO 114
<211> LENGTH: 12
<212> TYPE: PRT
<213> ORGANISM: Artificial Sequence
<220> FEATURE:
<223> OTHER INFORMATION: synthetic construct

<400> SEQUENCE: 114

Ala Ala Phe Thr Glu Cys Cys Gln Ala Ala Asp Lys
1               5                   10

<210> SEQ ID NO 115
<211> LENGTH: 12
<212> TYPE: PRT
<213> ORGANISM: Artificial Sequence
<220> FEATURE:
<223> OTHER INFORMATION: synthetic construct

<400> SEQUENCE: 115

Glu Thr Tyr Gly Glu Met Ala Asp Cys Cys Ala Lys
1               5                   10

<210> SEQ ID NO 116
<211> LENGTH: 21
<212> TYPE: PRT

```
<213> ORGANISM: Artificial Sequence
<220> FEATURE:
<223> OTHER INFORMATION: synthetic construct

<400> SEQUENCE: 116

Gln Glu Pro Glu Arg Asn Glu Cys Phe Leu Gln His Lys Asp Asp Asn
1               5                   10                  15

Pro Asn Leu Pro Arg
            20

<210> SEQ ID NO 117
<211> LENGTH: 12
<212> TYPE: PRT
<213> ORGANISM: Artificial Sequence
<220> FEATURE:
<223> OTHER INFORMATION: synthetic construct

<400> SEQUENCE: 117

Tyr Ile Cys Glu Asn Gln Asp Ser Ile Ser Ser Lys
1               5                   10

<210> SEQ ID NO 118
<211> LENGTH: 13
<212> TYPE: PRT
<213> ORGANISM: Artificial Sequence
<220> FEATURE:
<223> OTHER INFORMATION: synthetic construct

<400> SEQUENCE: 118

Ala Asp Asp Lys Glu Thr Cys Phe Ala Glu Glu Gly Lys
1               5                   10

<210> SEQ ID NO 119
<211> LENGTH: 8
<212> TYPE: PRT
<213> ORGANISM: Artificial Sequence
<220> FEATURE:
<223> OTHER INFORMATION: synthetic construct

<400> SEQUENCE: 119

Asn Glu Cys Phe Leu Gln His Lys
1               5

<210> SEQ ID NO 120
<211> LENGTH: 9
<212> TYPE: PRT
<213> ORGANISM: Artificial Sequence
<220> FEATURE:
<223> OTHER INFORMATION: synthetic construct

<400> SEQUENCE: 120

Cys Cys Thr Glu Ser Leu Val Asn Arg
1               5

<210> SEQ ID NO 121
<211> LENGTH: 24
<212> TYPE: PRT
<213> ORGANISM: Artificial Sequence
<220> FEATURE:
<223> OTHER INFORMATION: synthetic construct

<400> SEQUENCE: 121

Leu Ala Lys Thr Tyr Glu Thr Thr Leu Glu Lys Cys Cys Ala Ala Ala
1               5                   10                  15

Asp Pro His Glu Cys Tyr Ala Lys
            20
```

<210> SEQ ID NO 122
<211> LENGTH: 21
<212> TYPE: PRT
<213> ORGANISM: Artificial Sequence
<220> FEATURE:
<223> OTHER INFORMATION: synthetic construct

<400> SEQUENCE: 122

Met Pro Cys Ala Glu Asp Tyr Leu Ser Val Val Leu Asn Gln Leu Cys
1               5                   10                  15

Val Leu His Glu Lys
            20

<210> SEQ ID NO 123
<211> LENGTH: 14
<212> TYPE: PRT
<213> ORGANISM: Artificial Sequence
<220> FEATURE:
<223> OTHER INFORMATION: synthetic construct

<400> SEQUENCE: 123

His Pro Tyr Phe Tyr Ala Pro Glu Leu Leu Phe Phe Ala Lys
1               5                   10

<210> SEQ ID NO 124
<211> LENGTH: 17
<212> TYPE: PRT
<213> ORGANISM: Artificial Sequence
<220> FEATURE:
<223> OTHER INFORMATION: synthetic construct

<400> SEQUENCE: 124

Ser Leu His Thr Leu Phe Gly Asp Lys Leu Cys Thr Val Ala Thr Leu
1               5                   10                  15

Arg

<210> SEQ ID NO 125
<211> LENGTH: 12
<212> TYPE: PRT
<213> ORGANISM: Artificial Sequence
<220> FEATURE:
<223> OTHER INFORMATION: synthetic construct

<400> SEQUENCE: 125

Leu Lys Glu Cys Cys Glu Lys Pro Leu Leu Glu Lys
1               5                   10

<210> SEQ ID NO 126
<211> LENGTH: 21
<212> TYPE: PRT
<213> ORGANISM: Artificial Sequence
<220> FEATURE:
<223> OTHER INFORMATION: synthetic construct

<400> SEQUENCE: 126

Ala Leu Val Leu Ile Ala Phe Ala Gln Tyr Leu Gln Gln Cys Pro Phe
1               5                   10                  15

Glu Asp His Val Lys
            20

<210> SEQ ID NO 127
<211> LENGTH: 14
<212> TYPE: PRT
<213> ORGANISM: Artificial Sequence

```
<220> FEATURE:
<223> OTHER INFORMATION: synthetic construct

<400> SEQUENCE: 127

Ala Asp Asp Lys Glu Thr Cys Phe Ala Glu Glu Gly Lys Lys
1               5                   10

<210> SEQ ID NO 128
<211> LENGTH: 19
<212> TYPE: PRT
<213> ORGANISM: Artificial Sequence
<220> FEATURE:
<223> OTHER INFORMATION: synthetic construct

<400> SEQUENCE: 128

Glu Phe Asn Ala Glu Thr Phe Thr Phe His Ala Asp Ile Cys Thr Leu
1               5                   10                  15

Ser Glu Lys

<210> SEQ ID NO 129
<211> LENGTH: 13
<212> TYPE: PRT
<213> ORGANISM: Artificial Sequence
<220> FEATURE:
<223> OTHER INFORMATION: synthetic construct

<400> SEQUENCE: 129

Asp Val Phe Leu Gly Met Phe Leu Tyr Glu Tyr Ala Arg
1               5                   10

<210> SEQ ID NO 130
<211> LENGTH: 9
<212> TYPE: PRT
<213> ORGANISM: Artificial Sequence
<220> FEATURE:
<223> OTHER INFORMATION: synthetic construct

<400> SEQUENCE: 130

Leu Asp Glu Leu Arg Asp Glu Gly Lys
1               5

<210> SEQ ID NO 131
<211> LENGTH: 13
<212> TYPE: PRT
<213> ORGANISM: Artificial Sequence
<220> FEATURE:
<223> OTHER INFORMATION: synthetic construct

<400> SEQUENCE: 131

Cys Cys Ala Ala Ala Asp Pro His Glu Cys Tyr Ala Lys
1               5                   10

<210> SEQ ID NO 132
<211> LENGTH: 19
<212> TYPE: PRT
<213> ORGANISM: Artificial Sequence
<220> FEATURE:
<223> OTHER INFORMATION: synthetic construct

<400> SEQUENCE: 132

Asn Tyr Ala Glu Ala Lys Asp Val Phe Leu Gly Met Phe Leu Tyr Glu
1               5                   10                  15

Tyr Ala Arg

<210> SEQ ID NO 133
```

```
<211> LENGTH: 13
<212> TYPE: PRT
<213> ORGANISM: Artificial Sequence
<220> FEATURE:
<223> OTHER INFORMATION: synthetic construct

<400> SEQUENCE: 133

Thr Cys Val Ala Asp Glu Ser Ala Glu Asn Cys Asp Lys
1               5                   10

<210> SEQ ID NO 134
<211> LENGTH: 21
<212> TYPE: PRT
<213> ORGANISM: Artificial Sequence
<220> FEATURE:
<223> OTHER INFORMATION: synthetic construct

<400> SEQUENCE: 134

Glu Phe Asn Ala Glu Thr Phe Thr Phe His Ala Asp Ile Cys Thr Leu
1               5                   10                  15

Ser Glu Lys Glu Arg
            20

<210> SEQ ID NO 135
<211> LENGTH: 8
<212> TYPE: PRT
<213> ORGANISM: Artificial Sequence
<220> FEATURE:
<223> OTHER INFORMATION: synthetic construct

<400> SEQUENCE: 135

Asp Leu Gly Glu Glu Asn Phe Lys
1               5

<210> SEQ ID NO 136
<211> LENGTH: 13
<212> TYPE: PRT
<213> ORGANISM: Artificial Sequence
<220> FEATURE:
<223> OTHER INFORMATION: synthetic construct

<400> SEQUENCE: 136

Val Asn Val Asp Ala Val Gly Gly Glu Ala Leu Gly Arg
1               5                   10

<210> SEQ ID NO 137
<211> LENGTH: 12
<212> TYPE: PRT
<213> ORGANISM: Artificial Sequence
<220> FEATURE:
<223> OTHER INFORMATION: synthetic construct

<400> SEQUENCE: 137

Leu Leu Gly Asn Val Leu Val Cys Val Leu Ala Arg
1               5                   10

<210> SEQ ID NO 138
<211> LENGTH: 13
<212> TYPE: PRT
<213> ORGANISM: Artificial Sequence
<220> FEATURE:
<223> OTHER INFORMATION: synthetic construct

<400> SEQUENCE: 138

Gly Thr Phe Ser Gln Leu Ser Glu Leu His Cys Asp Lys
1               5                   10
```

<210> SEQ ID NO 139
<211> LENGTH: 21
<212> TYPE: PRT
<213> ORGANISM: Artificial Sequence
<220> FEATURE:
<223> OTHER INFORMATION: synthetic construct

<400> SEQUENCE: 139

```
Leu Leu Gln Asp Glu Phe Pro Gly Ile Pro Ser Pro Leu Asp Ala Ala
1               5                   10                  15

Val Glu Cys His Arg
            20
```

<210> SEQ ID NO 140
<211> LENGTH: 16
<212> TYPE: PRT
<213> ORGANISM: Artificial Sequence
<220> FEATURE:
<223> OTHER INFORMATION: synthetic construct

<400> SEQUENCE: 140

```
Ser Gly Ala Gln Ala Thr Trp Thr Glu Leu Pro Trp Pro His Glu Lys
1               5                   10                  15
```

<210> SEQ ID NO 141
<211> LENGTH: 10
<212> TYPE: PRT
<213> ORGANISM: Artificial Sequence
<220> FEATURE:
<223> OTHER INFORMATION: synthetic construct

<400> SEQUENCE: 141

```
Gln Gly His Asn Ser Val Phe Leu Ile Lys
1               5                   10
```

<210> SEQ ID NO 142
<211> LENGTH: 24
<212> TYPE: PRT
<213> ORGANISM: Artificial Sequence
<220> FEATURE:
<223> OTHER INFORMATION: synthetic construct

<400> SEQUENCE: 142

```
Glu Val Gly Thr Pro His Gly Ile Ile Leu Asp Ser Val Asp Ala Ala
1               5                   10                  15

Phe Ile Cys Pro Gly Ser Ser Arg
            20
```

<210> SEQ ID NO 143
<211> LENGTH: 11
<212> TYPE: PRT
<213> ORGANISM: Artificial Sequence
<220> FEATURE:
<223> OTHER INFORMATION: synthetic construct

<400> SEQUENCE: 143

```
Asn Phe Pro Ser Pro Val Asp Ala Ala Phe Arg
1               5                   10
```

<210> SEQ ID NO 144
<211> LENGTH: 11
<212> TYPE: PRT
<213> ORGANISM: Artificial Sequence
<220> FEATURE:
<223> OTHER INFORMATION: synthetic construct

```
<400> SEQUENCE: 144

Gly Gly Tyr Thr Leu Val Ser Gly Tyr Pro Lys
1               5                   10

<210> SEQ ID NO 145
<211> LENGTH: 15
<212> TYPE: PRT
<213> ORGANISM: Artificial Sequence
<220> FEATURE:
<223> OTHER INFORMATION: synthetic construct

<400> SEQUENCE: 145

Gly Glu Cys Gln Ala Glu Gly Val Leu Phe Phe Gln Gly Asp Arg
1               5                   10                  15

<210> SEQ ID NO 146
<211> LENGTH: 12
<212> TYPE: PRT
<213> ORGANISM: Artificial Sequence
<220> FEATURE:
<223> OTHER INFORMATION: synthetic construct

<400> SEQUENCE: 146

Val Ser Phe Leu Ser Ala Leu Glu Glu Tyr Thr Lys
1               5                   10

<210> SEQ ID NO 147
<211> LENGTH: 11
<212> TYPE: PRT
<213> ORGANISM: Artificial Sequence
<220> FEATURE:
<223> OTHER INFORMATION: synthetic construct

<400> SEQUENCE: 147

Thr His Leu Ala Pro Tyr Ser Asp Glu Leu Arg
1               5                   10

<210> SEQ ID NO 148
<211> LENGTH: 11
<212> TYPE: PRT
<213> ORGANISM: Artificial Sequence
<220> FEATURE:
<223> OTHER INFORMATION: synthetic construct

<400> SEQUENCE: 148

Gln Gly Leu Leu Pro Val Leu Glu Ser Phe Lys
1               5                   10

<210> SEQ ID NO 149
<211> LENGTH: 13
<212> TYPE: PRT
<213> ORGANISM: Artificial Sequence
<220> FEATURE:
<223> OTHER INFORMATION: synthetic construct

<400> SEQUENCE: 149

Asp Tyr Val Ser Gln Phe Glu Gly Ser Ala Leu Gly Lys
1               5                   10

<210> SEQ ID NO 150
<211> LENGTH: 16
<212> TYPE: PRT
<213> ORGANISM: Artificial Sequence
<220> FEATURE:
<223> OTHER INFORMATION: synthetic construct

<400> SEQUENCE: 150
```

```
Glu Gln Leu Gly Pro Val Thr Gln Glu Phe Trp Asp Asn Leu Glu Lys
1               5                   10                  15
```

<210> SEQ ID NO 151
<211> LENGTH: 14
<212> TYPE: PRT
<213> ORGANISM: Artificial Sequence
<220> FEATURE:
<223> OTHER INFORMATION: synthetic construct

<400> SEQUENCE: 151

```
Leu Leu Asp Asn Trp Asp Ser Val Thr Ser Thr Phe Ser Lys
1               5                   10
```

<210> SEQ ID NO 152
<211> LENGTH: 11
<212> TYPE: PRT
<213> ORGANISM: Artificial Sequence
<220> FEATURE:
<223> OTHER INFORMATION: synthetic construct

<400> SEQUENCE: 152

```
Asp Leu Ala Thr Val Tyr Val Asp Val Leu Lys
1               5                   10
```

<210> SEQ ID NO 153
<211> LENGTH: 7
<212> TYPE: PRT
<213> ORGANISM: Artificial Sequence
<220> FEATURE:
<223> OTHER INFORMATION: synthetic construct

<400> SEQUENCE: 153

```
Phe Leu Glu Asn Glu Asp Arg
1               5
```

<210> SEQ ID NO 154
<211> LENGTH: 18
<212> TYPE: PRT
<213> ORGANISM: Artificial Sequence
<220> FEATURE:
<223> OTHER INFORMATION: synthetic construct

<400> SEQUENCE: 154

```
Val Phe Ser Asn Gly Ala Asp Leu Ser Gly Val Thr Glu Glu Ala Pro
1               5                   10                  15

Leu Lys
```

<210> SEQ ID NO 155
<211> LENGTH: 10
<212> TYPE: PRT
<213> ORGANISM: Artificial Sequence
<220> FEATURE:
<223> OTHER INFORMATION: synthetic construct

<400> SEQUENCE: 155

```
Leu Ser Ile Thr Gly Thr Tyr Asp Leu Lys
1               5                   10
```

<210> SEQ ID NO 156
<211> LENGTH: 8
<212> TYPE: PRT
<213> ORGANISM: Artificial Sequence
<220> FEATURE:
<223> OTHER INFORMATION: synthetic construct

```
<400> SEQUENCE: 156

Ala Val Leu Thr Ile Asp Glu Lys
1               5

<210> SEQ ID NO 157
<211> LENGTH: 15
<212> TYPE: PRT
<213> ORGANISM: Artificial Sequence
<220> FEATURE:
<223> OTHER INFORMATION: synthetic construct

<400> SEQUENCE: 157

Leu Gln His Leu Glu Asn Glu Leu Thr His Asp Ile Ile Thr Lys
1               5                   10                  15

<210> SEQ ID NO 158
<211> LENGTH: 8
<212> TYPE: PRT
<213> ORGANISM: Artificial Sequence
<220> FEATURE:
<223> OTHER INFORMATION: synthetic construct

<400> SEQUENCE: 158

Ser Ala Ser Leu His Leu Pro Lys
1               5

<210> SEQ ID NO 159
<211> LENGTH: 10
<212> TYPE: PRT
<213> ORGANISM: Artificial Sequence
<220> FEATURE:
<223> OTHER INFORMATION: synthetic construct

<400> SEQUENCE: 159

Ser Val Leu Gly Gln Leu Gly Ile Thr Lys
1               5                   10

<210> SEQ ID NO 160
<211> LENGTH: 15
<212> TYPE: PRT
<213> ORGANISM: Artificial Sequence
<220> FEATURE:
<223> OTHER INFORMATION: synthetic construct

<400> SEQUENCE: 160

Thr Asp Thr Ser His His Asp Gln Asp His Pro Thr Phe Asn Lys
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: synthetic construct

<400> SEQUENCE: 161

Asp Thr Glu Glu Glu Asp Phe His Val Asp Gln Val Thr Thr Val Lys
1               5                   10                  15

<210> SEQ ID NO 162
<211> LENGTH: 18
<212> TYPE: PRT
<213> ORGANISM: Artificial Sequence
<220> FEATURE:
<223> OTHER INFORMATION: synthetic construct

<400> SEQUENCE: 162
```

```
Leu Tyr His Ser Glu Ala Phe Thr Val Asn Phe Gly Asp Thr Glu Glu
1               5                   10                  15

Ala Lys

<210> SEQ ID NO 163
<211> LENGTH: 10
<212> TYPE: PRT
<213> ORGANISM: Artificial Sequence
<220> FEATURE:
<223> OTHER INFORMATION: synthetic construct

<400> SEQUENCE: 163

Asp Gly Ala Gly Asp Val Ala Phe Val Lys
1               5                   10

<210> SEQ ID NO 164
<211> LENGTH: 8
<212> TYPE: PRT
<213> ORGANISM: Artificial Sequence
<220> FEATURE:
<223> OTHER INFORMATION: synthetic construct

<400> SEQUENCE: 164

Ala Ser Tyr Leu Asp Cys Ile Arg
1               5

<210> SEQ ID NO 165
<211> LENGTH: 14
<212> TYPE: PRT
<213> ORGANISM: Artificial Sequence
<220> FEATURE:
<223> OTHER INFORMATION: synthetic construct

<400> SEQUENCE: 165

Ser Val Ile Pro Ser Asp Gly Pro Ser Val Ala Cys Val Lys
1               5                   10

<210> SEQ ID NO 166
<211> LENGTH: 15
<212> TYPE: PRT
<213> ORGANISM: Artificial Sequence
<220> FEATURE:
<223> OTHER INFORMATION: synthetic construct

<400> SEQUENCE: 166

Ile Glu Cys Val Ser Ala Glu Thr Thr Glu Asp Cys Ile Ala Lys
1               5                   10                  15

<210> SEQ ID NO 167
<211> LENGTH: 8
<212> TYPE: PRT
<213> ORGANISM: Artificial Sequence
<220> FEATURE:
<223> OTHER INFORMATION: synthetic construct

<400> SEQUENCE: 167

Asp Ser Ala His Gly Phe Leu Lys
1               5

<210> SEQ ID NO 168
<211> LENGTH: 11
<212> TYPE: PRT
<213> ORGANISM: Artificial Sequence
<220> FEATURE:
<223> OTHER INFORMATION: synthetic construct
```

```
<400> SEQUENCE: 168

Ser Ala Ser Asp Leu Thr Trp Asp Asn Leu Lys
1               5                   10

<210> SEQ ID NO 169
<211> LENGTH: 8
<212> TYPE: PRT
<213> ORGANISM: Artificial Sequence
<220> FEATURE:
<223> OTHER INFORMATION: synthetic construct

<400> SEQUENCE: 169

Asp Asp Thr Val Cys Leu Ala Lys
1               5

<210> SEQ ID NO 170
<211> LENGTH: 14
<212> TYPE: PRT
<213> ORGANISM: Artificial Sequence
<220> FEATURE:
<223> OTHER INFORMATION: synthetic construct

<400> SEQUENCE: 170

Phe Asp Glu Phe Phe Ser Glu Gly Cys Ala Pro Gly Ser Lys
1               5                   10

<210> SEQ ID NO 171
<211> LENGTH: 11
<212> TYPE: PRT
<213> ORGANISM: Artificial Sequence
<220> FEATURE:
<223> OTHER INFORMATION: synthetic construct

<400> SEQUENCE: 171

Glu Phe Gln Leu Phe Ser Ser Pro His Gly Lys
1               5                   10

<210> SEQ ID NO 172
<211> LENGTH: 11
<212> TYPE: PRT
<213> ORGANISM: Artificial Sequence
<220> FEATURE:
<223> OTHER INFORMATION: synthetic construct

<400> SEQUENCE: 172

Cys Asp Glu Trp Ser Val Asn Ser Val Gly Lys
1               5                   10

<210> SEQ ID NO 173
<211> LENGTH: 8
<212> TYPE: PRT
<213> ORGANISM: Artificial Sequence
<220> FEATURE:
<223> OTHER INFORMATION: synthetic construct

<400> SEQUENCE: 173

Phe Tyr Tyr Ile Tyr Asn Glu Lys
1               5

<210> SEQ ID NO 174
<211> LENGTH: 20
<212> TYPE: PRT
<213> ORGANISM: Artificial Sequence
<220> FEATURE:
<223> OTHER INFORMATION: synthetic construct

<400> SEQUENCE: 174
```

```
Asp Thr Trp Val Glu His Trp Pro Glu Glu Asp Glu Cys Gln Asp Glu
1               5                   10                  15

Glu Asn Gln Lys
            20

<210> SEQ ID NO 175
<211> LENGTH: 22
<212> TYPE: PRT
<213> ORGANISM: Artificial Sequence
<220> FEATURE:
<223> OTHER INFORMATION: synthetic construct

<400> SEQUENCE: 175

Glu Pro Gly Gln Asp Leu Val Val Leu Pro Leu Ser Ile Thr Thr Asp
1               5                   10                  15

Phe Ile Pro Ser Phe Arg
            20

<210> SEQ ID NO 176
<211> LENGTH: 13
<212> TYPE: PRT
<213> ORGANISM: Artificial Sequence
<220> FEATURE:
<223> OTHER INFORMATION: synthetic construct

<400> SEQUENCE: 176

Ser Ser Leu Ser Val Pro Tyr Val Ile Val Pro Leu Lys
1               5                   10

<210> SEQ ID NO 177
<211> LENGTH: 9
<212> TYPE: PRT
<213> ORGANISM: Artificial Sequence
<220> FEATURE:
<223> OTHER INFORMATION: synthetic construct

<400> SEQUENCE: 177

Asn Thr Leu Ile Ile Tyr Leu Asp Lys
1               5

<210> SEQ ID NO 178
<211> LENGTH: 19
<212> TYPE: PRT
<213> ORGANISM: Artificial Sequence
<220> FEATURE:
<223> OTHER INFORMATION: synthetic construct

<400> SEQUENCE: 178

Gln Leu Tyr Asn Val Glu Ala Thr Ser Tyr Ala Leu Leu Ala Leu Leu
1               5                   10                  15

Gln Leu Lys

<210> SEQ ID NO 179
<211> LENGTH: 10
<212> TYPE: PRT
<213> ORGANISM: Artificial Sequence
<220> FEATURE:
<223> OTHER INFORMATION: synthetic construct

<400> SEQUENCE: 179

Ile His Trp Glu Ser Ala Ser Leu Leu Arg
1               5                   10

<210> SEQ ID NO 180
```

```
<211> LENGTH: 16
<212> TYPE: PRT
<213> ORGANISM: Artificial Sequence
<220> FEATURE:
<223> OTHER INFORMATION: synthetic construct

<400> SEQUENCE: 180

Asp Ile Cys Glu Glu Gln Val Asn Ser Leu Pro Gly Ser Ile Thr Lys
1               5                   10                  15

<210> SEQ ID NO 181
<211> LENGTH: 9
<212> TYPE: PRT
<213> ORGANISM: Artificial Sequence
<220> FEATURE:
<223> OTHER INFORMATION: synthetic construct

<400> SEQUENCE: 181

Phe Ile Ser Leu Gly Glu Ala Cys Lys
1               5

<210> SEQ ID NO 182
<211> LENGTH: 13
<212> TYPE: PRT
<213> ORGANISM: Artificial Sequence
<220> FEATURE:
<223> OTHER INFORMATION: synthetic construct

<400> SEQUENCE: 182

Val Phe Leu Asp Cys Cys Asn Tyr Ile Thr Glu Leu Arg
1               5                   10

<210> SEQ ID NO 183
<211> LENGTH: 8
<212> TYPE: PRT
<213> ORGANISM: Artificial Sequence
<220> FEATURE:
<223> OTHER INFORMATION: synthetic construct

<400> SEQUENCE: 183

Gln Gly Ala Leu Glu Leu Ile Lys
1               5

<210> SEQ ID NO 184
<211> LENGTH: 10
<212> TYPE: PRT
<213> ORGANISM: Artificial Sequence
<220> FEATURE:
<223> OTHER INFORMATION: synthetic construct

<400> SEQUENCE: 184

Asp Ser Cys Val Gly Ser Leu Val Val Lys
1               5                   10

<210> SEQ ID NO 185
<211> LENGTH: 9
<212> TYPE: PRT
<213> ORGANISM: Artificial Sequence
<220> FEATURE:
<223> OTHER INFORMATION: synthetic construct

<400> SEQUENCE: 185

Gly Leu Glu Val Thr Ile Thr Ala Arg
1               5

<210> SEQ ID NO 186
<211> LENGTH: 16
```

```
<212> TYPE: PRT
<213> ORGANISM: Artificial Sequence
<220> FEATURE:
<223> OTHER INFORMATION: synthetic construct

<400> SEQUENCE: 186

Glu Tyr Val Leu Pro Ser Phe Glu Val Ile Val Glu Pro Thr Glu Lys
1               5                   10                  15

<210> SEQ ID NO 187
<211> LENGTH: 12
<212> TYPE: PRT
<213> ORGANISM: Artificial Sequence
<220> FEATURE:
<223> OTHER INFORMATION: synthetic construct

<400> SEQUENCE: 187

Glu Val Val Ala Asp Ser Val Trp Val Asp Val Lys
1               5                   10

<210> SEQ ID NO 188
<211> LENGTH: 12
<212> TYPE: PRT
<213> ORGANISM: Artificial Sequence
<220> FEATURE:
<223> OTHER INFORMATION: synthetic construct

<400> SEQUENCE: 188

Val Ser His Ser Glu Asp Asp Cys Leu Ala Phe Lys
1               5                   10

<210> SEQ ID NO 189
<211> LENGTH: 12
<212> TYPE: PRT
<213> ORGANISM: Artificial Sequence
<220> FEATURE:
<223> OTHER INFORMATION: synthetic construct

<400> SEQUENCE: 189

Ser Gly Ser Asp Glu Val Gln Val Gly Gln Gln Arg
1               5                   10

<210> SEQ ID NO 190
<211> LENGTH: 14
<212> TYPE: PRT
<213> ORGANISM: Artificial Sequence
<220> FEATURE:
<223> OTHER INFORMATION: synthetic construct

<400> SEQUENCE: 190

Leu Val Ala Tyr Tyr Thr Leu Ile Gly Ala Ser Gly Gln Arg
1               5                   10

<210> SEQ ID NO 191
<211> LENGTH: 12
<212> TYPE: PRT
<213> ORGANISM: Artificial Sequence
<220> FEATURE:
<223> OTHER INFORMATION: synthetic construct

<400> SEQUENCE: 191

Thr Ile Tyr Thr Pro Gly Ser Thr Val Leu Tyr Arg
1               5                   10

<210> SEQ ID NO 192
<211> LENGTH: 9
<212> TYPE: PRT
```

<213> ORGANISM: Artificial Sequence
<220> FEATURE:
<223> OTHER INFORMATION: synthetic construct

<400> SEQUENCE: 192

Gly Tyr Thr Gln Gln Leu Ala Phe Arg
1               5

<210> SEQ ID NO 193
<211> LENGTH: 19
<212> TYPE: PRT
<213> ORGANISM: Artificial Sequence
<220> FEATURE:
<223> OTHER INFORMATION: synthetic construct

<400> SEQUENCE: 193

Asp Ala Pro Asp His Gln Glu Leu Asn Leu Asp Val Ser Leu Gln Leu
1               5                   10                  15

Pro Ser Arg

<210> SEQ ID NO 194
<211> LENGTH: 16
<212> TYPE: PRT
<213> ORGANISM: Artificial Sequence
<220> FEATURE:
<223> OTHER INFORMATION: synthetic construct

<400> SEQUENCE: 194

Val Glu Leu Leu His Asn Pro Ala Phe Cys Ser Leu Ala Thr Thr Lys
1               5                   10                  15

<210> SEQ ID NO 195
<211> LENGTH: 11
<212> TYPE: PRT
<213> ORGANISM: Artificial Sequence
<220> FEATURE:
<223> OTHER INFORMATION: synthetic construct

<400> SEQUENCE: 195

Ala Cys Glu Pro Gly Val Asp Tyr Val Tyr Lys
1               5                   10

<210> SEQ ID NO 196
<211> LENGTH: 10
<212> TYPE: PRT
<213> ORGANISM: Artificial Sequence
<220> FEATURE:
<223> OTHER INFORMATION: synthetic construct

<400> SEQUENCE: 196

Asp Glu Trp Ser Val Asn Ser Val Gly Lys
1               5                   10

<210> SEQ ID NO 197
<211> LENGTH: 16
<212> TYPE: PRT
<213> ORGANISM: Artificial Sequence
<220> FEATURE:
<223> OTHER INFORMATION: synthetic construct

<400> SEQUENCE: 197

Ser Asn Leu Asp Glu Asp Ile Ile Ala Glu Glu Asn Ile Val Ser Arg
1               5                   10                  15

<210> SEQ ID NO 198
<211> LENGTH: 13

```
<212> TYPE: PRT
<213> ORGANISM: Artificial Sequence
<220> FEATURE:
<223> OTHER INFORMATION: synthetic construct

<400> SEQUENCE: 198

Val Tyr Ala Tyr Tyr Asn Leu Glu Glu Ser Cys Thr Arg
1               5                   10

<210> SEQ ID NO 199
<211> LENGTH: 11
<212> TYPE: PRT
<213> ORGANISM: Artificial Sequence
<220> FEATURE:
<223> OTHER INFORMATION: synthetic construct

<400> SEQUENCE: 199

Val Thr Ile Lys Pro Ala Pro Glu Thr Glu Lys
1               5                   10

<210> SEQ ID NO 200
<211> LENGTH: 10
<212> TYPE: PRT
<213> ORGANISM: Artificial Sequence
<220> FEATURE:
<223> OTHER INFORMATION: synthetic construct

<400> SEQUENCE: 200

Asp Phe Asp Phe Val Pro Pro Val Val Arg
1               5                   10

<210> SEQ ID NO 201
<211> LENGTH: 9
<212> TYPE: PRT
<213> ORGANISM: Artificial Sequence
<220> FEATURE:
<223> OTHER INFORMATION: synthetic construct

<400> SEQUENCE: 201

Thr Gly Leu Gln Glu Val Glu Val Lys
1               5

<210> SEQ ID NO 202
<211> LENGTH: 12
<212> TYPE: PRT
<213> ORGANISM: Artificial Sequence
<220> FEATURE:
<223> OTHER INFORMATION: synthetic construct

<400> SEQUENCE: 202

Ala Pro Ser Thr Trp Leu Thr Ala Tyr Val Val Lys
1               5                   10

<210> SEQ ID NO 203
<211> LENGTH: 16
<212> TYPE: PRT
<213> ORGANISM: Artificial Sequence
<220> FEATURE:
<223> OTHER INFORMATION: synthetic construct

<400> SEQUENCE: 203

Val His Gln Tyr Phe Asn Val Glu Leu Ile Gln Pro Gly Ala Val Lys
1               5                   10                  15

<210> SEQ ID NO 204
<211> LENGTH: 22
<212> TYPE: PRT
```

<213> ORGANISM: Artificial Sequence
<220> FEATURE:
<223> OTHER INFORMATION: synthetic construct

<400> SEQUENCE: 204

Val Pro Val Ala Val Gln Gly Glu Asp Thr Val Gln Ser Leu Thr Gln
1               5                   10                  15

Gly Asp Gly Val Ala Lys
            20

<210> SEQ ID NO 205
<211> LENGTH: 16
<212> TYPE: PRT
<213> ORGANISM: Artificial Sequence
<220> FEATURE:
<223> OTHER INFORMATION: synthetic construct

<400> SEQUENCE: 205

Ser Gly Ile Pro Ile Val Thr Ser Pro Tyr Gln Ile His Phe Thr Lys
1               5                   10                  15

<210> SEQ ID NO 206
<211> LENGTH: 11
<212> TYPE: PRT
<213> ORGANISM: Artificial Sequence
<220> FEATURE:
<223> OTHER INFORMATION: synthetic construct

<400> SEQUENCE: 206

Gln Pro Ser Ser Ala Phe Ala Ala Phe Val Lys
1               5                   10

<210> SEQ ID NO 207
<211> LENGTH: 11
<212> TYPE: PRT
<213> ORGANISM: Artificial Sequence
<220> FEATURE:
<223> OTHER INFORMATION: synthetic construct

<400> SEQUENCE: 207

Ala Asp Ile Gly Cys Thr Pro Gly Ser Gly Lys
1               5                   10

<210> SEQ ID NO 208
<211> LENGTH: 13
<212> TYPE: PRT
<213> ORGANISM: Artificial Sequence
<220> FEATURE:
<223> OTHER INFORMATION: synthetic construct

<400> SEQUENCE: 208

Ala Ala Val Tyr His His Phe Ile Ser Asp Gly Val Arg
1               5                   10

<210> SEQ ID NO 209
<211> LENGTH: 26
<212> TYPE: PRT
<213> ORGANISM: Artificial Sequence
<220> FEATURE:
<223> OTHER INFORMATION: synthetic construct

<400> SEQUENCE: 209

Leu Asn Asn Leu Thr Phe Leu Tyr Leu Asp His Asn Ala Leu Glu Ser
1               5                   10                  15

Val Pro Leu Asn Leu Pro Glu Ser Leu Arg
            20                  25

```
<210> SEQ ID NO 210
<211> LENGTH: 18
<212> TYPE: PRT
<213> ORGANISM: Artificial Sequence
<220> FEATURE:
<223> OTHER INFORMATION: synthetic construct

<400> SEQUENCE: 210

Leu Asp Phe Thr Gly Asn Leu Ile Glu Asp Ile Glu Asp Gly Thr Phe
1               5                   10                  15

Ser Lys

<210> SEQ ID NO 211
<211> LENGTH: 16
<212> TYPE: PRT
<213> ORGANISM: Artificial Sequence
<220> FEATURE:
<223> OTHER INFORMATION: synthetic construct

<400> SEQUENCE: 211

Leu Ser Leu Leu Glu Glu Leu Ser Leu Ala Glu Asn Gln Leu Leu Lys
1               5                   10                  15

<210> SEQ ID NO 212
<211> LENGTH: 9
<212> TYPE: PRT
<213> ORGANISM: Artificial Sequence
<220> FEATURE:
<223> OTHER INFORMATION: synthetic construct

<400> SEQUENCE: 212

Asp Phe Ala Asp Ile Pro Asn Leu Arg
1               5

<210> SEQ ID NO 213
<211> LENGTH: 17
<212> TYPE: PRT
<213> ORGANISM: Artificial Sequence
<220> FEATURE:
<223> OTHER INFORMATION: synthetic construct

<400> SEQUENCE: 213

Glu Gly Pro Tyr Ser Ile Ser Val Leu Tyr Gly Asp Glu Glu Val Pro
1               5                   10                  15

Arg

<210> SEQ ID NO 214
<211> LENGTH: 11
<212> TYPE: PRT
<213> ORGANISM: Artificial Sequence
<220> FEATURE:
<223> OTHER INFORMATION: synthetic construct

<400> SEQUENCE: 214

Glu Ala Thr Thr Glu Phe Ser Val Asp Ala Arg
1               5                   10

<210> SEQ ID NO 215
<211> LENGTH: 23
<212> TYPE: PRT
<213> ORGANISM: Artificial Sequence
<220> FEATURE:
<223> OTHER INFORMATION: synthetic construct

<400> SEQUENCE: 215
```

```
Phe Asn Glu Glu His Ile Pro Asp Ser Pro Phe Val Val Pro Val Ala
1               5                   10                  15

Ser Pro Ser Gly Asp Ala Arg
            20

<210> SEQ ID NO 216
<211> LENGTH: 16
<212> TYPE: PRT
<213> ORGANISM: Artificial Sequence
<220> FEATURE:
<223> OTHER INFORMATION: synthetic construct

<400> SEQUENCE: 216

Ala Phe Gly Pro Gly Leu Gln Gly Gly Ser Ala Gly Ser Pro Ala Arg
1               5                   10                  15

<210> SEQ ID NO 217
<211> LENGTH: 22
<212> TYPE: PRT
<213> ORGANISM: Artificial Sequence
<220> FEATURE:
<223> OTHER INFORMATION: synthetic construct

<400> SEQUENCE: 217

Val Ser Gly Gln Gly Leu His Glu Gly His Thr Phe Glu Pro Ala Glu
1               5                   10                  15

Phe Ile Ile Asp Thr Arg
            20

<210> SEQ ID NO 218
<211> LENGTH: 16
<212> TYPE: PRT
<213> ORGANISM: Artificial Sequence
<220> FEATURE:
<223> OTHER INFORMATION: synthetic construct

<400> SEQUENCE: 218

Val Ala Asn Pro Ser Gly Asn Leu Thr Glu Thr Tyr Val Gln Asp Arg
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: synthetic construct

<400> SEQUENCE: 219

Ser Pro Phe Ser Val Ala Val Ser Pro Ser Leu Asp Leu Ser Lys
1               5                   10                  15

<210> SEQ ID NO 220
<211> LENGTH: 12
<212> TYPE: PRT
<213> ORGANISM: Artificial Sequence
<220> FEATURE:
<223> OTHER INFORMATION: synthetic construct

<400> SEQUENCE: 220

Phe Asn Gly Thr His Ile Pro Gly Ser Pro Phe Lys
1               5                   10

<210> SEQ ID NO 221
<211> LENGTH: 52
<212> TYPE: PRT
```

```
<213> ORGANISM: Artificial Sequence
<220> FEATURE:
<223> OTHER INFORMATION: synthetic construct

<400> SEQUENCE: 221

Val Gly Glu Pro Gly His Gly Gly Asp Pro Gly Leu Val Ser Ala Tyr
1               5                   10                  15

Gly Ala Gly Leu Glu Gly Gly Val Thr Gly Asn Pro Ala Glu Phe Val
            20                  25                  30

Val Asn Thr Ser Asn Ala Gly Ala Gly Ala Leu Ser Val Thr Ile Asp
        35                  40                  45

Gly Pro Ser Lys
    50

<210> SEQ ID NO 222
<211> LENGTH: 29
<212> TYPE: PRT
<213> ORGANISM: Artificial Sequence
<220> FEATURE:
<223> OTHER INFORMATION: synthetic construct

<400> SEQUENCE: 222

Val Gly Ser Ala Ala Asp Ile Pro Ile Asn Ile Ser Glu Thr Asp Leu
1               5                   10                  15

Ser Leu Leu Thr Ala Thr Val Val Pro Pro Ser Gly Arg
            20                  25

<210> SEQ ID NO 223
<211> LENGTH: 10
<212> TYPE: PRT
<213> ORGANISM: Artificial Sequence
<220> FEATURE:
<223> OTHER INFORMATION: synthetic construct

<400> SEQUENCE: 223

Glu Asn Gly Val Tyr Leu Ile Asp Val Lys
1               5                   10

<210> SEQ ID NO 224
<211> LENGTH: 33
<212> TYPE: PRT
<213> ORGANISM: Artificial Sequence
<220> FEATURE:
<223> OTHER INFORMATION: synthetic construct

<400> SEQUENCE: 224

Asp Gly Ser Cys Ser Val Glu Tyr Ile Pro Tyr Glu Ala Gly Thr Tyr
1               5                   10                  15

Ser Leu Asn Val Thr Tyr Gly Gly His Gln Val Pro Gly Ser Pro Phe
            20                  25                  30

Lys

<210> SEQ ID NO 225
<211> LENGTH: 14
<212> TYPE: PRT
<213> ORGANISM: Artificial Sequence
<220> FEATURE:
<223> OTHER INFORMATION: synthetic construct

<400> SEQUENCE: 225

Tyr Asn Glu Gln His Val Pro Gly Ser Pro Phe Thr Ala Arg
1               5                   10
```

```
<210> SEQ ID NO 226
<211> LENGTH: 8
<212> TYPE: PRT
<213> ORGANISM: Artificial Sequence
<220> FEATURE:
<223> OTHER INFORMATION: synthetic construct

<400> SEQUENCE: 226

Val Lys Glu Thr Ala Asp Phe Lys
1               5

<210> SEQ ID NO 227
<211> LENGTH: 12
<212> TYPE: PRT
<213> ORGANISM: Artificial Sequence
<220> FEATURE:
<223> OTHER INFORMATION: synthetic construct

<400> SEQUENCE: 227

Tyr Gly Gly Gln Pro Val Pro Asn Phe Pro Ser Lys
1               5                   10

<210> SEQ ID NO 228
<211> LENGTH: 19
<212> TYPE: PRT
<213> ORGANISM: Artificial Sequence
<220> FEATURE:
<223> OTHER INFORMATION: synthetic construct

<400> SEQUENCE: 228

Asp Ala Gly Glu Gly Leu Leu Ala Val Gln Ile Thr Asp Pro Glu Gly
1               5                   10                  15

Lys Pro Lys

<210> SEQ ID NO 229
<211> LENGTH: 11
<212> TYPE: PRT
<213> ORGANISM: Artificial Sequence
<220> FEATURE:
<223> OTHER INFORMATION: synthetic construct

<400> SEQUENCE: 229

Asn Gly His Val Gly Ile Ser Phe Val Pro Lys
1               5                   10

<210> SEQ ID NO 230
<211> LENGTH: 10
<212> TYPE: PRT
<213> ORGANISM: Artificial Sequence
<220> FEATURE:
<223> OTHER INFORMATION: synthetic construct

<400> SEQUENCE: 230

Gly Thr Val Glu Pro Gln Leu Glu Ala Arg
1               5                   10

<210> SEQ ID NO 231
<211> LENGTH: 24
<212> TYPE: PRT
<213> ORGANISM: Artificial Sequence
<220> FEATURE:
<223> OTHER INFORMATION: synthetic construct

<400> SEQUENCE: 231

Ala Ser Gly Pro Gly Leu Asn Thr Thr Gly Val Pro Ala Ser Leu Pro
1               5                   10                  15
```

Val Glu Phe Thr Ile Asp Ala Lys
            20

<210> SEQ ID NO 232
<211> LENGTH: 13
<212> TYPE: PRT
<213> ORGANISM: Artificial Sequence
<220> FEATURE:
<223> OTHER INFORMATION: synthetic construct

<400> SEQUENCE: 232

Ile Ala Asn Leu Gln Thr Asp Leu Ser Asp Gly Leu Arg
1               5                   10

<210> SEQ ID NO 233
<211> LENGTH: 24
<212> TYPE: PRT
<213> ORGANISM: Artificial Sequence
<220> FEATURE:
<223> OTHER INFORMATION: synthetic construct

<400> SEQUENCE: 233

Gly Leu Val Glu Pro Val Asp Val Val Asp Asn Ala Asp Gly Thr Gln
1               5                   10                  15

Thr Val Asn Tyr Val Pro Ser Arg
            20

<210> SEQ ID NO 234
<211> LENGTH: 16
<212> TYPE: PRT
<213> ORGANISM: Artificial Sequence
<220> FEATURE:
<223> OTHER INFORMATION: synthetic construct

<400> SEQUENCE: 234

Glu Ala Gly Ala Gly Gly Leu Ala Ile Ala Val Glu Gly Pro Ser Lys
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: synthetic construct

<400> SEQUENCE: 235

Thr Gly Val Ala Val Asn Lys Pro Ala Glu Phe Thr Val Asp Ala Lys
1               5                   10                  15

<210> SEQ ID NO 236
<211> LENGTH: 21
<212> TYPE: PRT
<213> ORGANISM: Artificial Sequence
<220> FEATURE:
<223> OTHER INFORMATION: synthetic construct

<400> SEQUENCE: 236

Asp Gly Ser Cys Gly Val Ala Tyr Val Val Gln Glu Pro Gly Asp Tyr
1               5                   10                  15

Glu Val Ser Val Lys
            20

<210> SEQ ID NO 237
<211> LENGTH: 33
<212> TYPE: PRT
<213> ORGANISM: Artificial Sequence

```
<220> FEATURE:
<223> OTHER INFORMATION: synthetic construct

<400> SEQUENCE: 237

Glu Glu Gly Pro Tyr Glu Val Glu Val Thr Tyr Asp Gly Val Pro Val
1               5                   10                  15

Pro Gly Ser Pro Phe Pro Leu Glu Ala Val Ala Pro Thr Lys Pro Ser
            20                  25                  30

Lys

<210> SEQ ID NO 238
<211> LENGTH: 28
<212> TYPE: PRT
<213> ORGANISM: Artificial Sequence
<220> FEATURE:
<223> OTHER INFORMATION: synthetic construct

<400> SEQUENCE: 238

Phe Gly Gly Glu His Val Pro Asn Ser Pro Phe Gln Val Thr Ala Leu
1               5                   10                  15

Ala Gly Asp Gln Pro Ser Val Gln Pro Pro Leu Arg
            20                  25

<210> SEQ ID NO 239
<211> LENGTH: 13
<212> TYPE: PRT
<213> ORGANISM: Artificial Sequence
<220> FEATURE:
<223> OTHER INFORMATION: synthetic construct

<400> SEQUENCE: 239

Val Glu Pro Gly Leu Gly Ala Asp Asn Ser Val Val Arg
1               5                   10

<210> SEQ ID NO 240
<211> LENGTH: 9
<212> TYPE: PRT
<213> ORGANISM: Artificial Sequence
<220> FEATURE:
<223> OTHER INFORMATION: synthetic construct

<400> SEQUENCE: 240

Leu Tyr Ser Val Ser Tyr Leu Leu Lys
1               5

<210> SEQ ID NO 241
<211> LENGTH: 9
<212> TYPE: PRT
<213> ORGANISM: Artificial Sequence
<220> FEATURE:
<223> OTHER INFORMATION: synthetic construct

<400> SEQUENCE: 241

Ser Pro Phe Glu Val Tyr Val Asp Lys
1               5

<210> SEQ ID NO 242
<211> LENGTH: 27
<212> TYPE: PRT
<213> ORGANISM: Artificial Sequence
<220> FEATURE:
<223> OTHER INFORMATION: synthetic construct

<400> SEQUENCE: 242

Ser Ala Asp Phe Val Val Glu Ala Ile Gly Asp Asp Val Gly Thr Leu
```

```
                1               5                   10                  15
Gly Phe Ser Val Glu Gly Pro Ser Gln Ala Lys
                20                  25
```

<210> SEQ ID NO 243
<211> LENGTH: 9
<212> TYPE: PRT
<213> ORGANISM: Artificial Sequence
<220> FEATURE:
<223> OTHER INFORMATION: synthetic construct

<400> SEQUENCE: 243

```
Ala Gly Val Ala Pro Leu Gln Val Lys
1               5
```

<210> SEQ ID NO 244
<211> LENGTH: 30
<212> TYPE: PRT
<213> ORGANISM: Artificial Sequence
<220> FEATURE:
<223> OTHER INFORMATION: synthetic construct

<400> SEQUENCE: 244

```
Ala Glu Ile Ser Cys Thr Asp Asn Gln Asp Gly Thr Cys Ser Val Ser
1               5                   10                  15
Tyr Leu Pro Val Leu Pro Gly Asp Tyr Ser Ile Leu Val Lys
                20                  25                  30
```

<210> SEQ ID NO 245
<211> LENGTH: 16
<212> TYPE: PRT
<213> ORGANISM: Artificial Sequence
<220> FEATURE:
<223> OTHER INFORMATION: synthetic construct

<400> SEQUENCE: 245

```
Asp Ala Gly Glu Gly Gly Leu Ser Leu Ala Ile Glu Gly Pro Ser Lys
1               5                   10                  15
```

<210> SEQ ID NO 246
<211> LENGTH: 11
<212> TYPE: PRT
<213> ORGANISM: Artificial Sequence
<220> FEATURE:
<223> OTHER INFORMATION: synthetic construct

<400> SEQUENCE: 246

```
Ala His Val Val Pro Cys Phe Asp Ala Ser Lys
1               5                   10
```

<210> SEQ ID NO 247
<211> LENGTH: 11
<212> TYPE: PRT
<213> ORGANISM: Artificial Sequence
<220> FEATURE:
<223> OTHER INFORMATION: synthetic construct

<400> SEQUENCE: 247

```
Leu Pro Gln Leu Pro Ile Thr Asn Phe Ser Arg
1               5                   10
```

<210> SEQ ID NO 248
<211> LENGTH: 13
<212> TYPE: PRT
<213> ORGANISM: Artificial Sequence
<220> FEATURE:

<223> OTHER INFORMATION: synthetic construct

<400> SEQUENCE: 248

Ala Trp Gly Pro Gly Leu Glu Gly Gly Val Val Gly Lys
1               5                   10

<210> SEQ ID NO 249
<211> LENGTH: 22
<212> TYPE: PRT
<213> ORGANISM: Artificial Sequence
<220> FEATURE:
<223> OTHER INFORMATION: synthetic construct

<400> SEQUENCE: 249

Tyr Thr Pro Val Gln Gln Gly Pro Val Gly Val Asn Val Thr Tyr Gly
1               5                   10                  15

Gly Asp Pro Ile Pro Lys
            20

<210> SEQ ID NO 250
<211> LENGTH: 14
<212> TYPE: PRT
<213> ORGANISM: Artificial Sequence
<220> FEATURE:
<223> OTHER INFORMATION: synthetic construct

<400> SEQUENCE: 250

Phe Ala Asp Gln His Val Pro Gly Ser Pro Phe Ser Val Lys
1               5                   10

<210> SEQ ID NO 251
<211> LENGTH: 7
<212> TYPE: PRT
<213> ORGANISM: Artificial Sequence
<220> FEATURE:
<223> OTHER INFORMATION: synthetic construct

<400> SEQUENCE: 251

Asp Gln Glu Phe Thr Val Lys
1               5

<210> SEQ ID NO 252
<211> LENGTH: 8
<212> TYPE: PRT
<213> ORGANISM: Artificial Sequence
<220> FEATURE:
<223> OTHER INFORMATION: synthetic construct

<400> SEQUENCE: 252

Ala Glu Ile Ser Phe Glu Asp Arg
1               5

<210> SEQ ID NO 253
<211> LENGTH: 15
<212> TYPE: PRT
<213> ORGANISM: Artificial Sequence
<220> FEATURE:
<223> OTHER INFORMATION: synthetic construct

<400> SEQUENCE: 253

Val Asn Gln Pro Ala Ser Phe Ala Val Ser Leu Asn Gly Ala Lys
1               5                   10                  15

<210> SEQ ID NO 254
<211> LENGTH: 15
<212> TYPE: PRT

```
<213> ORGANISM: Artificial Sequence
<220> FEATURE:
<223> OTHER INFORMATION: synthetic construct

<400> SEQUENCE: 254

Thr Phe Ser Val Trp Tyr Val Pro Glu Val Thr Gly Thr His Lys
1               5                   10                  15

<210> SEQ ID NO 255
<211> LENGTH: 19
<212> TYPE: PRT
<213> ORGANISM: Artificial Sequence
<220> FEATURE:
<223> OTHER INFORMATION: synthetic construct

<400> SEQUENCE: 255

Cys Ala Pro Gly Val Val Gly Pro Ala Glu Ala Asp Ile Asp Phe Asp
1               5                   10                  15

Ile Ile Arg

<210> SEQ ID NO 256
<211> LENGTH: 10
<212> TYPE: PRT
<213> ORGANISM: Artificial Sequence
<220> FEATURE:
<223> OTHER INFORMATION: synthetic construct

<400> SEQUENCE: 256

Leu Asp Val Gln Phe Ser Gly Leu Thr Lys
1               5                   10

<210> SEQ ID NO 257
<211> LENGTH: 24
<212> TYPE: PRT
<213> ORGANISM: Artificial Sequence
<220> FEATURE:
<223> OTHER INFORMATION: synthetic construct

<400> SEQUENCE: 257

Asn Gly Gln His Val Ala Ser Ser Pro Ile Pro Val Val Ile Ser Gln
1               5                   10                  15

Ser Glu Ile Gly Asp Ala Ser Arg
            20

<210> SEQ ID NO 258
<211> LENGTH: 17
<212> TYPE: PRT
<213> ORGANISM: Artificial Sequence
<220> FEATURE:
<223> OTHER INFORMATION: synthetic construct

<400> SEQUENCE: 258

Val Thr Ala Gln Gly Pro Gly Leu Glu Pro Ser Gly Asn Ile Ala Asn
1               5                   10                  15

Lys

<210> SEQ ID NO 259
<211> LENGTH: 16
<212> TYPE: PRT
<213> ORGANISM: Artificial Sequence
<220> FEATURE:
<223> OTHER INFORMATION: synthetic construct

<400> SEQUENCE: 259

Asp Ala Gly Tyr Gly Gly Leu Ser Leu Ser Ile Glu Gly Pro Ser Lys
```

```
<210> SEQ ID NO 260
<211> LENGTH: 12
<212> TYPE: PRT
<213> ORGANISM: Artificial Sequence
<220> FEATURE:
<223> OTHER INFORMATION: synthetic construct

<400> SEQUENCE: 260

Trp Gly Asp Glu His Ile Pro Gly Ser Pro Tyr Arg
1               5                   10

<210> SEQ ID NO 261
<211> LENGTH: 15
<212> TYPE: PRT
<213> ORGANISM: Artificial Sequence
<220> FEATURE:
<223> OTHER INFORMATION: synthetic construct

<400> SEQUENCE: 261

Asp Val Asp Ile Ile Asp His His Asp Asn Thr Tyr Thr Val Lys
1               5                   10                  15

<210> SEQ ID NO 262
<211> LENGTH: 18
<212> TYPE: PRT
<213> ORGANISM: Artificial Sequence
<220> FEATURE:
<223> OTHER INFORMATION: synthetic construct

<400> SEQUENCE: 262

Gly Ala Gly Thr Gly Gly Leu Gly Leu Ala Val Glu Gly Pro Ser Glu
1               5                   10                  15

Ala Lys

<210> SEQ ID NO 263
<211> LENGTH: 22
<212> TYPE: PRT
<213> ORGANISM: Artificial Sequence
<220> FEATURE:
<223> OTHER INFORMATION: synthetic construct

<400> SEQUENCE: 263

Thr His Ile Gln Asp Asn His Asp Gly Thr Tyr Thr Val Ala Tyr Val
1               5                   10                  15

Pro Asp Val Thr Gly Arg
            20

<210> SEQ ID NO 264
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: Carbamidomethylated cysteine

<400> SEQUENCE: 264

Leu Leu Gly Asn Val Leu Val Cys Val Leu Ala Arg
1               5                   10

<210> SEQ ID NO 265
<211> LENGTH: 13
```

```
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: Carbamidomethylated cysteine

<400> SEQUENCE: 265

Gly Thr Phe Ser Gln Leu Ser Glu Leu His Cys Asp Lys
1               5                   10

<210> SEQ ID NO 266
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (19)..(19)
<223> OTHER INFORMATION: Carbamidomethylated cysteine

<400> SEQUENCE: 266

Leu Leu Gln Asp Glu Phe Pro Gly Ile Pro Ser Pro Leu Asp Ala Ala
1               5                   10                  15

Val Glu Cys His Arg
            20

<210> SEQ ID NO 267
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (19)..(19)
<223> OTHER INFORMATION: Carbamidomethylated cysteine

<400> SEQUENCE: 267

Glu Val Gly Thr Pro His Gly Ile Ile Leu Asp Ser Val Asp Ala Ala
1               5                   10                  15

Phe Ile Cys Pro Gly Ser Ser Arg
            20

<210> SEQ ID NO 268
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 268

Gly Glu Cys Gln Ala Glu Gly Val Leu Phe Phe Gln Gly Asp Arg
1               5                   10                  15

<210> SEQ ID NO 269
<211> LENGTH: 8
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (6)..(6)
<223> OTHER INFORMATION: Carbamidomethylated cysteine

<400> SEQUENCE: 269

Ala Ser Tyr Leu Asp Cys Ile Arg
1               5

<210> SEQ ID NO 270
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (12)..(12)
<223> OTHER INFORMATION: Carbamidomethylated cysteine

<400> SEQUENCE: 270

Ser Val Ile Pro Ser Asp Gly Pro Ser Val Ala Cys Val Lys
1               5                   10

<210> SEQ ID NO 271
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine
<220> FEATURE:
<221> NAME/KEY: MOD_RES
<222> LOCATION: (12)..(12)
<223> OTHER INFORMATION: Carbamidomethylated cysteine

<400> SEQUENCE: 271

Ile Glu Cys Val Ser Ala Glu Thr Thr Glu Asp Cys Ile Ala Lys
1               5                   10                  15

<210> SEQ ID NO 272
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine

<400> SEQUENCE: 272

Asp Asp Thr Val Cys Leu Ala Lys
1               5

<210> SEQ ID NO 273
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: Carbamidomethylated cysteine

<400> SEQUENCE: 273

Phe Asp Glu Phe Phe Ser Glu Gly Cys Ala Pro Gly Ser Lys
```

```
<210> SEQ ID NO 274
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Carbamidomethylated cysteine

<400> SEQUENCE: 274

Cys Asp Glu Trp Ser Val Asn Ser Val Gly Lys
1               5                   10

<210> SEQ ID NO 275
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: Carbamidomethylated cysteine

<400> SEQUENCE: 275

Asp Thr Trp Val Glu His Trp Pro Glu Glu Asp Glu Cys Gln Asp Glu
1               5                   10                  15

Glu Asn Gln Lys
            20

<210> SEQ ID NO 276
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 276

Asp Ile Cys Glu Glu Gln Val Asn Ser Leu Pro Gly Ser Ile Thr Lys
1               5                   10                  15

<210> SEQ ID NO 277
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: Carbamidomethylated cysteine

<400> SEQUENCE: 277

Phe Ile Ser Leu Gly Glu Ala Cys Lys
1               5

<210> SEQ ID NO 278
<211> LENGTH: 13
<212> TYPE: PRT
<213> ORGANISM: Artificial Sequence
<220> FEATURE:
```

```
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine
<220> FEATURE:
<221> NAME/KEY: MOD_RES
<222> LOCATION: (6)..(6)
<223> OTHER INFORMATION: Carbamidomethylated cysteine

<400> SEQUENCE: 278

Val Phe Leu Asp Cys Cys Asn Tyr Ile Thr Glu Leu Arg
1               5                   10

<210> SEQ ID NO 279
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 279

Asp Ser Cys Val Gly Ser Leu Val Val Lys
1               5                   10

<210> SEQ ID NO 280
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: Carbamidomethylated cysteine

<400> SEQUENCE: 280

Val Ser His Ser Glu Asp Asp Cys Leu Ala Phe Lys
1               5                   10

<210> SEQ ID NO 281
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (10)..(10)
<223> OTHER INFORMATION: Carbamidomethylated cysteine

<400> SEQUENCE: 281

Val Glu Leu Leu His Asn Pro Ala Phe Cys Ser Leu Ala Thr Thr Lys
1               5                   10                  15

<210> SEQ ID NO 282
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: Carbamidomethylated cysteine

<400> SEQUENCE: 282
```

```
Ala Cys Glu Pro Gly Val Asp Tyr Val Tyr Lys
1               5                   10

<210> SEQ ID NO 283
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: Carbamidomethylated cysteine

<400> SEQUENCE: 283

Val Tyr Ala Tyr Tyr Asn Leu Glu Glu Ser Cys Thr Arg
1               5                   10

<210> SEQ ID NO 284
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine

<400> SEQUENCE: 284

Ala Asp Ile Gly Cys Thr Pro Gly Ser Gly Lys
1               5                   10

<210> SEQ ID NO 285
<211> LENGTH: 33
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine

<400> SEQUENCE: 285

Asp Gly Ser Cys Ser Val Glu Tyr Ile Pro Tyr Glu Ala Gly Thr Tyr
1               5                   10                  15

Ser Leu Asn Val Thr Tyr Gly Gly His Gln Val Pro Gly Ser Pro Phe
            20                  25                  30

Lys

<210> SEQ ID NO 286
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine

<400> SEQUENCE: 286

Asp Gly Ser Cys Gly Val Ala Tyr Val Val Gln Glu Pro Gly Asp Tyr
1               5                   10                  15

Glu Val Ser Val Lys
            20
```

```
<210> SEQ ID NO 287
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine
<220> FEATURE:
<221> NAME/KEY: MOD_RES
<222> LOCATION: (13)..(13)
<223> OTHER INFORMATION: Carbamidomethylated cysteine

<400> SEQUENCE: 287

Ala Glu Ile Ser Cys Thr Asp Asn Gln Asp Gly Thr Cys Ser Val Ser
1               5                   10                  15

Tyr Leu Pro Val Leu Pro Gly Asp Tyr Ser Ile Leu Val Lys
            20                  25                  30

<210> SEQ ID NO 288
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: Carbamidomethylated cysteine

<400> SEQUENCE: 288

Ala His Val Val Pro Cys Phe Asp Ala Ser Lys
1               5                   10

<210> SEQ ID NO 289
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Carbamidomethylated cysteine

<400> SEQUENCE: 289

Cys Ala Pro Gly Val Val Gly Pro Ala Glu Ala Asp Ile Asp Phe Asp
1               5                   10                  15

Ile Ile Arg

<210> SEQ ID NO 290
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine

<400> SEQUENCE: 290

Asp Gly Pro Cys Gly Thr Val Leu Thr Arg
1               5                   10
```

<210> SEQ ID NO 291
<211> LENGTH: 15
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (10)..(10)
<223> OTHER INFORMATION: Carbamidomethylated cysteine

<400> SEQUENCE: 291

Ser Thr Glu Tyr Gly Glu Gly Tyr Ala Cys Asp Thr Asp Leu Arg
1               5                   10                  15

<210> SEQ ID NO 292
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine

<400> SEQUENCE: 292

Met Ala Glu Thr Cys Val Pro Val Leu Arg
1               5                   10

<210> SEQ ID NO 293
<211> LENGTH: 5
<212> TYPE: PRT
<213> ORGANISM: Artificial Sequence
<220> FEATURE:
<223> OTHER INFORMATION: synthetic construct

<400> SEQUENCE: 293

Gln Thr Ala Leu Val
1               5

<210> SEQ ID NO 294
<211> LENGTH: 5
<212> TYPE: PRT
<213> ORGANISM: Artificial Sequence
<220> FEATURE:
<223> OTHER INFORMATION: synthetic construct

<400> SEQUENCE: 294

Leu Val Asn Glu Val
1               5

<210> SEQ ID NO 295
<211> LENGTH: 5
<212> TYPE: PRT
<213> ORGANISM: Artificial Sequence
<220> FEATURE:
<223> OTHER INFORMATION: synthetic construct

<400> SEQUENCE: 295

Val Phe Asp Glu Phe
1               5

<210> SEQ ID NO 296
<211> LENGTH: 5
<212> TYPE: PRT
<213> ORGANISM: Artificial Sequence
<220> FEATURE:
<223> OTHER INFORMATION: synthetic construct

```
<400> SEQUENCE: 296

Leu Val Ala Ala Ser
1               5

<210> SEQ ID NO 297
<211> LENGTH: 5
<212> TYPE: PRT
<213> ORGANISM: Artificial Sequence
<220> FEATURE:
<223> OTHER INFORMATION: synthetic construct

<400> SEQUENCE: 297

Asp Asp Asn Pro Asn
1               5

<210> SEQ ID NO 298
<211> LENGTH: 27
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine
<220> FEATURE:
<221> NAME/KEY: MOD_RES
<222> LOCATION: (12)..(12)
<223> OTHER INFORMATION: Oxidized methionine

<400> SEQUENCE: 298

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25

<210> SEQ ID NO 299
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 299

Arg Pro Cys Phe Ser Ala Leu Glu Val Asp Glu Thr Tyr Val Pro Lys
1               5                   10                  15

<210> SEQ ID NO 300
<211> LENGTH: 27
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 300

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25
```

```
<210> SEQ ID NO 301
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 301

Gln Asn Cys Glu Leu Phe Glu Gln Leu Gly Glu Tyr Lys
1               5                   10

<210> SEQ ID NO 302
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine
<220> FEATURE:
<221> NAME/KEY: MOD_RES
<222> LOCATION: (17)..(17)
<223> OTHER INFORMATION: Carbamidomethylated cysteine

<400> SEQUENCE: 302

Arg Met Pro Cys Ala Glu Asp Tyr Leu Ser Val Val Leu Asn Gln Leu
1               5                   10                  15

Cys Val Leu His Glu Lys
            20

<210> SEQ ID NO 303
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine
<220> FEATURE:
<221> NAME/KEY: MOD_RES
<222> LOCATION: (6)..(6)
<223> OTHER INFORMATION: Carbamidomethylated cysteine
<220> FEATURE:
<221> NAME/KEY: MOD_RES
<222> LOCATION: (13)..(13)
<223> OTHER INFORMATION: Carbamidomethylated cysteine

<400> SEQUENCE: 303

Val His Thr Glu Cys Cys His Gly Asp Leu Leu Glu Cys Ala Asp Asp
1               5                   10                  15

Arg

<210> SEQ ID NO 304
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
```

<223> OTHER INFORMATION: Carbamidomethylated cysteine

<400> SEQUENCE: 304

Leu Cys Thr Val Ala Thr Leu Arg
1               5

<210> SEQ ID NO 305
<211> LENGTH: 23
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (10)..(10)
<223> OTHER INFORMATION: Carbamidomethylated cysteine

<400> SEQUENCE: 305

Leu Val Arg Pro Glu Val Asp Val Met Cys Thr Ala Phe His Asp Asn
1               5                   10                  15

Glu Glu Thr Phe Leu Lys Lys
            20

<210> SEQ ID NO 306
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: Carbamidomethylated cysteine
<220> FEATURE:
<221> NAME/KEY: MOD_RES
<222> LOCATION: (3)..(3)
<223> OTHER INFORMATION: Carbamidomethylated cysteine

<400> SEQUENCE: 306

Glu Cys Cys Glu Lys Pro Leu Leu Glu Lys
1               5                   10

<210> SEQ ID NO 307
<211> LENGTH: 23
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: Oxidized methionine
<220> FEATURE:
<221> NAME/KEY: MOD_RES
<222> LOCATION: (10)..(10)
<223> OTHER INFORMATION: Carbamidomethylated cysteine
<220> FEATURE:
<221> NAME/KEY: MOD_RES
<222> LOCATION: (11)..(11)
<223> OTHER INFORMATION: Phosphorylated threonine

<400> SEQUENCE: 307

Leu Val Arg Pro Glu Val Asp Val Met Cys Thr Ala Phe His Asp Asn
1               5                   10                  15

Glu Glu Thr Phe Leu Lys Lys
            20

<210> SEQ ID NO 308
<211> LENGTH: 22

```
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine
<220> FEATURE:
<221> NAME/KEY: MOD_RES
<222> LOCATION: (8)..(8)
<223> OTHER INFORMATION: Phosphorylated tyrosine
<220> FEATURE:
<221> NAME/KEY: MOD_RES
<222> LOCATION: (17)..(17)
<223> OTHER INFORMATION: Carbamidomethylated cysteine

<400> SEQUENCE: 308

Arg Met Pro Cys Ala Glu Asp Tyr Leu Ser Val Val Leu Asn Gln Leu
1               5                   10                  15

Cys Val Leu His Glu Lys
            20

<210> SEQ ID NO 309
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (10)..(10)
<223> OTHER INFORMATION: Carbamidomethylated cysteine

<400> SEQUENCE: 309

Leu Val Arg Pro Glu Val Asp Val Met Cys Thr Ala Phe His Asp Asn
1               5                   10                  15

Glu Glu Thr Phe Leu Lys
            20

<210> SEQ ID NO 310
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Carbamidomethylated cysteine
<220> FEATURE:
<221> NAME/KEY: MOD_RES
<222> LOCATION: (6)..(6)
<223> OTHER INFORMATION: Carbamidomethylated cysteine
<220> FEATURE:
<221> NAME/KEY: MOD_RES
<222> LOCATION: (13)..(13)
<223> OTHER INFORMATION: Carbamidomethylated cysteine

<400> SEQUENCE: 310

Val His Thr Glu Cys Cys His Gly Asp Leu Leu Glu Cys Ala Asp Asp
1               5                   10                  15

Arg Ala Asp Leu Ala Lys
            20

<210> SEQ ID NO 311
<211> LENGTH: 16
<212> TYPE: PRT
<213> ORGANISM: Artificial Sequence
<220> FEATURE:
```

```
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 311

Asn Glu Cys Phe Leu Gln His Lys Asp Asp Asn Pro Asn Leu Pro Arg
1               5                   10                  15

<210> SEQ ID NO 312
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: Carbamidomethylated cysteine
<220> FEATURE:
<221> NAME/KEY: MOD_RES
<222> LOCATION: (7)..(7)
<223> OTHER INFORMATION: Carbamidomethylated cysteine

<400> SEQUENCE: 312

Ala Ala Phe Thr Glu Cys Cys Gln Ala Ala Asp Lys
1               5                   10

<210> SEQ ID NO 313
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: Carbamidomethylated cysteine
<220> FEATURE:
<221> NAME/KEY: MOD_RES
<222> LOCATION: (10)..(10)
<223> OTHER INFORMATION: Carbamidomethylated cysteine

<400> SEQUENCE: 313

Glu Thr Tyr Gly Glu Met Ala Asp Cys Cys Ala Lys
1               5                   10

<210> SEQ ID NO 314
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: Carbamidomethylated cysteine

<400> SEQUENCE: 314

Gln Glu Pro Glu Arg Asn Glu Cys Phe Leu Gln His Lys Asp Asp Asn
1               5                   10                  15

Pro Asn Leu Pro Arg
            20

<210> SEQ ID NO 315
<211> LENGTH: 12
<212> TYPE: PRT
<213> ORGANISM: Artificial Sequence
<220> FEATURE:
```

<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 315

Tyr Ile Cys Glu Asn Gln Asp Ser Ile Ser Ser Lys
1               5                   10

<210> SEQ ID NO 316
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: Carbamidomethylated cysteine

<400> SEQUENCE: 316

Ala Asp Asp Lys Glu Thr Cys Phe Ala Glu Glu Gly Lys
1               5                   10

<210> SEQ ID NO 317
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine

<400> SEQUENCE: 317

Asn Glu Cys Phe Leu Gln His Lys
1               5

<210> SEQ ID NO 318
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Carbamidomethylated cysteine
<220> FEATURE:
<221> NAME/KEY: MOD_RES
<222> LOCATION: (2)..(2)
<223> OTHER INFORMATION: Carbamidomethylated cysteine

<400> SEQUENCE: 318

Cys Cys Thr Glu Ser Leu Val Asn Arg
1               5

<210> SEQ ID NO 319
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Phosphorylated threonine
<220> FEATURE:
<221> NAME/KEY: MOD_RES

```
<222> LOCATION: (5)..(5)
<223> OTHER INFORMATION: Phosphorylated tyrosine
<220> FEATURE:
<221> NAME/KEY: MOD_RES
<222> LOCATION: (7)..(7)
<223> OTHER INFORMATION: Phosphorylated threonine
<220> FEATURE:
<221> NAME/KEY: MOD_RES
<222> LOCATION: (12)..(12)
<223> OTHER INFORMATION: Carbamidomethylated cysteine
<220> FEATURE:
<221> NAME/KEY: MOD_RES
<222> LOCATION: (13)..(13)
<223> OTHER INFORMATION: Carbamidomethylated cysteine
<220> FEATURE:
<221> NAME/KEY: MOD_RES
<222> LOCATION: (21)..(21)
<223> OTHER INFORMATION: Carbamidomethylated cysteine

<400> SEQUENCE: 319

Leu Ala Lys Thr Tyr Glu Thr Thr Leu Glu Lys Cys Cys Ala Ala Ala
1               5                   10                  15

Asp Pro His Glu Cys Tyr Ala Lys
            20

<210> SEQ ID NO 320
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Oxidized methionine
<220> FEATURE:
<221> NAME/KEY: MOD_RES
<222> LOCATION: (3)..(3)
<223> OTHER INFORMATION: Carbamidomethylated cysteine
<220> FEATURE:
<221> NAME/KEY: MOD_RES
<222> LOCATION: (16)..(16)
<223> OTHER INFORMATION: Carbamidomethylated cysteine

<400> SEQUENCE: 320

Met Pro Cys Ala Glu Asp Tyr Leu Ser Val Val Leu Asn Gln Leu Cys
1               5                   10                  15

Val Leu His Glu Lys
            20

<210> SEQ ID NO 321
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Carbamidomethylated cysteine
<220> FEATURE:
<221> NAME/KEY: MOD_RES
<222> LOCATION: (16)..(16)
<223> OTHER INFORMATION: Carbamidomethylated cysteine

<400> SEQUENCE: 321

Met Pro Cys Ala Glu Asp Tyr Leu Ser Val Val Leu Asn Gln Leu Cys
1               5                   10                  15

Val Leu His Glu Lys
            20
```

```
<210> SEQ ID NO 322
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: Carbamidomethylated cysteine

<400> SEQUENCE: 322

Ser Leu His Thr Leu Phe Gly Asp Lys Leu Cys Thr Val Ala Thr Leu
1               5                   10                  15

Arg

<210> SEQ ID NO 323
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: Carbamidomethylated cysteine
<220> FEATURE:
<221> NAME/KEY: MOD_RES
<222> LOCATION: (5)..(5)
<223> OTHER INFORMATION: Carbamidomethylated cysteine

<400> SEQUENCE: 323

Leu Lys Glu Cys Cys Glu Lys Pro Leu Leu Glu Lys
1               5                   10

<210> SEQ ID NO 324
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: Oxidized methionine
<220> FEATURE:
<221> NAME/KEY: MOD_RES
<222> LOCATION: (9)..(9)
<223> OTHER INFORMATION: Carbamidomethylated cysteine
<220> FEATURE:
<221> NAME/KEY: MOD_RES
<222> LOCATION: (10)..(10)
<223> OTHER INFORMATION: Carbamidomethylated cysteine

<400> SEQUENCE: 324

Glu Thr Tyr Gly Glu Met Ala Asp Cys Cys Ala Lys
1               5                   10

<210> SEQ ID NO 325
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: Carbamidomethylated cysteine

<400> SEQUENCE: 325
```

Ala Leu Val Leu Ile Ala Phe Ala Gln Tyr Leu Gln Gln Cys Pro Phe
1               5                   10                  15

Glu Asp His Val Lys
                20

<210> SEQ ID NO 326
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: Carbamidomethylated cysteine

<400> SEQUENCE: 326

Ala Asp Asp Lys Glu Thr Cys Phe Ala Glu Glu Gly Lys Lys
1               5                   10

<210> SEQ ID NO 327
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: Carbamidomethylated cysteine

<400> SEQUENCE: 327

Glu Phe Asn Ala Glu Thr Phe Thr Phe His Ala Asp Ile Cys Thr Leu
1               5                   10                  15

Ser Glu Lys

<210> SEQ ID NO 328
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Carbamidomethylated cysteine
<220> FEATURE:
<221> NAME/KEY: MOD_RES
<222> LOCATION: (2)..(2)
<223> OTHER INFORMATION: Carbamidomethylated cysteine
<220> FEATURE:
<221> NAME/KEY: MOD_RES
<222> LOCATION: (10)..(10)
<223> OTHER INFORMATION: Carbamidomethylated cysteine

<400> SEQUENCE: 328

Cys Cys Ala Ala Ala Asp Pro His Glu Cys Tyr Ala Lys
1               5                   10

<210> SEQ ID NO 329
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: Oxidized methionine
<220> FEATURE:

```
<221> NAME/KEY: MOD_RES
<222> LOCATION: (4)..(4)
<223> OTHER INFORMATION: Carbamidomethylated cysteine
<220> FEATURE:
<221> NAME/KEY: MOD_RES
<222> LOCATION: (17)..(17)
<223> OTHER INFORMATION: Carbamidomethylated cysteine

<400> SEQUENCE: 329

Arg Met Pro Cys Ala Glu Asp Tyr Leu Ser Val Val Leu Asn Gln Leu
1               5                   10                  15

Cys Val Leu His Glu Lys
            20

<210> SEQ ID NO 330
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: Oxidized methionine
<220> FEATURE:
<221> NAME/KEY: MOD_RES
<222> LOCATION: (10)..(10)
<223> OTHER INFORMATION: Carbamidomethylated cysteine

<400> SEQUENCE: 330

Leu Val Arg Pro Glu Val Asp Val Met Cys Thr Ala Phe His Asp Asn
1               5                   10                  15

Glu Glu Thr Phe Leu Lys
            20

<210> SEQ ID NO 331
<211> LENGTH: 27
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Phosphorylated serine
<220> FEATURE:
<221> NAME/KEY: MOD_RES
<222> LOCATION: (3)..(3)
<223> OTHER INFORMATION: Carbamidomethylated cysteine
<220> FEATURE:
<221> NAME/KEY: MOD_RES
<222> LOCATION: (12)..(12)
<223> OTHER INFORMATION: Oxidized methionine

<400> SEQUENCE: 331

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25

<210> SEQ ID NO 332
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: Oxidized methionine
```

<400> SEQUENCE: 332

Ala Val Met Asp Asp Phe Ala Ala Phe Val Glu Lys
1               5                   10

<210> SEQ ID NO 333
<211> LENGTH: 31
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: Oxidized methionine
<220> FEATURE:
<221> NAME/KEY: MOD_RES
<222> LOCATION: (10)..(10)
<223> OTHER INFORMATION: Carbamidomethylated cysteine

<400> SEQUENCE: 333

Leu Val Arg Pro Glu Val Asp Val Met Cys Thr Ala Phe His Asp Asn
1               5                   10                  15

Glu Glu Thr Phe Leu Lys Lys Asn Glu Glu Thr Phe Leu Lys Lys
            20                  25                  30

<210> SEQ ID NO 334
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: Carbamidomethylated cysteine
<220> FEATURE:
<221> NAME/KEY: MOD_RES
<222> LOCATION: (11)..(11)
<223> OTHER INFORMATION: Carbamidomethylated cysteine

<400> SEQUENCE: 334

Thr Cys Val Ala Asp Glu Ser Ala Glu Asn Cys Asp Lys
1               5                   10

<210> SEQ ID NO 335
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: Oxidized methionine

<400> SEQUENCE: 335

Asp Val Phe Leu Gly Met Phe Leu Tyr Glu Tyr Ala Arg
1               5                   10

<210> SEQ ID NO 336
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: Carbamidomethylated cysteine

<400> SEQUENCE: 336

Glu Phe Asn Ala Glu Thr Phe Thr Phe His Ala Asp Ile Cys Thr Leu
1               5                   10                  15

Ser Glu Lys Glu Arg
            20

<210> SEQ ID NO 337
<211> LENGTH: 5
<212> TYPE: PRT
<213> ORGANISM: Artificial Sequence
<220> FEATURE:
<223> OTHER INFORMATION: synthetic construct

<400> SEQUENCE: 337

Phe Gln Asn Ala Leu
1               5

<210> SEQ ID NO 338
<211> LENGTH: 5
<212> TYPE: PRT
<213> ORGANISM: Artificial Sequence
<220> FEATURE:
<223> OTHER INFORMATION: synthetic construct

<400> SEQUENCE: 338

Ser Leu His Thr Leu
1               5

<210> SEQ ID NO 339
<211> LENGTH: 5
<212> TYPE: PRT
<213> ORGANISM: Artificial Sequence
<220> FEATURE:
<223> OTHER INFORMATION: synthetic construct

<400> SEQUENCE: 339

Ala Glu Phe Ala Glu
1               5

<210> SEQ ID NO 340
<211> LENGTH: 5
<212> TYPE: PRT
<213> ORGANISM: Artificial Sequence
<220> FEATURE:
<223> OTHER INFORMATION: synthetic construct

<400> SEQUENCE: 340

Thr Tyr Glu Thr Thr
1               5

<210> SEQ ID NO 341
<211> LENGTH: 5
<212> TYPE: PRT
<213> ORGANISM: Artificial Sequence
<220> FEATURE:
<223> OTHER INFORMATION: synthetic construct

<400> SEQUENCE: 341

Tyr Leu Tyr Glu Ile
1               5

CORRELATED PEPTIDES FOR QUANTITATIVE MASS SPECTROMETRY

CROSS-REFERENCE TO RELATED APPLICATIONS

This application is a National Phase of International Application No. PCT/US2016/035117 filed May 31, 2016, which designated the U.S. and that International Application was published under PCT Article 21(2) in English, which also includes a claim of priority under 35 U.S.C. § 119(e) to U.S. provisional patent application No. 62/168,671, filed on May 29, 2015, the entirety of which is hereby incorporated by reference.

STATEMENT REGARDING FEDERALLY SPONSORED RESEARCH OR DEVELOPMENT

This invention was made with government support under Grant No. HHSN268201000032C awarded by the National Institutes of Health. The government has certain rights in the invention.

FIELD OF INVENTION

This invention relates to the identification of correlated signature peptides for quantification.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Selected reaction monitoring (SRM), also known as multiple reaction monitoring, is a quantitative mass spectrometry (MS) technique that targets predefined precursor and product ions specific to a particular analyte of interest. Proteins are typically quantified by cleaving them into peptides with a specific protease such as trypsin, measuring the concentration of one or more signature peptides, and then inferring the concentration of the parent protein.

Uromodulin was selected as an exemplary target to test SRM peptide selection workflows because of its physiological importance, biological complexity and association with disease phenotypes. Uromodulin, also known as UMOD or Tamm-Horsfall Glycoprotein, is the most abundant protein in normal human urine, but its functions remain incompletely understood. Data from genetically modified mice suggests that uromodulin protects against urinary tract infections and calcium oxalate crystals, and participates in the regulation of sodium reuptake to control blood pressure and glomerulocystic kidney disease. In these diseases, abnormal uromodulin processing leads to its accumulation in the ER. Additionally, common uromodulin variants are associated with chronic kidney disease and hypertension, possibly via effects on salt reabsorption in the kidney. Some disease-associated variants are present at lower concentrations in urine. Exact quantitation of urinary uromodulin as a novel biomarker of susceptibility to CKD and hypertension is therefore of clinical interest and may represent a future readout to monitor blood pressure lowering treatment.

Uromodulin is well-represented in proteomic MS databases. For example, aside from a 99 amino acid N-terminal region with only one tryptic cleavage site, Peptide Atlas has MS data representing 97% of the mature protein. Nevertheless, MS analysis is complicated by the existence of four major isoforms, a variety of silent, protective, and disease-associated SNPs and mutations, and multiple glycosylation sites and disulfide bonds. In addition, urine is challenging to analyze because its pH is inconsistent between samples and there are widely varying concentrations of uromodulin, serum albumin, total protein, urea, salts, creatinine, and other metabolites.

SWATH (sequential window acquisition of all theoretical fragment ion spectra) is a new strategy for high throughput, label-free protein quantification. It generates global, quantitative protein maps using data-independent acquisition of collision-induced dissociation (CID) spectra of all precursor ions. As a data-independent acquisition (DIA) method, SWATH-MS has a greater coverage of peptide identification compared to classical discovery approaches.

Using known fingerprints of target peptides comprising precursor mass, chromatographic retention time and MRM transitions, SWATH protein maps can be interrogated for targeted quantification of proteins of interest based on high resolution MRM-like signatures. SWATH acquires all MRM transitions of all precursors and thus does not require tedious assay development and allows for a more dynamic data interpretation compared to classical MRM experiments. New proteins can be added to the list of targets during the process of data interpretation without the requirement of additional data acquisition.

How does SWATH work? The mass spectrometer does not select and isolate a specific precursor ion for CID but fragments everything within a mass window such as m/z 25 to acquire a single CID fragment-ion spectrum. To cover the full mass range between m/z 400-1250 the mass spectrometer sequentially acquires one full MS spectrum and about 34 CID-MS/MS spectra with isolation windows of m/z 25 during one cycle of roughly 3.5 seconds. Theoretically fragment ions of all precursor ions detectable throughout the selected mass range and along the chromatographic elution period are recorded. Such complex CID data however, cannot be matched to peptide sequences from databases through the commonly used search engines like Mascot, SEQUEST, ProteinPilot etc. Instead SWATH MS/MS data are searched against spectral libraries which can be generated from previous discovery data of data-dependent acquisitions.

A variety of methods have been previously used to identify signature peptides for protein quantification. One common approach is to target peptides that were identified in a data-dependent MS screen on related samples, as these peptides are guaranteed to be detectable by MS. A limitation of this approach is that discovery MS and quantitative MS are traditionally performed on different types of MS instruments with different LC systems, ionization, collision cells, and fragmentation patterns. Consequently, the dominant peptides that provide for highly confident protein identification on one instrument do not always yield sufficient MS signals for quantitation on a different instrument. In addition, long peptides (e.g. >10 aa) generally yield more MS/MS fragment ions for confident identification, whereas shorter peptides are more likely to yield a limited number of dominant fragment ions for sensitive SRM quantitation. A related approach is to target peptides found in spectral peptide libraries. Available libraries contain spectra representing many thousands of peptides collected from hundreds of MS runs, thereby facilitating the selection of target peptides and transitions that have been reproducibly observed (see e.g. http://chemdata.nist.gov/dokuwiki/doku.php?id=peptidew:start). However, current MS spectral databases are primarily populated with data from discovery MS instruments and are therefore not directly applicable to SRM assays. SRMAtlas, an online resource designed to overcome this limitation, has MS spectra from natural and synthetic peptides that were collected on a triple quadrupole mass spectrometer, the most common instrument for SRM. A pre-publication SRMAtlas preview covers 99.9% of the human proteome. A third approach, in silico prediction of proteotypic peptides based solely upon a protein's amino acid sequence, provides an alternative to relying on previously acquired spectra that is especially useful for pioneering work on biological samples that have not been subjected to extensive proteomic analysis.

Peptide selection for a quantitative MS assay requires more that the mere identification of detectable peptides. If the goal of the experiment is to quantify the total protein concentration, the selected peptides should not contain genetically encoded variations, and should not be susceptible to in vivo or in vitro post-translational modifications. On the other hand, if the goal is to monitor a specific isoform, SNP or post-translational modification, peptide selection is constrained by the need to target specific peptides that may have relatively weak MS signals and therefore require extensive optimization.

Here we demonstrate that unpredictable confounding factors can interfere with MS quantitation. Thus, selection of peptides for a robust assay requires experimental data. We present an empirical peptide selection workflow to identify surrogate peptides suitable for determining the concentration of targeted proteins in a complex biological milieu by identifying peptides with highly correlated MS signals.

SUMMARY OF THE INVENTION

The following embodiments and aspects thereof are described and illustrated in conjunction with systems, compositions and methods which are meant to be exemplary and illustrative, not limiting in scope.

Various embodiments of the present invention provide a method for identifying signature peptides for quantifying a polypeptide in a sample by selecting peptides with MS signals that are highly correlated with the MS signals of other peptides derived from the same polypeptide. In a preferred embodiment, the MS signal is a peak area. In another preferred embodiment, the MS signal is calculated by dividing the peak area of the peptide by the peak area of an SIL internal standard peptide of the same sequence. In various embodiments, the correlation between the MS signals of a pair of peptides is determined by parametric methods such as the Pearson r correlation or by nonparametric methods such as Kendall rank correlation and Spearman rank correlation. In a preferred embodiment, correlations are measured by determining the coefficient of determination ($r^2$).

Various embodiments of the present invention provide a method of identifying signature fragments for quantifying a macromolecule in a sample. The method may comprise: acquiring mass spectrometry (MS) data on multiple candidate fragments of the macromolecule from multiple samples; using the MS data to calculate correlation values for pairwise comparisons between each of the multiple candidate fragments; and identifying the highly correlated fragments among the multiple candidate fragments as the signature fragments for quantifying the macromolecule. In some embodiments, the macromolecule is a polypeptide. In some embodiments, the macromolecule is a nucleic acid. In some embodiments, the macromolecule is a polysaccharide. In some embodiments, the correlation values are coefficient of determination ($r^2$) values.

Various embodiments of the present invention provide a method of identifying signature peptides for quantifying a polypeptide in a sample. The method may comprise: acquiring mass spectrometry (MS) data on multiple candidate peptides derived from the polypeptide in multiple samples; using the MS data to calculate correlation values for pairwise comparisons among the multiple candidate peptides; and identifying the highly correlated peptides among the multiple candidate peptides as the signature peptides for quantifying the polypeptide. In some embodiments, the correlation values are coefficient of determination ($r^2$) values.

In some embodiments, the MS data is acquired through targeted acquisition methods such as Selective Reaction Monitoring (SRM) and Multiple Reaction Monitoring (MRM). In other embodiments, the MS data is acquired through data-independent acquisition methods such as SWATH. In various embodiments, the MS data is SRM data and/or MRM data. In various embodiments, the MS data is SWATH MS data, Shotgun CID MS data, Original DIA MS Data, MSE MS data, p2CID MS Data, PAcIFIC MS Data, AIF MS Data, XDLA MS Data, or FT-ARM MS Data, or a combination thereof. In various embodiments, the MS data comprises raw MS data obtained from a mass spectrometer and/or processed MS data in which peptides and their fragments (e.g., transitions and MS peaks) are already identified, analyzed and/or quantified.

Various embodiments of the present invention provide a method of quantifying a polypeptide in a sample. The method may comprise: cleaving the polypeptide to yield one or more signature peptide identified according to a method as described herein; analyzing the sample on a mass spectrometer; detecting MS signals of the signature peptide; and quantifying the polypeptide based on the detected MS signals. In some embodiments, multiple polypeptides in a complex sample are quantified.

Various embodiments of the present invention provide a kit for quantifying a polypeptide in a sample. The kit comprises an internal standard of a signature peptide identified for the polypeptide according to a method as described herein; and instructions for using the internal standard to quantify the polypeptide in the sample. In some embodiments, the kit targets a single polypeptide. In other embodiments, the kit targets multiple polypeptides (multiplexing). In various embodiments, the kit further comprises a protease for cleaving the polypeptide to yield the signature peptide. In various embodiments, the kit further comprises an antibody specifically binding to the signature peptide. In certain embodiments, such a kit can be used for SISCAPA. In some embodiments, the kit comprises multiple internal standards. In some embodiments, the kit quantifies multiple polypeptides in a complex sample.

Various embodiments of the present invention provide a system for identifying signature peptides for quantifying a polypeptide. The system may comprises: a mass spectrometer configured for acquiring mass spectrometry (MS) data on multiple candidate peptides derived from the polypeptide in multiple samples; and a computer configured for using the MS data to calculate correlation values for pairwise comparisons among the multiple candidate peptides; and for identifying the highly correlated peptides among the multiple candidate peptides as the signature peptides for quantifying the polypeptide, wherein the mass spectrometer and the computer are connected via a communication link. In some embodiments, the computer is configured for processing the MS data to identify, analyze and/or quantify the multiple candidate peptides and fragments thereof (e.g., transitions and MS peaks) before calculating correlation values. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for using mass spectrometry (MS) data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the correlation values are coefficient of determination ($r^2$) values.

Various embodiments of the present invention provide a computer. The computer may comprises: a memory configured for storing a program; and a processor configured for executing the program, wherein the program comprises instructions for using mass spectrometry (MS) data to calculate correlation values for pairwise comparisons between each of multiple candidate peptides for quantifying a polypeptide, and for identifying the highly correlated peptides among the multiple candidate peptides as the signature peptides for quantifying the polypeptide. Various embodiments of the present invention provide a computer implemented method. The method may comprise: providing a computer as described herein; inputting mass spectrometry (MS) data into the computer; and operating the computer to use the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for operating a mass spectrometer to acquire mass spectrometry (MS) data, for using the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the correlation values are coefficient of determination ($r^2$) values.

Various embodiments of the present invention provide a computer. The computer comprises: a memory configured for storing a program; and a processor configured for executing the program, wherein the program comprises instructions for operating a mass spectrometer to acquire mass spectrometry (MS) data, for using the MS data to calculate correlation values for pairwise comparisons between each of multiple candidate peptides for quantifying a polypeptide, and for identifying the highly correlated peptides among the multiple candidate peptides as the signature peptides for quantifying the polypeptide. Various embodiments of the present invention provide a computer implemented method. The method comprises: providing a computer as described herein; connecting the computer via a communication link to a mass spectrometer; and operating the computer to operate the mass spectrometer to acquire mass spectrometry (MS) data, to use the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for processing MS data to identify, analyze and/or quantify a signature peptide of a polypeptide and for quantify the polypeptide based on the signature peptide.

Various embodiments of the present invention provide a computer, comprising: a memory configured for storing a program; and a processor configured for executing the program, wherein the program comprises instructions for processing MS data to identify, analyze and/or quantify a signature peptide of a polypeptide and for quantify the polypeptide based on the signature peptide. Various embodiments of the present invention provide a computer implemented method, comprising: providing a computer as described herein; inputting MS data into the computer; and operating the computer to process MS data to identify, analyze and/or quantify a signature peptide of a polypeptide and to quantify the polypeptide based on the signature peptide.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for operating a mass spectrometer to detect MS signals of a signature peptide for quantifying a polypeptide, and quantifying the polypeptide based on the detected MS signals.

Various embodiments of the present invention provide a computer. The computer may comprise: a memory configured for storing a program; and a processor configured for executing the program, wherein the program comprises instructions for operating a mass spectrometer to detect MS signals of a signature peptide for quantifying a polypeptide, and quantifying the polypeptide based on the detected MS signals. Various embodiments of the present invention provide a computer implemented method. The method may comprise: providing a computer as described herein; connecting the computer via a communication link to a mass spectrometer; and operating the computer to operate the mass spectrometer to detect MS signals of a signature peptide for quantifying a polypeptide, and to quantify the polypeptide based on the detected MS signals.

Various embodiments of the present invention provide a method of producing an antibody. The method comprises: providing a signature peptide identified according to a method as described herein; and immunizing an animal using the signature peptide, thereby producing the antibody.

In various embodiments, the method further comprises isolating and/or purifying the antibody from the immunized animal.

Various embodiments of the present invention provide an antibody specifically binding to a signature peptide identified according to a method as described herein, or an antigen-binding fragment thereof.

Various embodiments of the present invention provide a method of quantifying a polypeptide in a sample. The method may comprise: contacting the sample with an antibody as described herein or an antigen-binding fragment thereof; detecting the binding between the polypeptide and the antibody or the antigen-binding fragment thereof; and quantifying the polypeptide based on the detected binding.

Various embodiments of the present invention provide a kit quantifying a polypeptide in a sample. The kit comprises: an antibody specifically binding to a signature peptide identified according to a method as described herein; and instructions for using the antibody to quantify the polypeptide in the sample.

In certain embodiments, the polypeptide is uromodulin, serum albumin or any one listed in Table 18. In certain embodiments, the signature peptide is any one listed in Tables 9, 15, or 19.

BRIEF DESCRIPTION OF FIGURES

Exemplary embodiments are illustrated in referenced figures. It is intended that the embodiments and figures disclosed herein are to be considered illustrative rather than restrictive.

FIG. 1A depicts, in accordance with various embodiments of the present invention, amino acid sequence features of uromodulin 1. Candidate tryptic peptides of 6-21 amino acids include two signature peptides reporting the concentration of total uromodulin (thin outline), two signature peptides that discriminate between uromodulin isoforms (bold outline), three peptides identified by data dependent acquisition that were found to have nonlinear responses (thin dashed outline), and six other peptides included in the correlation matrix (bold dashed outline). Potential posttranslational modifications include N-linked glycosylation (bold font surround with gray box), disulfide bonds (hollow font), and methionine oxidation (bold font).

FIG. 2A-FIG. 2C depict, in accordance with various embodiments of the present invention, that absolute quantification of uromodulin is reproducible. Four uromodulin peptides were quantified by SRM in 40 urine samples using SIL internal standards for normalization to a standard curve. For presentation, the samples are arranged according to the concentration of the DWVSV (SEQ. ID NO: 5) peptide. Absolute concentration (m/ml) and reproducibility (% CV) are compared between (FIG. 2A) LC-MS injections (n=3) for quantitation of the DWVSV-y7 (SEQ. ID NO: 5) transition in each digest, (FIG. 2B) Trypsin digests (n=3), and (FIG. 2C) different SRM transitions (n=2, 3, or 4) for the same peptide. See Table 9 for a list of transitions for each peptide.

FIG. 12A: SIL peptides (100 fmol/μl) were desalted on C18 or C4 OMIX pipet tips or on WCX or HLB Oasis microplates. Recovery was calculated by comparing SRM peak areas before and after desalting. FIG. 12B: Various concentrations of SIL peptides in 50 μl of trypsin-digested urine were desalted on an HLB plate.

FIG. 14 depicts, in accordance with various embodiments of the present invention, an example of TOF MS parameters for TripleTOF MS instruments.

FIG. 17 depicts, in accordance with various embodiments of the present invention, example of typical processing settings for SWATH analysis using PeakView software.

DESCRIPTION OF THE INVENTION

Figure 1B:
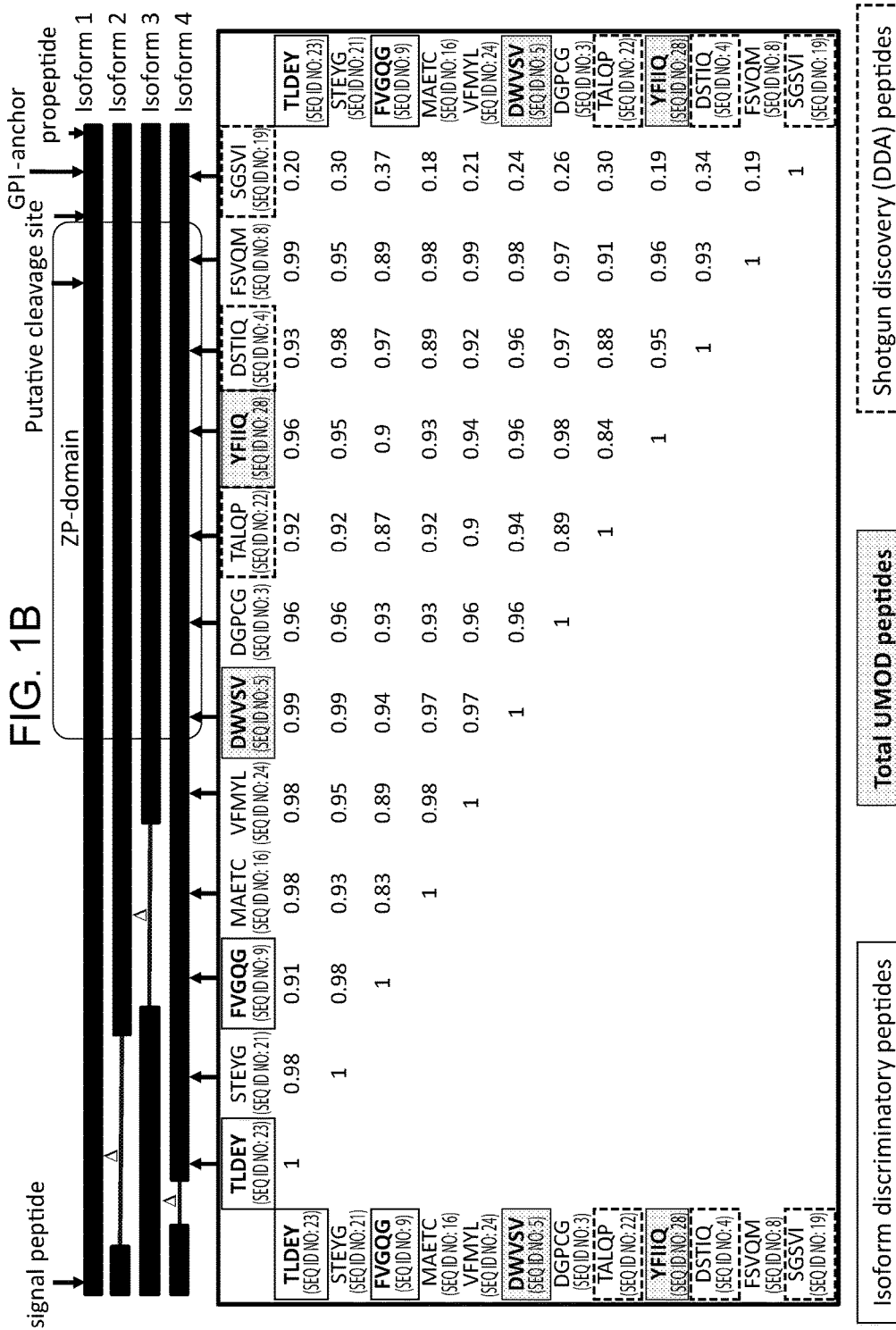
FIG. 1B depicts, in accordance with various embodiments of the present invention, a coefficients of determination ($r^2$) matrix for uromodulin. The schema at top presents structural features of the 4 uromodulin isoforms and identifies the location of 12 candidate peptides, which are identified by their first 5 amino acids. To empirically identify signature peptides that can accurately report the concentration of uromodulin protein, each peptide was individually compared with every other peptide for a total of 72 (12×12/2) comparisons. For each peptide pair, a plot was constructed using SRM measurements from 9 urine samples. Values for the area under the curve for one peptide were plotted on the x axis and values for the area under the curve for the other peptide were plotted on the y axis. A line was fit to the 9 data points, and a coefficient of determination ($r^2$) was calculated and entered into the matrix.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application.

For references on mass spectrometry and proteomics, see e.g., Salvatore Sechi, *Quantitative Proteomics by Mass Spectrometry (Methods in Molecular Biology)* 2nd ed. 2016 Edition, Humana Press (New York, N.Y., 2009); Daniel Martins-de-Souza, *Shotgun Proteomics: Methods and Protocols* 2014 *edition*, Humana Press (New York, N.Y., 2014); Jörg Reinders and Albert Sickmann, *Proteomics: Methods and Protocols (Methods in Molecular Biology)* 2009 *edition*, Humana Press (New York, N.Y., 2009); and Jörg Reinders, *Proteomics in Systems Biology: Methods and Protocols (Methods in Molecular Biology)* 1$^{st}$ ed. 2016 edition, Humana Press (New York, N.Y., 2009).

For references on how to prepare antibodies, see e.g., Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

The term "sample" or "biological sample" as used herein denotes a sample taken or isolated from a biological organism, e.g., a tumor sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; tissue sample; tumor sample; and/or tumor biopsy etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

As used herein, SRM stands for selected reaction monitoring. As used herein, MRM stands for multiple reaction monitoring. As used herein, SWATH stands for sequential window acquisition of all theoretical fragment ion spectra. As used herein, DIA stands for data-independent analysis. As used herein, MS stands for mass spectrometry. As used herein, ARIC stands for atherosclerosis risk in communities. As used herein, PDAY stands for Pathobiological Determinants of Atherosclerosis in Youth. As used herein, PTM stands for post-translational modifications. As used herein, SIL stands for stable isotope-labeled.

As used herein, "MS data" can be raw MS data obtained from a mass spectrometer and/or processed MS data in which peptides and their fragments (e.g., transitions and MS peaks) are already identified, analyzed and/or quantified. MS data can be Selective Reaction Monitoring (SRM) data, Multiple Reaction Monitoring (MRM) data, Shotgun CID MS data, Original DIA MS Data, MSE MS data, p2CID MS Data, PAcIFIC MS Data, AIF MS Data, XDLA MS Data, SWATH MS data, or FT-ARM MS Data, or their combinations.

As used herein, "acquiring MS data" can be accomplished without operating a mass spectrometer (for example, through retrieving results from MS experiments run previously and/or MS databases), or can be accomplished through operating a mass spectrometer to run MS experiments on samples.

As used herein, a pairwise correlation matrix refers to a matrix in which multiple candidate peptides are placed on a top (or bottom) row and a left (or right) column in the same order, and correlation values for each pair of candidate peptides are placed at their column-row intersections. The multiple candidate peptides can be derived from a single polypeptide or multiple polypeptides (for examples, protein isoforms, variants, or a family of related proteins). In some embodiments, the correlation values are coefficient of determination ($r^2$) values.

As used herein, the terms "correlation", "correlation value" and "correlation coefficient" can be used interchangeably to refer to any statistical measure that indicates the extent to which two or more variables fluctuate together. Non-limiting examples of "correlation value" include parametric methods such as the Pearson correlation coefficient; and nonparametric methods such as Kendall rank correlation coefficient and Spearman rank correlation coefficient. In preferred embodiments of the present invention, the "correlation value" is a coefficient of determination ($r^2$) value.

This approach of the present invention, based on SRM and/or SWATH MS, allows for the detection and accurate quantification of specific peptides in complex mixtures.

Selected Reaction Monitoring or Multiple Reaction Monitoring (SRM/MRM) mass spectrometry is a technology with the potential for reliable and comprehensive quantification of substances of low abundance in complex samples. SRM is performed on triple quadrupole-like instruments, in which increased selectivity is obtained through collision-induced dissociation. It is a non-scanning mass spectrometry technique, where two mass analyzers are used as static mass filters, to monitor a particular fragment of a selected precursor. The specific pair of mass-over-charge (m/z) values associated to the precursor and fragment ions selected is referred to as a "transition". The detector acts as a counting device for the ions matching the selected transition thereby returning an intensity distribution over time. MRM is when multiple SRM transitions are measured within the same experiment on the chromatographic time scale by rapidly switching between the different precursor/fragment pairs. Typically, the triple quadrupole instrument cycles through a series of transitions and records the signal of each transition as a function of the elution time. The method allows for additional selectivity by monitoring the chromatographic co-elution of multiple transitions for a given analyte.

SWATH MS a data independent acquisition (DIA) method which aims to complement traditional mass spectrometry-based proteomics techniques such as shotgun and SRM methods. In essence, it allows a complete and permanent recording of all fragment ions of the detectable peptide precursors present in a biological sample. It thus combines the advantages of shotgun (high throughput) with those of SRM (high reproducibility and consistency).

In a preferred embodiment, the developed assays can be applied to the quantification of polypeptides(s) in biological sample(s). Any kind of biological samples comprising polypeptides can be the starting point and be analyzed in the above procedure. Indeed any protein/peptide containing sample can be used for and analyzed by the assays produced here (cells, tissues, body fluids, waters, food, terrain, synthetic preparations, etc.). The assays can also be used with peptide mixtures obtain by digestion or with any non-digested sample. Digestion of a polypeptide includes any kind of cleavage strategies, such as, enzymatic, chemical, physical or combinations thereof.

The deciding factors of which polypeptide will be the one of interest varies. It can be decided by performing a literature search and identifying proteins that are functionally related, are candidate protein biomarkers which can be used in screening for drug discovery, biomarker discovery and/or disease clinical phase trials or are diagnostic markers to screen for pharmaceutical/medical purposes. The polypeptide of interest may be determined by experimental analysis. The selection of the polypeptides is done at the beginning, and used in the invention to develop assays to specifically monitor quantitatively the set of polypeptides in samples of interest.

According to a preferred embodiment, the following parameters of the assay are determined: trypsin digestion and peptide clean up, best responding polypeptides, best responding fragments, fragment intensity ratios (increased high and reproducible peak intensities), optimal collision energies, and all the optimal parameters to maximize sensitivity and/or specificity of the assays.

In another preferred embodiment, quantification of the polypeptides and/or of the corresponding proteins or activity/regulation of the corresponding proteins is desired. A selected peptide is labeled with a stable-isotope and used as an internal standard to achieve absolute quantification of a protein of interest. The addition of a quantified stable-labeled peptide analogue of the tag to the peptide sample in known amount; and subsequently the tag and the peptide of interest is quantified by mass spectrometry and absolute quantification of the endogenous levels of the proteins is obtained.

According to a preferred embodiment, the analysis and/or comparison is done on protein samples of wild-type or physiological/healthy origin with protein samples of mutant or pathological origin.

The present invention supports the use of SRM and SWATH as platform and uses a correlation matrix to identify signature polypeptides for quantitative proteomics. The approach is applicable to the analysis of proteins from all organisms, from cells, organs, body fluids, and in the context of in vivo and/or in vitro analyses. Examples of applications of the invention include the development, use and commercialization of quantitative assays for sets of polypeptides of interest. The invention can be beneficial for the pharmaceutical industry (e.g. drug development and assessment), the biotechnology industry (e.g. assay design and development and quality control), and in clinical applications (e.g. identification of biomarkers of disease and quantitative analysis for diagnostic, prognostic and/or therapeutic use). The invention can also be applied to water, drink, food and food ingredient testing, for example, quantifying nutrients, contaminants, toxins, antibiotics, steroids, hormones, pathogens, and allergens in water, drinks, foods and food ingredients.

Methods of the Invention

Various embodiments of the present invention provide for a method for identifying signature peptides for quantifying a polypeptide of interest in a sample. The methods include cleaving the polypeptide into peptides; detecting a multiplicity of the peptides with a quantitative analytical instrument; comparing the linearity of signals attributable to pairs of the peptides in a multiplicity of samples; and selecting signature peptides from a group of peptides with more highly correlated signals. In some embodiments, the quantitative analytical instrument is a mass spectrometer configured for selected reaction monitoring. In other exemplary embodiments, the mass spectrometer is a Triple-Time Of Flight (Triple-TOF) mass spectrometer configured for SWATH.

In various embodiments, the samples are biological samples or complex biological samples. In exemplary embodiments, the complex samples include, but are not limited to urine, blood fractions, tissues and/or tissue extracts, cells, body fluids, waters, food, terrain and/or synthetic preparations.

In some embodiments, coefficients of determination are calculated to quantify the linearity of the signals attributable to pairs of peptides in the multiplicity of samples.

In various embodiments, the peptides are derived by proteolysis or chemical cleavage of the polypeptide. In an embodiment, a protease is utilized to cleave the polypeptide into peptides. For example, the protease is trypsin. In additional embodiments, other proteases or cleavage agents may be used including but not limited to chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, NTCB, or a combination thereof.

In various other embodiments, a list of candidate peptides to be targeted for detection on the analytical instrument is generated by modeling protein cleavage. In exemplary embodiments, a list of candidate peptides to be targeted for detection on the analytical instrument is generated by modeling trypsin digestion of the polypeptide. In some embodiments, the list of candidate peptides is narrowed by eliminating peptides that, for example, cannot be detected on the analytical instrument. In some embodiments, a list of candidate peptides is narrowed by eliminating: a peptide that has not been previously detected on a mass spectrometer, a peptide susceptible to a modification that interferes with accurate quantitation, a miscleaved peptide comprising an internal protease recognition site, a peptide with relatively inaccessible ends evidenced by the presence of miscleaved peptides, a peptide that is not unique to the sequence of the protein of interest, a peptide not present in the mature protein, or a combination thereof.

In an embodiment, the detection of a peptide is improved by changing the conditions for fragmenting that peptide prior to detecting a multiplicity of the peptides with the mass spectrometer. In exemplary embodiments, the fragmentation condition is the collision energy.

In some embodiments, the selected signature peptides (i) have higher intensity signals than non-selected peptides in the group of peptides with correlated highly correlated signals, (ii) have signals that can be robustly detected above background noise and contaminants, and/or (iii) can discriminate between forms of the protein of interest and/or a combination thereof.

In various other embodiments, the method further comprises adding a stable isotope-labeled peptide to the sample prior to mass spectrometry. In some embodiments, the absolute amount of a peptide in the sample is determined by comparing the MS signals of natural and stable isotope-labeled peptides.

Various other embodiments of the present invention also provide a method for identifying signature fragments for quantifying a macromolecule of interest in a sample. The method includes cleaving the macromolecule into fragments; detecting a multiplicity of the fragments with a quantitative analytical instrument; comparing the linearity of signals attributable to pairs of the fragments in a multiplicity of samples; and selecting signature fragments from a group of fragments with more highly correlated signals.

Various embodiments of the present invention provide for a method for identifying signature peptides for quantifying a polypeptide of interest comprising: identifying one or more polypeptides of interest; establishing a list of candidate peptides in silico; digesting the polypeptide of interest with a protease to obtain a mixture of peptides; analyzing the mixture of peptides on a mass spectrometer to identify transitions with high and reproducible peak intensities; optimizing collision energy for each transition with high and reproducible peak intensities; using the optimized parameters to assay a digested complex sample using mass spectrophotometry; calculating correlation values for pairs of target peptide; determining correlated signature peptides that have high coefficients of determination; and quantitatively assessing the signature peptides in varying experimental situations. In other embodiments, optimization is performed when the signal is marginal and not performed if the signal is strong. In another embodiment, multiple complex samples are digested so that there are enough points on the graph to compare the signals between a pair of peptides to make a linear fit. In some embodiments, the correlation values are coefficient of determination ($r^2$) values.

In various other embodiments, the lengths of the lengths of the peptides are within the range of 6 and 21 amino acids.

In other embodiments, the comprehensive list of candidate peptides is narrowed by eliminating peptides. In other embodiments, conventional criteria are used to eliminate peptides from the comprehensive list of candidate peptides by eliminating peptides that: (i) were never detected by MS on any instrument, (ii) are not unique to the sequence of the protein of interest, (iii) are not located within the mature protein, (iv) contain amino acid residues such as methionine, cysteine, and/or asparagine that are subjected to posttranslational modifications that interfere with accurate quantitation by mass spectrometry, (v) are miscleaved or partially cleaved, (vi) are post-translationally modified in vivo, (vii) and/or a combination thereof.

In various other embodiments, transitions for each peptide with high and reproducible peak intensities are identified. In other embodiments, the collision energy for each transition is optimized. In other embodiments, mass spectrometry comprises selected reaction monitoring (SRM), also known as multiple reaction monitoring (MRM). In other embodiments, SRM or MRM is performed on a triple quadrapole mass spectrometer. In other embodiments, the peptides uniquely associated with the polypeptide of interest are those with high correlations, strong signals, high signal/noise and/or sequences unique to the protein of interest.

In various other embodiments, an average is calculated from the coefficients of determination for each peptide in a correlation matrix. Signature peptides are then selected from among those peptides with the highest 30%, 40%, 50%, 60%, 70%, 80% or 90% of averages.

In various other embodiments, a subset of correlated peptides is selected from among the set of peptides in a correlation matrix. Members of the subset all have coefficients of determination of more than 0.60, 0.65, 0.70, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or 0.99 for pairwise combinations with all other members of the subset. Signature peptides are then selected from the subset of correlated peptides.

In various other embodiments, stable isotope-labeled peptide standards for absolute quantification are used. In other embodiments, the peptide labeled with a stable isotope is used as an internal standard to obtain absolute quantification of the polypeptide of interest. In other embodiments, the peptides are quantified and then the amount of the parent protein present is inferred before digesting the sample with trypsin. In other embodiments, MS responses are used to determine an upper limit of quantification (ULOQ) and a lower limit of quantification (LLOQ).

Various embodiments of the present invention provide a method of identifying signature fragments for quantifying a macromolecule in a sample. The method comprises: acquiring mass spectrometry (MS) data on multiple candidate fragments of the macromolecule from multiple samples; using the MS data to calculate correlation values for pairwise comparisons between each of the multiple candidate fragments; and identifying the highly correlated fragments among the multiple candidate fragments as the signature fragments for quantifying the macromolecule. In some embodiments, the macromolecule is a polysaccharide. In some embodiments, the macromolecule is a nucleic acid such as DNA and RNA. In some embodiments, the macromolecule is a polypeptide or protein. In some embodiments, the macromolecule is a glycopeptide. In some embodiments, the macromolecule is a metabolic intermediate. In various embodiments, the multiple candidate peptides are derived by proteolysis or chemical cleavage of the polypeptide. In various embodiments, the macromolecule is digested with an enzyme or chemical to yield the multiple candidate fragments. In some embodiments, the enzyme is a nuclease. In some embodiments, the enzyme is a protease. In certain embodiments, the protease is trypsin. In various embodiments, the MS data comprises raw MS data obtained from a mass spectrometer and/or processed MS data in which peptides and their fragments (e.g., transitions and MS peaks) are already identified, analyzed and/or quantified. In various embodiments, the MS data is Selective Reaction Monitoring (SRM) data and/or Multiple Reaction Monitoring (MRM) data. In various embodiments, the MS data is Shotgun CID MS data, Original DIA MS Data, MSE MS data, p2CID MS Data, PAcIFIC MS Data, AIF MS Data, XDLA MS Data, SWATH MS data, or FT-ARM MS Data, or a combination thereof. In some embodiments, the method further comprising processing the MS data to identify, analyze and/or quantify the multiple candidate peptides and fragments thereof (e.g., transitions and MS peaks) before calculating correlation values. In some embodiments, the correlation values are coefficient of determination ($r^2$) values.

Various embodiments of the present invention provide a method of identifying signature peptides for quantifying a polypeptide in a sample. The method comprises: acquiring mass spectrometry (MS) data on multiple candidate peptides derived from the polypeptide in multiple samples; using the MS data to calculate correlation values for pairwise comparisons among the multiple candidate peptides; and identifying the highly correlated peptides among the multiple candidate peptides as the signature peptides for quantifying the polypeptide. In various embodiments, the multiple candidate peptides are derived by proteolysis or chemical cleavage of the polypeptide. In various embodiments, the polypeptide is digested with an enzyme or chemical to yield the multiple candidate fragments. In various embodiments, the MS data comprises raw MS data obtained from a mass spectrometer and/or processed MS data in which peptides and their fragments (e.g., transitions and MS peaks) are already identified, analyzed and/or quantified. In various embodiments, the MS data is Selective Reaction Monitoring (SRM) data and/or Multiple Reaction Monitoring (MRM) data. In various embodiments, the MS data is Shotgun CID MS Data, Original DIA MS Data, MSE MS data, p2CID MS Data, PAcIFIC MS Data, AIF MS Data, XDLA MS Data, SWATH MS data, or FT-ARM MS Data, or a combination thereof. In some embodiments, the method further comprising processing the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a method for identifying signature peptides for quantifying a polypeptide in a sample by selecting peptides with MS signals that are highly correlated with the MS signals of other peptides derived from the same polypeptide. In a preferred embodiment, the MS signal is a peak area. In another preferred embodiment, the MS signal is calculated by dividing the peak area of the peptide by the peak area of an SIL internal standard peptide of the same sequence. In various embodiments, the correlation between the MS signals of a pair of peptides is determined by parametric methods such as the Pearson r correlation or by nonparametric methods such as Kendall rank correlation and Spearman rank correlation. In a preferred embodiment, correlations are measured by determining the coefficient of determination ($r^2$).

Data Independent Acquisition on TripleTOF Mass Spectrometers (SWATH)

Data independent acquisition (DIA) is an emerging technology in the field of mass spectrometry based proteomics. Although the concept of DIA has been around for over a decade, recent advancements, in particular an improved speed of acquisition, of mass analyzers has pushed the technique into the spotlight and allowed for high quality DIA data to be routinely acquired by proteomics labs. Described herein are exemplar protocols used for DIA acquisition using the Sciex TripleTOF mass spectrometers and data analysis using the Sciex processing software.

I. GENERAL

Figure 13:
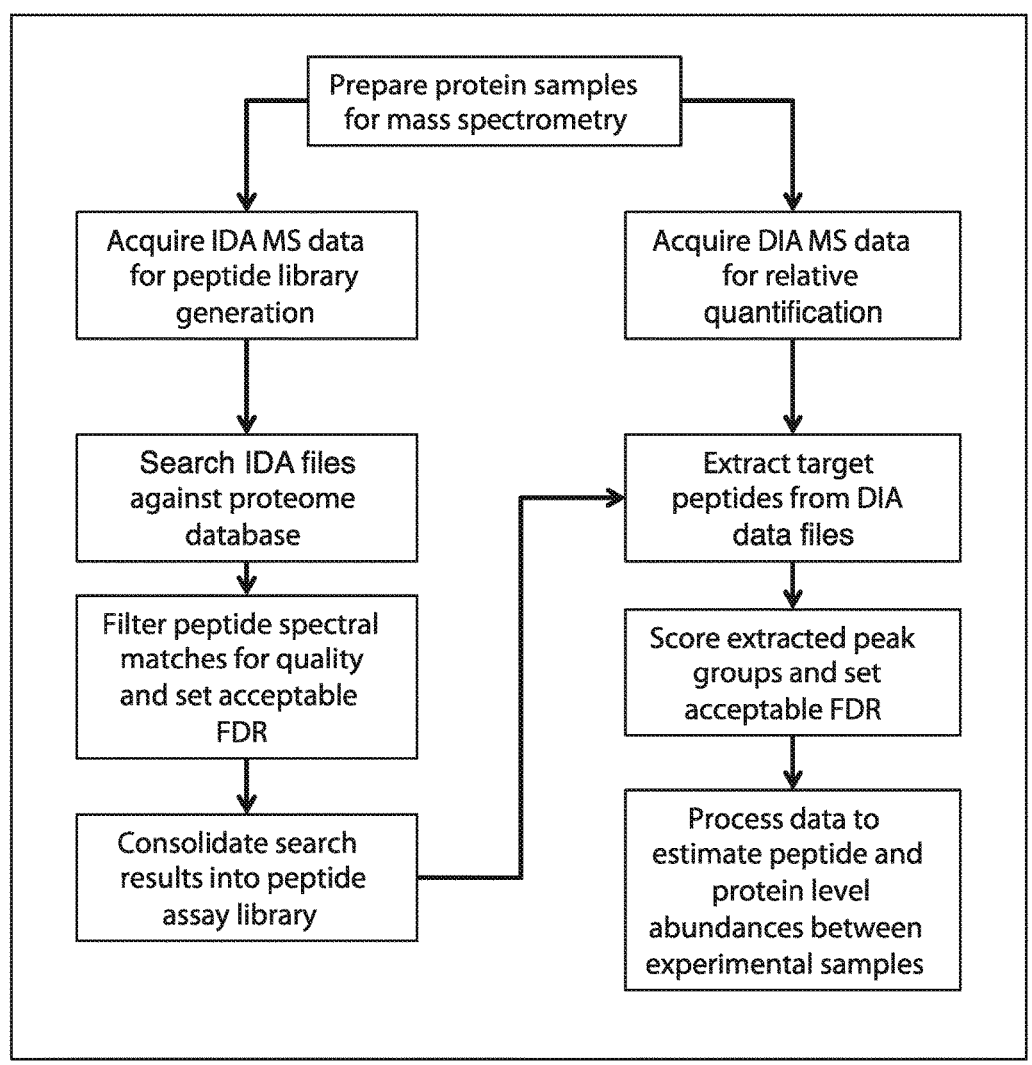
FIG. 13 depicts, in accordance with various embodiments of the present invention, a schematic of general workflow for SWATH-MS acquisition and analysis.

Data Independent Acquisition Mass Spectrometry (DIA-MS) is a long-standing technique (1, 2) that has garnered increased attention recently due to the development of new pipelines for extracting, identifying, and quantifying peptides using a targeted analysis approach (3, 4). SWATH™ couples DIA-MS with direct searching of individual samples against an established, and often a more exhaustive, peptide MS spectral library (3, 5, 6). SWATH™ is, therefore, a two-step process (FIG. 13), development of the MS spectral library, most often on a pooled sample representing the breath of the experimental collection, using information dependent acquisition (IDA) (see Note 1) and then the subsequent analysis of each individual sample by DIA. Thus, a major advantage of SWATH™ is that it can maximize the peptides observed both within an individual sample and across all of the samples in an experimental set, thereby increasing proteome coverage, experimental efficiency, reducing quantitative variability, and minimizing missing data across an experimental matrix. It is important to note that SWATH™ is an emerging approach and methods for estimating peptide identification confidence and false discovery rates as well as the ideal approach for estimating peptide and protein quantity from transition extracted ion chromatograms are continuing to evolve along with the sensitivity and capabilities of the instrumentation itself. As with any large-scale quantitative screening method, care should be taken to confirm and validate the biological differences and conclusions that are derived from a SWATH™ experiment.

In a SWATH™ experiment, proteins are digested and either directly infused or, more often, separated by liquid chromatography (LC) prior to analysis on a TripleTOF mass spectrometers (5600 or 6600, Sciex), a Q-Exactive mass spectrometer (Thermo Scientific), or any instrument with sufficiently high scan speed and a quadrupole mass filter. On the Triple TOF instruments, precursor peptide ion selection is performed by filtering precursors collectively through mass-to-charge windows, typically 4-10 m/z wide, sequentially across the entire m/z range of interest rather than selectively isolating a single precursor mass/charge (m/z) per MS/MS scan as performed in IDA-MS experiments. Due to the typically wider isolation windows used in DIA experiments, two or more co-eluting precursors are often fragmented collectively to produce an MS2 spectrum containing a convoluted mixture of fragment ions from multiple precursor ions.

One approach used to increase the ability to find and confidently identify peptides from these complex mixed spectra is to associate specific peptides with defined regions within the chromatographic elution profile. In order to accomplish this, retention time (RT) determination and alignments across samples is a key aspect of searching IDA data. Exogenous supplied RT standards (6) or endogenous RT (7) that are composed of peptides consistently observed across large number of samples must be used for RT calibration in order to properly align individual ion chromatograms across the entire sample's elution profile.

Optimization of m/z window number and dwell time/ion accumulation time per window is performed so that the instrument cycles through the entire desired precursor m/z range (e.g., 400-1250 m/z). This is largely instrument and sample specific. For the 6600 triple TOF, you can go up to 2250 m/z but we typically analyze between 400-1250 m/z for tryptic digests. When analyzing middle down or any peptides larger than the average tryptic peptides the full range can be used with the appropriate considerations to SWATH™ windows and cycle times. Ultimately, the key is to allow the instrument to cycle rapidly enough to capture multiple observations across the chromatographic elution profile for a given ion.

The data are subsequently searched against a sample specific peptide library that allows a set number of transition ion chromatograms to be extracted for a peptide within the window of its predicted RT (determined by its observed or normalized RT from the peptide library). The peak groups are scored according to several factors intended to discriminate a "true" peptide target from non-specific noise, and the distribution of these target scores are modeled against the distribution of scores attributed to decoy peak groups to determine a score cut off resulting in an acceptable false discovery rate. Relative peptide abundance is then inferred from the aggregate of the area under the curve for each transition extracted ion chromatograms (XICs), and various statistical approaches are used to roll transition intensity XICs into peptide intensity estimates, which can then be used to estimate the overall protein intensity. In this chapter, we present the typical workflow used currently by our group to prepare, acquire, and analyze proteomic data for a DIA-MS experiment of cell or tissue samples. For simplicity and pragmatism we present the workflow as completed using SCIEX TripleTOF® instruments and data analysis platform exclusively, with mention of alternative approaches as appropriate.

1.1 Quality Assurance and Quality Control (QA/QC) Considerations

Robust quality assurance (QA) or quality control (QC) protocols are essential to monitor instrument performance and improve reproducibility and reliability of data. A QC standard run can be analyzed at fixed times such as the beginning and end of an experiment or day to assess variation in a variety of quality control metrics (8). For the TripleTOF instruments, we conduct internal mass calibrations of mass accuracy and sensitivity for both MS1 and MS2 scans every 3-5 runs by monitoring at least 8 peptides from 100 fmols digested beta-galactosidase standard (Sciex) and 7 transition ions from the 729.3652 $[M+2H]^{2+}$ ion (Table 1).

TABLE 1

Beta-galactosidase peptides used for autocalibration and quality control.

| Beta-Galactosidase Peptide sequence | $[M + 2H]^{2+}$ | transition ions for 729.36Fragment |
|---|---|---|
| YSQQQLMETSHR (SEQ ID NO: 71) | 503.2368 | |
| RDWENPGVTQLNR (SEQ ID NO: 72) | 528.9341 | |
| GDFQFNISR (SEQ ID NO: 73) | 542.2654 | |
| IDPNAWVER (SEQ ID NO: 74) | 550.2802 | |
| DVSLLHKPTTQISDFHVATR (SEQ ID NO: 75) | 567.0565 | |
| VDEDQPFPAVPK (SEQ ID NO: 76) | 671.3379 | |

TABLE 1-continued

Beta-galactosidase peptides used for autocalibration and quality control.

| Beta-Galactosidase Peptide sequence | $[M + 2H]^{2+}$ | transition ions for 729.36Fragment |
|---|---|---|
| DWENPGVTQLNR (SEQ ID NO: 77) | 714.8469 | |
| APLDNDIGVSEATR (SEQ ID NO: 78) | 729.3652 | |
| | | 175.1190 y1 |
| | | 347.2037 Y3 |
| | | 563.2784 Y5 |
| | | 729.3652 b7 |
| | | 832.4523 y8 |
| | | 1061.5222 y10 |
| | | 1289.6332 y12 |

What also needs to be tracked is sample processing to ensure the quality to what is being analyzed, which is not addressed at in this manuscript but is well established in targeted multiple and selective monitoring work flows. To do this one can include a exogenously protein, such as beta galactosidase, is added into the sample prior to digestion. Beta-galactosidase elected peptides can be quantified (if $^{15}$N labeled peptides are added after digestion to the sample) or assessed in each sample (for more details see Chen et al., in Salvatore Sechi, *Quantitative Proteomics by Mass Spectrometry* (Methods in Molecular Biology) 2nd ed. 2016 Edition, Humana Press (New York, N.Y., 2009))

Internal peptide retention time (RT) standards are an essential component of both peptide library generation and SWATH™ data analysis, and must be 1) detectable across all individual samples and 2) spread evenly across the chromatogram. Retention time of a given peptide from the library is used to set an extraction window for its peak group identification from the SWATH™ data file, and subsequently also used in scoring the confidence of a given peak group assignment to a peptide sequence from the library. If SWATH™ data files and peptide library files are collected absolutely sequentially with nearly identical chromatography, one might bypass the use of RT alignment standards. Much more commonly, differences in sample matrix, chromatographic set-ups, timing of instrument batch acquisitions, and many other factors can contribute to imperfect chromatographic alignment necessitating RT standards to normalize peptide assay library retention time to SWATH™ acquisition file retention time. Used alone or in combination with retention time standards that are spiked into a sample, endogenous reference peptides can also be used for the calibration of retention times across samples (7). These can be unique to a specific library (sample), however, there are common and conserved peptides that may be present in most, if not all, mammalian cells and tissues which can be used as a complement or replacement to synthetic, externally spiked RT reference peptides (7). QC tools are available to assess quality control metrics in a shotgun or targeted proteomic workflow that allows chromatographic performance and systemic error to be monitored (9). Tracking RT standards across sample runs can also server to assess instrument performance.

As larger numbers of individual samples are analyzed adopting other routine QC such as randomization or blocking of sampled to minimize sample analysis bias and regular collection of quality control samples spaced evenly and strategically throughout acquisition batches can be necessary components of SWATH™ experimental design.

1.2 Spectral Library Building—Data Generation

The use of a spectral ion library is most often used for the targeted analysis of SWATH™ data, although other methods are being explored and developed (10, 11), and can be primarily cell or tissue and species specific or a broader library assembled from all relevant peptide observations from a given species (5). Spectral ion libraries are most commonly built using traditional shotgun proteomics in information dependent acquisition (IDA) MS mode. In some cases spectral ion libraries previously generated have been made available to the public from various labs (5, 12, 13). Here we describe the creation of new spectral ion libraries from IDA analysis of proteolytic digestions. Additional detailed information regarding the generation of spectral ion libraries, including the management of protein redundancy and isoform specificity, can be found in Schubert et al (5). It is important to consider differences in peptide fragmentation patterns between instruments, and ideally use IDA data acquired on the same instrument from which you perform your SWATH™ acquisition (14).

Spectral ion libraries can be constructed in a number of ways. The first and most straightforward way to create an ion library is to analyze a proteolytic digestion in IDA mode of a pooled sample created from all of the individual samples that can be subsequently analyzed by DIA or of samples composing the extremes of the phenotype. This can give the most basic ion library comprising the peptides identified in a single IDA run that can then be used against the SWATH™ acquired version of itself and any other SWATH™ acquired sample of the same general proteome. In an attempt to expand the number of ions selected for fragmentation for library generation from a single IDA run of the pooled sample, multiple runs or technical replicates might help increase the proteome coverage provided to the sample library beyond what may be obtained from a single run and thus may help compensate for the error in sampling that is inherent to DIA methods. Alternatively, deeper and more inclusive ion libraries can be constructed post-digestion using off-line peptide fractionation and analysis of these fractions independently in IDA mode. The IDA runs are then combined to create a more complete and inclusive ion library for the given sample proteome and should ultimately increase the power of DIA-base protein identifications by increasing the number of peptides used to quantitate highly abundant proteins while harnessing the sensitivity of MS2-based quantitation necessary of low abundance proteins and peptides. Some methods commonly used for peptide fractionation are basic-reverse phase HPLC (bRP-HPLC) (15), strong cation exchange (SCX), and strong anion exchange (SAX) (16) (see Notes 2 and 3). Our lab typically uses bRP-HPLC or a solid phase extraction SCX (17) method for peptide fractionation prior to MS analysis. For SWATH™ analysis of post-translational modifications it is recommended to employ enrichment strategies (if applicable) either independently or in combination with the peptide fractionation techniques described and as typically performed in shotgun experiments.

The following exemplar protocol is for library generation using Sciex TripleTOF™ systems with an Eksigent® 415 nano LC and ekspert 400 autosampler, although alternative LC and autosamplers may be used with the TripleTOF systems.

II. MATERIALS

Proteolytic peptide mixture, most often MS-grade trypsin (Promega)
5600 or 6600 TripleTOF system
Nano-LC and autosampler (e.g. Eksigent® 415 nano LC, ekspert 400 autosampler) and ekspert cHiPLC (optional)
Trap and analytical LC columns (Eksigent P/N 804-00006 and 804-00001)
Proteolytic peptide mixture, most often MS-grade trypsin (Promega)
5600 or 6600 TripleTOF system
Retention time standards, either commercial peptides that are spiked in right before MS analysis (e.g. Biogynosis cat# KI-3002-2) or endogenous peptides present in all samples can be used (Parker et al, in press) (see Note 4).
Software Needed (see Note 5)
Analyst TF 1.7
PeakView 2.0 or higher
Variable Window Calculator
Protein Pilot 4.5 or higher
SWATH™ microapp
Microsoft Excel
MarkerView (optional)

III. METHODS 3.1 IDA Analysis of Proteolytic Digests for Spectral Ion Library Building 3.1.1 Create an IDA method in Analyst TF 1.7 with 1 survey scan and 20 candidate ion scans per cycle (see Note 6). Check the Rolling Collision Energy box.

3.1.2 For TOF MS (MS1)

Figure 14:
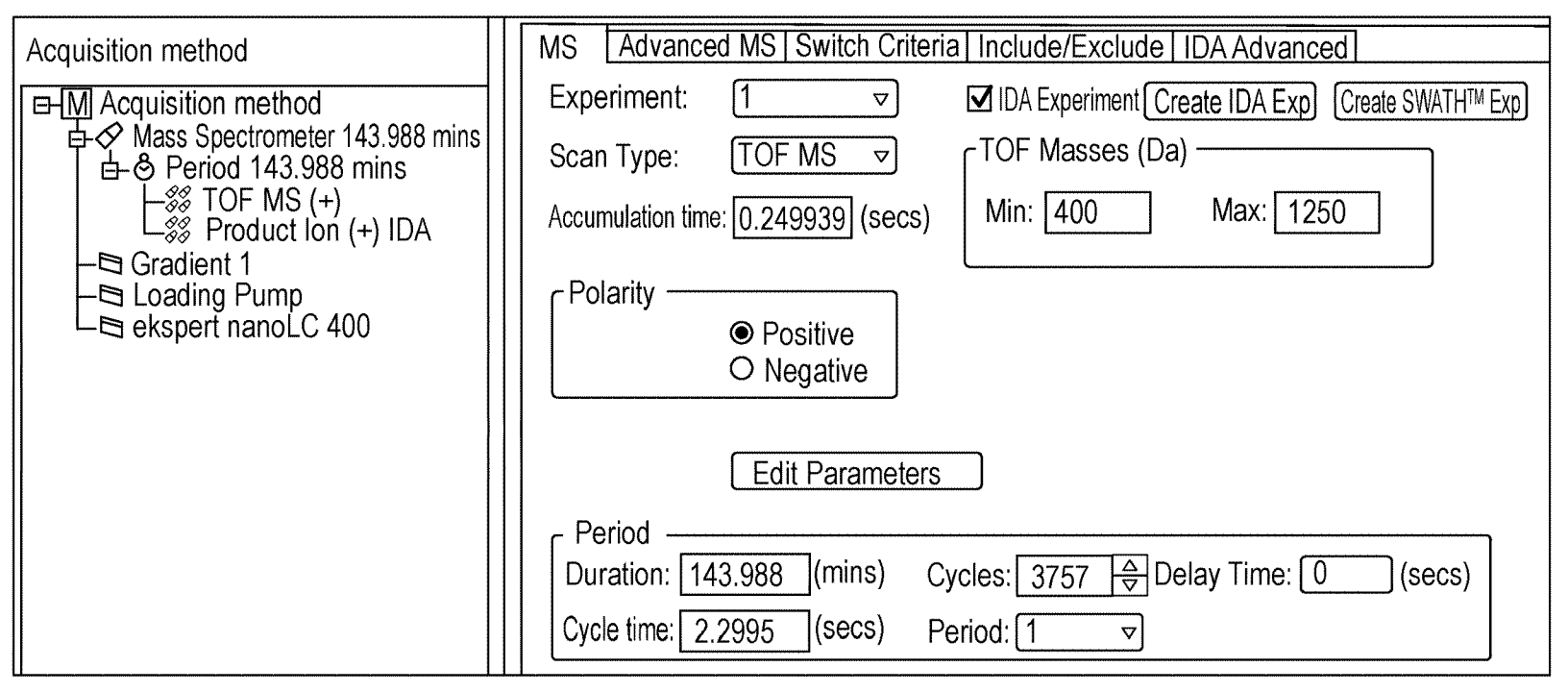

Under the MS Tab set the accumulation time to 250 ms and the mass range from 400-1250 Da (FIG. 14, see Note 7). Set the method duration to match the length of your LC gradient method.

Figure 15:
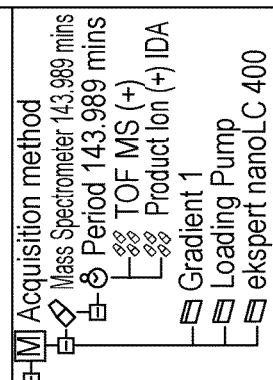
FIG. 15 depicts, in accordance with various embodiments of the present invention, an example of Switch Criteria parameters for TripleTOF MS instruments.

Under the Switch Criteria tab set the range to match what you selected under the above window, monitor charge states from 2 to 5 which exceed 150 counts, set the mass tolerance to 50 ppm, and set your exclusion criteria (FIG. 15, see Note 8).

Under the Include/Exclude tab put in any masses you want to monitor or exclude in your analysis.

Under the IDA Advanced tab make sure Rolling Collision Energy is checked and make any other necessary changes that would be pertinent to your experiment.

Default settings do not need to be changed under the Advanced MS tab.

3.1.3 For Product Ion (MS2)

Under the MS Tab set the accumulation time to 100 ms and the mass range from 100-1800 Da$^7$ and check whether you want high resolution or high sensitivity (the high sensitivity function is most commonly selected for proteomics experiments).

All other tabs should maintain the same parameters as for the TOF MS and do not need to be changed.

3.1.4 Load the sample appropriate Gradient, Loading Pump, and auto-sampler methods and save your Acquisition File.

3.1.5 Analyze your peptide samples.

3.2 SWATH-MS Data Acquisition

3.2.1 Creation of Variable Window SWATH™ methods

Optimized SWATH™ methods can be constructed for specific samples using the Sciex Variable Window Calculator application. The steps for creating the customized SWATH™ variable windows for a specific sample are listed in the Variable Window Calculator under the Instructions and Controls tab. After following these directions select the number of variable windows (see Note 9) you want to analyze in your method and the mass range of the SWATH™ analysis. For general proteomics experiments the window overlap is usually left at 1 Da and the collision energy spread (CES) is usually left at 5. The minimum window width should be set no lower than 4 due to the default parameters in the PeakView software. After the Variable Window calculator is finished creating the optimal windows for your analysis go to the OUTPUT for Analyst tab and copy columns A, B, and C into a new Excel file and save as a Text (Tab Deliminated) file which can then be loaded into the SWATH™ method within Analyst TF 1.7.

3.2.2 Creation of a SWATH™ method in Analyst TF 1.7

3.2.2.1 In Analyst TF 1.7 go to the Build Acquisition Method tab on the left hand side of the window. Click on TOF MS and select Create SWATH™ Exp button then select the Manual tab within this window.

3.2.2.2 Under SWATH™ Analysis Parameters select the mass range of the analysis (typically 400-1250 Da for tryptic peptides). Under Fragmentation Conditions make sure Rolling Collision energy is checked (the CES set in the Variable Window Calculator can overwrite the CES value inputted on this screen). Under SWATH™ Detection Parameters select the mass range to monitor for the SWATH™ MS2 spectra (typically 100-1800 Da) and the accumulation time for each window (typically for 100 VW 30 ms is adequate) (see Note 10). Lastly, click the Read SWATH™ Windows from Text File box and load in your .txt file create in the Variable Window Calculator.

The accumulation time for the MS1 can be set between 50-150 ms to give a quick survey scan for each cycle (see Note 11). Select the appropriate loading pump, gradient, and auto-sampler methods for the file (see Note 12). The gradient method chosen should be the same one that was used during the IDA analysis preformed to generate the proteome specific spectral library.

3.3 SWATH™ Data Analysis Using PeakView 2.1 and SWATH™ Microapp 2.0

3.3.1 Introduction to SWATH™ data analysis procedure

As with many methodologies, there are several options for processing SWATH™ data and analyzing results. Here, we present the protocol to process data through the SCIEX proprietary software. In our lab, we also regularly utilize two alternative pipelines, Skyline (18) and OpenSWATH (4). Skyline is a free and open-source tool built in Windows computing environments for analysis of multiple MS data types, including DIA. OpenSWATH™ is a free and open-source built within the openMS data analysis tool space, and operates optimally in a linux computing environment. A summary of the basic information pertaining to using these two alternate data analysis pathways is provided in Table 2.

TABLE 20

Selected alternative DIA-MS data analysis approaches

| Parameters | Skyline[1] | OpenSWATH[2] |
|---|---|---|
| Input DIA File format | .WIFF | .mzML/.mzXML[3] |
| Peptide Ion Library | Built from DDA search result files (e.g., pep.xml, .group) or imported as a "transition list" | Built using TPP tools and custom Python scripts[4] |
| SWATH Workflow Output File Format | Internal to Skyline .csv transition report | OpenSwathWorkflow.exe .tsv transition report |
| Visualization | Internal to Skyline | TAPIR[5] |
| Peak Picking Algorithm | mProphet[6] adaptation | pyProphet[7] |
| Multi-Run Alignment | — | Feature Alignment[8] |
| Quantitative Statistics | Linked External Tool MSstats[9] | External Tools (eg. MapDIA[10], MSstats) |

[1]MacLean, B. et al. Skyline: an open source document editor for creating and analyzing targeted proteomics experiments. Bioinformatics 26, 966-968 (2010).
[2]Röst HL et al OpenSWATH ™ enables automated, targeted analysis of data-independent acquisition MS data. Nature Biotechnology 10; 32(3): 219-23 (2014)
[3]Conversion to mzML or mzXML can be done using the tool msconvert, available at: (http://proteowizard.sourceforge.net/tools/msconvert.html). Do not select peak picking, files may expand 10x or more from raw file size.
[4]Schubert OT et al., Building high-quality assay libraries for targeted analysis of SWATH ™ MS data. Nature Protocols, 10(3): 426-41 (2015). Note: libraries generated using the pipeline described in the Schubert et al paper can be formatted for use in the PeakView microapp, and substituted in the workflow above.
[5]https://github.com/msproteomicstools/msproteomicstools/blob/master/gui/TAPIR.py
[6]http://www.mprophet.org/
[7]https://pypi.python.org/pypi/pyprophet
[8]python script, available to download from https://github.com/msproteomicstools, found in folder msproteomicstools/analysis/alignment/feature_alignment.py
[9]http://www.msstats.org/
[10]httpp://mapdia.sourceforge.net/Main.html In this section, we provide a summary specific to the approach used in our lab for the general implementation of the SCIEX software tools. We recommend referring to the SCIEX software user manuals for additional guidance.

3.3.2 Creation of Spectral Ion Library using Protein Pilot Paragon Method 3.3.2.1 Prepare the protein reference database that you use for matching DDA spectra to peptide sequences. For instance, FASTA documents for annotated proteomes can be downloaded from the Uniprot website: (http://www.uniprot.org/proteomes). Typically, we chose to use the curated, or reference proteomes, for a given organism of interest.

If external retention time standards were used in the experiment, such as the Biognosys iRT (see Note 13) peptides, copy their sequences and append to your FASTA file by opening it in a text editor. FASTA proteome databases should be saved in the appropriate folder within the Protein Pilot software files on your computer as per the software manual instructions.

3.3.2.2 In Protein Pilot, select the option for an LC MS search and prepare a database search method appropriate for your experiment, including all of the raw data files you would like to include to build the ion library.

3.3.2.3 Once the search is completed open the "FDR report" generated for the search and record the number of proteins identified at 1% Global FDR to be used as input in the following section.

Figure 16:
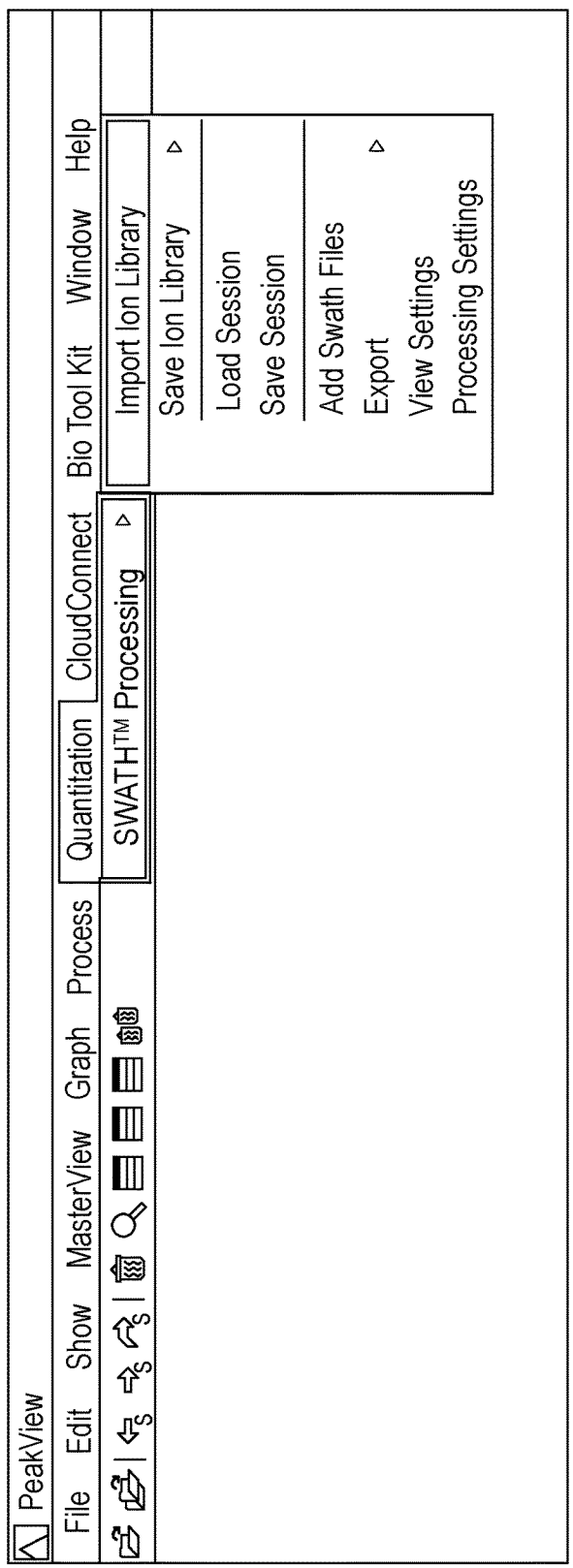
FIG. 16 depicts, in accordance with various embodiments of the present invention, schematic for importing ion library into PeakView software.

3.3.3 Importing Ion Libraries into the SWATH™ microapp and analyzing SWATH™ data 3.3.3.1 Open PeakView and using the tabs at the top of the screen, navigate to Quantitation→SWATH™ Processing→Import Ion Library (FIG. 16).

3.3.3.2 Find the .group file produced from the Protein Pilot search and set the number of proteins to import to the 1% Global FDR (see Note 14) recorded in the previous section from the FDR report generated by Protein Pilot.

Typically peptides shared by more than one protein are not imported. Under Select sample type, chose the option appropriate for whether the samples were unlabeled (typical) or labeled with a chemical tag (i.e. iTRAQ, SILAC, etc. . . . ).

3.3.3.3 Select all of the SWATH™ files to be analyzed for a given experiment.

3.3.3.4 Set your processing settings. For protein quantitation analysis, examples of typical parameter settings are given in FIG. 17 (see Note 15):

3.3.3.5 After setting your processing settings click "Process" to analyze your SWATH™ data.

Figure 18:
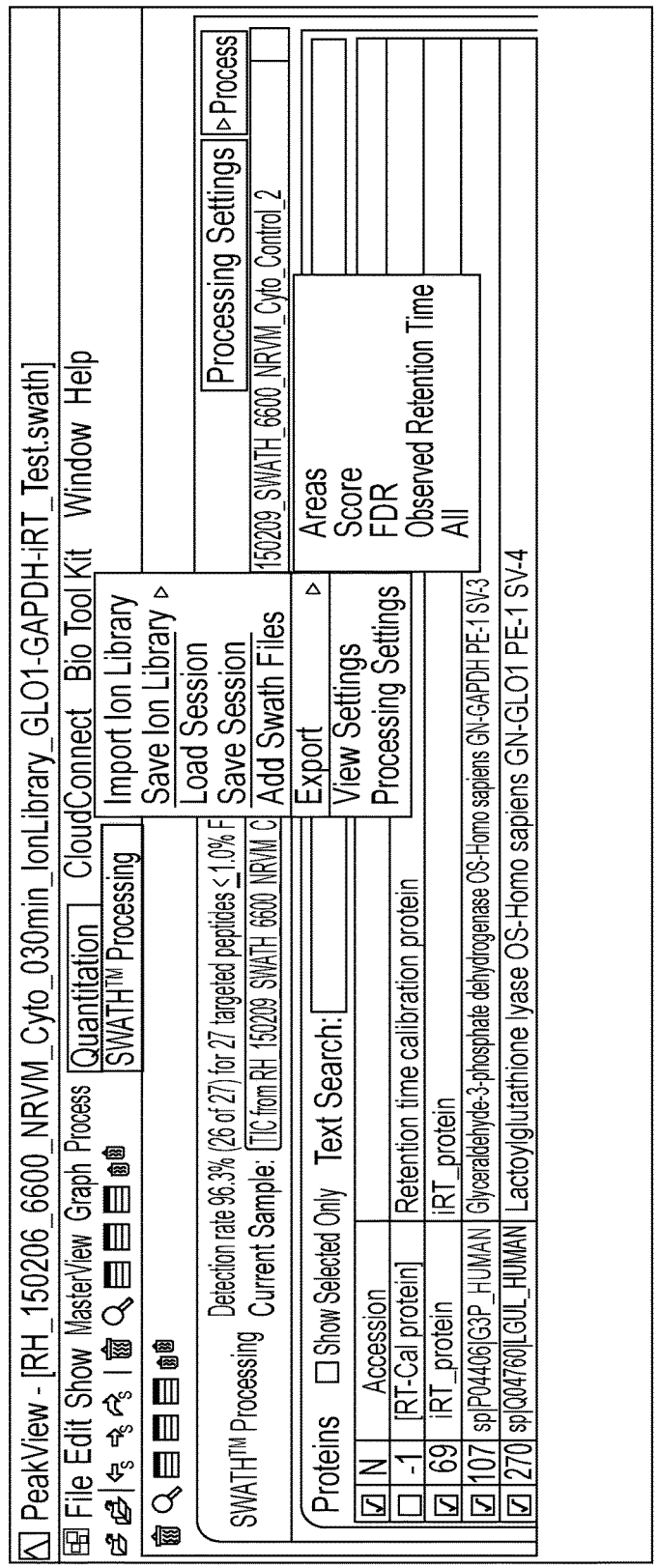
FIG. 18 depicts, in accordance with various embodiments of the present invention, schematic for exporting SWATH results from PeakView software.

3.3.3.6 Once completed you can export the data for visualization in MarkerView by clicking Quantitation→SWATH™ Processing→Export→Areas or Export→All to get a complete list of all parameters for the analysis in Excel format (FIG. 18).

IV. NOTES

1. The Sciex terminology Information Dependent Acquisition (IDA) is the same as Data Dependent Acquisition (DDA) and this is the terminology used in the Sciex software for shotgun proteomics experiments. Here, we use the IDA acronym to be consistent with the Sciex terminology and software.
2. bRP-HPLC fractionation may be preferred over SCX or SAX fractionation if downstream phospho-peptide enrichment or analysis of other negatively charged peptides is desired. This is due to a more equal distribution of phospho-peptides throughout basic-RP fractions compared to SCX and SAX fractions, in which phospho-peptides are most dense in the early and late fractions, respectively.
3. The SCX method published by Dephoure and Gygi (17) was based on 10 mg of starting material and was used upstream of phosphopeptide enrichment. Our lab has used this method for both phosphoproteomic and general proteomic analysis and we have scaled back the protocol for 1 mg of starting material, in which we have cut the reagents used in the Dephoure & Gygi paper by ¹⁄₁₀th. If using less than 1 mg of starting material scale back the reagents accordingly (13).
4. If large number of samples include beta-galactosidease for sample preparation assessment and N15 labeled peptides to track (see Chen et al., in Salvatore Sechi, *Quantitative Proteomics by Mass Spectrometry* (*Methods in Molecular Biology*) 2nd ed. 2016 Edition, Humana Press (New York, N.Y., 2009)).
5. Sciex software can be downloaded at http://www.absciex.com/downloads/software-downloads
6. The number of survey scans desired for the analysis of concatenated or single run samples for library generation is a matter of user discretion but a typical IDA method on a TripleTOF system uses 20 candidate ions.
7. The 5600 TripleTOF system can go up to 1250 m/z and the 6600 TripleTOF can go up to 2250 m/z. However, we find that for tryptic digests there is little additional peptide data obtained above 1250 m/z. The larger mass range on the 6600 system is beneficial when doing large protein modifications such as glycoproteomics or when using alternative proteolytic methods that produce larger peptides (i.e. Lys-C, CNBr).
8. These values are meant to be used as a general guide in setting up an IDA method. Optimization for individual systems and sample types may be required for optimal results. For PTM and low abundant peptide analysis the accumulation times may be adjusted to allow for increased signal in both the MS1 and MS2 scans.
9. The number of variable windows chosen should be considered carefully as the more windows selected the shorter the dwell time has to be for each window. For general purposes 100 VW and a 30 ms dwell time should be sufficient to yield good quantitation of peptides.
10. If accumulation times less than 30 ms are desired it is recommended that they be tested prior to large scale sample analysis to ensure the accumulation time chosen can give adequate signal for quantitation.
11. If using the 5600 TripleTOF system, the minimum accumulation time for the MS1 should be set to 150 ms to ensure the MS1 quality is sufficient to perform the background calibrations during the run. The 6600 TripleTOF system does not use this background calibration so a shorter MS1 accumulation time (50 ms) may be used to get a quick survey scan.
12. The LC and auto-sampler methods can vary between labs and the gradient lengths can vary depending on the complexity of the samples. Typically, for complex mixtures a gradient of 5-35% B over 90-120 minutes is suitable and for less complex samples (i.e. immunoprecipitations, purified proteins) shorter gradients between 30 and 60 minutes may be sufficient.
13. iRT FASTA sequence is available at www.biognosys.com, or type the following into your FASTA file:

13.1.1. >Biognosys iRT Kit Fusion (SEQ ID NO: 81)
AGGSSEPVTGLADKVEATFGVDESANKYILAGVESNKDAVTPADFSEWSK

FLLQFGAQGSPLFKLGGNETQVRTPVISGGPYYERTPVITGAPYYERGDL

DAASYYAPVRTGFIIDPGGVIRGTFIIDPAAIVR

14. FDR threshold can be set higher or lower depending on the user preference, the higher the FDR is set the more proteins can be incorporated into the library but the confidence of these proteins cannot be as high as if a lower FDR threshold is used.
15. These parameters are meant as a guideline and can be adjusted based on user preferences. Refer to the Sciex PeakView software documentation and the literature regarding optimizing these settings for your particular experiment. Importantly, for PTM analysis, un-check the Exclude Modified Peptides box and increase the number of peptides per protein to a larger value (i.e. 100) to import all peptides identified at the confidence level selected or create a PTM enriched peptide library.

V. REFERENCES

1. Venable J D, Dong M Q, Wohlschlegel J, Dillin A, Yates J R (2004) Automated approach for quantitative analysis of complex peptide mixtures from tandem mass spectra. Nature methods 1 (1):39-45. doi:10.1038/nmeth705
2. Dong M Q, Venable J D, Au N, Xu T, Park S K, Cociorva D, Johnson J R, Dillin A, Yates J R, 3rd (2007) Quantitative mass spectrometry identifies insulin signaling targets in *C. elegans*. Science 317 (5838):660-663. doi:10.1126/science.1139952
3. Gillet L C, Navarro P, Tate S, Rost H, Selevsek N, Reiter L, Bonner R, Aebersold R (2012) Targeted data extraction of the MS/MS spectra generated by data-independent acquisition: a new concept for consistent and accurate proteome analysis. Molecular & cellular proteomics: MCP 11 (6):0111 016717. doi:10.1074/mcp.0111.016717

4. Rost H L, Rosenberger G, Navarro P, Gillet L, Miladinovic S M, Schubert O T, Wolski W, Collins B C, Malmstrom J, Malmstrom L, Aebersold R (2014) OpenSWATH enables automated, targeted analysis of data-independent acquisition MS data. Nat Biotechnol 32 (3):219-223. doi:10.1038/nbt.2841
5. Schubert O T, Gillet L C, Collins B C, Navarro P, Rosenberger G, Wolski W E, Lam H, Amodei D, Mallick P, MacLean B, Aebersold R (2015) Building high-quality assay libraries for targeted analysis of SWATH MS data. Nature protocols 10 (3):426-441. doi:10.1038/nprot.2015.015
6. Wang J, Perez-Santiago J, Katz J E, Mallick P, Bandeira N (2010) Peptide identification from mixture tandem mass spectra. Molecular & cellular proteomics: MCP 9 (7):1476-1485. doi:10.1074/mcp.M000136-MCP201
7. Parker S, Rost H, Rosenberger G, Collins B C, Maelstrom L, Amodei D, Venkatramen V, Raedschelders K, Van Eyk J, Aebersold R (2015) Identification of a Set of Conserved Eukaryotic Internal Retention Time Standards for Data-Independent Acquisition Mass Spectrometry. Molecular & cellular proteomics: MCP Conditionally Accepted
8. Bereman M S (2015) Tools for monitoring system suitability in LCMS/MS centric proteomic experiments. Proteomics 15 (5-6):891-902. doi:10.1002/pmic.201400373
9. Bereman M S, Johnson R, Bollinger J, Boss Y, Shulman N, MacLean B, Hoofnagle A N, MacCoss M J (2014) Implementation of statistical process control for proteomic experiments via LCMS/MS. J Am Soc Mass Spectrom 25 (4):581-587. doi:10.1007/s13361-013-0824-5
10. Tsou C C, Avtonomov D, Larsen B, Tucholska M, Choi H, Gingras A C, Nesvizhskii A I (2015) DIA-Umpire: comprehensive computational framework for data-independent acquisition proteomics. Nature methods 12 (3): 258-264, 257 p following 264. doi:10.1038/nmeth.3255
11. Ting S, Egertson J, MacLean B, Kim S, Payne S, Noble W, MacCoss M J Pecan: Peptide Identification Directly from Data-Independent Acquisition (DIA) MS/MS Data. In: American Society for Mass Spectrometry, Baltimore, Md., 2014.
12. Toprak U H, Gillet L C, Maiolica A, Navarro P, Leitner A, Aebersold R (2014) Conserved peptide fragmentation as a benchmarking tool for mass spectrometers and a discriminating feature for targeted proteomics. Molecular & cellular proteomics: MCP 13 (8):2056-2071. doi: 10.1074/mcp.O113.036475
13. Kirk J A, Holewinski R J, Kooij V, Agnetti G, Tunin R S, Witayavanitkul N, de Tombe P P, Gao W D, Van Eyk J, Kass D A (2014) Cardiac resynchronization sensitizes the sarcomere to calcium by reactivating GSK-3beta. The Journal of clinical investigation 124 (1):129-138. doi: 10.1172/JCI69253
14. Escher C, Reiter L, MacLean B, Ossola R, Herzog F, Chilton J, MacCoss M J, Rinner O (2012) Using iRT, a normalized retention time for more targeted measurement of peptides. Proteomics 12 (8):1111-1121. doi:10.1002/pmic.201100463
15. Wang Y, Yang F, Gritsenko M A, Wang Y, Clauss T, Liu T, Shen Y, Monroe M E, Lopez-Ferrer D, Reno T, Moore R J, Klemke R L, Camp D G, 2nd, Smith R D (2011) Reversed-phase chromatography with multiple fraction concatenation strategy for proteome profiling of human MCF10A cells. Proteomics 11 (10):2019-2026. doi: 10.1002/pmic.201000722
16. Han G, Ye M, Zhou H, Jiang X, Feng S, Jiang X, Tian R, Wan D, Zou H, Gu J (2008) Large-scale phosphoproteome analysis of human liver tissue by enrichment and fractionation of phosphopeptides with strong anion exchange chromatography. Proteomics 8 (7):1346-1361. doi:10.1002/pmic.200700884
17. Dephoure N, Gygi S P (2011) A solid phase extraction-based platform for rapid phosphoproteomic analysis. Methods 54 (4):379-386. doi:10.1016/j.ymeth.2011.03.008
18. MacLean B, Tomazela D M, Shulman N, Chambers M, Finney G L, Frewen B, Kern R, Tabb D L, Liebler D C, MacCoss M J (2010) Skyline: an open source document editor for creating and analyzing targeted proteomics experiments. Bioinformatics 26 (7):966-968. doi: 10.1093/bioinformatics/btq054

In some embodiments, acquiring MS data does not require operating a mass spectrometer. For examples, MS data can be acquired from MS experiments run previously and/or MS databases. In some embodiments, previously acquired SWATH MS data can be queried with a more comprehensive library to identify additional MS peaks derived from different and macromolecules.

In various embodiments, acquiring MS data comprises operating a TripleTOF mass spectrometer, a triple quadrupole mass spectrometer, a liquid chromatography-mass spectrometry (LC-MS) system, a gas chromatography-mass spectrometry (GC-MS) system, or a tandem mass spectrometry (MS/MS) system, a dual time-of-flight (TOF-TOF) mass spectrometer, or a combination thereof.

In various embodiments, acquiring MS data comprises operating a mass spectrometer. Examples of the mass spectrometer include but are not limited to high-resolution instruments such as Triple-TOF, Orbitrap, Fourier transform, and tandem time-of-flight (TOF/TOF) mass spectrometers; and high-sensitivity instruments such as triple quadrupole, ion trap, quadrupole TOF (QTOF), and Q trap mass spectrometers; and their hybrid and/or combination. High-resolution instruments are used to maximize the detection of peptides with minute mass-to-charge ratio (m/z) differences. Conversely, because targeted proteomics emphasize sensitivity and throughput, high-sensitivity instruments are used. In some embodiments, the mass spectrometer is a TripleTOF mass spectrometer. In some embodiments, the mass spectrometer is a triple quadrupole mass spectrometer.

In various embodiments, the MS data is collected by a targeted acquisition method. Examples of the targeted acquisition method include but are not limited to Selective Reaction Monitoring (SRM) and/or Multiple Reaction Monitoring (MRM) methods. In various embodiments, acquiring MS data comprises acquiring Selective Reaction Monitoring (SRM) data and/or Multiple Reaction Monitoring (MRM) data.

In various embodiments, the MS data is collected by a data independent acquisition method. Examples of the independent acquisition (DIA) method including but not limited to Shotgun CID (see. e.g., Purvine et al. 2003), Original DIA (see e.g., Venable et al. 2004), $MS^E$ (see e.g., Silva et al. 2005), p2CID (see e.g., Ramos et al. 2006), PAcIFIC (see e.g., Panchaud et al. 2009), AIF (see e.g., Geiger et al. 2010), XDLA (see e.g., Carvalho et al. 2010), SWATH (see e.g., Gillet et al. 2012), and FT-ARM (see e.g., Weisbrod et al. 2012). More information can be found in, for example, Chapman et al. (*Multiplexed and data-independent tandem mass spectrometry for global proteome profiling*, Mass Spectrom Rev. 2014 November-December; 33(6):452-70). In various embodiments, acquiring MS data comprises acquiring Shotgun CID MS data, Original DIA MS Data, $MS^E$ MS data, p2CID MS Data, PAcIFIC MS Data, AIF MS Data, XDLA MS Data, SWATH MS data, or FT-ARM MS Data, or a combination thereof. In certain embodiments, acquiring MS data comprises acquiring MS data comprises acquiring SWATH MS data.

In various embodiments, the sample is food, water, cheek swab, blood, serum, plasma, urine, saliva, semen, cell sample, tissue sample, or tumor sample, or a combination thereof.

In various embodiments, the highly correlated peptides form a subset of all queried peptides and have correlation values when compared with other members of the subset that are more than 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88 or 0.89. In various embodiments, the highly correlated peptides form a subset of all queried peptides and have correlation values when compared with other members of the subset that are more than 0.90, 0.91, 0.92, 0.93, 0.94, 0.95, 0.96, 0.97, 0.98 or 0.99. In some embodiments, the correlation values are coefficient of determination ($r^2$) values.

In various embodiments, the method further comprises ranking the correlation values of the multiple candidate peptides. In various embodiments, the highly correlated peptides have correlation values ranked in the top 2, 3, 4, 5, 6, 7, 8, 9, 10, 11, 12, 13, 14, 15, 16, 17, 18, 19, o 20 among the multiple candidate peptides. In various embodiments, the highly correlated peptides have correlation values ranked in the top 10%, 9%, 8%, 7%, 6%, 5%, 4%, 3%, 2%, or 1% among the multiple candidate peptides. In various embodiments, the highly correlated peptides have correlation values ranked in the top 90%, 85%, 80%, 75%, 70%, 65%, 60%, 55%, 50%, 45%, 40%, 30% or 20% among the multiple candidate peptides. In certain embodiments, the highly correlated peptides have correlation values ranked in the top 2, 3, 4, 5, 6, 7, 8, 9, or 10 among the multiple candidate peptides. In certain embodiments, the highly correlated peptides have correlation values ranked in the top 80%, 70%, 60%, 50%, 40%, 30% or 20% among the multiple candidate peptides. In some embodiments, the correlation values are coefficient of determination ($r^2$) values.

In various embodiments, all of the correlation values of a candidate peptide are considered as indicators for the candidate peptide's correlation level. In various embodiments, a highly correlated peptide has all or half of its correlation values more than 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88 or 0.89. In various embodiments, a highly correlated peptide has all or half of its correlation values more than 0.90, 0.91, 0.92, 0.93, 0.94, 0.95, 0.96, 0.97, 0.98 or 0.99. In various embodiments, a highly correlated peptide has all or half of its correlation values more than 0.990, 0.991, 0.992, 0.993, 0.994, 0.995, 0.996, 0.997, 0.998 or 0.999. In various embodiments, a highly correlated peptide has all or half of its correlation values ranked in the top 2, 3, 4, 5, 6, 7, 8, 9, or 10 among the multiple candidate peptides. In various embodiments, a highly correlated peptide has all or half of its correlation values ranked in the top 10%, 9%, 8%, 7%, 6%, 5%, 4%, 3%, 2%, or 1% among the multiple candidate peptides. In various embodiments, a highly correlated peptide has all or half of its correlation values ranked in the top 80%, 70%, 60%, 50%, 40%, 30% or 20% among the multiple candidate peptides. In some embodiments, the correlation values are coefficient of determination ($r^2$) values.

In various other embodiments, a subset of correlated peptides is selected from among the set of peptides in a correlation matrix. Members of the subset all have correlation values of more than 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or 0.99 for pairwise combinations with all other members of the subset. Signature peptides are then selected from the subset of correlated peptides. In various other embodiments, an average is calculated from the correlation values for each peptide in a correlation matrix. Signature peptides are then selected from among those peptides with the highest 30%, 40%, 50%, 60%, 70%, 80% or 90% of averages. In some embodiments, the correlation values are coefficient of determination ($r^2$) values.

In various embodiments, the correlation values of a candidate peptide are used to calculate the candidate peptide's mean or media correlation value, which is then considered as an indicator of the candidate peptide's correlation level. In various embodiments, a highly correlated peptide has a mean or median correlation value more than 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88 or 0.89. In various embodiments, a highly correlated peptide has a mean or median correlation value more than 0.90, 0.91, 0.92, 0.93, 0.94, 0.95, 0.96, 0.97, 0.98 or 0.99. In various embodiments, a highly correlated peptide has a mean or median correlation value more than 0.990, 0.991, 0.992, 0.993, 0.994, 0.995, 0.996, 0.997, 0.998 or 0.999. In some embodiments, the correlation values are coefficient of determination ($r^2$) values.

In various embodiments, the method further comprises ranking the mean or median correlation values of the multiple candidate peptides. In various embodiments, a highly correlated peptide has a mean or median correlation value ranked in the top 2, 3, 4, 5, 6, 7, 8, 9, or 10 among the multiple candidate peptides. In various embodiments, a highly correlated peptide has a mean or median correlation value ranked in the top 10%, 9%, 8%, 7%, 6%, 5%, 4%, 3%, 2%, or 1% among the multiple candidate peptides. In various embodiments, the highly correlated peptide has a mean or median correlation values ranked in the top 80%, 70%, 60%, 50%, 40%, 30% or 20% among the multiple candidate peptides. In certain embodiments, the highly correlated peptides have mean or median correlation values ranked in the top 2, 3, 4, 5, 6, 7, 8, 9, or 10 among the multiple candidate peptides. In certain embodiments, the highly correlated peptides have mean or median correlation values ranked in the top 80%, 70%, 60%, 50%, 40%, 30% or 20% among the multiple candidate peptides. In some embodiments, the correlation values are coefficient of determination ($r^2$) values.

In various embodiments, a method as described herein is an iterative process. For a non-limiting example, an initial set of multiple candidate peptides are subject to a first round of signature peptide identification according to a method as described herein, including but not limited to the steps of: (1) using the MS data to calculate correlation values for pairwise comparisons among the complete initial set of multiple candidate peptides; (2) calculating each candidate peptide's mean or median correlation value; (3) ranking the multiple candidate peptides' mean or median correlation values; and (4) retaining those candidate peptides with mean or median correlation values among the top 90%, 80%, 70%, 60%, or 50% as the second set of multiple candidate peptides. Then, the second set of multiple candidate peptides are subject a second round of signature peptide identification, with the above steps (1)-(4) being repeated. This iterative process continues until reaching the final set of highly correlated peptides that are hence identified as the signature peptides for quantifying the polypeptide. In various embodiments, there can be 2, 3, 4, 5, 6, 7, 8, 9, or 10, or more rounds of signature peptide identification. In various embodiments, the final set of highly correlated peptides have mean or median correlation value more than 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or 0.99. In various embodiments, the final set of highly correlated peptides have mean or median correlation value more than 0.990, 0.991, 0.992, 0.993, 0.994, 0.995, 0.996, 0.997, 0.998 or 0.999. In some embodiments, the correlation values are coefficient of determination ($r^2$) values.

In various embodiments, the multiple candidate peptides are obtained from a data-dependent MS screen, data-independent MS data, targeted peptides data, MS spectral database, or proteotypic peptide prediction, or a combination thereof. In some embodiments, the proteotypic peptide prediction is a prediction of protease digestion of the polypeptide. In some embodiments, the proteotypic peptide prediction is a prediction of trypsin digestion of the polypeptide.

In various embodiments, the method further comprises eliminating peptides that satisfy one or more of the following criteria: (i). not previously detected by MS; (ii). not unique to the polypeptide; (iii). absent from the polypeptide's mature form; (iv.) containing an uncleaved protease recognition site; (v). susceptible to post-translational modification (PTM), or known to be post-translationally modified in some forms of the protein; (vi.) containing methionine and/or cysteine residues; (vii.) sensitive to endogenous proteases, or miscleaved or incompletely cleaved; (viii.) having m/z values lower than the quantifiable range for the mass spectrometer or sample type (for example, an m/z bottom cutoff value); (ix.) having m/z values higher than the quantifiable range for the mass spectrometer or sample type (for example, an m/z top cutoff value); and (x.) having signal intensities lower than an intensity bottom cutoff value in the acquired MS data (for example, less than 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, or 20-fold higher than the background noise in the MS data).

Examples of PTMs include but are not limited to N-linked glycosylation, O-linked glycosylation, C-mannosylation, GPI anchors (glypiation), phosphorylation on tyrosine, serine or threonine, disulfide bonds, deamidation of asparagine, and methionine oxidation. In various embodiments, one or more of these elimination criteria are applied before acquiring the MS data. In various embodiments, one or more of these elimination criteria are applied before calculating correlation values. In various embodiments, one or more of these elimination criteria are applied after acquiring the MS data. In various embodiments, one or more of these elimination criteria are used after calculating correlation values.

In various embodiments, the m/z bottom cutoff value is about 100, 110, 120 130, 140, 150, 160, 170, 180, 190, 200, 210, 220, 230, 240, 250, 260, 270, 280, 290, or 300. In one embodiment, the m/z bottom cutoff value is about 200.

In various embodiments, the m/z top cutoff value is about 1500, 1550, 1600, 1650, 1700, 1750, 1800, 1850, 1900, 1950, 2000, 2050, 2100, 2150, 2200, 2250, 2300, 2350, 2400, 2450, or 2500. In various embodiments, the m/z top cutoff value is about 2000.

In some embodiments, the intensity bottom cutoff value is the background noise' intensity value. In some embodiments, the intensity bottom cutoff values is 2, 3, 4, 5, 6, 7, 8, 9, 10, 11, 12, 13, 14, 15, 16, 17, 18, 19, or 20 times of the background noise' intensity value. In one embodiments, the intensity bottom cutoff values 10 times of the background noise' intensity value.

In various embodiments, the identified signature peptides have high and reproducible signal intensities in the acquired MS data. In some embodiments, the identified signature peptides have peak areas of more than 100, 200, 300, 400, 500, 600, 700, 800, 1000, 1250, 1500, 1600, 1700, 1800, 1900, 2000, 2100, 2200, 2300, 2400, 2500, 3000, 3500 or 4000. In one embodiment, the identified signature peptides have signal intensities more than 2000.

Various cutoff values described herein (e.g., the m/z bottom cutoff value, the m/z top cutoff value, and the intensity bottom cutoff value) can have variations for different samples and instruments. It is contemplated that an ordinarily skilled artisan will recognize characteristics of different samples and instruments and apply appropriate cutoff values with respect to those characteristics.

The identified signature peptides can be used to build quantitative assays of the polypeptide. Various embodiments of the present invention also provide a method of quantifying a polypeptide in a sample. The method comprises: cleaving the polypeptide to yield a signature peptide identified according to a method as described herein; analyzing the sample on a mass spectrometer; detecting MS signals of the signature peptide; and quantifying the polypeptide based on the detected MS signals. In some embodiments, multiple polypeptides in a complex sample are quantified.

In various embodiments, the method further comprises spiking the sample with an internal standard of the signature peptide and detecting the internal standard's MS signals in the sample. In some embodiments, the internal standard comprises the signature peptide labeled with a stable isotope. Examples of the stable isotope include but are not limited to $^5N$ (nitrogen-15), $^{13}C$ (carbon-13), and $^2H$ (deuterium). In various embodiments, the method further comprises normalizing the signature peptide's MS signals detected in the sample to the internal standard's MS signals detected in the sample.

Internal Standards and Methods of Making Internal Standards

Stable Isotope Labeled (SIL) peptides, small molecules and lipids, including but not limited to peptides synthesized with $^{13}C/^{15}N$ universally-labeled Arg (+10) and Lys (+8).

Stable Isotope Labeled (SIL) proteins, including but not limited to $^{15}N$ labeled proteins, $^{15}N$-$^{13}C$ labeled proteins, and $^{15}N$-$^{13}C$-$^2H$-labeled proteins.

Metabolically labeled proteins. There are multiple methods of this type of in vivo labeling. One exemplar method is Stable Isotope Labeling by Amino acids in Cell culture (SILAC). Cells are cultured in growth medium that contains $^{13}C_6$-lysine and/or $^{13}C_6$-arginine. Another exemplar method is to feed carnivores with $^{13}C_6$-lysine and/or $^{13}C_6$-arginine to animals.

Stable isotopic labeling. Chemical or enzymatic stable isotopic labeling methods are used for samples that are not amenable to metabolic labeling (e.g., clinical samples) and/or when experimental time is limited. Non-limiting examples include adding isotopic atoms or isotope-coded tags to peptides or proteins.

As one non-limiting example: enzymatic labeling with $^{18}O$ takes advantage of the proteolytic mechanism of trypsin to incorporate two heavy oxygen atoms from $H_2^{18}O$ at the C-terminus of every newly digested peptide.

As another non-limiting example: Global Internal Standard Technology (GIST), which uses deuterated ($^2H$) acylating agents such as N-acetoxysuccinimide (NAS) to label primary amino groups on digested peptides. Acylation of these groups, though, changes the ionic states of peptides and may affect the ionization efficiency of peptides with C-terminal lysines.

As another non-limiting example: chemical labeling by stable isotope dimethylation. This approach uses formaldehyde in deuterated water to label primary amines with deuterated methyl groups.

As another non-limiting example: Isotope-Coded Affinity Tags (ICAT). This method originally comprised a sulfhydryl-reactive chemical crosslinking group, linkers with various amounts of heavy (deuterated) isotopes, and a biotin molecule for collection of labelled peptides on a streptavidin matrix.

As another non-limiting example: isobaric mass tags. A benefit of isobaric mass tags is the multiplex capabilities and thus increased throughput potential of this approach. Commercially available isobaric mass tags (e.g., TMT*, iTRAQ*)

The Isobaric tags for relative and absolute quantitation (iTRAQ) method is based on the covalent labeling of the N-terminus and side chain amines of peptides from trypsin digested proteins with tags of varying mass. This method offers the simultaneous analysis of 4, 6 or 8 biological samples. While the exact tags used vary depending on manufacturer, the basic components of all isobaric mass tag reagents consist of a mass reporter (tag) that has a unique number of $^{13}C$ substitutions, a mass normalizer that has a unique mass that balances the mass of the tag to make all of the tags equal in mass.

Tandem mass tags (TMT or TMTs) are chemical labels. The tags contain four regions, namely a mass reporter region (M), a cleavable linker region (F), a mass normalization region (N) and a protein reactive group (R). The chemical structures of all the tags are identical but each contains isotopes substituted at various positions, such that the mass reporter and mass normalization regions have different molecular masses in each tag. The combined M-F-N-R regions of the tags have the same total molecular weights and structure so that during chromatographic or electrophoretic separation and in single MS mode, molecules labelled with different tags are indistinguishable. Upon fragmentation in MS/MS mode, sequence information is obtained from fragmentation of the peptide back bone and quantification data are simultaneously obtained from fragmentation of the tags, giving rise to mass reporter ions.

Isotope-Coded Protein Label (ICPL) isobaric mass tagging has also been adapted for use with protein labeling. ICPL is based on tagging stable isotope derivatives at the free amino groups of intact proteins, the method is applicable to any protein sample, including tissue extracts and body fluids. Some commercially available kits also offer isobaric tags with sulfhydryl-reactivity and anti-TMT antibody for affinity purification of cysteine-tagged peptides prior to LC-MS/MS.

In various embodiments, the method further comprises generating a standard curve for the polypeptide using external standards. Examples of the external standards include but are not limited to a series of known concentrations of the polypeptide to be quantified. In various embodiments, the method further comprises spiking the external standards with an internal standard of the signature peptide and detecting the internal standard's MS signals in the external standards. In various embodiments, the method further comprises normalizing the signature peptide's MS signals detected in the external standards to the internal standard's MS signals detected in the external standards. In various embodiments, the method further comprises quantifying the polypeptide in a sample based on the detected MS signals in the sample and the generated standard curve. In various embodiments, the same MS protocol or technique is used to analyze the external standards to generate the standard curve and to analyze the sample to quantify the polypeptide.

Systems and Computers of the Invention

Various embodiments of the present invention provide a system for identifying signature peptides for quantifying a polypeptide. The system comprises: a mass spectrometer configured for acquiring mass spectrometry (MS) data on multiple candidate peptides derived from the polypeptide in multiple samples; and a computer configured for using the MS data to calculate correlation values for pairwise comparisons among the multiple candidate peptides; and for identifying the highly correlated peptides among the multiple candidate peptides as the signature peptides for quantifying the polypeptide, wherein the mass spectrometer and the computer are connected via a communication link. In some embodiments, the computer is also configured for processing the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a system for identifying signature peptides for quantifying a polypeptide. The system comprises: a mass spectrometer configured for acquiring mass spectrometry (MS) data on multiple candidate peptides derived from the polypeptide in multiple samples; a first computer configured for processing the MS data to identify, analyze and/or quantify the multiple candidate peptides and fragments thereof (e.g., transitions and MS peaks); and a second computer configured for using the processed MS data to calculate correlation values for pairwise comparisons among the multiple candidate peptides; and for identifying the highly correlated peptides among the multiple candidate peptides as the signature peptides for quantifying the polypeptide, wherein the mass spectrometer and the computers are connected via a communication link. In some embodiments, the first and second computers are the same computer. In other embodiments, the first and second computers are separate computers. In certain embodiments, the polypeptide is uromodulin, serum albumin or any one listed in Table 18. In some embodiments, the correlation values are coefficient of determination ($r^2$) values.

In various embodiments, the computer comprises: a memory configured for storing a program; and a processor configured for executing the program, wherein the program comprises instructions for using the MS data to calculate correlation values for pairwise comparisons among the multiple candidate peptides; and for identifying the highly correlated peptides among the multiple candidate peptides as the signature peptides for quantifying the polypeptide. In some embodiments, the program further comprises instructions for processing the MS data to identify, analyze and/or quantify the multiple candidate peptides and fragments thereof (e.g., transitions and MS peaks) before calculating correlation values. In certain embodiments, the signature peptide is any one listed in Tables 9, 15, or 19. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for using mass spectrometry (MS) data to calculate correlation values for pairwise comparisons between each of multiple candidate peptides for quantifying a polypeptide, and for identifying the highly correlated peptides among the multiple candidate peptides as the signature peptides for quantifying the polypeptide. In various embodiments, the MS data comprises raw MS data obtained from a mass spectrometer and/or processed MS data in which peptides and their fragments (e.g., transitions and MS peaks) are already identified, analyzed and/or quantified. In some embodiments, the program further comprises instructions for processing the MS data to identify, analyze and/or quantify the multiple candidate peptides and fragments thereof (e.g., transitions and MS peaks) before calculating correlation values. In some embodiments, the program further comprises instructions for operating a mass spectrometer to acquire MS data. In certain embodiments, the polypeptide is uromodulin, serum albumin or any one listed in Table 18. In some embodiments, the correlation values are coefficient of determination ($r^2$) values.

Various embodiments of the present invention provide a computer. The computer comprises: a memory configured for storing a program; and a processor configured for executing the program, wherein the program comprises instructions for using mass spectrometry (MS) data to calculate correlation values for pairwise comparisons between each of multiple candidate peptides for quantifying a polypeptide, and for identifying the highly correlated peptides among the multiple candidate peptides as the signature peptides for quantifying the polypeptide. In various embodiments, the MS data comprises raw MS data obtained from a mass spectrometer and/or processed MS data in which peptides and their fragments (e.g., transitions and MS peaks) are already identified, analyzed and/or quantified. In some embodiments, the program further comprises instructions for processing the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a computer implemented method. The method comprises: providing a computer as described herein; inputting mass spectrometry (MS) data into the computer; and operating the computer to use the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the method further comprises operating the computer to process the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for operating a mass spectrometer to acquire mass spectrometry (MS) data, for using the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In various embodiments, the MS data comprises raw MS data obtained from a mass spectrometer and/or processed MS data in which peptides and their fragments (e.g., transitions and MS peaks) are already identified, analyzed and/or quantified. In some embodiments, the program further comprises instructions for processing the MS data to identify, analyze and/or quantify the multiple candidate peptides and fragments thereof (e.g., transitions and MS peaks) before calculating correlation values. In some embodiments, the program further comprises instructions for operating a mass spectrometer to acquire MS data. In certain embodiments, the polypeptide is uromodulin, serum albumin or any one listed in Table 18. In some embodiments, the correlation values are coefficient of determination ($r^2$) values.

Various embodiments of the present invention provide a computer. The computer comprises: a memory configured for storing a program; and a processor configured for executing the program, wherein the program comprises instructions for operating a mass spectrometer to acquire mass spectrometry (MS) data, for using the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In various embodiments, the MS data comprises raw MS data obtained from a mass spectrometer and/or processed MS data in which peptides and their fragments (e.g., transitions and MS peaks) are already identified, analyzed and/or quantified. In some embodiments, the program further comprises instructions for processing the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a computer implemented method. The method comprises: providing a computer as described herein; connecting the computer via a communication link to a mass spectrometer; and operating the computer to operate the mass spectrometer to acquire mass spectrometry (MS) data, to use the MS data to calculate correlation values for pairwise comparisons between each of multiple candidate peptides for quantifying a polypeptide, and for identifying the highly correlated peptides among the multiple candidate peptides as the signature peptides for quantifying the polypeptide. In some embodiments, the method further comprises operating the computer to process the MS data to identify, analyze and/or quantify the multiple candidate peptides and fragments thereof (e.g., transitions and MS peaks) before calculating correlation values. In certain embodiments, the polypeptide is uromodulin, serum albumin or any one listed in Table 18. In some embodiments, the correlation values are coefficient of determination ($r^2$) values.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for processing MS data to identify, analyze and/or quantify a signature peptide of a polypeptide and for quantify the polypeptide based on the signature peptide. In certain embodiments, the polypeptide is uromodulin, serum albumin or any one listed in Table 19. In certain embodiments, the signature peptide is any one listed in Tables 9, 15, or 19.

Various embodiments of the present invention provide a computer, comprising: a memory configured for storing a program; and a processor configured for executing the program, wherein the program comprises instructions for processing MS data to identify, analyze and/or quantify a signature peptide of a polypeptide and for quantify the polypeptide based on the signature peptide. In certain embodiments, the polypeptide is uromodulin, serum albumin or any one listed in Table 19. In certain embodiments, the signature peptide is any one listed in Tables 9, 15, or 19.

Various embodiments of the present invention provide a computer implemented method, comprising: providing a computer as described herein; inputting MS data into the computer; and operating the computer to process MS data to identify, analyze and/or quantify a signature peptide of a polypeptide and to quantify the polypeptide based on the signature peptide. In certain embodiments, the polypeptide is uromodulin, serum albumin or any one listed in Table 19. In certain embodiments, the signature peptide is any one listed in Tables 9, 15, or 19.

Various embodiments of the present invention provide a non-transitory computer-readable storage medium, wherein the non-transitory computer-readable storage medium is configured for storing a program, wherein the program is configured for execution by a processor of a computer, and wherein the program comprises instructions for operating a mass spectrometer to detect MS signals of a signature peptide for quantifying a polypeptide, and quantifying the polypeptide based on the detected MS signals. In certain embodiments, the polypeptide is uromodulin, serum albumin or any one listed in Table 19. In certain embodiments, the signature peptide is any one listed in Tables 9, 15, or 19.

Various embodiments of the present invention provide a computer. The computer comprises: a memory configured for storing a program; and a processor configured for executing the program, wherein the program comprises instructions for operating a mass spectrometer to detect MS signals of a signature peptide for quantifying a polypeptide, and quantifying the polypeptide based on the detected MS signals. In certain embodiments, the polypeptide is uromodulin, serum albumin or any one listed in Table 19. In certain embodiments, the signature peptide is any one listed in Tables 9, 15, or 19.

Various embodiments of the present invention provide a computer implemented method. The method comprises: providing a computer as described herein; connecting the computer via a communication link to a mass spectrometer; and operating the computer to operate the mass spectrometer to detect MS signals of a signature peptide for quantifying a polypeptide, and to quantify the polypeptide based on the detected MS signals. In certain embodiments, the polypeptide is uromodulin, serum albumin or any one listed in Table 19. In certain embodiments, the signature peptide is any one listed in Tables 9, 15, or 19.

In accordance with the present invention, a "communication link," as used in this disclosure, means a wired and/or wireless medium that conveys data or information between at least two points. The wired or wireless medium may include, for example, a metallic conductor link, a radio frequency (RF) communication link, an Infrared (IR) communication link, an optical communication link, or the like, without limitation. The RF communication link may include, for example, WiFi, WiMAX, IEEE 802.11, DECT, 0G, 1G, 2G, 3G or 4G cellular standards, Bluetooth, and the like.

Computers and computing devices typically include a variety of media, which can include computer-readable storage media and/or communications media, in which these two terms are used herein differently from one another as follows.

Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computer sand computing devices. The term article of manufacture, as used herein, is intended to encompass a computer program accessible from any computer-readable device or storage media.

Capturing Reagents, Antibodies and Immunoassays of the Invention

Various embodiments of the present invention provide a method of producing a capturing reagent. The method comprises: providing a signature peptide identified according to a method as described herein; and producing the capturing reagent specifically binding to the signature peptide. In some embodiments, the capturing reagent is an antibody. In other embodiments, the capturing reagent is an aptamer. In various embodiments, the aptamer is DNA aptamer, RNA aptamer, XNA aptamer, or peptide aptamer, or a combination thereof. In various embodiments, the method further comprises using the signature peptide to screen an aptamer library; and identifying an aptamer specifically binding to the signature peptide. In certain embodiments, the signature peptide is any one listed in Tables 9, 15, or 19. In various embodiments, the aptamer specifically binds to the polypeptide to which the signature peptide is identified for. In certain embodiments, the polypeptide is uromodulin, serum albumin or any one listed in Table 19.

Various embodiments of the present invention provide a capturing reagent specifically binding to a signature peptide identified according to a method as described herein. In some embodiments, the capturing reagent is an antibody. In other embodiments, the capturing reagent is an aptamer. In various embodiments, the aptamer is DNA aptamer, RNA aptamer, XNA aptamer, or peptide aptamer, or a combination thereof. In certain embodiments, the signature peptide is any one listed in Tables 9, 15, or 19.

As used herein, aptamers refer to oligonucleotide or peptide molecules that bind to a specific target molecule. Aptamers are usually created by selecting them from a large random sequence pool. Aptamers can be classified as: DNA or RNA or XNA aptamers, which comprise (usually short) strands of oligonucleotides; and peptide aptamers, which comprise a short variable peptide domain, attached at both ends to a protein scaffold.

Various embodiments of the present invention provide a method of producing an antibody. The method comprises: providing a signature peptide identified according to a method as described herein; and immunizing an animal using the signature peptide, thereby producing the antibody. In various embodiments, the method further comprises isolating and/or purifying the antibody from the immunized animal. In various embodiments, the antibody specifically binds to the signature peptide. In certain embodiments, the signature peptide is any one listed in Tables 9, 15, or 19. In various embodiments, the antibody specifically binds to the polypeptide to which the signature peptide is identified for. In certain embodiments, the polypeptide is uromodulin, serum albumin or any one listed in Table 19.

Various embodiments of the present invention provide an antibody specifically binding to a signature peptide identified according to a method as described herein, or an antigen-binding fragment thereof. In various embodiments, the antibody is a polyclonal antibody or a monoclonal antibody. In various embodiments, the antibody can be of any animal origin. Examples of the animal origin include but are not limited to human, non-human primate, monkey, mouse, rat, guinea pig, dog, cat, rabbit, pig, cow, horse, goat, and donkey. In some embodiments, the antibody is a humanized antibody. In some embodiments, the antibody is a chimeric antibody. In certain embodiments, the signature peptide is any one listed in Tables 9, 15, or 19.

Various embodiments of the present invention provide a method of quantifying a polypeptide in a sample. The method comprises: contacting the sample with an antibody as descried herein or an antigen-binding fragment thereof; detecting the binding between the polypeptide and the antibody or the antigen-binding fragment thereof; and quantifying the polypeptide based on the detected binding. In various embodiments, the method further comprises generating a standard curve for the polypeptide using external standards. Examples of the external standards include but are not limited to a series of known concentrations of the polypeptide to be quantified. In certain embodiments, the polypeptide is uromodulin, serum albumin or any one listed in Table 19. In certain embodiments, the signature peptide is any one listed in Tables 9, 15, or 19.

In various embodiments, quantifying a polypeptide in a sample comprises contacting the sample with an antibody as described herein and thereby forming antigen-antibody complexes. In the methods and assays of the invention, the quantity of a polypeptide can be determined using an antibody as described herein and detecting immunospecific binding of the antibody to the polypeptide. Examples of quantitative assays based on the antibody include but are not limited to western blot, enzyme-linked immunosorbent assay (ELISA) and radioimmunoassay.

Various embodiments of the present invention provide a method of quantifying a polypeptide in a sample. The method comprises using an antibody as described herein with SISCAPA (Stable Isotope Standards and Capture by Anti-Peptide Antibodies). SISCAPA applies existing mass spectrometry quantitation methods (e.g., MRM) to the measurement of signature peptides of protein biomarkers. It improves sensitivity by capture of these signature peptides on immobilized anti-peptide antibodies.

In various embodiments, the method comprise: cleaving the polypeptide in the sample to yield a signature peptide identified according to a method as described herein; spiking the sample with an internal standard of the signature peptide; capturing the signature peptide and internal standard with a capturing reagent specifically binding to the signature peptide; analyzing the captured signature peptide and internal standard on a mass spectrometer; detecting MS signals of the signature peptide the internal standard; and quantifying the signature peptide based on the detected MS signals. In some embodiments, the capturing reagent is an antibody or an antigen-binding fragment thereof specifically binding to the signature peptide. In other embodiments, the capturing reagent is an aptamer specifically binding to the signature peptide. In some embodiments, capturing the signature peptide and internal standard comprises forming an antigen-antibody complex between the antibody or its fragment and the signature peptide and an antigen-antibody complex between the antibody or its fragment and the internal standard; isolating the antigen-antibody complexes from the sample; and dissociating the signature peptide and the internal standard from the antibody or its fragment. In various embodiments, the antibody or its fragment is attached to a magnetic bead for capturing the signature peptide and internal standard. In some embodiments, capturing the signature peptide and internal standard comprises forming a target-aptamer complex between the aptamer and the signature peptide and a target-aptamer complex between the aptamer and the internal standard; isolating the target-aptamer complexes from the sample; and dissociating the signature peptide and the internal standard from the aptamer. In various embodiments, the aptamer is attached to a magnetic bead for capturing the signature peptide and internal standard. In certain embodiments, the polypeptide is uromodulin, serum albumin or any one listed in Table 19. In certain embodiments, the signature peptide is any one listed in Tables 9, 15, or 19.

SISCAPA technology is the smart shortcut to sensitive quantitation of protein biomarkers and targets. SISCAPA assays combine the precision of MRM mass spectrometry with the power of affinity enrichment to deliver a superior alternative to conventional immunoassays for protein quantitation. The SISCAPA workflow is highly automated and exploits familiar LC-MS/MS platforms widely used for drug and metabolite quantitation. SISCAPA provides a range of practical advantages over conventional ligand binding immunoassays. Sensitivity: SISCAPA improves peptide multiple reaction monitoring (MRM) sensitivity by 3-4 orders of magnitude over non-enriched samples. Specificity: SISCAPA combines antibody immunocapture selectivity with the near-absolute structural specificity of MRM mass spectrometry. Standardization: SISCAPA employs true internal standards (stable isotope labeled synthetic peptides) within each assay for reliable quantitation. Multiplexing: SISCAPA assays can be combined in mix-and-match panels without cross-reactions common in sandwich immunoassays. Throughput: SISCAPA delivers highly purified peptide analytes, free of matrix components, for decreased LC times and higher throughput. Development: SISCAPA assay development is faster, less expensive and more straightforward than sandwich immunoassay development. More information on SISCAPA can be found in U.S. Pat. No. 9,274,124 and Anderson, N. L. et al. (Mass Spectrometric Quantitation of Peptides and Proteins Using Stable Isotope Standards and Capture by Anti-Peptide Antibodies (SISCAPA), Journal of Proteome Research 3: 235-44 (2004)), which are incorporated herein by reference in their entirety as though fully set forth.

As a non-limiting example, serum or plasma samples to be analyzed by Siscapa MRM are first subjected to proteolytic digestion, yielding a complex mixture of peptides from which one or more signature peptides are selected as targets. Digestion is accomplished by unfolding the proteins in a chaotropic solvent and then adding an enzyme such as trypsin which specifically cleaves the sample proteins at lysine and arginine residues. A synthetic stable isotope labeled version of a target signature peptide is added in known amount to serve as an internal standard for quantitation. The target signature peptide and its corresponding internal standard are then captured by sequence specific anti-peptide antibodies (e.g., an anti-signature peptide antibody as described herein) attached to magnetic beads. A low-abundance target signature peptide can be captured from a large massive digest, extending detection sensitivity by orders of magnitude compared to unfractionated digests. The magnetic beads, with their peptide cargo can then be easily removed from the digest, washed extensively, and then finally placed in an acidic eluent solution in which the peptides disassociate from the antibodies. This specific capture process enriches the target signature peptide and corresponding internal standard by more than 100,000 fold while retaining the quantitative ratio between them. This ratio can then be measured precisely in a mass spectrometer providing a quantitation of the bio marker protein in the original sample. By providing an almost pure sample of the desired target signature peptide for analysis, detection sensitivity is maximized while shortening LC-MS cycle time for higher throughput.

Antibodies, both polyclonal and monoclonal, can be produced by a skilled artisan either by themselves using well known methods or they can be manufactured by service providers who specialize making antibodies based on known protein sequences. In the present invention, the signature peptide sequences are identified and thus production of antibodies against them is a matter of routine.

For example, production of monoclonal antibodies can be performed using the traditional hybridoma method by first immunizing mice with an antigen which may be an isolated peptide of choice or fragment thereof (for example, a signature peptide as described herein) and making hybridoma cell lines that each produce a specific monoclonal antibody. The antibodies secreted by the different clones are then assayed for their ability to bind to the antigen using, e.g., ELISA or Antigen Microarray Assay, or immuno-dot blot techniques. The antibodies that are most specific for the detection of the signature peptide can be selected using routine methods and using the antigen used for immunization and other antigens as controls. The antibody that most specifically detects the desired antigen and no other antigens are selected for the processes, assays and methods described herein. The best clones can then be grown indefinitely in a suitable cell culture medium. They can also be injected into mice (in the peritoneal cavity, surrounding the gut) where they produce an antibody-rich ascites fluid from which the antibodies can be isolated and purified. The antibodies can be purified using techniques that are well known to one of ordinary skill in the art.

Any suitable immunoassay method may be utilized, including those which are commercially available, to determine the level of a polypeptide assayed according to the invention. Extensive discussion of the known immunoassay techniques is not required here since these are known to those of skill in the art. Typical suitable immunoassay techniques include sandwich enzyme-linked immunoassays (ELISA), radioimmunoassays (RIA), competitive binding assays, homogeneous assays, heterogeneous assays, etc.

For example, in the assays of the invention, "sandwich-type" assay formats can be used. An alternative technique is the "competitive-type" assay. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule.

The antibodies can be labeled. In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease.

The antibody can be attached to a surface. Examples of useful surfaces on which the antibody can be attached for the purposes of detecting the desired antigen include nitrocellulose, PVDF, polystyrene, and nylon.

In some embodiments of the processes, assays and methods described herein, detecting the binding of an antibody to a polypeptide includes contacting the sample with an antibody as described herein that specifically binds a signature peptide, forming an antigen-antibody complex between the antibody and the polypeptide present in the sample, washing the sample to remove the unbound antibody, adding a detection antibody that is labeled and is reactive to the antibody bound to the polypeptide in the sample, washing to remove the unbound labeled detection antibody and converting the label to a detectable signal, wherein the detectable signal is indicative of the quantity of the polypeptide in the sample. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The quantity of the polypeptide may be obtained by assaying a light scattering intensity resulting from the formation of an antigen-antibody complex formed by a reaction of the polypeptide in the sample with the antibody, wherein the light scattering intensity of at least 10% above a control light scattering intensity indicates the likelihood of chemotherapy resistance.

Kits of the Invention

Various embodiments of the present invention provide a kit for quantifying a polypeptide in a sample. The kit comprises an internal standard of a signature peptide identified for the polypeptide according to a method as described herein; and instructions for using the internal standard to quantify the polypeptide in the sample. In various embodiments, the kit further comprises a protease for cleaving the polypeptide to yield the signature peptide. In certain embodiments, the polypeptide is uromodulin, serum albumin or any one listed in Table 19. In certain embodiments, the signature peptide is any one listed in Tables 9, 15, or 19. In some embodiments, the kit comprises multiple internal standards. In some embodiments, the kit quantifies multiple polypeptides in a complex sample.

In accordance with the present invention, "a" should be construed to cover both the singular and the plural. In some embodiments, the kit targets a single polypeptide. In various embodiments, the kit includes one or more signature peptides for the single polypeptide.

In other embodiments, the kit targets multiple polypeptides (multiplexing). In some embodiments, the multiple polypeptides are related by their functions or pathways. When the kit targets multiple polypeptides, the kit includes multiple internal standards of multiple signature peptides for multiple polypeptides.

As a non-limiting example, for Uromodulin, a kit includes an internal standard for quantifying a UMOD signature peptide. In other examples, the kit would have signature peptides representing multiple target polypeptides or proteins, and the concentration of each signature peptide would be either identical, or balanced to approximate the concentration of the target polypeptides or proteins.

In various embodiments, the kit can be used for MRM assays for greater sensitivity. In some embodiments, the signature peptides is identified by SRM, and/or MRM, and/or SWATH.

In various embodiments, the kit further comprises an antibody specifically binding to the signature peptide. In certain embodiments, such a kit can be used for SISCAPA.

Various embodiments of the present invention provide a kit quantifying a polypeptide in a sample. The kit comprises: a protease for cleaving the polypeptide to yield a signature peptide identified according to a method as described herein; an internal standard of the signature peptide; and instructions for using the protease and the internal standard to quantify the polypeptide in the sample. In certain embodiments, the polypeptide is uromodulin, serum albumin or any one listed in Table 19. In certain embodiments, the signature peptide is any one listed in Tables 9, 15, or 19. In some embodiments, multiple polypeptides in a complex sample are quantified.

In various embodiments, the internal standard comprises the signature peptide labeled with a stable isotope. Examples of the stable isotope include but are not limited to $^{15}N$ (nitrogen-15), $^{13}C$ (carbon-13), and $^{2}H$ (deuterium). In various embodiments, the kit further comprises external standards. Examples of the external standards include but are not limited to a series of known concentrations of the polypeptide to be quantified. In various embodiments, the external standards can be used to generate a standard curve for quantifying the polypeptide in the sample.

Various embodiments of the present invention provide a kit quantifying a polypeptide in a sample. The kit comprises: an antibody specifically binding to a signature peptide identified according to a method as described herein; and instructions for using the antibody to quantify the polypeptide in the sample. Examples of quantitative assays based on the antibody include but are not limited to western blot, enzyme-linked immunosorbent assay (ELISA), radioimmunoassay and SISCAPA. In various embodiments, the kit further comprises external standards. Examples of the external standards include but are not limited to a series of known concentrations of the polypeptide to be quantified. In various embodiments, the external standards can be used to generate a standard curve for quantifying the polypeptide in the sample. In certain embodiments, the polypeptide is uromodulin, serum albumin or any one listed in Table 19. In certain embodiments, the signature peptide is any one listed in Tables 9, 15, or 19.

Various other embodiments of the present invention also provide for a kit for quantifying proteins of interest. The kit comprises stable isotope-labeled peptides and/or polypeptides matching the sequence of peptides with highly correlated signals; reagents to prepare a sample for mass spectrometry; and instructions for using said kit.

In some embodiments, the kit further comprises orthologous proteins from species other than the species to which the sample belongs as a control for digestion. For example, non-human protein and peptides (e.g., β-galactosidase and its corresponding SIL peptides) can be included in the kit as a digestion control. In various embodiments, the SIL peptides are a pre-defined mixture appropriate for quantitation, approximating the concentration of peptide in a digested biological sample. In other words, the SIL peptides are provided at concentrations ranges that encompass target protein's levels generally detected in samples.

In various embodiments, the instructions describe target peptide and fragment masses for the signature peptide and internal standard (e.g., SIL peptides). In some embodiments, the instructions describe methods for achieving complete digestion, etc.

The present invention is also directed to a kit to quantify signature polypeptides in a sample. The kit is useful for practicing the inventive method of accurately quantifying correlated polypeptides. The kit is an assemblage of materials or components, including at least one of the inventive compositions. Thus, in some embodiments the kit contains a composition including the signature polypeptide, as described above.

The exact nature of the components configured in the inventive kit depends on its intended purpose. For example, some embodiments are configured for assaying different types of samples, such as but not limited to cells, tissues, body fluids, waters, food, terrain and/or synthetic preparations.

Instructions for use may be included in the kit. "Instructions for use" typically include a tangible expression describing the technique to be employed in using the components of the kit to effect a desired outcome, such as to identify and quantify polypeptides. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in proteomics. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing the signature peptides. The packaging material generally has an external label which indicates the contents and/or purpose of the kit and/or its components.

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." As one non-limiting example, one of ordinary skill in the art would generally consider a value difference (increase or decrease) no more than 5% to be in the meaning of the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 an Empirical Approach to Signature Peptide Choice for Selected Reaction Monitoring: Quantification of Uromodulin in Urine There are many proposed avenues for a seamless transition between biomarker discovery data and selected reaction monitoring (SRM) assays for biomarker validation. Unfortunately, studies with the abundant urinary protein uromodulin showed that these methods do not converge on a consistent set of surrogate peptides for targeted MS. As an alternative, we present an empirical peptide selection workflow for robust protein quantitation.

The relative SRM signal intensity of 12 uromodulin-derived peptides was compared between tryptic digests of 9 urine specimens. Pairwise coefficients of variation between the 12 peptides ranged from 0.19 to 0.99. A correlation matrix was utilized to identify peptides that reproducibly track the amount of uromodulin protein. Four peptides with robust and highly-correlated SRM signals were selected. Absolute quantitation was performed using stable-isotope labeled versions of these peptides as internal standards and a standard curve prepared from a tryptic digest of purified uromodulin.

Absolute quantification of uromodulin in 40 clinical urine specimens yielded inter-peptide correlations of ≥0.984 and correlations of ≥0.912 with ELISA data. The SRM assays were linear over >3 orders of magnitude and had typical inter-digest CV's of <10%, inter-injection CV's of <7%, and inter-transition CV's of <7%.

Comparing the apparent abundance of a plurality of peptides derived from the same target protein makes it possible to select signature peptides that are unaffected by the unpredictable confounding factors that are inevitably present in biological samples.

Urine Samples

Pooled normal human urine and 10 urine samples from healthy males were purchased from Bioreclamation, Inc. Clinical urine specimens were obtained from 42 participants of the Atherosclerosis Risk in Communities (ARIC) study, detailed description of sample selection and characteristics was published (see e.g., The atherosclerosis risk in communities (ARIC) study: Design and objectives. The aric investigators. American journal of epidemiology 1989; 129:687-702; and Kottgen A, Hwang S J, Larson M G, Van Eyk J E, Fu Q, Benjamin E J, et al. Uromodulin levels associate with a common UMOD variant and risk for incident ckd. J Am Soc Nephrol 2010; 21:337-44).

Urine Sample Preparation

Figure 5:
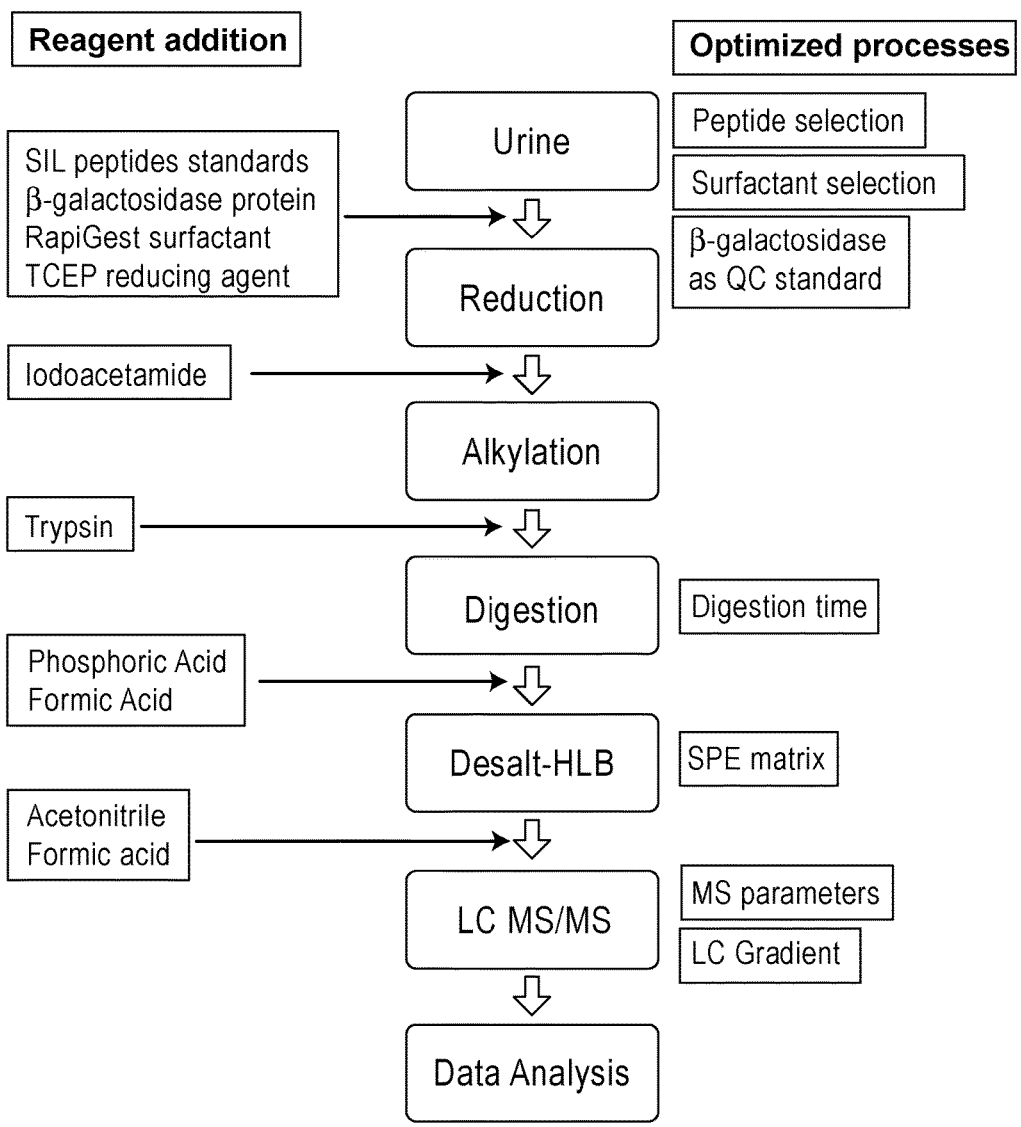
FIG. 5 depicts, in accordance with various embodiments of the present invention, a sample processing workflow highlighting the order of reagent addition and each step where conditions were optimized.

The sample preparation process is illustrated in FIG. 5. To prepare urine for MS analysis, specimens stored at −80° C. were thawed, gently mixed, and then centrifuged for 10 minutes at 10,000×g at room temperature. 5 μl of urine was supplemented with 3 μl of NH4HCO3 (1M), 5 μl water, 2 μl RapiGest (1%), 2 μl of SIL peptides (1000 fmole/μl), and 0.16 μl of β-galactosidase (0.5 μg/μl), which was used as a quality control probe to monitor the consistency of sample processing and analysis. Proteins were reduced with 1 μl TCEP (100 mM) for 30 minutes at 60° C., alkylated in the dark with 1 μl iodoacetamide (50 mM) for 30 minutes at 37° C., and then incubated with 0.8 μl trypsin (0.125 μg/μl, Promega Gold) in a 37° C. shaker for 6 hours. Digested peptides were purified on an HLB microplate and resuspended in MS loading buffer.

Mass Spectrometry

SRM assays were performed on an LC/MS system comprising a high flow HPLC (Shimadzu Prominence) with an)(Bridge BEH 30 C18 reverse-phase column (Waters) linked to a triple quadrapole mass spectrometer (Q-Trap 6500 or Q-Trap 5500, Sciex) with a TurboV ion source (Sciex). A detailed description of SRM LC-MS/MS methods and parameters is provided herein. The SRM data was processed using Multiquant (Sciex).

Data-dependent MS experiments for discovery were performed on an Orbitrap Elite MS (Thermo Scientific, USA) coupled to an Easy-nLC 1000 chromatography system (Thermo Scientific, USA), and a TripleTOF® 5600 MS (Sciex) coupled to an Ekspert nanoLC 415 chromatography system as described herein. Data was processed through SORCERER™ (Sage-N-Research Inc.), ProteinPilot™ (Sciex), or PASS (Integrated Analysis Inc.) software.

Quantitation of Uromodulin

The absolute concentration of uromodulin was determined using stable isotope-labeled (SIL) peptides as internal standards and purified uromodulin (EMD Milipore) as an external standard, as described herein.

Peptide Selection Methods

For data-dependent LC MS/MS, a tryptic digest of purified uromodulin was analyzed on an Orbitrap MS, in both higher-energy collisional dissociation (HCD) and collision induced dissociation (CID) fragmentation modes, and on a Triple-TOF MS. Proteome Discoverer was used to search MS spectra files and rank peptides. Peptides are commonly ranked by intensity and spectral counting. These methods can give different results, so both were compared. The database methods involved searching human proteome databases from National Institute of Standards and Technology (NIST), PeptideAtlas, and SRMAtlas for uromodulin peptides. Predictions were obtained through the PeptideAtlas interface.

Optimization of Urine Sample Preparation

FIG. 5 presents an overview of the sample preparation workflow highlighting each parameter that was optimized to standardize the trypsin digestion and peptide cleanup procedures.

Figure 11:
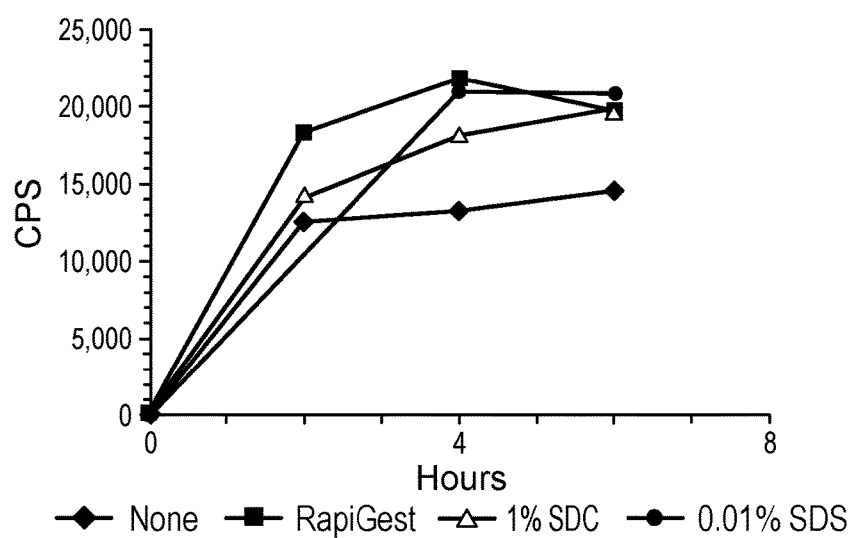
FIG. 11 depicts, in accordance with various embodiments of the present invention, a selection of surfactants. Pooled human urine was supplemented with various surfactants and then reduced, alkylated, and digested with typsin. The resulting peptides were desalted on an HLB plate and analyzed by SRM. Data is presented for a representative transition targeting the y10 fragment of the DSTIQVVEN-GESSQGR (SEQ. ID. NO: 69) peptide.

(a) Surfactants. Three different surfactants (0.1% RapiGest, 1% sodium deoxycholate (SDC) and 0.01% sodium dodecyl sulfate (SDS) were tested (FIG. 11). All of the surfactants increased the SRM signal of the DSTIQ (SEQ ID NO: 4) uromodulin peptide when compared with a no surfactant control. RapiGest provided the highest and most consistent response. Surfactants may help to disassemble large UMOD aggregates, thereby increasing the accessibility of trypsin cleavage sites, and may stabilize peptides after digestion. RapiGest has an additional advantage in that it degrades at low pH, so it doesn't interfere with MS like other detergents. In comparison with urea, which is generally used to denature proteins prior to trypsin digestion, surfactants do not modify proteins covalently and are added at a much lower concentration.

(b) Digestion time. The signals for two uromodulin peptides selected from data-dependent MS discovery data reached a plateau after 4-6 hours. Reduced signals detected after 16 hours in trypsin suggest that these uromodulin-derived peptides are either unstable or susceptible to cleavage by an endogenous protease. In the optimized procedure, urine was supplemented with RapiGest (0.01%) and digested with trypsin for 6 hours.

(c) Excess trypsin to overcome inhibitors in urine. To optimize trypsin digestion conditions and insure that incomplete proteolysis did not compromise protein quantitation, pooled urine and a mixture of purified uromodulin and serum albumin were digested with varying amounts of trypsin and then analyzed with an SRM assay targeting 12 uromodulin peptides. In general, more trypsin was required to release peptides from the native uromodulin in urine than from the pure protein mix, even though there was twice as much uromodulin protein in the pure samples. This difference suggests that urine contains a trypsin inhibitor. The amount of this unidentified inhibitor could vary between urine specimens in an uncontrolled manner. For quantitative analysis, urine was digested with a three-fold excess over the amount of trypsin required for compete digestion of the most trypsin-resistant sites.

Figure 6:
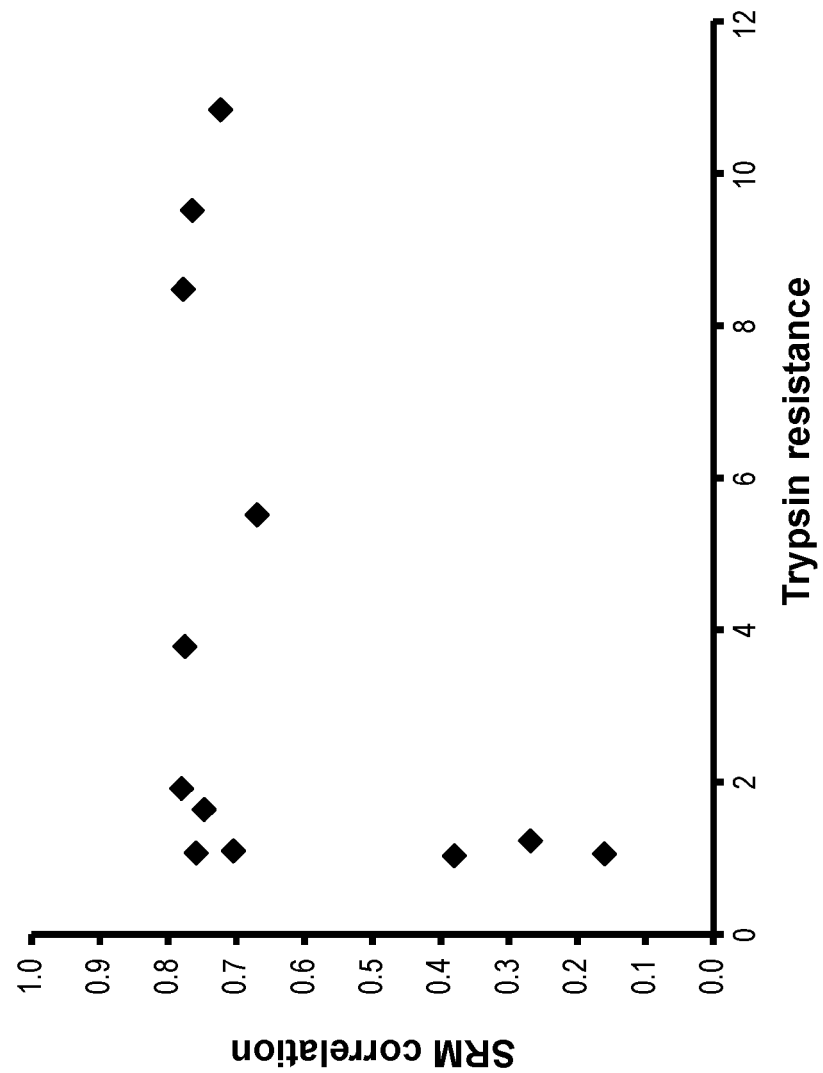
FIG. 6 depicts, in accordance with various embodiments of the present invention, that some trypsin-sensitive peptides have low SRM correlations. For each peptide, an average SRM correlation was calculated from the coefficients of variation presented in FIG. 1B. Trypsin resistance was defined as the ratio of the SRM signal from a digest with 4 µl trypsin compared to the signal from a digest with 1 µl trypsin. Trypsin-sensitive peptides had a low score because digestion was complete with 1 µl trypsin.

(d) Inconsistent results with peptides from protease-sensitive unfolded domains. The amount of trypsin required for complete release of different uromodulin peptides varied by more than 10-fold (FIG. 6). As expected, the most trypsin-resistant peptides were derived from folded domains of the uromodulin protein (see FIG. 1B). Notably, the three uromodulin peptides with the most disparately variable SRM signals were completely released by a low concentration of trypsin (FIG. 6). These peptides may arise from unfolded regions of the protein that are sensitive to natural proteases in urine, which could have different activity in different individuals.

Figure 12B:
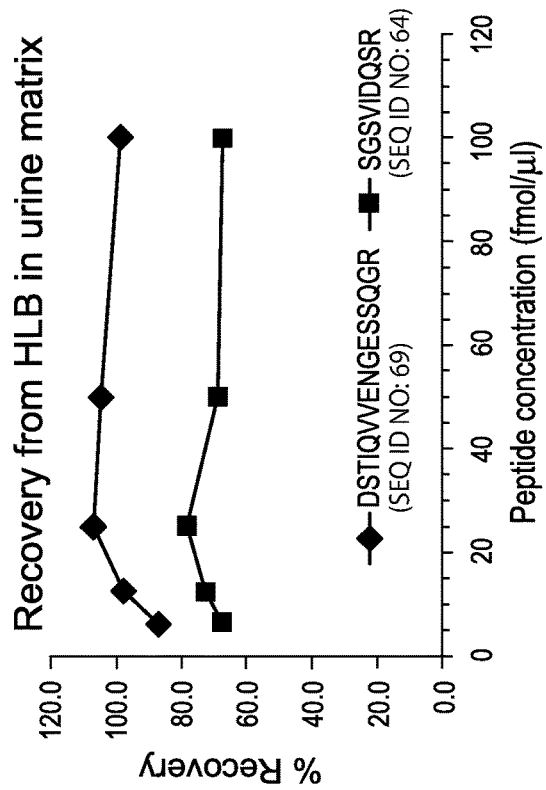
FIG. 12A-FIG. 12B depict, in accordance with various embodiments of the present invention, peptide desalting on HLB resin.
Figure 12A:
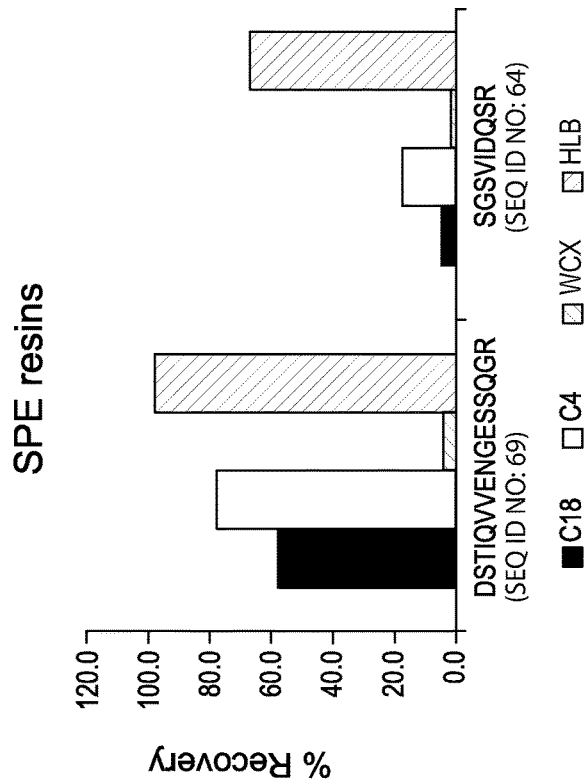

(e) Selecting HLB as the SPE resin for peptide desalting. The yield of uromodulin peptides after desalting on various SPE resins was evaluated using SIL peptides. HLB resin had the highest yield of the DSTIQVVENGESSQGR (SEQ ID NO: 69) and SGSVIDQSR (SEQ ID NO: 64) peptides (FIG. 12A). Recovery of the SIL peptides from HLB resin was consistent for peptide concentrations ranging from 6.25 to 100 fmol/μl in 50 μl urine (FIG. 12B). Desalting on these SPE resins was performed following the manufacturers' suggested protocols. C4 and C18 OMIX Tips (Agilent) fit on a standard pipette. Liquid is passed through the resin by pipetting in and out. Tips were conditioned twice with 10 μl 50% acetonitrile, 0.1% trifluoracetic acid (TFA) and equilibrated twice with 10 μl 0.1% TFA. SIL peptides were acidified with 0.1% TFA, loaded five times on the C4 or C18 resin, washed with 0.1% TFA, eluted with 75% acetonitrile, 0.5% formic acid, dried in a speed-vac, and then dissolved in MS loading buffer. For weak cation exchange (WCX), a 96 well microplate (Waters) was wetted with 200 μl methanol, equilibrated with 200 μl water, loaded with SIL peptides in 4% H3PO4, washed three times with 200 μl of 25 mM KH2PO4/K2HPO4 (pH7), and washed again with 200 μl methanol. Peptides were eluted with 50 μl 2% formic acid in methanol, dried in a speed vac, and resuspended in MS loading buffer. The HLB resin was wetted with 200 μl methanol and then equilibrated three times with 200 μl of 0.1% formic acid. SIL peptides in 200 μl of 4% H3PO4 were loaded on the microplate, washed three times with 200 μl 0.1% formic acid, and then slowly eluted with 200 μl of 80% acetonitrile, 0.1% formic acid. The eluates were dried in a speed-vacuum and then dissolved in MS loading buffer.

Figure 9:
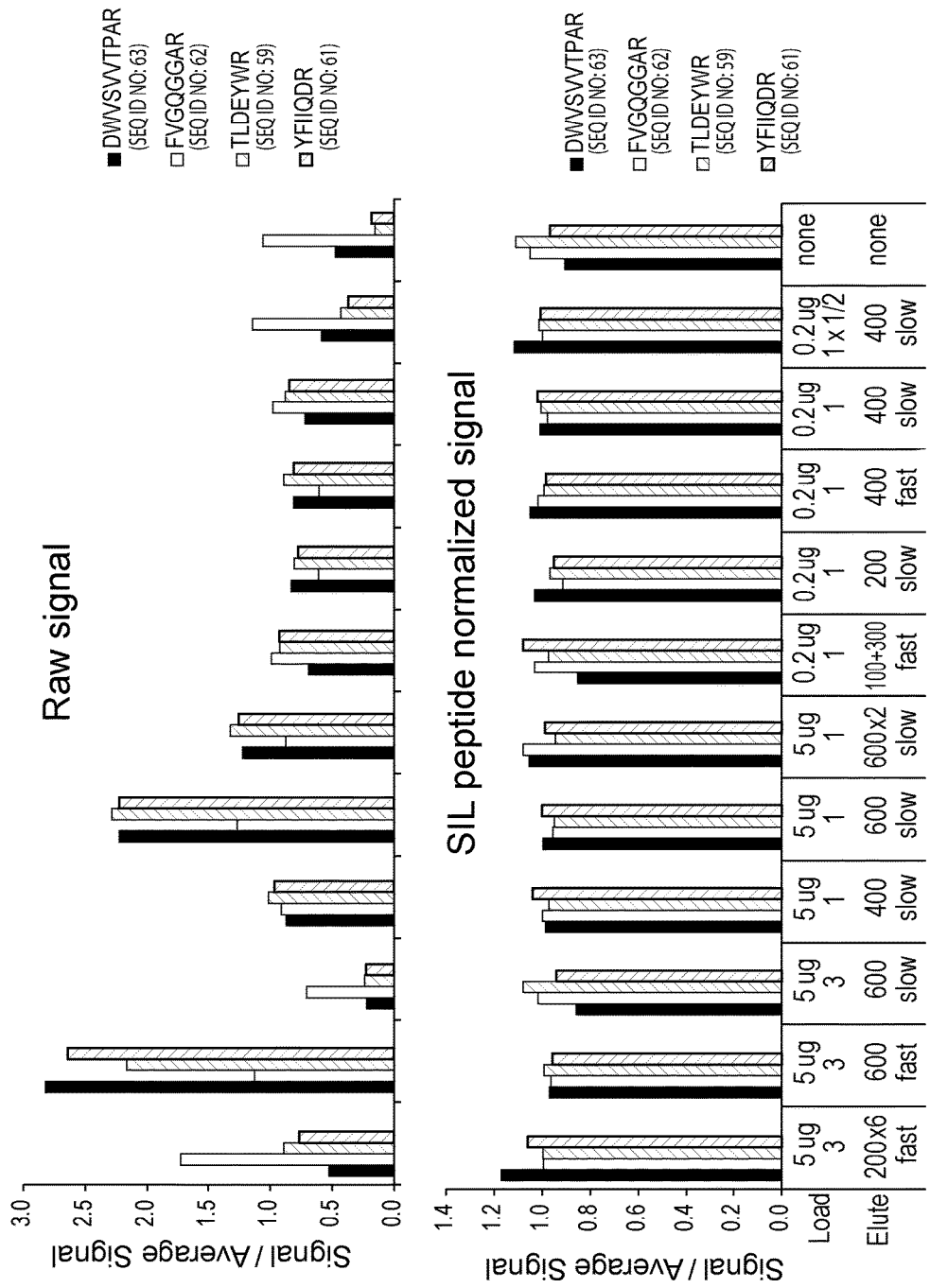
FIG. 9 depicts, in accordance with various embodiments of the present invention, normalization with SIL internal standards. Pooled urine was spiked with a mixture of SIL peptide standards, digested with trypsin, and then divided into aliquots that were desalted on different wells of an HLB microplate. The desalting conditions were altered by varying the total amount of urine protein applied, the number of times each aliquot was passed through the HLB resin, the volume of elution buffer, the number of times the elution buffer was passed through the HLB resin, and the flow rate during elution. Each eluate was dried, resuspended in MS buffer, and then analyzed with an SRM assay targeting the four empirically selected uromodulin peptides and two peptides from human serum albumin. The resuspension volume was adjusted to compensate for differences in the amounts of input peptides. Upper panel: Raw area-under-the-curve data; Lower panel: normalized data calculated by dividing the signal from native peptides by data from the corresponding SIL peptide standard. To compensate for differences between the SRM response for different peptides, all data was divided by the average signal for the corresponding peptide.

(f) Normalization to SIL peptide internal standards. Theoretically, SIL peptides should behave identically to native peptides with the same sequence. Thus, any losses of native peptides during sample processing due to peptide instability, insolubility, or low yield after SPE should be accompanied by loss of an equal fraction of the SIL peptide. The utility of SIL peptides as internal standards was tested in an experiment where the desalting conditions were intentionally varied using techniques expected to affect peptide recovery (FIG. 9). SIL peptides were added to a large batch of pooled urine, which was digested with trypsin and then divided into aliquots. Each aliquot was separately desalted under different conditions and then analyzed with an SRM assay tracking 6 peptides. As expected, the absolute and relative amounts of native peptides recovered varied tremendously (upper panel). However, a more consistent ratio was observed after normalization to the SIL peptide internal standards (lower panel). These results demonstrate that normalization is highly effective, and highlight the importance of consistent desalting procedures, which were employed in all other experiments.

(g) Spiked β-galactosidase as a probe for quality control. For quality control, urine samples were spiked with 0.08 μg β-galactosidase protein and 2 pmol β-galactosidase SIL peptides prior to reduction, alkylation, trypsin digestion, and desalting. The consistency of sample processing was judged by comparing the ratio between digested natural peptide and SIL internal standard peptide for 3 tryptic peptides from β-galactosidase: WVGYGQDSR (SEQ ID NO: 79), IDPNAWVER (SEQ ID NO: 74), and GDFQFNIS (SEQ ID NO: 80). The % CVs for these three peptides were 16.9%, 4.9%, and 3.4%, respectively, in the experiment where uromodulin was quantified in 42 urine samples.

MS Methods to Identify Detectable Uromodulin Peptides

The data-dependent acquisition MS experiment for initial peptide selection was performed on an Orbitrap XL mass spectrometer (ThermoFisher) with an on-line nano-HPLC system (1200 Series, Agilent Technologies). Peptides were separated on a reverse-phase analytical column packed with 10 cm of C18 beads (Biobasic C18 PicoFrit column, New Objective, Woburn, Mass.). A linear AB gradient comprising 5-60% B for 25 min was used where solvent A was 0.1% formic acid and solvent B was 90% acetonitrile in 0.1% formic acid, followed by 100% B for 2 min. The flow rate was 300 nl/min. The instrument was operated in a data-dependent mode in which a full scan was followed by MS/MS scans of the five most intensive ions, which were automatically selected for collision-induced dissociation (CID). Data analysis was performed on a Sorcerer server using Sequest.

To compare peptides identifications, the same digested and desalted peptide mixture was run in duplicate on Orbitrap, Triple-TOF, and Triple-Quadrupole instruments. Specifically, the sample was analyzed using an Orbitrap Elite mass spectrometer (Thermo Scientific, USA) online coupled to an Easy-nLC 1000 system (Thermo Scientific, USA). The injection volume was 10 μL of the sample, representing 0.2 μg of peptides. After injection the samples were preconcentrated with 0.1% TFA on a trap column (Acclaim PepMap 100, 300 μm×5 mm, C18, 5 μm, 100 Å; maxiam pressure 800bar). Subsequently, the peptides were transferred to the analytical column (Acclaim PepMap RSLC, 75 μm×15 cm, nano Viper, C18, 2 μm, 100 Å) and separated by a 2% to 30% gradient over 70 mins (solvent A: 0.1% FA in water, solvent B: 0.1% FA in acetonitrile; flow rate 350 nL/min; column oven temperature 45° C.). The MS was operated in a data-dependent mode. Full scan MS spectra were acquired at a resolution of 60,000 in the Orbitrap analyzer, followed by tandem mass spectra of the 20 most abundant peaks in the linear ion trap after peptide fragmentation by collision-induced dissociation (CID) or high-energy collision dissociation (HCD). For 5600 Triple-TOF, source conditions were as follows: Spray voltage was set to 2.3 kV, source gas was set to 15, curtain gas was set to 20, interface heater temperature was set to 160, and declustering potential was set to 100. Rolling collision energy was used for MS2 experiments and the 20 most abundant ions were selected for fragmentation. Peptides were loaded onto an Eksigent Ekspert™ 415 nanoLC equipped with Ekspert™ cHiPLC and Ekspert™ nanoLC 400 autosampler. Samples were separated using a nano cHiPLC 200 μm×15 cm ChromXP C18-CL 3 μm 120 Å column using a flow rate of 1000 nL/min and a linear gradient of 5-35% solvent B (0.1% formic acid in acetonitrile) for 123 min, 35-95% B for 3 minutes, holding at 95% for 10 minutes, then re-equilibration at 5% B for 15 minutes.

LC MS/MS data-dependent acquisition spectral data were searched on Mascot against a Human database and the results were imported into Proteome Discoverer, which allowed peptides to be ranked according to their intensity or spectral count. SEQUEST searches were conducted using the SORCERER platform by Sage-N. The human proteome database from NIST was also imported into Proteome Discoverer. The SRM Atlas and PeptideAtlas online resources were queried for uromodulin. The consensus prediction amalgamates the results from five predictive algorithms, including STEPP (see e.g., Webb-Robertson et al., A support vector machine model for the prediction of proteotypic peptides for accurate mass and time proteomics, Bioinformatics. 2010 Jul. 1; 26(13):1677-83.)

MS Methods for Targeting Uromodulin

SRM assays were performed on an LC/MS system with a reverse-phase column (XBridge BEH 30 C18 column, 2.1 mm×100 mm, 3.5 µm, Waters, Milford, Mass.) plumbed into an HPLC (Shimadzu Prominence) linked to a triple quadrapole mass spectrometer (Q-Trap 6500 or Q-Trap 5500, Sciex) with a TurboV ion source (Sciex). Peptides (5 µl) were injected in triplicate at a rate of 0.2 ml/min. The chromatography buffers were 0.1% formic acid (buffer A) and 95% acetonitrile in 0.1% formic acid (buffer B). The % buffer A increased from 18 to 27% over 7 minutes.

Uromodulin peptides and transitions were identified using Skyline software (see e.g., MacLean B, Tomazela D M, Shulman N, Chambers M, Finney G L, Frewen B, et al. Skyline: An open source document editor for creating and analyzing targeted proteomics experiments. Bioinformatics 2010; 26:966-8), and then imported into Analyst 2.1 software (Sciex). An initial set of six transitions for each peptide was identified from the NIST spectral library. The best two to five of these were selected based upon signal intensity on a triple quadrupole MS. Synthetic stable-isotope peptides were obtained once the final peptides were selected. The collision energy and collision cell exit potential were then optimized using the Autotune function in Analyst with a continuous infusion of synthetic peptides.

Transitions (Table 8) were initially selected based upon high signal intensity. Two transitions were subsequently eliminated because they had overlapping interferences and/or misshapen peaks. Of note, some of the remaining transitions report on b2 or a2 fragment ions with short sequences and fragment m/z<parent m/z, making them prone to interference. However, we used these transitions because of their high signal intensity. To validate the fragment m/z<parent m/z transitions, we showed that (1) they co-elute with fragment m/z>parent m/z transitions from the same peptide, (2) have symmetrical peaks, (3) no spurious noise was observed, even in urine samples with low uromodulin concentrations and (4) the correlation between the measured amounts of different transitions from the same peptide in 9 urine samples, including with transitions having fragment m/z>parent m/z, was nearly perfect ($r^2$>0.995).

Absolute Quantification of Uromodulin

The concentration of uromodulin was determined by comparison to a standard curve prepared from purified uromodulin through the use of stable isotope-labeled (SIL) internal standard peptides. The SIL peptides had a C-terminal [$^{15}$N]-Lys or [$^{15}$N]-Arg and were synthesized and HPLC-purified by New England Peptide. A mixture of $^{15}$N peptides (3 nmoles each) from uromodulin (4 peptides), and β-galatosidase (3 peptides) was prepared in 20% acetonitrile, 0.1% formic acid and then divided into 100 pmoles aliquots. Each aliquot was dried in a speed-vacuum and then stored at −80° C. until use. Peptides were re-suspended as a 10× stock (2 pmole/µl) in 50 µl of MS loading buffer (20% acetonitrile, 0.1% formic acid, and 15 µg/ml glucagon). Glucagon was included as a carrier to stabilize low concentration peptides.

Standard curves were prepared from human uromodulin purified from pooled urine (EMD Millipore, marketed as Human Tamm-Horsfall Glycoprotein) and recombinant β-galactosidase (Sigma). The concentrations of these proteins were determined by the manufacturers. 100 pmoles each of protein were dissolved in 150 mM NH4HCO3 with 0.1% RapiGest (Waters). The proteins were reduced with 5 mM tris(2-carboxyethyl)phosphine (TCEP, Pierce) for 30 minutes at 60° C., alkylated in the dark with 5 mM iodoacetamide for 30 minutes at 37° C., and then incubated overnight with 1.5 µg Trypsin (Promega Gold) in a final volume of 50 µl in a shaker block at 37° C.

Digested peptides were desalted on an HLB microplate in a vacuum manifold (Waters). The HLB resin was wetted with 700 µl methanol and then equilibrated three times with 700 µl of 0.1% formic acid. The peptide solution was diluted to 300 µl in 0.1% formic acid, further acidified with 300 µl of 4% H3PO4, loaded on the microplate, and then slowly aspirated through the HLB resin. The resin was washed three times with 0.1% formic acid and then slowly eluted with 400 µl of 80% acetonitrile, 0.1% formic acid. The eluates were dried in a speed-vacuum, dissolved at 1 pmole/µl in MS loading buffer supplemented with 1×SIL peptide standards, and then serially diluted 1:$\sqrt{10}$ in MS buffer with 1×SIL peptide standards.

Reproducibility and Recovery

Reproducibility and recovery of the SRM assay were established in a different laboratory with different lots of sample preparation reagents on a different MS instrument by a different operator. These experiments tracked the same MS transitions using the same mixture of SIL internal standard peptides, the same LC method, and the same standard curve. The volume of urine digested for each sample was increased from 5 µl to 20 µl.

The reproducibility test compared pooled normal human urine with a pool of diseased urine created by mixing urine specimens with high uromodulin from the ARIC study. On five separate days, five samples from each pool were digested with tyrpsin, desalted, and analyzed on a Q-Trap 6500 MS. Inter-assay CV's were calculated by comparing pools that were run on five different days (Table 10, top). Intra-assay CV's were calculated by comparing five pools run on the same day (Table 10, middle). Total CV's were calculated from the sum of squares of the mean inter- and intra-assay CVs (Table 10, bottom) (see e.g., Grant RP, Hoofnagle AN. From lost in translation to paradise found: Enabling protein biomarker method transfer by mass spectrometry. Clin Chem 2014; 60:941-4). Total CVs were <20%, satisfying the best practice acceptance criterion (see e.g., Lee J W, Devanarayan V, Barrett Y C, Weiner R, Allinson J, Fountain S, et al. Fit-for-purpose method development and validation for successful biomarker measurement. Pharmaceutical research 2006; 23:312-28).

SRM results with the four uromodulin peptides showed that diseased urine pool had a 2.5-3.0-fold higher uromodulin concentration than healthy urine (Table 11, top). Linearity and recovery were determined using mixtures having healthy to diseased ratios of 1:3, 1:1, and 3:1 (Table 11, bottom). For each mixture, an expected concentration for each peptide was calculated assuming a linear response. Observed and expected concentrations were then compared to calculate the percent recovery. The mean percent recovery of was 104%, with a standard deviation of 6%.

Commonly Used Signature Peptide Selection Methods Yield Divergent Results

The first major step in developing an SRM assay is to choose signature peptides for the quantitative analysis. In uromodulin-1, there are 27 predicted tryptic peptides with lengths in the useful range of between 6 and 21 amino acids (FIG. 1A). From these, potential signature peptides were identified by data-dependent acquisition, database, and predictive methods. Remarkably, these methods yielded almost completely different results. No clear patterns emerge when comparing the top 10 uromodulin peptides selected using 12 different, but not entirely independent, peptide selection methods (Table 3). Urine matrix and the choice of algorithm for searching discovery data also had a profound influence on peptide ranking (Table 4). There was, however, modest overlap in the ranking of transitions based on fragment ion intensity (Table 5). These results demonstrate that current peptide selection methods do not converge upon a consistent set of recommended peptides and transitions for quantitative analysis.

An exemplar sequence of uromodulin is shown as SEQ ID NO:82 below:

```
  1  mgqpsltwml mvvvaswfit taatdtsear wcsechsnat
     ctedeavttc tcqegftgdg
 61  ltcvdldeca ipgahncsan sscvntpgsf scvcpegfrl
     spglgctdvd ecaepglshc
121  halatcvnvv gsylcvcpag yrgdgwhcec spgscgpgld
     cvpegdalvc adpcqahrtl
181  deywrsteyg egyacdtdlr gwyrfvgqgg armaetcvpv
     lloctaapmw lngthpssde
241  givsrkacah wsghcclwda svqvkacagg yyvynltapp
     echlayctdp ssvegtceec
301  sidedcksnn grwhcqckqd fnitdislle hrlecgandm
     kvslgkcqlk slgfdkvfmy
361  lsdsrcsgfn drdnrdwvsv vtpardgpcg tvltrnetha
     tysntlylad eiiirdlnik
421  infacsypld mkvslktalq pmvsalnirv ggtgmftvrm
     alfqtpsytq pyqgssvtls
481  teaflyvgtm ldggdlsrfa llmtncyatp ssnatdplky
     fiiqdrcpht rdstiqvven
541  gessqgrfsv qmfrfagnyd lvylhcevyl cdtmnekckp
     tcsgtrfrsg svidqsrvln
601  lgpitrkgvq atvsrafssl gllkvwlpll lsatltltfq
```

TABLE 3

Comparison of SRM peptide selection methods[a]

| peptide ranking | Discovery | | | | | | | | Database | | | |
|---|---|---|---|---|---|---|---|---|---|---|---|---|
| | Triple TOF | | Orbi HCD | | Orbi CID | | NIST library | | Peptide-Atlas | SRM Atlas | Method Prediction | |
| | Inten-sity | Count | Inten-sity | Count | Inten-sity | Count | Inten-sity | Count | | | PeptideAtlas Consensus | STEPP |
| #1 | VGGTG (SEQ ID NO: 25) | TALQP (SEQ ID NO: 22) | VGGTG (SEQ ID NO: 25) | VLNLG (SEQ ID NO: 26) | SGSVI (SEQ ID NO: 19) | DGPCG (SEQ ID NO: 3) | DSTIQ (SEQ ID NO: 4) | TALQP (SEQ ID NO: 22) | FAGNY (SEQ ID NO: 6) | VFMYL (SEQ ID NO: 24) | DSTIQ (SEQ ID NO: 4) | QDFNI (SEQ ID NO: 18) |
| #2 | SLGFD (SEQ ID NO: 20) | INFAC (SEQ ID NO: 12) | STEYG (SEQ ID NO: 21) | SGSVI (SEQ ID NO: 19) | INFAC (SEQ ID NO: 12) | VGGTG (SEQ ID NO: 25) | ACAHW (SEQ ID NO: 1) | DSTIQ (SEQ ID NO: 4) | DSTIQ (SEQ ID NO: 4) | TALQP (SEQ ID NO: 22) | TALQP (SEQ ID NO: 22) | DSTIQ (SEQ ID NO: 4) |
| #3 | FSVQM (SEQ ID NO: 8) | DGPCG (SEQ ID NO: 3) | INFAC (SEQ ID NO: 12) | VGGTG (SEQ ID NO: 25) | FSVQM (SEQ ID NO: 8) | STEYG (SEQ ID NO: 21) | INFAC (SEQ ID NO: 12) | INFAC (SEQ ID NO: 12) | STEYG (SEQ ID NO: 21) | STEYG (SEQ ID NO: 21) | QDFNI (SEQ ID NO: 18) | NETHA (SEQ ID NO: 17) |
| #4 | LECGA (SEQ ID NO: 15) | YFIIQ (SEQ ID NO: 28) | YFIIQ (SEQ ID NO: 28) | DGPCG (SEQ ID NO: 3) | YFIIQ (SEQ ID NO: 28) | VLNLG (SEQ ID NO: 26) | DWVSV (SEQ ID NO: 5) | STEYG (SEQ ID NO: 21) | VFMYL (SEQ ID NO: 24) | VGGTG (SEQ ID NO: 25) | NETHA (SEQ ID NO: 17) | VWLPL (SEQ ID NO: 27) |
| #5 | DWVSV (SEQ ID NO: 5) | VGGTG (SEQ ID NO: 25) | FSVQM (SEQ ID NO: 8) | TALQP (SEQ ID NO: 22) | TALQP (SEQ ID NO: 22) | DWVSV (SEQ ID NO: 5) | STEYG (SEQ ID NO: 21) | VFMYL (SEQ ID NO: 24) | INFAC (SEQ ID NO: 12) | QDFNI (SEQ ID NO: 18) | STEYG (SEQ ID NO: 21) | VLNLG (SEQ ID NO: 26) |
| #6 | GVQAT (SEQ ID NO: 11) | SGSVI (SEQ ID NO: 19) | DSTIQ (SEQ ID NO: 4) | FSVQM (SEQ ID NO: 8) | VFMYL (SEQ ID NO: 24) | DSTIQ (SEQ ID NO: 4) | VFMYL (SEQ ID NO: 24) | DWVSV (SEQ ID NO: 5) | FSVQM (SEQ ID NO: 8) | DWVSV (SEQ ID NO: 5) | DWVSV (SEQ ID NO: 5) | TALQP (SEQ ID NO: 22) |

TABLE 3-continued

Comparison of SRM peptide selection methods[a]

| | Discovery | | | | | | Database | | | | Method Prediction | |
|---|---|---|---|---|---|---|---|---|---|---|---|---|
| | Triple TOF | | Orbi HCD | | Orbi CID | | NIST library | | | | | |
| peptide ranking | Intensity | Count | Intensity | Count | Intensity | Count | Intensity | Count | Peptide-Atlas | SRM Atlas | PeptideAtlas Consensus | STEPP |
| #7 | VLNLG (SEQ ID NO: 26) | VLNLG (SEQ ID NO: 26) | VFMYL (SEQ ID NO: 24) | STEYG (SEQ ID NO: 21) | VLNLG (SEQ ID NO: 26) | YFIIQ (SEQ ID NO: 28) | FSVQM (SEQ ID NO: 8) | YFIIQ (SEQ ID NO: 28) | ACAHW (SEQ ID NO: 1) | FALLM (SEQ ID NO: 7) | VGGTG (SEQ ID NO: 25) | AFSSL (SEQ ID NO: 2) |
| #8 | TALQP (SEQ ID NO: 22) | DWVSV (SEQ ID NO: 5) | TALQP (SEQ ID NO: 22) | VFMYL (SEQ ID NO: 24) | VGGTG (SEQ ID NO: 25) | TALQP (SEQ ID NO: 22) | VLNLG (SEQ ID NO: 26) | VGGTG (SEQ ID NO: 25) | VGGTG (SEQ ID NO: 25) | FSVQM (SEQ ID NO: 8) | AFSSL (SEQ ID NO: 2) | DWVSV (SEQ ID NO: 5) |
| #9 | VFMYL (SEQ ID NO: 24) | VFMYL (SEQ ID NO: 24) | VLNLG (SEQ ID NO: 26) | DWVSV (SEQ ID NO: 5) | MAETC (SEQ ID NO: 16) | VFMYL (SEQ ID NO: 24) | DGPCG (SEQ ID NO: 3) | TLDEY (SEQ ID NO: 23) | DWVSV (SEQ ID NO: 5) | VLNLG (SEQ ID NO: 26) | VWLPL (SEQ ID NO: 27) | SLGFD (SEQ ID NO: 20) |
| #10 | FVGQG (SEQ ID NO: 9) | LECGA (SEQ ID NO: 15) | DGPCG (SEQ ID NO: 3) | INFAC (SEQ ID NO: 12) | DWVSV (SEQ ID NO: 5) | INFAC (SEQ ID NO: 12) | MAETC (SEQ ID NO: 16) | VLNLG (SEQ ID NO: 26) | FVGQG (SEQ ID NO: 9) | NETHA (SEQ ID NO: 17) | VLNLG (SEQ ID NO: 26) | VGGTG (SEQ ID NO: 25) |

[a]Peptides are identified by the sequence of their first 5 amino acid residues. See Table 5 for the full sequence and amino acid numbers of each peptide.

TABLE 4

Effects of urine matrix and the search algorithm on peptide ranking of Orbitrap after CID fragmentation and data-dependent acquisition

| | Intensity | | | | Count | | | |
|---|---|---|---|---|---|---|---|---|
| | Pure UMOD* | | Urine | | Pure UMOD* | | Urine | |
| Rank | Mascot | SEQUEST | Mascot | SEQUEST | Mascot | SEQUEST | Mascot | SEQUEST |
| 1 | SGSVI (SEQ ID NO: 19) | VLNLG (SEQ ID NO: 26) | VLNLG (SEQ ID NO: 26) | DGPCG (SEQ ID NO: 3) | MAETC (SEQ ID NO: 16) | VGGTG (SEQ ID NO: 25) | | |
| 2 | INFAC (SEQ ID NO: 12) | VGGTG (SEQ ID NO: 25) | MAETC (SEQ ID NO: 16) | VGGTG (SEQ ID NO: 25) | STEYG (SEQ ID NO: 21) | DGPCG (SEQ ID NO: 3) | | |
| 3 | FSVQM (SEQ ID NO: 8) | DGPCG (SEQ ID NO: 3) | GDGWH (SEQ ID NO: 10) | STEYG (SEQ ID NO: 21) | DSTIQ (SEQ ID NO: 4) | MAETC (SEQ ID NO: 16) | | |
| 4 | YFIIQ (SEQ ID NO: 28) | TALQP (SEQ ID NO: 22) | SGSVI (SEQ ID NO: 19) | VLNLG (SEQ ID NO: 26) | VGGTG (SEQ ID NO: 25) | DSTIQ (SEQ ID NO: 4) | | |
| 5 | TALQP (SEQ ID NO: 22) | MAETC (SEQ ID NO: 16) | TALQP (SEQ ID NO: 22) | DWVSV (SEQ ID NO: 5) | TALQP (SEQ ID NO: 22) | STEYG (SEQ ID NO: 21) | | |
| 6 | VFMYL (SEQ ID NO: 24) | KGVQA (SEQ ID NO: 14) | VGGTG (SEQ ID NO: 25) | DSTIQ (SEQ ID NO: 4) | DWVSV (SEQ ID NO: 5) | KGVQA (SEQ ID NO: 14) | | |
| 7 | VLNLG (SEQ ID NO: 26) | SGSVI (SEQ ID NO: 19) | DWVSV (SEQ ID NO: 5) | YFIIQ (SEQ ID NO: 28) | VLNLG (SEQ ID NO: 26) | TALQP (SEQ ID NO: 22) | | |
| 8 | VGGTG (SEQ ID NO: 25) | KACAH (SEQ ID NO: 13) | INFAC (SEQ ID NO: 12) | TALQP (SEQ ID NO: 22) | INFAC (SEQ ID NO: 12) | INFAC (SEQ ID NO: 12) | | |
| 9 | MAETC (SEQ ID NO: 16) | INFAC (SEQ ID NO: 12) | LECGA (SEQ ID NO: 15) | VFMYL (SEQ ID NO: 24) | VFMYL (SEQ ID NO: 24) | VLNLG (SEQ ID NO: 26) | | |
| 10 | DWVSV (SEQ ID NO: 5) | ACAHW (SEQ ID NO: 1) | VFMYL (SEQ ID NO: 24) | INFAC (SEQ ID NO: 12) | SGSVI (SEQ ID NO: 19) | DWVSV (SEQ ID NO: 5) | | |

*The same MS data (.RAW) file was searched with both Mascot and SEQUEST.

TABLE 5

Fragmentation comparison

| | Triple Quad | Triple TOF | Orbi HCD | Orbi CID | NIST Library | Peptide Atlas | SRM Atlas | Fragmentation rank |
|---|---|---|---|---|---|---|---|---|
| TLDEYWR | y5 | y5 | | | y5 | y5 | y2 | 1 |
| (SEQ ID | y4 | a2 | | | a2 | b2 | y5 | 2 |
| NO: 59) | y3 | y4 | | | b2 | y4 | b2 | 3 |
| | (-H2O) | b2 | | | y4 | y3 | y3 | 4 |
| | b3 | y3 | | | y3 | y2 | y3 | 5 |
| | y6 | y6 | | | y2 | b4 | y4 | 6 |
| FVGQGGAR | y6 | y6 | | | y6 | y6 | | 1 |
| (SEQ ID | y7 | a2 | | | a2 | b2 | | 2 |
| NO: 52) | y4 | a1 | | | a1 | a2 | | 3 |
| | (-H2O) | b2 | | | b2 | b6 | | 4 |
| | y5 | y7 | | | b6 | y4 | | 5 |
| | | y4 | | | y4 | b4 | | 6 |
| DWVSVVTPAR | b2 | y7 | y7 | y5 | y5 | y5 | b2 | 1 |
| (SEQ ID | y7 | b2 | a2 | y7 | y4 | y7 | y1 | 2 |
| NO: 63) | y5 | a2 | b2 | y4 | y7 | b6 | y5 | 3 |
| | a2 | y8 | y8 | b2 | b6 | b7 | y3 | 4 |
| | y8 | y5 | Y5 | b6 | y3 | y8 | y4 | 5 |
| | b3 | y4 | a3 | y8 | b7 | b5 | y6 | 6 |
| YFIIQDR | a2 | y5 | a1 | y5 | y5 | y5 | b2 | 1 |
| (SEQ ID | y5 | a2 | y5 | y4 | y4 | y4 | y2 | 2 |
| NO: 61) | b2 | y4 | a2 | b2 | a2 | b2 | y5 | 3 |
| | y4 | b2 | y4 | a2 | b2 | a2 | y3 | 4 |
| | y3 | a1 | y6 | b3 | y3 | y3 | y4 | 5 |
| | y6 | y6 | y1 | y3 | b3 | b3 | y3 | 6 |

An Empirical Workflow for SRM Peptide Selection

In order to identify the best signature peptides for quantifying uromodulin in urine, the first step was to eliminate peptides that were never detected by MS on any instrument, were not unique to uromodulin, or were located within a C-terminal region thought to be absent from the mature protein. Several peptides with methionine or cysteine residues, which are susceptible to in vivo and in vitro modifications affecting their m/z ratio were also eliminated. This process narrowed the original set of 27 theoretical peptides down to 12 candidates for further testing (Table 6).

TABLE 5

Summary of the peptide selection process

| Peptide ID | Theoretical UMOD tryptic peptides 27 tryptic peptides (6-21 a.a.) | Round I-selecting 12 peptides (Why excluded from round I) | Round II-selecting final 4 peptides (why exculde from round II) | Final selection Isoform specificity |
|---|---|---|---|---|
| TLDEY (SEQ ID NO: 23) | R.TLDEYWR.S [178, 184] (SEQ ID NO: 32) | | | Isoforms 1, 3, and 4 |
| STEYG (SEQ ID NO: 21) | R.STEYGEGYACDTDLR.G [185, 199] (SEQ ID NO: 33) | | Low signal and Cys | |
| FVGQG (SEQ ID NO: 9) | R.FVGQGGAR.M [204, 211] (SEQ ID NO: 34) | | | Isoforms 1, 2, and 4 |
| MAETC (SEQ ID NO: 16) | R.MAETCVPVLR.C [212, 221] (SEQ ID NO: 35) | | low signal and MetOx | |
| ACAHW (SEQ ID NO: 1) | K.ACAHWSGHCCLWDASVQVK.A [246, 264] (SEQ ID NO: 36) | 3 Cys, conserved | | |

TABLE 5-continued

Summary of the peptide selection process

| Peptide ID | Theoretical UMOD tryptic peptides 27 tryptic peptides (6-21 a.a.) | Round I-selecting 12 peptides (Why excluded from round I) | Round II-selecting final 4 peptides (why exculde from round II) | Final selection Isoform specificity |
|---|---|---|---|---|
| WHCQC (SEQ ID NO: 29) | R.WHCQCK.Q [312, 317] (SEQ ID NO: 37) | Low m/z, 2 cys | | |
| QDFNI (SEQ ID NO: 18) | K.QDFNITDISLLEHR.L [318, 331] (SEQ ID NO: 38) | No Spectra | | |
| LECGA (SEQ ID NO: 15) | R.LECGANDMK.V [332, 340] (SEQ ID NO: 39) | MetOx | | |
| SLGFD (SEQ ID NO: 20) | K.SLGFDK.V [350, 355] (SEQ ID NO: 40) | Low m/z, not unique (published) | | |
| VFMYL (SEQ ID NO: 24) | K.VFMYLSDSR.C [356, 364] (SEQ ID NO: 41) | | low signal and MetOx | |
| CSGFN (SEQ ID NO: 30) | R.CSGFNDR.D [365, 371] (SEQ ID NO: 42) | no spectra | | |
| DWVSV (SEQ ID NO: 5) | R.DWVSVVTPAR.D [375, 384] (SEQ ID NO: 43) | | | Universal peptide |
| DGPCG (SEQ ID NO: 3) | R.DGPCGTVLTR.N [385, 394] (SEQ ID NO: 44) | | Cys, glycosylated tryptic site | |
| NETHA (SEQ ID NO: 17) | R.NETHATYSNTLYLADEIIIR.D [395, 414] (SEQ ID NO: 45) | No Spectra | | |
| INFAC (SEQ ID NO: 12) | K.INFACSYPLDMK.V [420, 431] (SEQ ID NO: 46) | MetOx | | |
| TALQP (SEQ ID NO: 22) | K.TALQPMVSALNIR.V [436, 448] (SEQ ID NO: 47) | | low signal and MetOx | |
| VGGTG (SEQ ID NO: 25) | R.VGGTGMFTVR.M [449, 458] (SEQ ID NO: 48) | MetOx | | |
| FALLM (SEQ ID NO: 7) | R.FALLMTNCYATPSSNATDPLK.Y [498, 518] (SEQ ID NO: 49) | MetOx, high m/z | | |
| YFIIQ (SEQ ID NO: 28) | K.YFIIQDR.C [519, 525] (SEQ ID NO: 50) | | | Universal peptide |

TABLE 5-continued

Summary of the peptide selection process

| Peptide ID | Theoretical UMOD tryptic peptides 27 tryptic peptides (6-21 a.a.) | Round I-selecting 12 peptides (Why excluded from round I) | Round II-selecting final 4 peptides (why exculde from round II) | Final selection Isoform specificity |
|---|---|---|---|---|
| DSTIQ (SEQ ID NO: 4) | R.DSTIQVVENGESSQGR.F [531, 546] (SEQ ID NO: 51) | | Low correlation | |
| FSVQM (SEQ ID NO: 8) | R.FSVQMFR.F [547, 553] (SEQ ID NO: 52) | | low signal and MetOx | |
| CKPTC (SEQ ID NO: 31) | K.CKPTCSGTR.F [577, 585] (SEQ ID NO: 53) | Post CT cleavage | not in the processed form low correlation and not in | |
| SGSVI (SEQ ID NO: 19) | R.SGSVIDQSR.V [588, 596] (SEQ ID NO: 54) | | he processed form | |
| VLNLG (SEQ ID NO: 26) | R.VLNLGPITR.K [597, 605] (SEQ ID NO: 55) | Post CT cleavage | not in the processed form | |
| GVQAT (SEQ ID NO: 11) | K.GVQATVSR.A [607, 614] (SEQ ID NO: 56) | Post CT cleavage | not in the processed form | |
| AFSSL (SEQ ID NO: 2) | R.AFSSLGLLK.V [615, 623] (SEQ ID NO: 57) | Post CT cleavage | not in the processed form | |
| VWLPL (SEQ ID NO: 27) | K.VWLPLLLSATLTLTFQ.- [624, 639] (SEQ ID NO: 58) | No spectra, Post CT cleavage | not in the processed form | |

A tryptic digest of purified uromodulin was used identify a set of transitions for each peptide that had high and reproducible peak intensities on a triple quadrapole mass spectrometer. The digest was then repeatedly injected to optimize the collision energy for each transition. The resulting parameters were used to investigate the performance of the 12 candidates in urine matrices. After establishing robust procedures for trypsin digestion and peptide cleanup, each peptide was evaluated in a set of tryptic digests of urine specimens obtained from healthy individuals. For this initial analysis, raw area-under-the-peak measurements were compared without normalization.

The measured amounts of the uromodulin signature peptides used for quantifying uromodulin protein should be linearly related to the amount of input protein and to the amount of other well-behaved signature peptides. To identify peptides with this property, coefficients of determination ($r^2$) were calculated for pairwise comparisons between each of the 12 candidate peptides across 9 urine samples (FIG. 1B). As expected, $r^2$ values for pairs of transitions from the same peptide were always >0.998, indicating that any variations from true linearity were due to the effects of differences between individual urine samples on the overall detectability of specific peptides. In contrast, low correlations were observed between several pairs of peptides, indicating that at least one peptide in each of these pairs was not accurately reporting the protein concentration. The identity of the peptides with poor correlations could not have been predicted from SRM chromatograms, as all of the peptides had symmetrical and unambiguously quantifiable peaks with no indication of interference in all urine samples.

Notably, the peptides with the lowest correlations were highly accessible to trypsin digestion, suggesting that these peptides may be derived from regions of the protein that are sensitive to endogenous proteases that vary between individuals (FIG. 6). Also, the poorly correlated SGSVIDQSR (SEQ ID NO: 64) peptide, although routinely detected in urine and purified uromodulin, is thought to be located within a C-terminal propeptide associated with the GPI anchor and may be absent from the mature protein.

Figure 7:
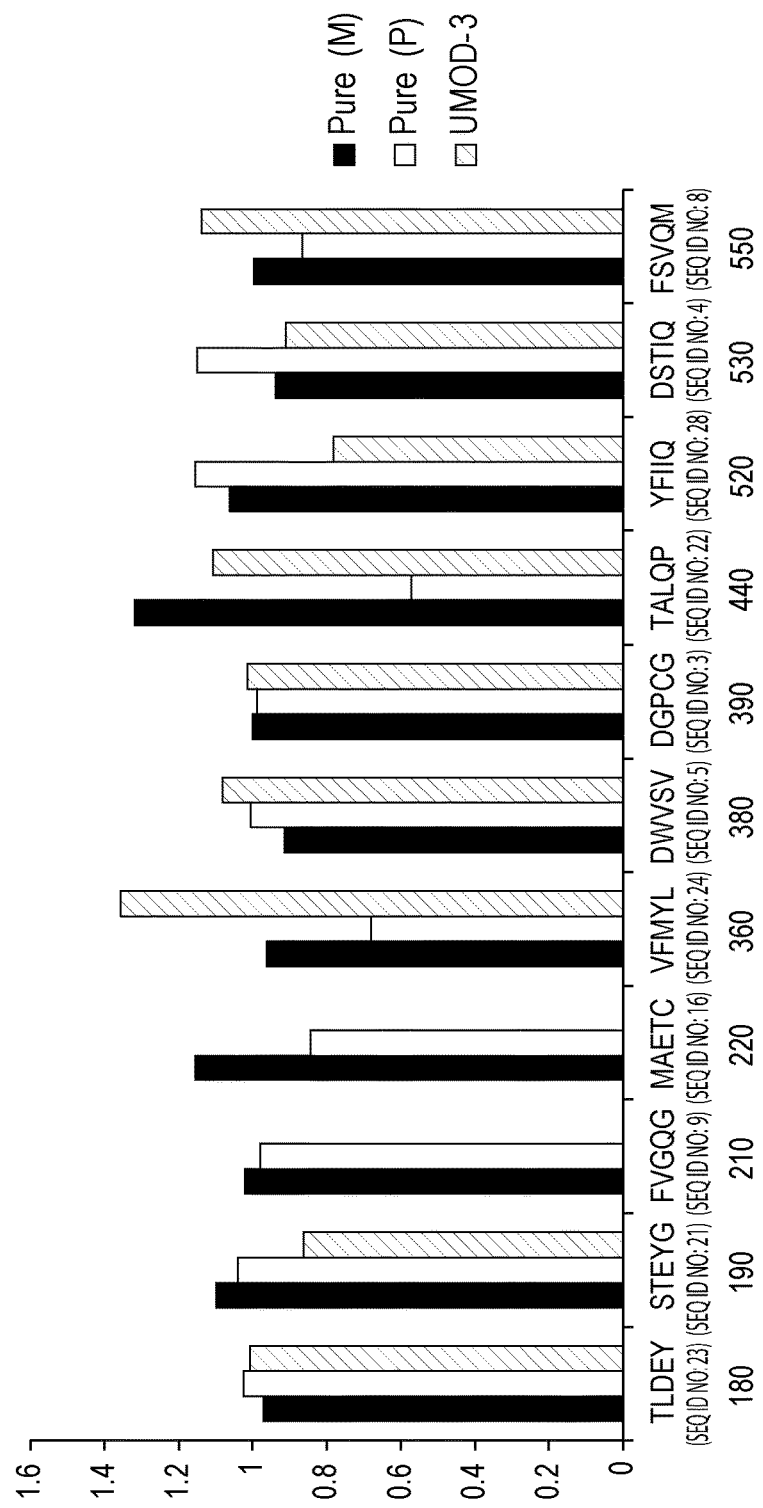
FIG. 7 depicts, in accordance with various embodiments of the present invention, that SRM can distinguish between uromodulin isoforms. Uromodulin purified from urine by Millipore (M) and Prospec Bio (P) was compared with recombinant uromodulin-3 (Abnova). A trypsin digest of each protein was analyzed with an SRM assay targeting 11 uromodulin-derived peptides. To normalize the results for each target peptide, raw SRM area-under-the-curve data was divided by the average signal for those samples with detectable peptide.
Figure 8:
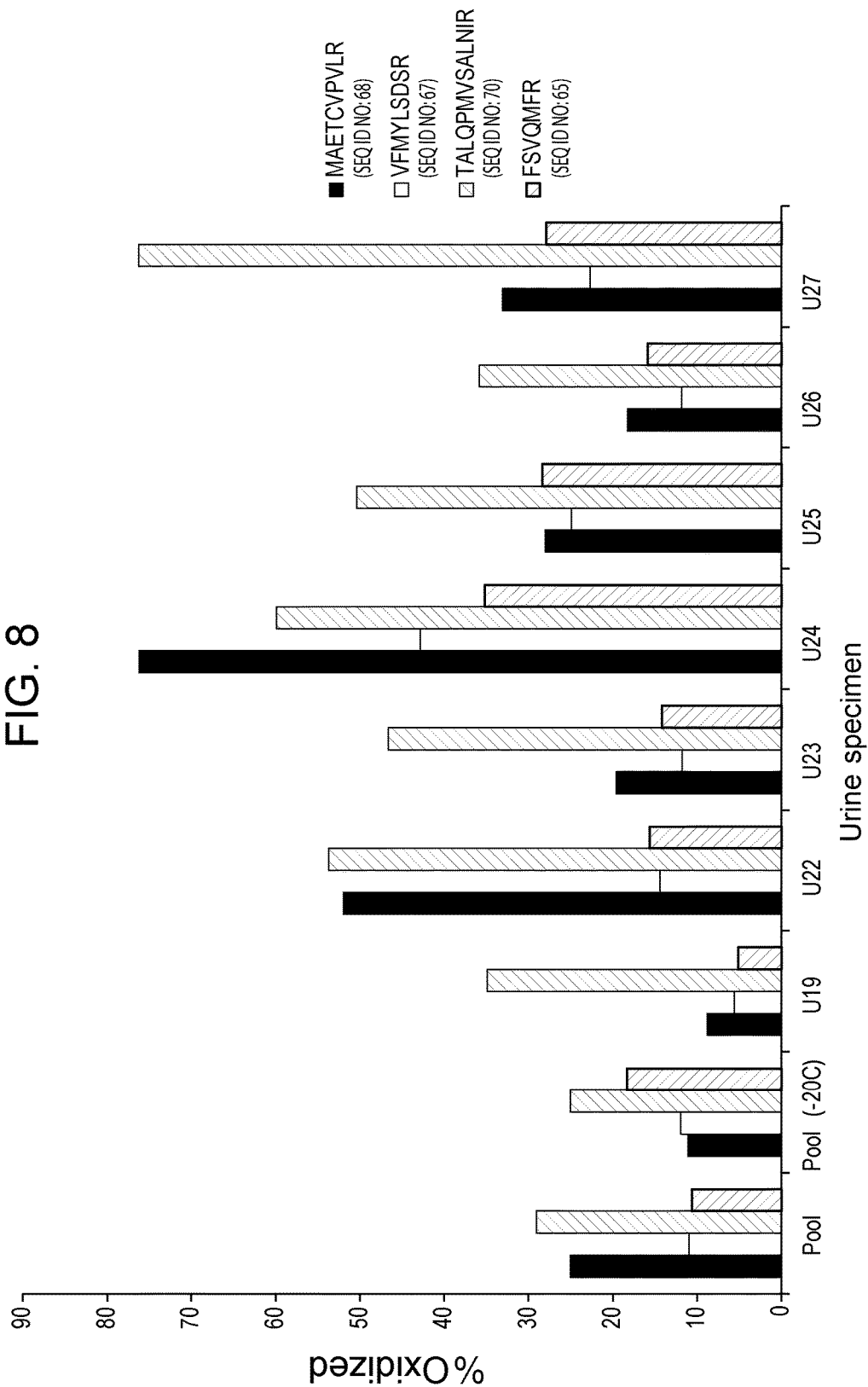
FIG. 8 depicts, in accordance with various embodiments of the present invention, variability in methionine oxidation. Native and oxidized forms of four uromodulin peptides were quantified by comparing equivalent transitions from raw SRM (area under the curve) data. The urine specimens included pooled normal urine from a −80° C. stock, with and without thawing and storage at −20° C. for one month, and seven randomly selected clinical urine specimens.

From the $r^2$ data, we selected a set of four signature peptides that were all highly correlated with each other, having $r^2$ values of at least 0.9. Two of these peptides, DWVSVVTPAR (SEQ ID NO: 63) (DWVSV) (SEQ ID NO: 5) and YFIIQDR (SEQ ID NO: 61) (YFIIQ) (SEQ ID NO: 28), were present in all uromodulin isoforms. The other two, TLDEYWR (SEQ ID NO: 59) (TLDEY) (SEQ ID NO: 23) and FVGQGGAR (SEQ ID NO: 62) (FVGQG) (SEQ ID NO: 9), can discriminate between isoforms (FIG. 1A-FIG. 1B and FIG. 7). In making our selections, we also considered the total SRM signal intensity of each peptide, background noise, LC retention time, and peak shape (Table 7). Additionally, four Met-containing peptides included in the empirical test had acceptable raw pairwise correlations, but were excluded because the extent of Met oxidation was highly variable (FIG. 8).

TABLE 7

SRM response for 12 individual peptides

|  | Total from top 3 transitions | | Best transition for each peptide | | |
|---|---|---|---|---|---|
|  | Peptide sequence | SRM signal | Peptide fragment | SRM signal | Selection |
| Uromodulin | TLDEYWR (SEQ ID NO: 59) | 222228 | TLDEYWR y5 (SEQ ID NO: 59) | 184155 | Yes |
|  | DGPC[+57]GTVLTR (SEQ ID NO: 290) | 210975 | DGPC[+57]GTVLTR y8 + 2 (SEQ ID NO: 290) | 132294 | No |
|  | YFIIQDR (SEQ ID NO: 61) | 202797 | YFIIQDR y5 (SEQ ID NO: 61) | 139368 | Yes |
|  | FVGQGGAR (SEQ ID NO: 62) | 189641 | FVGQGGAR y6 (SEQ ID NO: 62) | 168847 | Yes |
|  | DWVSVVTPAR (SEQ ID NO: 63) | 111931 | DWVSVVTPAR y7 (SEQ ID NO: 63) | 51717 | Yes |
|  | SGSVIDQSR (SEQ ID NO: 64) | 58652 | SGSVIDQSR y5 (SEQ ID NO: 64) | 33819 | No/yes for comparison |
|  | FSVQMFR (SEQ ID NO: 65) | 55306 | FSVQMFR y4 (SEQ ID NO: 62) | 22738 | No |
|  | STEYGEGYAC[+57]DTDLR (SEQ ID NO: 291) | 47853 | STEYGEGYAC[+57]DTDLR y9 (SEQ ID NO: 291) | 14321 | No |
|  | VFMYLSDSR (SEQ ID NO: 67) | 46293 | VFMYLSDSR y7 (SEQ ID NO: 67) | 24338 | No |
|  | MAETC[+57]VPVLR (SEQ ID NO: 292) | 28391 | MAETC[+57]VPVLR y4 (SEQ ID NO: 292) | 14637 | No |
|  | DSTIQVVENGESSQGR (SEQ ID NO: 69) | 13240 | DSTIQVVENGESSQGR y5 (SEQ ID NO: 69) | 4497 | No/yes for comparison |
|  | TALQPMVSALNIR (SEQ ID NO: 70) | 5146 | TALQPMVSALNIR y9 (SEQ ID NO: 70) | 3629 | No/yes for comparison |

Building a Quantitative SRM Assay

For absolute quantitation, SIL peptide versions of the empirically-selected uromodulin signature peptides were spiked into each trypsin digest and used to normalize the data. Our expectation was that the SIL peptides would behave similarly to natural peptides with the same sequence, such that any loss of natural peptides during sample processing would be accompanied by an equivalent loss of SIL peptides. Normalization was found to be remarkably effective in a test where peptide cleanup procedures were deliberately manipulated to alter peptide recovery (FIG. 9). The SIL peptides were also used to further optimize the MS parameters (Table 8).

TABLE 8

SRM parameters

| Protein | Q1 Mass (Da) | Q3 Mass (Da) | Acq. Time (ms) | Transition | DP (volts) | EP (volts) | CE (volts) | CXP (volts) |
|---|---|---|---|---|---|---|---|---|
| Uromodulin | 491.7 | 768.3 | 30 | TLDEYWR y5 (SEQ ID NO: 59) | 67 | 10 | 21 | 15 |
|  | 496.7 | 778.3 | 20 | TLDEYWR^ y5 (SEQ ID NO: 59) | 51 | 10 | 21 | 4 |
|  | 491.7 | 653.3 | 100 | TLDEYWR y4 (SEQ ID NO: 59) | 67 | 10 | 24 | 15 |
|  | 496.7 | 663.3 | 60 | TLDEYWR^ y4 (SEQ ID NO: 59) | 51 | 10 | 27 | 4 |
|  | 491.7 | 524.3 | 100 | TLDEYWR y3 (SEQ ID NO: 59) | 67 | 10 | 26 | 15 |
|  | 496.7 | 534.3 | 60 | TLDEYWR^ y3 (SEQ ID NO: 59) | 51 | 10 | 27 | 4 |
|  | 396.2 | 545.3 | 30 | FVGQGGAR y6 (SEQ ID NO: 62) | 41 | 10 | 19 | 4 |
|  | 401.2 | 555.3 | 20 | FVGQGGAR^ y6 (SEQ ID NO: 62) | 41 | 10 | 19 | 4 |
|  | 396.2 | 644.4 | 70 | FVGQGGAR y7 (SEQ ID NO: 62) | 41 | 10 | 21 | 16 |
|  | 401.2 | 654.4 | 60 | FVGQGGAR^ y7 (SEQ ID NO: 62) | 41 | 10 | 21 | 16 |
|  | 565.3 | 302.1 | 60 | DWVSVVTPAR b2 (SEQ ID NO: 63) | 46 | 10 | 27 | 8 |
|  | 570.3 | 302.1 | 30 | DWVSVVTPAR^ b2 (SEQ ID NO: 63) | 46 | 10 | 27 | 8 |
|  | 565.3 | 729.4 | 60 | DWVSVVTPAR y7 (SEQ ID NO: 63) | 72 | 10 | 26 | 15 |
|  | 570.3 | 739.4 | 40 | DWVSVVTPAR^ y7 (SEQ ID NO: 63) | 46 | 10 | 25 | 4 |

TABLE 8-continued

SRM parameters

| Protein | Q1 Mass (Da) | Q3 Mass (Da) | Acq. Time (ms) | Transition | DP (volts) | EP (volts) | CE (volts) | CXP (volts) |
|---|---|---|---|---|---|---|---|---|
| | 565.3 | 274.1 | 60 | DWVSVVTPAR a2 (SEQ ID NO: 63) | 46 | 10 | 37 | 8 |
| | 570.3 | 274.1 | 50 | DWVSVVTPAR^ a2 (SEQ ID NO: 63) | 46 | 10 | 37 | 8 |
| | 565.3 | 828.5 | 80 | DWVSVVTPAR y8 (SEQ ID NO: 63) | 72 | 10 | 26 | 15 |
| | 570.3 | 838.5 | 50 | DWVSVVTPAR^ y8 (SEQ ID NO: 63) | 46 | 10 | 25 | 18 |
| | 477.8 | 644.3 | 40 | YFIIQDR y5 (SEQ ID NO: 61) | 66 | 10 | 22 | 15 |
| | 482.8 | 654.4 | 20 | YFIIQDR^ y5 (SEQ ID NO: 61) | 56 | 10 | 21 | 4 |
| | 477.8 | 311.1 | 40 | YFIIQDR b2 (SEQ ID NO: 61) | 56 | 10 | 21 | 10 |
| | 482.8 | 311.0 | 20 | YFIIQDR^ b2 (SEQ ID NO: 61) | 56 | 10 | 21 | 10 |
| | 477.8 | 531.2 | 40 | YFIIQDR y4 (SEQ ID NO: 61) | 66 | 10 | 22 | 15 |
| | 482.8 | 541.3 | 30 | YFIIQDR^ y4 (SEQ ID NO: 61) | 56 | 10 | 21 | 4 |
| | 858.5 | 1072.5 | 20 | DSTIQVVENGESSQGR^ y10 (SEQ ID NO: 69) | 80 | 10 | 40 | 28 |
| | 858.5 | 973.5 | 20 | DSTIQVVENGESSQGR^ y9 (SEQ ID NO: 69) | 80 | 10 | 43 | 25 |
| | 479.4 | 515.2 | 20 | SGSVIDQSR^ y4 (SEQ ID NO: 64) | 80 | 10 | 25 | 14 |
| | 479.4 | 628.2 | 20 | SGSVIDQSR^ y5 (SEQ ID NO: 64) | 80 | 10 | 25 | 18 |
| | 712.4 | 414.4 | 20 | TALQPMVSALNIR^ b4 (SEQ ID NO: 70) | 76 | 10 | 29 | 32 |
| | 712.4 | 1010.4 | 20 | TALQPMVSALNIR^ y9 (SEQ ID NO: 70) | 76 | 10 | 35 | 26 |
| Galactosidase | 534.3 | 286.1 | 15 | WVGYGQDSR b2 (SEQ ID NO: 79) | 51 | 10 | 23 | 8 |
| | 539.3 | 286.1 | 15 | WVGYGQDSR^ b2 (SEQ ID NO: 79) | 51 | 10 | 23 | 8 |
| | 534.3 | 262.0 | 15 | WVGYGQDSR-y2 (SEQ ID NO: 79) | 51 | 10 | 37 | 8 |
| | 539.3 | 272.0 | 15 | WVGYGQDSR^ y2 (SEQ ID NO: 79) | 51 | 10 | 37 | 8 |
| | 534.3 | 562.1 | 15 | WVGYGQDSR-y5 (SEQ ID NO: 79) | 51 | 10 | 27 | 6 |
| | 539.3 | 572.1 | 15 | WVGYGQQSR^ y5 (SEQ ID NO: 79) | 51 | 10 | 27 | 6 |
| | 534.3 | 782.1 | 15 | WVGYGQDSR-y7 (SEQ ID NO: 79) | 51 | 10 | 25 | 6 |
| | 539.3 | 792.1 | 15 | WVGYGQDSR^ y7 (SEQ ID NO: 79) | 51 | 10 | 25 | 6 |
| | 550.3 | 774.2 | 15 | IDPNAWVER y6 (SEQ ID NO: 74) | 61 | 10 | 33 | 8 |
| | 555.4 | 784.2 | 15 | IDPNAWVER^ y6 (SEQ ID NO: 74) | 61 | 10 | 33 | 8 |
| | 550.3 | 871.2 | 15 | IDPNAWVER y7 (SEQ ID NO: 74) | 61 | 10 | 25 | 18 |
| | 555.4 | 881.2 | 15 | IDPNAWVER^ y7 (SEQ ID NO: 74) | 61 | 10 | 25 | 18 |
| | 550.3 | 436.1 | 15 | IDPNAWVER y7 + 2 (SEQ ID NO: 74) | 61 | 10 | 23 | 8 |
| | 555.4 | 441.1 | 15 | IDPNAWVER^ y7 + 2 (SEQ ID NO: 74) | 61 | 10 | 23 | 8 |
| | 542.3 | 262.1 | 15 | GDFQFNISR y2 (SEQ ID NO: 73) | 61 | 10 | 21 | 8 |
| | 547.3 | 272.1 | 15 | GDFQFNISR^ y2 (SEQ ID NO: 73) | 61 | 10 | 21 | 8 |
| | 542.3 | 636.0 | 15 | GDFQFNISR y5 (SEQ ID NO: 73) | 61 | 10 | 25 | 12 |
| | 547.3 | 646.0 | 15 | GDFQFNISR^ y5 (SEQ ID NO: 73) | 61 | 10 | 25 | 12 |
| | 542.3 | 764.2 | 15 | GDFQFNISR y6 (SEQ ID NO: 73) | 61 | 10 | 25 | 18 |
| | 547.3 | 774.2 | 15 | GDFQFNISR^ y6 (SEQ ID NO: 73) | 61 | 10 | 25 | 18 |

^15N-labeled amino acid residue at the C-terminus of a SIL peptide

Figure 10:
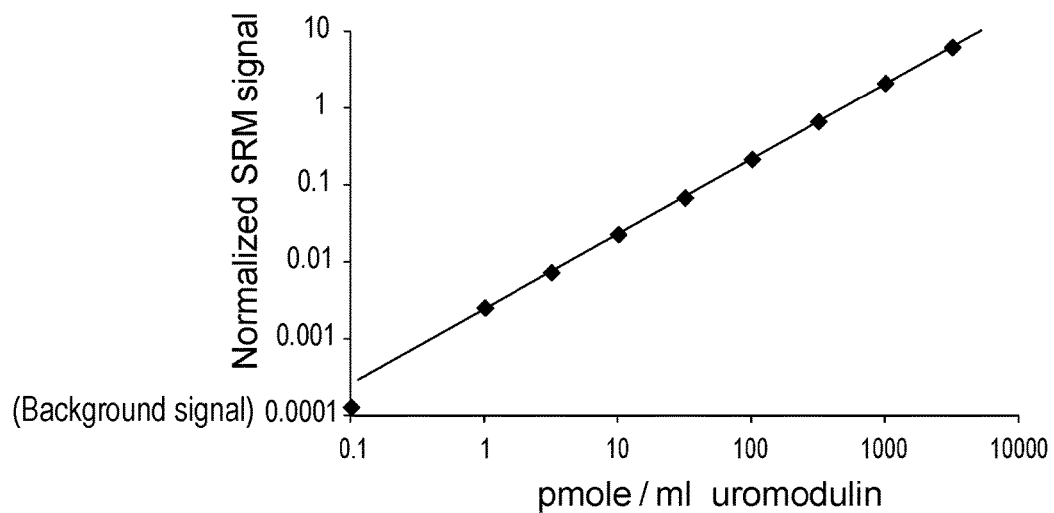
FIG. 10 depicts, in accordance with various embodiments of the present invention, linearity and range of the SRM assay. Purified uromodulin was digested with trypsin, desalted on HLB resin, and resuspended in MS loading buffer supplemented with a mixture of SIL peptides. Serial dilutions were prepared in supplemented loading buffer and then analyzed by SRM. Data is presented for a representative transition reporting on the y7 fragment of the DWVSV (SEQ. ID NO: 5) peptide.

On a standard curve constructed from a serial dilution of purified uromodulin, the SRM response for 12 abundant transitions representing the 4 signature uromodulin peptides was linear over at least 3 orders of magnitude, with a linearity of 0.998 (FIG. 10). The lower limits of quantitation (LLOQ) ranged between 0.4-14.1 μg/ml) (Table 9). The upper limit of quantification for all transitions was greater than 446.4 μg/ml, the highest concentration tested. At 446.4 μg/ml uromodulin, recoveries were nearly 100%, and CVs were <5%.

TABLE 9

LLOQ and ULOQ of Selected Uromodulin Peptides

| Signature Peptide | | | LLOQ (ug/ml) | | | ULOQ | | |
|---|---|---|---|---|---|---|---|---|
| Peptide | Fragment | Linearity | ug/ml | % Recovery[d] | % CV | ug/ml | % recovery | % CV |
| DWVSVVTPAR | y7 | 1.000 | 4.5 | 94.2 | 6.0 | 446.4 | 99.5 | 1.3 |
| (SEQ ID | y8 | 1.000 | 1.4 | 105.0 | 8.4 | 446.4 | 96.2 | 1.2 |
| NO: 63) | b2 | 0.998 | 1.4 | 97.9 | 8.0 | 446.4 | 100.8 | 2.0 |
| | a2 | 1.000 | 1.4 | 86.0 | 6.2 | 446.4 | 99.4 | 1.7 |
| FVGQGGAR | y6 | 0.999 | 14.1 | 109.1 | 14.4 | 446.4 | 100.0 | 4.6 |
| (SEQ ID | y7 | 1.000 | 4.5 | 102.0 | 8.6 | 446.4 | 100.0 | 3.6 |
| NO: 62) | | | | | | | | |
| TLDEYWR | Y5 | 0.999 | 1.4 | 87.8 | 14.9 | 446.4 | 97.1 | 2.1 |
| (SEQ ID | y4 | 1.000 | 1.4 | 87.1 | 12.9 | 446.4 | 100.7 | 1.9 |
| NO: 59) | Y3 | 1.000 | 4.5 | 94.0 | 5.6 | 446.4 | 99.2 | 1.9 |
| YFIIQDR | Y5 | 1.000 | 1.4 | 82.3 | 11.4 | 446.4 | 98.4 | 2.5 |
| (SEQ ID | y4 | 0.999 | 0.5 | 97.9 | 17.8 | 446.4 | 97.6 | 2.7 |
| NO: 61) | b2 | 0.999 | 1.4 | 84.1 | 12.8 | 446.4 | 96.8 | 2.0 | a. Linearity was determined across an 8 point 1: √10 dilution series of purified uromodulin
b. LLOQ, determined from the standard curve, is defined as the lowest concentration of calibrate at which recovery is 100% ± 20% and CV <20%.
c. ULOQ is defined as the highest concentration of the standard at which recover is 100% ± 20% and CV <20%.
[d] Recovery was calculated by back-fitting data to the standard curve. For each data point, the concentration calculated using the linear equation of best fit was compared with the known amount of input protein.

Reproducibility and Recovery

Uromodulin was quantified in pools of healthy and diseased serum to establish the reproducibility and recovery of the final method. For reproducibility, five aliquots of each pooled sample were processed on each of five different days. The inter-assay, intra-assay, and total CV's ranged from 1%-13%, 1%-11%, and 5%-13%, respectively (Table 10). For recovery, healthy and diseased serum was mixed at ratios of 1:3, 1:1, and 3:1. Recoveries ranged from 83% to 118%, with a mean and standard deviation of 104%±6% (Table 11).

TABLE 10

Reproducibility of the SRM method: Inter-Assay, Intra-Assay, and Total CV's

| Inter-Assay CV's[a] | | | | | |
|---|---|---|---|---|---|
| Sample type | Sample | DWVSVVTPAR | FVGQGGAR | TLDEYWR | YFIIQDR |
| Healthy pool | 1 | 4% | 7% | 6% | 4% |
| | 2 | 4% | 8% | 10% | 3% |
| | 3 | 3% | 13% | 3% | 5% |
| | 4 | 4% | 7% | 6% | 4% |
| | 5 | 1% | 11% | 8% | 2% |
| | mean | 3% | 9% | 7% | 4% |
| Sample type | Sample | DWVSVVTPAR | FVGQGGAR | TLDEYWR | YFIIQDR |
| ARIC pool | 1 | 4% | 6% | 5% | 7% |
| | 2 | 5% | 2% | 7% | 5% |
| | 3 | 6% | 3% | 7% | 4% |
| | 4 | 5% | 8% | 6% | 6% |
| | 5 | 4% | 6% | 8% | 6% |
| | mean | 5% | 5% | 7% | 6% |

TABLE 10-continued

Reproducibility of the SRM method: Inter-Assay, Intra-Assay, and Total CV's

Intra-Assay CV's[b]

| Sample type | Day | DWVSVVTPAR | FVGQGGAR | TLDEYWR | YFIIQDR |
|---|---|---|---|---|---|
| Healthy pool | 1 | 4% | 11% | 5% | 3% |
|  | 2 | 3% | 10% | 9% | 1% |
|  | 3 | 3% | 9% | 7% | 2% |
|  | 4 | 3% | 4% | 4% | 7% |
|  | 5 | 5% | 9% | 7% | 5% |
|  | mean | 4% | 9% | 6% | 4% |

| Sample type | Day | DWVSVVTPAR | FVGQGGAR | TLDEYWR | YFIIQDR |
|---|---|---|---|---|---|
| ARIC pool | 1 | 3% | 3% | 4% | 4% |
|  | 2 | 3% | 4% | 4% | 5% |
|  | 3 | 1% | 4% | 6% | 2% |
|  | 4 | 3% | 3% | 5% | 4% |
|  | 5 | 4% | 6% | 4% | 2% |
|  | mean | 3% | 4% | 5% | 3% |

Total CV's[c]

| Sample | DVWSWTPAR | FVGQGGAR | TLDEYWR | YFIIQDR |
|---|---|---|---|---|
| Healthy pool | 5% | 13% | 9% | 5% |
| ARIC pool | 7% | 8% | 8% | 7% |

[a]Inter-assay CV's were established for each sample of each pooled samples across 5 days. Experiments were repeated with 5 individual pooled healthy or 5 pooled diseased (2),
[b]Intra-assay CV's were established from each day 5 healthy pooled or 5 healthy diseased pooled, experiments were repeated 5 days for each pool (2).
[c]CV total = (mean CV$^2$intra + meanCV$^2$inter)$^{1/2}$ (2).

TABLE 11

Recovery

DWVSVVTPAR

| Sample | Observed[a] (µg/ml) | Calculated[b] | Recovery[c] |
|---|---|---|---|
| 15 µl healthy: 5 µl ARIC | 10.0 ± 0.6 | 9.8 | 102% ± 6% |
| 10 µl healthy: 10 µl ARIC | 12.7 ± 0.8 | 12.5 | 101% ± 7% |
| 5 µl healthy: 15 µl ARIC | 14.9 ± 1.5 | 15.3 | 98% ± 10% |

FVGQGGAR

| Sample | Observed (µg/ml) | Calculated | Recovery |
|---|---|---|---|
| 15 µl healthy: 5 µl ARIC | 27.4 ± 3.3 | 27.3 | 101% ± 12% |
| 10 µl healthy: 10 µl ARIC | 36.9 ± 3.7 | 34.5 | 101% ± 11% |
| 5 µl healthy: 15 µl ARIC | 45.9 ± 2.8 | 41.7 | 98% ± 7% |

TLDEYWR

| Sample | Observed (µg/ml) | Calculated | Recovery |
|---|---|---|---|
| 15 µl healthy: 5 µl ARIC | 13.2 ± 1.0 | 12.3 | 108% ± 8% |
| 10 µl healthy: 10 µl ARIC | 16.6 ± 1.2 | 15.7 | 106% ± 8% |
| 5 µl healthy: 15 µl ARIC | 20.9 ± 0.9 | 19.1 | 110% ± 5% |

YFIIQDR

| Sample | Observed (µg/ml) | Calculated | Recovery |
|---|---|---|---|
| 15 µl healthy: 5 µl ARIC | 10.8 ± 1.0 | 10.8 | 101% ± 2% |
| 10 µl healthy: 10 µl ARIC | 14.4 ± 0.5 | 14.4 | 100% ± 3% |
| 5 µl healthy: 15 µl ARIC | 17.8 ± 0.5 | 17.9 | 100% ± 3% |

[a]The observed concentrations were calculated using peptides as internal standards and purified uromodulin as an external standard, for each admixture sample, mean observed concentration is obtained from 4 replicate.
[b]Calculated concentration from each pool each determined by 25 samples (5 samples for 5 days) analyzed in Table 8
[c]Recovery = 100× (observed/calculated)

The Quantitative SRM Assay Yields Reproducible Results Comparable to an ELISA

The quantitative SRM assay was evaluated by measuring the uromodulin concentration in 42 urine specimens that had been previously analyzed using an ELISA assay (see e.g., Kottgen A, Hwang S J, Larson M G, Van Eyk J E, Fu Q, Benjamin E J, et al. Uromodulin levels associate with a common UMOD variant and risk for incident ckd. J Am Soc Nephrol 2010; 21:337-44). The absolute concentration for each peptide was calculated with reference to a standard curve prepared from data collected in the same sequence of MS runs. Three independent digests were prepared for each urine sample, and the SRM assay was run three times on each digest. Two urine specimens were eliminated from further analysis: one had a uromodulin concentration below the LLOQ, and the other was enriched for uromodulin isoforms 1 and 4 over isoforms 2 and 3, as shown by relatively high amounts of the TLDEY (SEQ ID NO: 23) and FVGQG (SEQ ID NO: 9) peptides.

The results for the remaining 40 samples, acquired from a total of 360 MS runs, were internally consistent (FIG. 2A-FIG. 2C). Coefficients of variation (CV) comparing the three digests for each sample were typically <10%, and CV's comparing the three injections for each digest were typically <7%. CV's comparing peptide concentrations measured using different transitions were typically <10%, with a trend towards higher CV's for low concentration peptides.

Notably, the UMOD concentration determined by SRM was greater than that determined by ELISA. This discrepancy could be due to i) inconsistency in the documented concentration of the standards used for SRM and ELISA, and/or ii) reduced antibody binding to endogenous uromodulin due to interference from unknown matrix components or structural modifications (e.g. post-translational modifications, proteolysis) lying within one of the uromodulin epitopes. In addition, the calculated concentration of the isoform-discriminatory FVGQG (SEQ ID NO: 9) peptide was consistently higher than that of the other peptides, suggesting that the purified uromodulin calibrator had a different ratio of isoforms than the clinical samples or lacked an interfering contaminant common to all urine specimens. Alternatively, the FVGQG (SEQ ID NO: 9) peptide could have a different decay rate than the other peptides.

Figure 3:
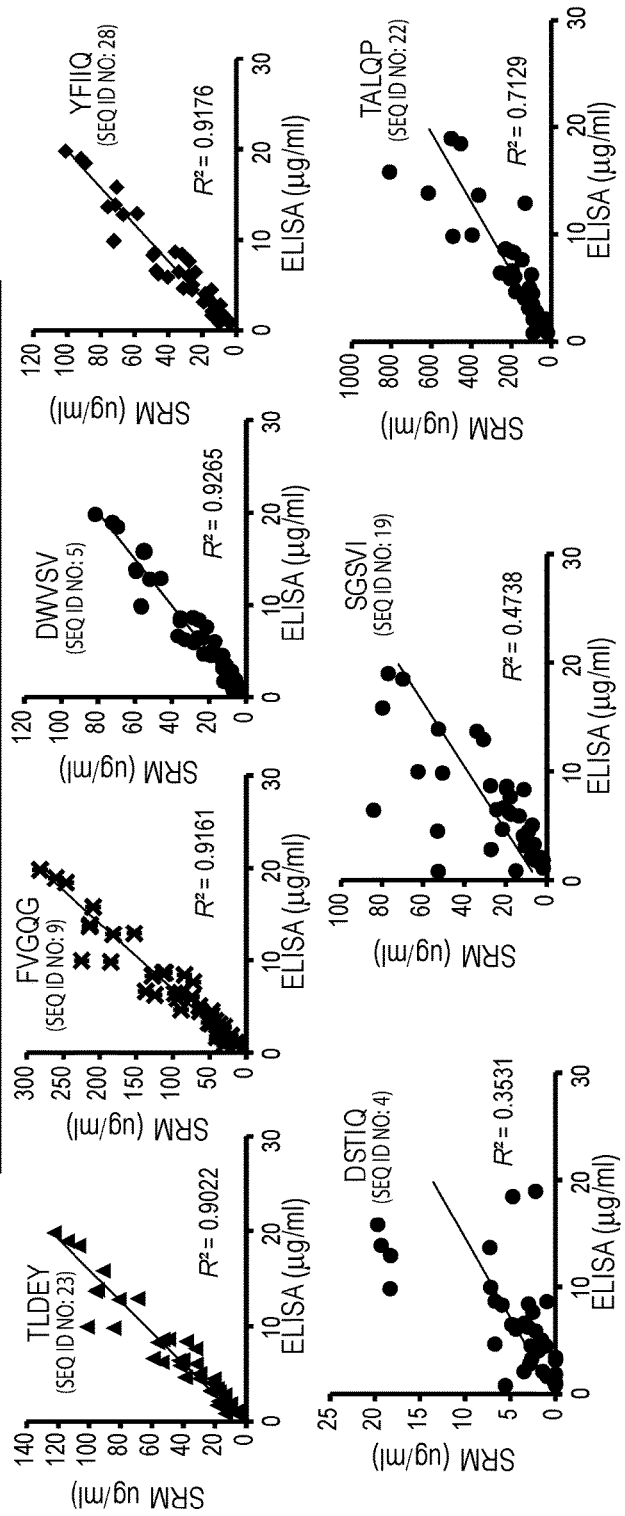
FIG. 3 depicts, in accordance with various embodiments of the present invention, that SRM quantification of the 4 empirically selected uromodulin peptides is internally consistent and correlates with ELISA results. Normalized SRM and ELISA data from 40 urine samples are presented as a correlation matrix.

There was a strong correlation (0.98) between the calculated concentrations of the 4 uromodulin signature peptides (FIG. 3). These results represents a significant improvement over the >0.90 correlations for these peptides observed during the peptide selection phase. This improvement was achieved by normalizing to the SIL internal standards, thereby controlling for variations in peptide recovery. In contrast to the superior results for the empirically selected signature peptides, normalized data for 3 peptides that had been previously selected from shotgun proteomics data correlated poorly with each other ($r^2$ 0.28-0.70) and with the 4 empirically selected peptides ($r^2$ 0.38-0.74). Significantly, there was also a high correlation between the SRM data for the four empirically selected peptides and results from an ELISA assay that had been performed 2 years earlier on the same samples (FIG. 3). These results demonstrate that choosing signature peptides based on experimental results generates more reliable SRM data.

The accuracy of protein quantitation by SRM, SWATH, and other MS techniques is completely dependent upon the selection of appropriate surrogate peptides to represent the protein of interest. Empirically testing a plurality of candidate peptides to identify those with correlated MS signals makes it possible to select peptides that will generate robust data in the real world. Reliance on other popular methods can lead to confounding results because unpredictable factors can interfere with accurate quantitation.

Using a Correlation Matrix to Identify Proteotypic Peptides

In principle, when a protein is completely digested into peptides, the derivative peptides should be present in equimolar amounts. Thus, if one complex biological sample has twice as much of a protein of interest as another, it should, after proteolysis, have twice as much of every derivative peptide. Consequently, in a set of unknown biological samples, the measured amounts of two peptides derived from the same protein should have a linear relationship regardless of the amount of protein in each sample. If the relationship deviates from linearity for any reason, at least one of the peptides is not suitable for determining the concentration of the parent protein.

Figure 4:
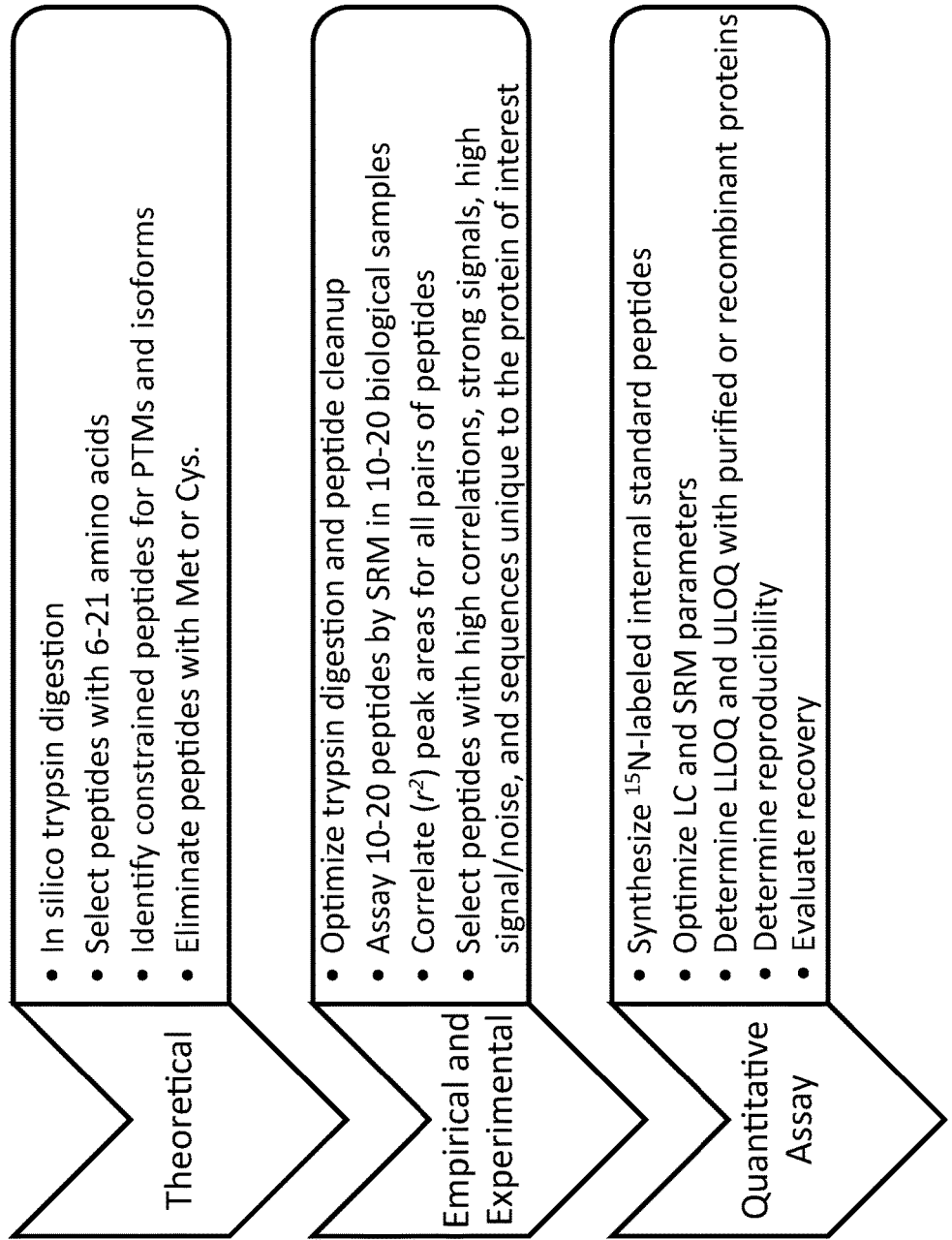
FIG. 4 depicts, in accordance with various embodiments of the present invention, a proposed workflow for empirical peptide selection.

We propose an efficient workflow to select representative peptides for absolute MS quantitation of a target protein (FIG. 4). The process begins by identifying the set of all potential peptides from an amino acid sequence that are within a detectable m/z range. If the goal of the experiment is to monitor a specific PTM, proteolytic cleavage, isoform, or mutation, peptides representing the desired feature must be retained. Otherwise, the initial set can be trimmed by eliminating peptides that are not be present in all forms of the protein to be quantified. Peptides subject to oxidation and other in vitro artifacts should also be eliminated, if possible.

Preliminary SRM assays are designed to target as many peptides as practically possible and then tested in biological samples representative of the milieu that will be used for quantitative assays. If the peptide is readily detected, these preliminary assays don't have to be fully optimized for MS performance or absolute quantitation, and they can be developed using purified protein, enriched protein or native biological samples. The goal is to quickly measure the relative amounts of each peptide in the full range of appropriate biological samples. A coefficient of correlation ($r^2$) is calculated for each pair of peptides and then arranged in a matrix, making it possible to identify a subset of well-behaved peptides that all have relatively high correlation scores with each other. The final signature peptides can then be selected based on practical criteria including signal strength and LC elution time.

There are many potential reasons for the measured amount of a peptide to vary from expectation. Differences in the chemical composition, pH, or ionic strength of the biological matrix can influence proteolysis, peptide stability, aggregation, or ionization in an MS instrument. Oxidation and other artifactual chemical modifications can change the mass of a peptide and thereby interfere with MS detection. Peptide mass can also be affected by unknown PTMs or polymorphisms. In addition, background noise could arise from unknown components in the biological matrix. By following the proposed workflow, peptides with poor correlations can be readily identified using a correlation matrix and then expeditiously eliminated without actually determining precisely why they are unsuitable for quantitation.

Limitations of Previous Peptide Selection Methods

The most important concept arising from this work is that one cannot take shortcuts in peptide selection and expect to be rewarded with a robust assay. A variety of common peptide selection methods were tested and gave wildly inconsistent results. Notably, 14 different uromodulin peptides were ranked among the top three by one or more methods (Table 3; see also Table 4), but none of these "top 3" peptides were included in the empirically derived SRM assay (Table 8). The most commonly recommended peptide, DSTIQVVENGESSQGR (SEQ ID NO: 69), with 6 different endorsements, had a low SRM signal and a relatively low correlation with other uromodulin peptides. Five other top 3 peptides, including two recommended by SRM Atlas, contained methionine residues, which can have a high degree of variability in the percentage of oxidation. Additionally, two top 3 peptides predicted by purely computational methods were not detected on any MS instruments.

Comparing SRM and ELISA Assays

All four uromodulin peptides in our final assay yielded quantitative SRM results comparable to those obtained with an ELISA (FIG. 3). The correlation between different peptides measured by SRM was somewhat higher than the correlation with the ELISA data. This difference may arise because the same tryptic digests were used for all peptides in the SRM assay, whereas the ELISA was performed 2 years earlier (see e.g., Kottgen A, Hwang S J, Larson M G, Van Eyk J E, Fu Q, Benjamin E J, et al. Uromodulin levels associate with a common umod UMOD variant and risk for incident ckd. J Am Soc Nephrol 2010; 21:337-44).

SRM assays have several advantages over ELISAs. Most importantly, ELISAs are completely dependent upon antibodies. It takes a long time to produce antibodies with sufficient affinity and specificity, and their corresponding epitopes may be suboptimal for quantitation due to incomplete accessibility, interferences, or variation between protein forms. These concerns are magnified by the fact that epitopes are not even disclosed for the commercially available ELISA assays targeting uromodulin. Furthermore, SRM assays are more flexible than ELISAs, as they can target multiple peptides including ones that discriminate between isoforms and post-translational modifications.

In conclusion, the empirical peptide selection workflow described in this paper is useful to identify signature peptides for quantitative MS assays that are demonstrably free from unpredictable artifacts that could interfere with accurate and reproducible quantitation.

Example 2 Peptide Selection from SWATH Data

Human aorta tissue was from the Pathobiological Determinants of Atherosclerosis in Youth (PDAY) study, an investigation of atherosclerotic lesions (Pathobiological Determinants of Atherosclerosis in Youth (PDAY) Research Group, Natural history of aortic and coronary atherosclerotic lesions in youth. Findings from the PDAY Study, Arterioscler Thromb. 1993 September; 13(9):1291-8). Proteins from 15 aortas were extracted by grinding with a mortar and pestle in 8M urea, 2M Thiourea, 4% CHAPS and 1% DTT. Samples were diluted to 0.8M urea with 100 mM NH4HCO3 buffer at pH 8.0 and digested overnight with trypsin. After digestion the samples were desalted by solid phase extraction on a 30 mg Oasis® HLB plate.

MS Data Acquisition

Chromatography: Peptides from 4 μg aortic protein were separated on a NanoLC™ 415 System (SCIEX) operating in trap-elute mode at microflow rates. A 0.3×150 cm ChromXP™ column (SCIEX) was used with a short gradient (3-35% solvent B in 60 min, B: 100% ACN, 0.1 formic acid in water) at 5 μL/min (total run time 75 min).

Mass Spectrometry: The MS analysis was performed on a TripleTOF® 6600 system (SCIEX) using a DuoSpray Source with a 25 μm I.D. hybrid electrodes (SCIEX). Variable window SWATH® Acquisition methods were built using Analyst® TF Software 1.7. 100 Q1 window across the mass range (400-1250) isolation for improved data quality through increased specificity. Variable sized Q1 windows optimized based on precursor density further increased specificity while ensuring broad mass range coverage.

Data-Independent Acquisition data analysis: Spectral library generation from data-dependent acquisition MS: Profile-mode .wiff files from shotgun data acquisition were converted to mzML format using the AB Sciex Data Converter (in proteinpilot mode) and then re-converted to mzXML format using ProteoWizard v.3.0.6002 (Kessner et al, 2008) for peaklist generation. The MS2 spectra were queried against the reviewed canonical Swiss-Prot Human complete proteome appended with iRT protein sequence and shuffled sequence decoys (Elias & Gygi, 2007). All data were searched using the X!Tandem Native v.2013.06.15.1, X! Tandem Kscore v.2013.06.15.1 (Craig & Beavis, 2004) and Comet v.2014.02 rev.2 (Eng et al, 2012). The search parameters included the following criteria: static modifications of Carbamidomethyl (C) and variable modifications of Oxidation (M), Phosphorylation (STY). The parent mass tolerance was set to be 50 p.p.m, and mono-isotopic fragment mass tolerance was 100 p.p.m (which was further filtered to be <0.05 Da for building spectral library); tryptic peptides with up to two missed cleavages were allowed. The identified peptides were processed and analyzed through Trans-Proteomic Pipeline v.4.8 (Keller et al, 2005) and was validated using the PeptideProphet (Keller et al, 2002) scoring. The PeptideProphet results were statistically refined using iProphet (Shteynberg et al, 2011). All the peptides were filtered at a false discovery rate (FDR) of 1% with a peptide probability cutoff>=0.99. The raw spectral libraries were generated from all valid peptide spectrum matches and then refined into non-redundant consensus libraries (Collins et al, 2013) using SpectraST v.4.0 (Lam et al, 2007). For each peptide, the retention time was mapped into the iRT space (Escher et al, 2012) with reference to a linear calibration constructed for each shotgun run as previously described (Collins et al, 2013). The MS assays, constructed from the Top six most intense transitions (from ion series: b and y and charge states: 1,2) with Q1 range from 400 to 1,200 m/z excluding the precursor SWATH window, were used for targeted data analysis of SWATH maps.

Targeted data analysis for SWATH-MS: SWATH-MS.wiff files from the data-independent acquisition were first converted to profile mzML using ProteoWizard v.3.0.6002 (Kessner et al, 2008). The whole process of SWATH-targeted data analysis was carried out using OpenSWATH v.2.0.0 (Rost et al, 2014) running on an internal computing cluster. OpenSWATH utilizes a target-decoy scoring system (PyProphet v.0.13.3) such as mProphet to estimate the identification of FDR. The best scoring classifier that was built from the sample of most protein identifications was utilized in this study. Based on our final spectral library, OpenSWATH firstly identified the peak groups from all individual SWATH maps at a global peptide FDR of 1% and aligned them between SWATH maps based on the clustering behaviors of retention time in each run with a non-linear alignment algorithm (Weisser et al, 2013). For this analysis, the MS runs were realigned to each other using LOcally WEighted Scatterplot Smoothing method and the peak group clustering was performed using "LocalMST" method. Specifically, only those peptide peak groups that deviate within 3 standard deviations from the retention time were reported and considered for alignment with the max FDR quality of 5% (quality cutoff to still consider a feature for alignment). Next, to obtain a high-quality quantitative data at the protein level, we discarded those proteins whose peptides were shared between multiple different proteins (non-proteotypic peptides) (Mallick et al, 2007). Quantitative peptide and protein level summary outputs were then used for all downstream biological analysis.

Selection of Highly-Correlated Signature Peptides

Transition Selection.

Prism software was used to calculate coefficients of determination between all possible pairs of the six transitions for each peptide. A correlation matrix was constructed, and the mean correlation for each peptide was calculated. Correlations were generally $r^2$>0.85. Any transition with a mean correlation 10% below the average mean for all transitions of the peptide was discarded. If any transitions were discarded, a revised correlation matrix was constructed and the mean correlations were recalculated.

Transitions were also ranked by mean peak area. The transition with the highest mean peak area was selected as the signature transition for the peptide if its mean correlation was within 5% of the highest mean correlation. If not, the transition having the highest peak area and also having a mean correlation within 5% of the highest mean correlation was selected.

Correlation Matrix Analysis.

A separate correlation matrix was created for each protein of interest. All quantifiable peptides derived from the protein were represented by the peak area from a single signature transition. Prism software was used to calculate coefficients of determination between all possible peptide pairs. The correlation data was transferred to a Microsoft Excel spreadsheet, and an average correlation was determined for each peptide.

Peptide Selection for Serum Albumin.

Serum albumin was selected as an exemplary protein to investigate the versatility of the peptide selection methodology because it is well studied in quantitative SRM assays. The PDAY SWATH dataset contains quantified peaks from 63 serum albumin peptides. Table 12 presents a truncated version of a 63×63 matrix of pairwise correlations between these peptides. Columns 5-9 show pairwise correlations for 5 exemplary peptides. Column 10 shows the average of pairwise correlations between the peptide shown in column 2 and the other 62 peptides.

TABLE 12

| Peak Area | Peptide sequence[a] | Frag z | Ion | QTALV (SEQ ID NO: 293) | LVNEV (SEQ ID NO: 294) | VFDEF (SEQ ID NO: 295) | LVAAS (SEQ ID NO: 296) | DDNPN (SEQ ID NO: 297) | Ave $r^2$ |
|---|---|---|---|---|---|---|---|---|---|
| 218306 | QTALVELVK (SEQ ID NO: 83) | 2 | y5 | | 0.958 | 0.941 | 0.933 | 0.916 | 0.937 |
| 136844 | SHC(CAM)IAEVENDEM(Ox)PADLPSLAADFVESK (SEQ ID NO: 298) | 3 | b3 | 0.979 | 0.912 | 0.945 | 0.879 | 0.866 | 0.916 |
| 739992 | LVNEVTEFAK (SEQ ID NO: 85) | 2 | y8 | 0.958 | | 0.905 | 0.906 | 0.934 | 0.926 |
| 441926 | RPC(CAM)FSALEVDETYVPK (SEQ ID NO: 299) | 3 | b6 | 0.950 | 0.903 | 0.932 | 0.888 | 0.860 | 0.907 |
| 114067 | SHC(CAM)IAEVENDEMPADLPSLAADFVESK (SEQ ID NO: 300) | 3 | y11 | 0.957 | 0.904 | 0.936 | 0.823 | 0.851 | 0.894 |
| 366357 | VFDEFKPLVEEPQNLIK (SEQ ID NO: 87) | 3 | y6 | 0.941 | 0.905 | | | 0.859 | 0.895 |
| 98707 | QNC(CAM)ELFEQLGEYK (SEQ ID NO: 301) | 2 | y4 | 0.935 | 0.942 | 0.899 | 0.906 | 0.899 | 0.916 |
| 238541 | AVMDDFAAFVEK (SEQ ID NO: 89) | 2 | y9 | 0.951 | 0.878 | 0.922 | 0.862 | 0.834 | 0.890 |
| 56772 | RMPC(CAM)AEDYLSVVLNQLC(CAM)VLHEK (SEQ ID NO: 302) | 4 | b7 | 0.946 | 0.879 | 0.868 | 0.921 | 0.880 | 0.899 |
| 21997 | KQTALVELVK (SEQ ID NO: 91) | 2 | y8 | 0.912 | 0.933 | 0.855 | 0.847 | 0.923 | 0.894 |
| 28179 | VHTEC(CAM)C(CAM)HGDLLEC(CAM)ADDR (SEQ ID NO: 303) | 4 | y4 | 0.913 | 0.944 | 0.910 | 0.850 | 0.944 | 0.912 |
| 419165 | LC(CAM)TVATLR (SEQ ID NO: 304) | 2 | y6 | 0.890 | 0.900 | 0.940 | 0.860 | 0.855 | 0.889 |
| 282837 | LVRPEVDVMC(CAM)TAFHDNEETFLKK (SEQ ID NO: 305) | 4 | b7 | 0.949 | 0.882 | 0.869 | 0.813 | 0.806 | 0.864 |
| 7661 | EC(CAM)C(CAM)EKPLLEK (SEQ ID NO: 306) | 3 | y5 | 0.943 | 0.946 | 0.838 | 0.848 | 0.898 | 0.895 |
| 53763 | LVAASQAALGL (SEQ ID NO: 96) | 2 | b8 | 0.933 | 0.906 | 0.859 | | 0.927 | 0.906 |
| 116552 | DDNPNLPR (SEQ ID NO: 97) | 2 | y5 | 0.916 | 0.934 | 0.876 | 0.927 | | 0.913 |
| 501275 | FQNALLVR (SEQ ID NO: 98) | 2 | y6 | 0.918 | 0.950 | 0.842 | 0.850 | 0.869 | 0.886 |
| 19645 | VPQVSTPTLVEVSR (SEQ ID NO: 99) | 2 | y8 | 0.920 | 0.971 | 0.841 | 0.865 | 0.897 | 0.899 |
| 18838 | RHPYFYAPELLFFAK (SEQ ID NO: 100) | 3 | b5 | 0.918 | 0.886 | 0.831 | 0.796 | 0.783 | 0.843 |
| 243203 | AEFAEVSK (SEQ ID NO: 101) | 2 | y6 | 0.883 | 0.875 | 0.902 | 0.857 | 0.884 | 0.880 |
| 69408 | SLHTLFGDK (SEQ ID NO: 102) | 2 | y7 | 0.866 | 0.918 | 0.911 | 0.809 | 0.858 | 0.873 |
| 14853 | LVRPEVDVM(Ox)C(CAM)T(p)AFHDNEETFLKK (SEQ ID NO: 307) | 5 | b7 | 0.903 | 0.837 | 0.888 | 0.859 | 0.868 | 0.871 |
| 7550 | RMPC(CAM)AEDY(p)LSVVLNQLC(CAM)VLHEK (SEQ ID NO: 308) | 4 | y3 | 0.880 | 0.923 | 0.811 | 0.897 | 0.930 | 0.888 |

TABLE 12-continued

| Peak Area | Peptide sequence[a] | z | Frag Ion | QTALV (SEQ ID NO: 293) | LVNEV (SEQ ID NO: 294) | VFDEF (SEQ ID NO: 295) | LVAAS (SEQ ID NO: 296) | DDNPN (SEQ ID NO: 297) | Ave $r^2$ |
|---|---|---|---|---|---|---|---|---|---|
| 368829 | KVPQVSTPTLVEVSR (SEQ ID NO: 103) | 3 | y4 | 0.894 | 0.888 | 0.923 | 0.739 | 0.777 | 0.844 |
| 2716 | KYLYEIAR (SEQ ID NO: 104) | 2 | y6 | 0.885 | 0.896 | 0.902 | 0.832 | 0.865 | 0.876 |
| 131057 | TYETTLEK (SEQ ID NO: 105) | 2 | y6 | 0.889 | 0.921 | 0.821 | 0.877 | 0.953 | 0.892 |
| 227882 | RHPDYSVVLLLR (SEQ ID NO: 106) | 3 | y5 | 0.904 | 0.877 | 0.820 | 0.780 | 0.716 | 0.819 |
| 15226 | HPDYSVVLLLR (SEQ ID NO: 107) | 3 | y4 | 0.877 | 0.849 | 0.886 | 0.928 | 0.842 | 0.876 |
| 4327 | KLVAASQAALGL (SEQ ID NO: 108) | 2 | b9 | 0.897 | 0.831 | 0.894 | 0.744 | 0.726 | 0.818 |
| 191879 | LVRPEVDVMC(CAM)TAFHDNE ETFLK (SEQ ID NO: 309) | 4 | b7 | 0.862 | 0.793 | 0.914 | 0.806 | 0.737 | 0.822 |
| 65813 | FKDLGEENFK (SEQ ID NO: 110) | 3 | y4 | 0.857 | 0.874 | 0.945 | 0.808 | 0.841 | 0.865 |
| 206640 | YLYEIAR (SEQ ID NO: 111) | 2 | y5 | 0.878 | 0.830 | 0.901 | 0.752 | 0.725 | 0.817 |
| 38305 | VHTEC(CAM)C(CAM)HGDLLE C(CAM)ADDRADLAK (SEQ ID NO: 310) | 5 | b9 | 0.840 | 0.776 | 0.919 | 0.844 | 0.850 | 0.846 |
| 4685 | NEC(CAM)FLQHKDDNPNLPR (SEQ ID NO: 311) | 4 | y3 | 0.855 | 0.779 | 0.853 | 0.804 | 0.806 | 0.820 |
| 21573 | AAFTEC(CAM)C(CAM)QAADK (SEQ ID NO: 312) | 2 | y7 | 0.821 | 0.866 | 0.807 | 0.816 | 0.891 | 0.840 |
| 17678 | ETYGEMADC(CAM)C(CAM)AK (SEQ ID NO: 313) | 2 | y7 | 0.826 | 0.773 | 0.897 | 0.773 | 0.790 | 0.812 |
| 7105 | QEPERNEC(CAM)FLQHKDDNP NLPR (SEQ ID NO: 314) | 5 | y4 | 0.858 | 0.798 | 0.858 | 0.878 | 0.892 | 0.857 |
| 22522 | YIC(CAM)ENQDSISSK (SEQ ID NO: 315) | 2 | y10 | 0.823 | 0.872 | 0.797 | 0.823 | 0.939 | 0.851 |
| 1836 | ADDKETC(CAM)FAEEGK (SEQ ID NO: 316) | 3 | y5 | 0.827 | 0.891 | 0.779 | 0.813 | 0.953 | 0.853 |
| 2995 | NEC(CAM)FLQHK (SEQ ID NO: 317) | 2 | y6 | 0.821 | 0.903 | 0.780 | 0.833 | 0.831 | 0.834 |
| 35989 | C(CAM)C(CAM)TESLVNR (SEQ ID NO: 318) | 2 | y7 | 0.801 | 0.797 | 0.753 | 0.819 | 0.808 | 0.795 |
| 30991 | LAKT(p)Y(p)ET(p)TLEKC(CAM) C(CAM)AAADPHEC(CAM)YAK (SEQ ID NO: 319) | 4 | y7 | 0.786 | 0.737 | 0.871 | 0.759 | 0.788 | 0.788 |
| 41379 | M(Ox)PC(CAM)AEDYLSVVLNQ LC(CAM)VLHEK (SEQ ID NO: 320) | 3 | y3 | 0.822 | 0.782 | 0.703 | 0.769 | 0.648 | 0.745 |
| 41376 | MPC(CAM)AEDYLSVVLNQL C(CAM)VLHEK (SEQ ID NO: 321) | 3 | y3 | 0.821 | 0.780 | 0.702 | 0.768 | 0.646 | 0.743 |
| 5762 | HPYFYAPELLFFAK (SEQ ID NO: 123) | 3 | b4 | 0.780 | 0.758 | 0.772 | 0.691 | 0.614 | 0.723 |

TABLE 12-continued

| Peak Area | Peptide sequence[a] | z | Frag Ion | QTALV (SEQ ID NO: 293) | LVNEV (SEQ ID NO: 294) | VFDEF (SEQ ID NO: 295) | LVAAS (SEQ ID NO: 296) | DDNPN (SEQ ID NO: 297) | Ave $r^2$ |
|---|---|---|---|---|---|---|---|---|---|
| 3066 | SLHTLFGDKLC(CAM)TVATLR (SEQ ID NO: 322) | 4 | y4 | 0.772 | 0.769 | 0.639 | 0.879 | 0.819 | 0.776 |
| 21003 | LKEC(CAM)C(CAM)EKPLLEK (SEQ ID NO: 323) | 3 | y5 | 0.740 | 0.830 | 0.650 | 0.745 | 0.882 | 0.769 |
| 3262 | ETYGEM(Ox)ADC(CAM)C(CAM)AK (SEQ ID NO: 324) | 2 | y6 | 0.753 | 0.749 | 0.851 | 0.714 | 0.795 | 0.772 |
| 37325 | ALVLIAFAQYLQQC(CAM)PFEDHVK (SEQ ID NO: 325) | 3 | y7 | 0.747 | 0.637 | 0.745 | 0.563 | 0.464 | 0.631 |
| 6779 | ADDKETC(CAM)FAEEGKK (SEQ ID NO: 326) | 4 | y6 | 0.729 | 0.671 | 0.749 | 0.775 | 0.712 | 0.727 |
| 35973 | EFNAETFTFHADIC(CAM)TLSEK (SEQ ID NO: 327) | 3 | y9 | 0.720 | 0.631 | 0.743 | 0.595 | 0.532 | 0.644 |
| 54535 | DVFLGMFLYEYAR (SEQ ID NO: 129) | 2 | y9 | 0.715 | 0.580 | 0.737 | 0.557 | 0.459 | 0.609 |
| 4731 | LDELRDEGK (SEQ ID NO: 130) | 2 | b6 | 0.657 | 0.627 | 0.688 | 0.630 | 0.652 | 0.651 |
| 7212 | C(CAM)C(CAM)AAADPHEC(CAM)YAK (SEQ ID NO: 328) | 3 | y7 | 0.677 | 0.600 | 0.685 | 0.663 | 0.618 | 0.649 |
| 2732 | RM(Ox)PC(CAM)AEDYLSVVLNQLC(CAM)VLHEK (SEQ ID NO: 329) | 4 | b7 | 0.589 | 0.651 | 0.420 | 0.605 | 0.564 | 0.566 |
| 4755 | LVRPEVDVM(Ox)C(CAM)TAFHDNEETFLK (SEQ ID NO: 330) | 4 | b7 | 0.516 | 0.594 | 0.414 | 0.505 | 0.436 | 0.493 |
| 6271 | S(p)HC(CAM)IAEVENDEM(Ox)PADLPSLAADFVESK (SEQ ID NO: 331) | 4 | y7 | 0.536 | 0.459 | 0.577 | 0.262 | 0.247 | 0.416 |
| 5672 | AVM(Ox)DDFAAFVEK (SEQ ID NO: 332) | 2 | y4 | 0.463 | 0.562 | 0.314 | 0.518 | 0.456 | 0.463 |
| 1422 | NYAEAKDVFLGMFLYEYAR (SEQ ID NO: 132) | 3 | y5 | 0.454 | 0.495 | 0.398 | 0.320 | 0.482 | 0.430 |
| 4000 | LVRPEVDVM(Ox)C(CAM)TAFHDNEETFLKK (SEQ ID NO: 333) | 5 | b7 | 0.426 | 0.489 | 0.280 | 0.464 | 0.342 | 0.400 |
| 5581 | TC(CAM)VADESAENC(CAM)DK (SEQ ID NO: 334) | 2 | y10 | 0.389 | 0.391 | 0.451 | 0.288 | 0.395 | 0.383 |
| 4571 | DVFLGM(Ox)FLYEYAR (SEQ ID NO: 335) | 2 | b3 | 0.372 | 0.352 | 0.284 | 0.299 | 0.123 | 0.286 |
| 3171 | EFNAETFTFHADIC(CAM)TLSEKER (SEQ ID NO: 336) | 4 | y5 | 0.322 | 0.182 | 0.175 | 0.447 | 0.386 | 0.302 |
| | Average coefficient of determination ($r^2$) | | | 0.799 | 0.784 | 0.771 | 0.751 | 0.748 | |

[a] Abbreviations: z, charge; (CAM), Carbamidomethylated; (Ox), Oxidized; (P), Phosphorylated Peptides containing methionine residues, missed cleavages, and/or phosphorylations were excluded, resulting in a 26×26 matrix of pairwise correlations. The peptides in this matrix were sorted again by the average of their correlations. Table 13 presents a truncated version of this matrix.

TABLE 13

| Average Peak Area | Peptide sequence[a] | Frag z Ion | QTALV (SEQ ID NO: 293) | LVNEV (SEQ ID NO: 294) | VFDEF (SEQ ID NO: 295) | DDNPN (SEQ ID NO: 297) | FQNAL (SEQ ID NO: 337) | LVAAS (SEQ ID NO: 296) | SLHTL (SEQ ID NO: 338) | AEFAE (SEQ ID NO: 339) | Ave $r^2$ |
|---|---|---|---|---|---|---|---|---|---|---|---|
| 218306 | QTALVELVK (SEQ ID NO: 83) | 2 y5 |  | 0.958 | 0.941 | 0.916 | 0.918 | 0.933 | 0.866 | 0.883 | 0.848 |
| 739992 | LVNEVTEFAK (SEQ ID NO: 85) | 2 y8 | 0.958 |  | 0.905 | 0.934 | 0.950 | 0.906 | 0.918 | 0.875 | 0.844 |
| 366357 | VFDEFKPLVEEPQNLIK (SEQ ID NO: 87) | 3 y6 | 0.941 | 0.905 |  | 0.876 | 0.842 | 0.859 | 0.911 | 0.902 | 0.829 |
| 98707 | QNC(CAM)ELFEQLGEYK (SEQ ID NO: 301) | 2 y4 | 0.935 | 0.942 | 0.899 | 0.899 | 0.920 | 0.906 | 0.895 | 0.794 | 0.822 |
| 28179 | VHTEC(CAM)C(CAM)HGDLLEC(CAM)ADDR (SEQ ID NO: 303) | 4 y4 | 0.913 | 0.944 | 0.910 | 0.944 | 0.905 | 0.850 | 0.896 | 0.905 | 0.821 |
| 441926 | RPC(CAM)FSALEVDETYVPK (SEQ ID NO: 299) | 3 b6 | 0.950 | 0.903 | 0.932 | 0.860 | 0.896 | 0.888 | 0.883 | 0.927 | 0.817 |
| 419165 | LC(CAM)TVATLR (SEQ ID NO: 304) | 2 y6 | 0.890 | 0.900 | 0.940 | 0.855 | 0.868 | 0.860 | 0.946 | 0.886 | 0.811 |
| 116552 | DDNPNLPR (SEQ ID NO: 97) | 2 y5 | 0.916 | 0.934 | 0.876 |  | 0.869 | 0.927 | 0.858 | 0.884 | 0.809 |
| 501275 | FQNALLVR (SEQ ID NO: 98) | 2 y6 | 0.918 | 0.950 | 0.842 | 0.869 |  | 0.850 | 0.865 | 0.821 | 0.806 |
| 19645 | VPQVSTPTLVEVSR (SEQ ID NO: 99) | 2 y8 | 0.920 | 0.971 | 0.841 | 0.897 | 0.960 | 0.865 | 0.855 | 0.843 | 0.803 |
| 53763 | LVAASQAALGL (SEQ ID NO: 96) | 2 b8 | 0.933 | 0.906 | 0.859 | 0.927 | 0.850 |  | 0.809 | 0.857 | 0.800 |
| 7661 | EC(CAM)C(CAM)EKPLLEK (SEQ ID NO: 306) | 3 y5 | 0.943 | 0.946 | 0.838 | 0.898 | 0.935 | 0.848 | 0.810 | 0.823 | 0.800 |
| 69408 | SLHTLFGDK (SEQ ID NO: 102) | 2 y7 | 0.866 | 0.918 | 0.911 | 0.858 | 0.865 | 0.809 |  | 0.853 | 0.794 |
| 243203 | AEFAEVSK (SEQ ID NO: 101) | 2 y6 | 0.883 | 0.875 | 0.902 | 0.884 | 0.821 | 0.857 | 0.853 |  | 0.790 |
| 131057 | TYETTLEK (SEQ ID NO: 105) | 2 y6 | 0.889 | 0.921 | 0.821 | 0.953 | 0.927 | 0.877 | 0.805 | 0.830 | 0.786 |
| 15226 | HPDYSVVLLLR (SEQ ID NO: 107) | 3 y4 | 0.877 | 0.849 | 0.886 | 0.842 | 0.800 | 0.928 | 0.864 | 0.776 | 0.770 |
| 21573 | AAFTEC(CAM)C(CAM)QAADK (SEQ ID NO: 312) | 2 y7 | 0.821 | 0.866 | 0.807 | 0.891 | 0.833 | 0.816 | 0.811 | 0.900 | 0.760 |
| 22522 | YIC(CAM)ENQDSISSK (SEQ ID NO: 315) | 2 y10 | 0.823 | 0.872 | 0.797 | 0.939 | 0.838 | 0.823 | 0.818 | 0.829 | 0.755 |
| 206640 | YLYEIAR (SEQ ID NO: 111) | 2 y5 | 0.878 | 0.830 | 0.901 | 0.725 | 0.817 | 0.752 | 0.789 | 0.835 | 0.743 |
| 2995 | NEC(CAM)FLQHK (SEQ ID NO: 317) | 2 y6 | 0.821 | 0.903 | 0.780 | 0.831 | 0.828 | 0.833 | 0.825 | 0.669 | 0.737 |
| 35989 | C(CAM)C(CAM)TESLVNR (SEQ ID NO: 318) | 2 y7 | 0.801 | 0.797 | 0.753 | 0.808 | 0.668 | 0.819 | 0.729 | 0.726 | 0.703 |
| 5762 | HPYFYAPELLFFAK (SEQ ID NO: 123) | 3 b4 | 0.780 | 0.758 | 0.772 | 0.614 | 0.820 | 0.691 | 0.769 | 0.586 | 0.676 |

TABLE 13-continued

| Average Peak Area | Peptide sequence[a] | Frag z Ion | QTALV (SEQ ID NO: 293) | LVNEV (SEQ ID NO: 294) | VFDEF (SEQ ID NO: 295) | DDNPN (SEQ ID NO: 297) | FQNAL (SEQ ID NO: 337) | LVAAS (SEQ ID NO: 296) | SLHTL (SEQ ID NO: 338) | AEFAE (SEQ ID NO: 339) | Ave $r^2$ |
|---|---|---|---|---|---|---|---|---|---|---|---|
| 35973 | EFNAETFTFHADIC(CAM)TLSEK (SEQ ID NO: 327) | 3 y9 | 0.720 | 0.631 | 0.743 | 0.532 | 0.571 | 0.595 | 0.656 | 0.597 | 0.596 |
| 37325 | ALVLIAFAQYLQQC(CAM)PFEDHVK (SEQ ID NO: 325) | 3 y7 | 0.747 | 0.637 | 0.745 | 0.464 | 0.623 | 0.563 | 0.626 | 0.608 | 0.587 |
| 7212 | C(CAM)C(CAM)AAADPHEC(CAM)YAK (SEQ ID NO: 328) | 3 y7 | 0.677 | 0.600 | 0.685 | 0.618 | 0.447 | 0.663 | 0.539 | 0.677 | 0.555 |
| 5581 | TC(CAM)VADESAENC(CAM)DK (SEQ ID NO: 334) | 2 y10 | 0.389 | 0.391 | 0.451 | 0.395 | 0.381 | 0.288 | 0.264 | 0.468 | 0.355 |
| Average coefficient of determination ($r^2$) | | | 0.848 | 0.844 | 0.829 | 0.809 | 0.806 | 0.800 | 0.794 | 0.790 | |

[a] Abbreviations: z, charge; (CAM), Carbamidomethylated; (Ox), Oxidized; (P), Phosphorylated Next, an iterative process was employed to remove peptides with low correlations. The peptide with the lowest average correlation was excluded. Then, the correlation matrix was resorted. This was repeated 6 times until the lowest average correlation was >0.78. After each poorly correlated peptide was removed from the matrix, the average correlations for the remaining peptides increased. Table 14 presents a portion of the data from this matrix.

TABLE 14

| Peak Area | Peptide sequence[a] | Frag z Ion | LVNEV (SEQ ID NO: 294) | QTALV (SEQ ID NO: 293) | DDNPN (SEQ ID NO: 297) | FQNAL (SEQ ID NO: 337) | VFDEF (SEQ ID NO: 295) | LVAAS (SEQ ID NO: 296) | SLHTL (SEQ ID NO: 338) | AEFAE (SEQ ID NO: 339) | Ave $r^2$ |
|---|---|---|---|---|---|---|---|---|---|---|---|
| 739992 | LVNEVTEFAK (SEQ ID NO: 85) | 2 y8 | | 0.958 | 0.934 | 0.950 | 0.905 | 0.906 | 0.918 | 0.875 | 0.910 |
| 218306 | QTALVELVK (SEQ ID NO: 83) | 2 y5 | 0.958 | | 0.916 | 0.918 | 0.941 | 0.933 | 0.866 | 0.883 | 0.899 |
| 28179 | VHTEC(CAM)C(CAM)HGDLLEC(CAM)ADDR (SEQ ID NO: 303) | 4 y4 | 0.944 | 0.913 | 0.944 | 0.905 | 0.910 | 0.850 | 0.896 | 0.905 | 0.895 |
| 116552 | DDNPNLPR (SEQ ID NO: 97) | 2 y5 | 0.934 | 0.916 | | 0.869 | 0.876 | 0.927 | 0.858 | 0.884 | 0.884 |
| 19645 | VPQVSTPTLVEVSR (SEQ ID NO: 99) | 2 y8 | 0.971 | 0.920 | 0.897 | 0.960 | 0.841 | 0.865 | 0.855 | 0.843 | 0.881 |
| 98707 | QNC(CAM)ELFEQLGEYK (SEQ ID NO: 301) | 2 y4 | 0.942 | 0.935 | 0.899 | 0.920 | 0.899 | 0.906 | 0.895 | 0.794 | 0.880 |
| 501275 | FQNALLVR (SEQ ID NO: 98) | 2 y6 | 0.950 | 0.918 | 0.869 | | 0.842 | 0.850 | 0.865 | 0.821 | 0.876 |
| 366357 | VFDEFKPLVEEPQNLIK (SEQ ID NO: 87) | 3 y6 | 0.905 | 0.941 | 0.876 | 0.842 | | 0.859 | 0.911 | 0.902 | 0.873 |
| 441926 | RPC(CAM)FSALEVDETYVPK (SEQ ID NO: 299) | 3 b6 | 0.903 | 0.950 | 0.860 | 0.896 | 0.932 | 0.888 | 0.883 | 0.927 | 0.871 |
| 131057 | TYETTLEK (SEQ ID NO: 105) | 2 y6 | 0.921 | 0.889 | 0.953 | 0.927 | 0.821 | 0.877 | 0.805 | 0.830 | 0.871 |
| 419165 | LC(CAM)TVATLR (SEQ ID NO: 304) | 2 y6 | 0.900 | 0.890 | 0.855 | 0.868 | 0.940 | 0.860 | 0.946 | 0.886 | 0.871 |
| 7661 | EC(CAM)C(CAM)EKPLLEK (SEQ ID NO: 306) | 3 y5 | 0.946 | 0.943 | 0.898 | 0.935 | 0.838 | 0.848 | 0.810 | 0.823 | 0.866 |
| 53763 | LVAASQAALGL (SEQ ID NO: 96) | 2 b8 | 0.906 | 0.933 | 0.927 | 0.850 | 0.859 | | 0.809 | 0.857 | 0.862 |
| 69408 | SLHTLFGDK (SEQ ID NO: 102) | 2 y7 | 0.918 | 0.866 | 0.858 | 0.865 | 0.911 | 0.809 | | 0.853 | 0.857 |

TABLE 14-continued

| Peak Area | Peptide sequence[a] | Frag z Ion | LVNEV (SEQ ID NO: 294) | QTALV (SEQ ID NO: 293) | DDNPN (SEQ ID NO: 297) | FQNAL (SEQ ID NO: 337) | VFDEF (SEQ ID NO: 295) | LVAAS (SEQ ID NO: 296) | SLHTL (SEQ ID NO: 338) | AEFAE (SEQ ID NO: 339) | Ave $r^2$ |
|---|---|---|---|---|---|---|---|---|---|---|---|
| 243203 | AEFAEVSK (SEQ ID NO: 101) | 2 y6 | 0.875 | 0.883 | 0.884 | 0.821 | 0.902 | 0.857 | 0.853 | | 0.847 |
| 22522 | YIC(CAM)ENQDSISSK (SEQ ID NO: 315) | 2 y10 | 0.872 | 0.823 | 0.939 | 0.838 | 0.797 | 0.823 | 0.818 | 0.829 | 0.834 |
| 21573 | AAFTEC(CAM)C(CAM)QAADK (SEQ ID NO: 312) | 2 y7 | 0.866 | 0.821 | 0.891 | 0.833 | 0.807 | 0.816 | 0.811 | 0.900 | 0.827 |
| 15226 | HPDYSVVLLLR (SEQ ID NO: 107) | 3 y4 | 0.849 | 0.877 | 0.842 | 0.800 | 0.886 | 0.928 | 0.864 | 0.776 | 0.818 |
| 2995 | NEC(CAM)FLQHK (SEQ ID NO: 317) | 2 y6 | 0.903 | 0.821 | 0.831 | 0.828 | 0.780 | 0.833 | 0.825 | 0.669 | 0.804 |
| 206640 | YLYEIAR (SEQ ID NO: 111) | 2 y5 | 0.830 | 0.878 | 0.725 | 0.817 | 0.901 | 0.752 | 0.789 | 0.835 | 0.780 |
| | Average coefficient of determination ($r^2$) | | 0.910 | 0.899 | 0.884 | 0.876 | 0.873 | 0.862 | 0.857 | 0.847 | |

[a]Abbreviations: z, charge; (CAM), Carbamidomethylated; (Ox), Oxidized; (P), Phosphorylated The final matrix of pairwise correlations between serum albumin peptides (Table 15) was created by excluding 10 additional peptides that contained cysteine residues and/or had an average peak area of <20,000.

TABLE 15

| Peak Area | Peptide sequence[a] | Frag z Ion | LVNEV (SEQ ID NO: 294) | QTALV (SEQ ID NO: 293) | VFDEF (SEQ ID NO: 295) | DDNPN (SEQ ID NO: 297) | FQNAL (SEQ ID NO: 337) | LVAAS (SEQ ID NO: 296) | AEFAE (SEQ ID NO: 339) | TYETT (SEQ ID NO: 340) | SLHTL (SEQ ID NO: 338) | YLYEI (SEQ ID NO: 341) | Ave $r^2$ |
|---|---|---|---|---|---|---|---|---|---|---|---|---|---|
| 739992 | LVNEVTEFAK (SEQ ID NO: 85) | 2 y8 | | 0.958 | 0.905 | 0.934 | 0.950 | 0.906 | 0.875 | 0.921 | 0.918 | 0.830 | 0.911 |
| 218306 | QTALVELVK (SEQ ID NO: 83) | 2 y5 | 0.958 | | 0.941 | 0.916 | 0.918 | 0.933 | 0.883 | 0.889 | 0.866 | 0.878 | 0.909 |
| 366357 | VFDEFKPLVEEPQNLIK (SEQ ID NO: 87) | 3 y6 | 0.905 | 0.941 | | 0.876 | 0.842 | 0.859 | 0.902 | 0.821 | 0.911 | 0.901 | 0.884 |
| 116552 | DDNPNLPR (SEQ ID NO: 97) | 2 y5 | 0.934 | 0.916 | 0.876 | | 0.869 | 0.927 | 0.884 | 0.953 | 0.858 | 0.725 | 0.883 |
| 501275 | FQNALLVR (SEQ ID NO: 98) | 2 y6 | 0.950 | 0.918 | 0.842 | 0.869 | | 0.850 | 0.821 | 0.927 | 0.865 | 0.817 | 0.873 |
| 53763 | LVAASQAALGL (SEQ ID NO: 96) | 2 b8 | 0.906 | 0.933 | 0.859 | 0.927 | 0.850 | | 0.857 | 0.877 | 0.809 | 0.752 | 0.863 |
| 243203 | AEFAEVSK (SEQ ID NO: 101) | 2 y6 | 0.875 | 0.883 | 0.902 | 0.884 | 0.821 | 0.857 | | 0.830 | 0.853 | 0.835 | 0.860 |
| 131057 | TYETTLEK (SEQ ID NO: 105) | 2 y6 | 0.921 | 0.889 | 0.821 | 0.953 | 0.927 | 0.877 | 0.830 | | 0.805 | 0.711 | 0.859 |
| 69408 | SLHTLFGDK (SEQ ID NO: 102) | 2 y7 | 0.918 | 0.866 | 0.911 | 0.858 | 0.865 | 0.809 | 0.853 | 0.805 | | 0.789 | 0.853 |
| 206640 | YLYEIAR (SEQ ID NO: 111) | 2 y5 | 0.830 | 0.878 | 0.901 | 0.725 | 0.817 | 0.752 | 0.835 | 0.711 | 0.789 | | 0.804 |
| | Average coefficient of determination ($r^2$) | | 0.911 | 0.909 | 0.884 | 0.883 | 0.873 | 0.863 | 0.860 | 0.859 | 0.853 | 0.804 | |

[a]Abbreviations: z, charge; (CAM) and *, Carbamidomethylated; (Ox) and $^{Ox}$, Oxidized; (P) and $^{P}$, Phosphorylated As undesirable and poorly correlated peptides were progressively excluded, the percentage of correlations with $r^2 > 0.85$ increased from 21.4% to 72.2%. Additional metrics showing increased correlations throughout the peptide selection process are presented in Table 16.

TABLE 16

| | All Peptides | Remove Miscleaved and Met$^{Ox}$ | Remove $r^2 < 0.78$ | Remove Cys and Peak < 20,000 |
|---|---|---|---|---|
| Peptides | 63 | 26 | 20 | 10 |
| Total correlations | 1953 | 325 | 190 | 45 |
| $r^2 > 0.90$ (%) | 9.2 | 18.5 | 31.6 | 37.8 |
| $r^2 > 0.85$ (%) | 21.4 | 35.1 | 58.9 | 72.2 |
| Highest mean $r^2$ | 0.799 | 0.848 | 0.910 | 0.911 |
| Lowest mean $r^2$ | 0.218 | 0.355 | 0.780 | 0.804 |

Validation of the Serum Albumin Signature Peptides.

The resulting collection of 10 serum albumin signature peptides was compared with results from previously validated SRM assays.

Two of the peptides, LVNEVTEFAK (SEQ ID NO: 85) and DDNPNLPR (SEQ ID NO: 97), were targeted in the SRM assays on 42 urine samples described in Example 1. Three transitions were monitored for each peptide. The assay included SIL peptide internal standards corresponding to the two serum albumin peptides. The correlation between normalized peak areas of the two serum albumin peptides was >98%, regardless of which transitions were compared.

Beasley-Green and colleagues selected 11 serum albumin peptides on the basis of retention time reproducibility, peak intensity, and the degree of sequence coverage. They built an SRM assay with SIL internal standards that targeted two transitions for each peptide. The linearity, precision, repeatability and accuracy of this SRM assay were extensively validated.

Eight out of the 10 highly correlated signature peptides shown in Table 15 were also targeted in Beasley-Green's SRM assay (Table 17). Two of the three Beasley-Green peptides that are not also found in Table 15 contain a cysteine amino acid residue. The third was not among the 63 quantifiable peptides in the PDAY SWATH data. The two Table 15 peptides that were also not targeted by Beasley-Green had the second and third lowest peak areas among Table 15 peptides.

TABLE 17

| Highly-correlated signature peptides | Beasley-Green signature peptides |
|---|---|
| LVNEVTEFAK (SEQ ID NO: 85) | LVNEVTEFAK (SEQ ID NO: 85) |
| QTALVELVK (SEQ ID NO: 83) | QTALVELVK (SEQ ID NO: 83) |
| VFDEFKPLVEEPQNLIK (SEQ ID NO: 87) | VFDEFKPLVEEPQNLIK (SEQ ID NO: 87) |
| DDNPNLPR (SEQ ID NO: 97) | |
| FQNALLVR (SEQ ID NO: 98) | FQNALLVR (SEQ ID NO: 98) |
| LVAASQAALGL (SEQ ID NO: 96) | LVAASQAALGL (SEQ ID NO: 96) |

TABLE 17-continued

| Highly-correlated signature peptides | Beasley-Green signature peptides |
|---|---|
| AEFAEVSK (SEQ ID NO: 101) | AEFAEVSK (SEQ ID NO: 101) |
| TYETTLEK (SEQ ID NO: 105) | TYETTLEK (SEQ ID NO: 105) |
| SLHTLFGDK (SEQ ID NO: 102) | |
| YLYEIAR (SEQ ID NO: 111) | YLYEIAR (SEQ ID NO: 111) |
| | DLGEENFK (SEQ ID NO: 135) |
| | LCTVATLR (SEQ ID NO: 93) |
| | RPCFSALEVDETYVPK (SEQ ID NO: 86) |

The broad applicability of the signature peptide selection method of the present invention is highlighted by the observation that serum albumin signature peptides selected from the SWATH data yield reliable results in SRM assays. This was true despite differences in sample origin (aortic tissue v urine), sample preparation (harsh extraction and denaturation with urea v gentle treatment with RapiGest), and MS instruments (Triple-TOF v triple quadrupole).

Signature Peptide Selection from Blood and Tissue Proteins

The SWATH dataset for the PDAY extracts includes data on 1,121 proteins. Six blood proteins and two tissue proteins were selected as exemplary proteins for the identification of highly-correlated signature peptides (Table 18). Several of these proteins have been implicated as biomarkers.

TABLE 18

| Principle Location | Protein | UniProt ID | Quantifiable Peptides | Correlated Signature Peptides |
|---|---|---|---|---|
| Blood | Hemoglobin delta | P02042 | 14 | 4 |
| | Hemopexin | P02790 | 14 | 7 |
| | Apolipoprotein A-I | P02647 | 22 | 7 |
| | Alpha-1-antitrypsin | P01009 | 35 | 12 |
| | Serotransferrin | P02787 | 45 | 10 |
| | Complement C3 | P01024 | 68 | 36 |
| Tissue | Mimecan | P20774 | 16 | 4 |
| | Filamin-A | P21333 | 104 | 51 |

For each protein, data from 6 transitions for all quantifiable peptides was imported into a Microsoft Excel spreadsheet. The average peak area was calculated for each transition and the transition with the strongest peak area was selected to represent the peptide. All pairwise correlations ($r^2$) between the peptides were calculated with Prism and transferred to the Excel spreadsheet to create a correlation matrix. Peptides within the matrix were sorted according to the average of their correlations. Peptides having an average of correlations of less than 0.5 were removed. The peptides were resorted according their average of correlations and peptides having an average of correlations of less than 0.6 were removed. The process was repeated a third time to exclude peptides having an average of correlations of less than 0.7. Peptides with missed cleavages or methionine residues were then removed, and the remaining peptides were again sorted according to their average of correlations. A summary of these results is presented in Table 19.

TABLE 19

| Protein/Sequence | Charge (z) | Fragment Ion | Average r² | Average Peak Area |
|---|---|---|---|---|
| Hemoglobin subunit delta | | | | |
| VNVDAVGGEALGR (SEQ ID NO: 136) | 3 | y4 | 0.911 | 2043 |
| LLGNVLVC(Cam)VLAR (SEQ ID NO: 264) | 2 | y7 | 0.911 | 3704 |
| GIFSQLSELHC(Cam)DK (SEQ ID NO: 265) | 2 | y3 | 0.855 | 1408 |
| VNVDAVGGEALGR (SEQ ID NO: 136) | 2 | y7 | 0.878 | 18575 |
| Hemopexin | | | | |
| LLQDEFPGIPSPLDAAVEC(CAM)HR (SEQ ID NO: 266) | 3 | y12 | 0.880 | 6013 |
| SGAQATWTELPWPHEK (SEQ ID NO: 140) | 3 | y4 | 0.849 | 6078 |
| QGHNSVFLIK (SEQ ID NO: 141) | 2 | y8 | 0.806 | 323 |
| EVGTPNGIILDSVDAAFIC(CAM)PGSSR (SEQ ID NO: 267) | 3 | y5 | 0.823 | 10191 |
| NFPSPVDAAFR (SEQ ID NO: 143) | 2 | y9 | 0.864 | 12780 |
| GGYTLVSGYPK (SEQ ID NO: 144) | 2 | y6 | 0.836 | 2963 |
| GEC(CAM)QAEGVLFFQGDR (SEQ ID NO: 268) | 2 | y7 | 0.796 | 1419 |
| Apolipoprotein A-I | | | | |
| VSFLSALEEYTK (SEQ ID NO: 146) | 2 | y8 | 0.927 | 13501 |
| THLAPYSDELR (SEQ ID NO: 147) | 2 | b3 | 0.920 | 3093 |
| QGLLPVLESFK (SEQ ID NO: 148) | 2 | y7 | 0.918 | 25313 |
| DYVSQFEGSALGK (SEQ ID NO: 149) | 2 | y10 | 0.896 | 6389 |
| EQLGPVTQEFWDNLEK (SEQ ID NO: 150) | 2 | y4 | 0.891 | 2299 |
| LLDNWDSVTSTFSK (SEQ ID NO: 151) | 2 | y6 | 0.888 | 6381 |
| DLATVYVDVLK (SEQ ID NO: 152) | 2 | y6 | 0.848 | 4235 |
| Alpha-1-antitrypsin | | | | |
| FLENEDR (SEQ ID NO: 153) | 2 | y5 | 0.902 | 1033 |
| VFSNGADLSGVTEEAPLK (SEQ ID NO: 154) | | y3 | 0.890 | 10629 |
| LSITGTYDLK (SEQ ID NO: 155) | 2 | y7 | 0.889 | 15263 |
| AVLTIDEK (SEQ ID NO: 156) | 2 | y6 | 0.875 | 28127 |
| LQHLENELTHDIITK (SEQ ID NO: 157) | 4 | b3 | 0.874 | 3774 |
| VFSNGADLSGVTEEAPLK (SEQ ID NO: 154) | | y3 | 0.871 | 1443 |
| SASLHLPK (SEQ ID NO: 158) | 2 | y6 | 0.867 | 2358 |
| SVLGQLGITK (SEQ ID NO: 159) | 2 | y8 | 0.847 | 28919 |
| TDTSHHDQDHPTFNK (SEQ ID NO: 160) | 4 | y5 | 0.832 | 575 |
| DTEEEDFHVDQVTTVK (SEQ ID NO: 161) | 3 | y7 | 0.824 | 1724 |
| LYHSEAFTVNFGDTEEAK (SEQ ID NO: 162) | | y7 | 0.744 | 1267 |
| LQHLENELTHDIITK (SEQ ID NO: 157) | 3 | b3 | 0.742 | 4044 |
| Serotransferrin | | | | |
| DGAGDVAFVK (SEQ ID NO: 163) | 2 | y7 | 0.815 | 15560 |
| ASYLDC(Cam)IR (SEQ ID NO: 269) | 2 | y4 | 0.796 | 7916 |
| SVIPSDGPSVAC(Cam)VK (SEQ ID NO: 270) | 2 | y11 | 0.791 | 11944 |
| IEC(Cam)VSAETTEDC(Cam)IAK (SEQ ID NO: 271) | 2 | b3 | 0.772 | 5663 |
| DSAHGFLK (SEQ ID NO: 167) | 2 | y4 | 0.769 | 898 |
| SASDLTWDNLK (SEQ ID NO: 168) | 2 | y6 | 0.753 | 7257 |
| DDTVC(Cam)LAK (SEQ ID NO: 272) | 2 | y6 | 0.753 | 3883 |
| FDEFFSEGC(Cam)APGSK (SEQ ID NO: 273) | 2 | y4 | 0.736 | 24477 |
| EFQLFSSPHGK (SEQ ID NO: 171) | 3 | y6 | 0.728 | 4093 |
| C(Cam)DEWSVNSVGK (SEQ ID NO: 274) | 2 | b3 | 0.710 | 926 |
| Complement C3 | | | | |
| FYYIYNEK (SEQ ID NO: 173) | 2 | y6 | 0.994 | 646 |
| DTWVEHWPEEDEC(Cam)QDEENQK (SEQ ID NO: 275) | 3 | y6 | 0.948 | 1379 |
| EPGQDLVVLPLSITTDFIPSFR (SEQ ID NO: 175) | 2 | y4 | 0.938 | 1234 |
| SSLSVPYVIVPLK (SEQ ID NO: 176) | 2 | y8 | 0.931 | 4660 |
| NTLIIYLDK (SEQ ID NO: 177) | 2 | y6 | 0.930 | 2245 |
| QLYNVEATSYALLALLQLK (SEQ ID NO: 178) | 3 | y6 | 0.929 | 311 |
| IHWESASLLR (SEQ ID NO: 179) | 3 | y4 | 0.925 | 2419 |
| DIC(Cam)EEQVNSLPGSITK (SEQ ID NO: 276) | 2 | y6 | 0.924 | 6151 |
| FISLGEAC(Cam)K (SEQ ID NO: 277) | 2 | y7 | 0.924 | 3834 |
| VFLDC(Cam)C(Cam)NYITELR (SEQ ID NO: 278) | 2 | y4 | 0.924 | 2124 |
| QGALELIK (SEQ ID NO: 183) | 2 | y4 | 0.923 | 2305 |
| DSC(Cam)VGSLVVK (SEQ ID NO: 279) | 2 | y6 | 0.918 | 3994 |
| GLEVTITAR (SEQ ID NO: 185) | 2 | y5 | 0.918 | 2041 |
| EYVLPSFEVIVEPTEK (SEQ ID NO: 186) | 2 | b3 | 0.917 | 4462 |
| EVVADSVWVDVK (SEQ ID NO: 187) | 2 | y5 | 0.913 | 1435 |
| VSHSEDDC(Cam)LAFK (SEQ ID NO: 280) | 3 | y3 | 0.913 | 1815 |
| SGSDEVQVGQQR (SEQ ID NO: 189) | 2 | y4 | 0.913 | 587 |
| LVAYYTLIGASGQR (SEQ ID NO: 190) | 3 | y6 | 0.912 | 1596 |
| TIYTPGSTVLYR (SEQ ID NO: 191) | 2 | y8 | 0.911 | 3207 |
| GYTQQLAFR (SEQ ID NO: 192) | 2 | y5 | 0.910 | 1039 |
| DAPDHQELNLDVSLQLPSR (SEQ ID NO: 193) | 3 | y7 | 0.909 | 2002 |
| VELLHNPAFC(Cam)SLATTK (SEQ ID NO: 281) | 3 | b6 | 0.906 | 1436 |
| AC(Cam)EPGVDYVYK (SEQ ID NO: 282) | 2 | y8 | 0.899 | 2000 |
| IPIEDGSGEVVLSR (SEQ ID NO: 196) | 2 | y11 | 0.890 | 2511 |
| SNLDEDIIAEENIVSR (SEQ ID NO: 197) | 2 | y9 | 0.886 | 3618 |

TABLE 19-continued

| Protein/Sequence | Charge (z) | Fragment Ion | Average r² | Average Peak Area |
|---|---|---|---|---|
| VYAYYNLEESC(Cam)TR (SEQ ID NO: 283) | 2 | y6 | 0.885 | 421 |
| VTIKPAPETEK (SEQ ID NO: 199) | 3 | y7 | 0.876 | 1163 |
| DFDFVPPVVR (SEQ ID NO: 200) | 2 | y5 | 0.876 | 18784 |
| TGLQEVEVK (SEQ ID NO: 201) | 2 | y6 | 0.861 | 2191 |
| APSTWLTAYVVK (SEQ ID NO: 202) | 2 | y7 | 0.859 | 365 |
| VHQYFNVELIQPGAVK (SEQ ID NO: 203) | 3 | y5 | 0.835 | 4037 |
| VPVAVQGEDTVQSLTQGDGVAK (SEQ ID NO: 204) | 2 | b4 | 0.833 | 5289 |
| SGIPIVTSPYQIHFTK (SEQ ID NO: 205) | 3 | y4 | 0.831 | 918 |
| QPSSAFAAFVK (SEQ ID NO: 206) | 2 | y6 | 0.829 | 1977 |
| ADIGC(Cam)TPGSGK (SEQ ID NO: 284) | 2 | y5 | 0.801 | 858 |
| AAVYHHFISDGVR (SEQ ID NO: 208) | 3 | y5 | 0.748 | 650 |
| Mimecan | | | | |
| LNNLTFLYLDHNALESVPLNLPESLR (SEQ ID NO: 209) | 3 | y5 | 0.842 | 269781 |
| LDFTGNLIEDIEDGTFSK (SEQ ID NO: 210) | 2 | y5 | 0.839 | 242667 |
| LSLLEELSLAENQLLK (SEQ ID NO: 211) | 3 | y7 | 0.824 | 280665 |
| DFADIPNLR (SEQ ID NO: 212) | 2 | y4 | 0.757 | 59975 |
| Filamin-A | | | | |
| EGPYSISVLYGDEEVPR (SEQ ID NO: 213) | 2 | y11 | 0.871 | 15559 |
| EATTEFSVDAR (SEQ ID NO: 214) | 2 | y6 | 0.869 | 19572 |
| FNEEHIPDSPFVVPVASPSGDAR (SEQ ID NO: 215) | 3 | y10 | 0.861 | 72916 |
| AFGPGLQGGSAGSPAR (SEQ ID NO: 216) | 2 | y9 | 0.858 | 17271 |
| VSGQGLHEGHTFEPAEFIIDTR (SEQ ID NO: 217) | 3 | y9 | 0.849 | 2064 |
| VANPSGNLTETYVQDR (SEQ ID NO: 218) | 2 | y8 | 0.849 | 11286 |
| SPFSVAVSPSLDLSK (SEQ ID NO: 219) | 2 | y7 | 0.845 | 15559 |
| FNGTHIPGSPFK (SEQ ID NO: 220) | 3 | y6 | 0.847 | 5564 |
| VGEPGHGGDPGLVSAYGAGLEGGVTGNPAEFVVNTSNAGAGALSVTIDGPSK (SEQ ID NO: 221) | 4 | y4 | 0.837 | 6776 |
| VGSAADIPINISETDLSLLTATVVPPSGR (SEQ ID NO: 222) | 3 | y5 | 0.839 | 76329 |
| ENGVYLIDVK (SEQ ID NO: 223) | 2 | y6 | 0.829 | 10363 |
| DGSC(CAM)SVEYIPYEAGTYSLNVTYGGHQVPGSPFK (SEQ ID NO: 285) | 3 | y6 | 0.831 | 13569 |
| YNEQHVPGSPFTAR (SEQ ID NO: 225) | 2 | y8 | 0.826 | 2831 |
| VKETADFK (SEQ ID NO: 226) | 2 | y6 | 0.819 | 1289 |
| YGGQPVPNFPSK (SEQ ID NO: 227) | 2 | y6 | 0.823 | 14928 |
| DAGEGLLAVQITDPEGKPK (SEQ ID NO: 228) | 2 | y6 | 0.817 | 12196 |
| NGHVGISFVPK (SEQ ID NO: 229) | 2 | y7 | 0.818 | 676 |
| GTVEPQLEAR (SEQ ID NO: 230) | 2 | y6 | 0.818 | 41503 |
| ASGPGLNTTGVPASLPVEFTIDAK (SEQ ID NO: 231) | 2 | y13 | 0.816 | 6897 |
| IANLQTDLSDGLR (SEQ ID NO: 232) | 2 | y8 | 0.817 | 32516 |
| GLVEPVDVVDNADGTQTVNYVPSR (SEQ ID NO: 233) | 3 | y3 | 0.811 | 39841 |
| EAGAGGLAIAVEGPSK (SEQ ID NO: 234) | 2 | y4 | 0.812 | 19210 |
| TGVAVNKPAEFTVDAK (SEQ ID NO: 235) | 2 | y9 | 0.810 | 2720 |
| DGSC(CAM)GVAYVVQEPGDYEVSVK (SEQ ID NO: 286) | 2 | y9 | 0.809 | 2266 |
| EEGPYEVEVTYDGVPVPGSPFPLEAVAPTKPSK (SEQ ID NO: 237) | 3 | y6 | 0.808 | 13995 |
| FGGEHVPNSPFQVTALAGDQPSVQPPLR (SEQ ID NO: 238) | 3 | y4 | 0.798 | 30580 |
| VEPGLGADNSVVR (SEQ ID NO: 239) | 2 | y11 | 0.798 | 38786 |
| LYSVSYLLK (SEQ ID NO: 240) | 2 | y7 | 0.794 | 17335 |
| SPFEVYVDK (SEQ ID NO: 241) | 2 | y7 | 0.799 | 16092 |
| SADFVVEAIGDDVGTLGFSVEGPSQAK (SEQ ID NO: 242) | 3 | y6 | 0.789 | 15162 |
| AGVAPLQVK (SEQ ID NO: 243) | 2 | y5 | 0.791 | 38022 |
| AEISC(CAM)TDNQDGTC(CAM)SVSYLPVLPGDYSILVK (SEQ ID NO: 287) | 3 | y9 | 0.774 | 15308 |
| DAGEGGLSLAIEGPSK (SEQ ID NO: 245) | 2 | y4 | 0.771 | 21033 |
| AHVVPC(CAM)FDASK (SEQ ID NO: 288) | 2 | y7 | 0.775 | 7011 |
| LPQLPITNFSR (SEQ ID NO: 247) | 2 | y7 | 0.771 | 95463 |
| AWGPGLEGGVVGK (SEQ ID NO: 248) | 2 | y11 | 0.760 | 15328 |
| YTPVQQGPVGVNVTYGGDPIPK (SEQ ID NO: 249) | 2 | y4 | 0.764 | 7271 |
| FADQHVPGSPFSVK (SEQ ID NO: 250) | 3 | y8 | 0.758 | 4813 |
| DQEFTVK (SEQ ID NO: 251) | 2 | y5 | 0.753 | 1425 |
| AEISFEDR (SEQ ID NO: 252) | 2 | y5 | 0.755 | 18604 |
| VNQPASFAVSLNGAK (SEQ ID NO: 253) | 2 | y12 | 0.752 | 3160 |
| TFSVWYVPEVTGTHK (SEQ ID NO: 254) | 2 | y8 | 0.747 | 3825 |
| C(CAM)APGVVGPAEADIDFDIIR (SEQ ID NO: 289) | 2 | y5 | 0.740 | 4577 |
| LDVQFSGLTK (SEQ ID NO: 256) | 2 | y6 | 0.728 | 9797 |
| NGQHVASSPIPVVISQSEIGDASR (SEQ ID NO: 257) | 3 | y10 | 0.739 | 1156 |
| VTAQGPGLEPSGNIANK (SEQ ID NO: 258) | 2 | y8 | 0.729 | 11129 |
| DAGYGGLSLSIEGPSK (SEQ ID NO: 259) | 2 | y4 | 0.722 | 2508 |
| WGDEHIPGSPYR (SEQ ID NO: 260) | 2 | y6 | 0.710 | 3121 |
| DVDIIDHHDNTYTVK (SEQ ID NO: 261) | 3 | y13 | 0.710 | 6653 |
| GAGTGGLGLAVEGPSEAK (SEQ ID NO: 262) | 2 | y6 | 0.707 | 17618 |
| THIQDNHDGTYTVAYVPDVTGR (SEQ ID NO: 263) | 3 | y6 | 0.712 | 1930 |

Persons of ordinary skill will recognize that this process can be repeated to identify correlated signature peptides for all 1,121 identified proteins in the PDAY SWATH data. The resulting correlated signature peptides will provide accurate and reproducible quantitative results for this and other MS datasets. Persons of ordinary skill will also realize that this approach will allow signature peptides to be selected from any database for every human (or other species) protein. Reproducibility can be enhanced by incorporating SIL peptides matching the sequence of the correlated signature peptides. Correlated signature peptides identified in SWATH data can also be targeted in higher sensitivity SRM assays.

REFERENCES

Kessner D, Chambers M, Burke R, Agus D, Mallick P. ProteoWizard: open source software for rapid proteomics tools development. Bioinformatics. 2008; 24:2534-2536.

Elias J E, Gygi S P. Target-decoy search strategy for increased confidence in large-scale protein identifications by mass spectrometry. Nat Methods. 2007; 4:207-214.

Craig R, Beavis R. TANDEM: matching proteins with tandem mass spectra. Bioinformatics.2004; 20:1466-1467.

Eng J K, Jahan T A, Hoopmann M R. Comet: an open source tandem mass spectrometry sequence database search tool. Proteomics. 2012 Nov. 12. doi: 10. 1002/pmic.201200439

Agger SA1, Marney L C, Hoofnagle A N, Simultaneous quantification of apolipoprotein A-I and apolipoprotein B by liquid-chromatography-multiple-reaction-monitoring mass spectrometry. Clin Chem. 2010 December; 56(12): 1804-13.

Keller, A., Eng, J Zhang, N., Li, X. J Aebersold, R., A uniform proteomics MS/MS analysis platform utilizing open XML file formats. Mol. Syst. Biol. 2005, 1, 2005 0017.

Keller, A., Nesvizhskii, A. I., Kolker, E., Aebersold, R., Empirical statistical model to estimate the accuracy of peptide identifications made by MS/MS and database search. Anal. Chem. 2002, 74, 5383-5392.

Shteynberg D., Deutsch E. W., Lam H., Eng J. K., Sun Z., Tasman N., Mendoza L., Moritz R. L., Aebersold R., Nesvizhskii A. I. iProphet: multi-level integrative analysis of shotgun proteomic data improves peptide and protein identification rates and error estimates. Mol Cell Proteomics. 2011, 10:M111.007690

Collins B C, Gillet L C, Rosenberger G, Rost H L, Vichalkovski A, Gstaiger M, Aebersold R. Quantifying protein interaction dynamics by SWATH mass spectrometry: application to the 14-3-3 system. Nat Methods. 2013; 10:1246-1253.

Lam H, Deutsch E W, Eddes J S, Eng J K, King N, Stein S E, Aebersold R. Development and validation of a spectral library searching method for peptide identification from MS/MS. Proteomics. 2007; 7:655-667.

scher C, Reiter L, MacLean B, Ossola R, Herzog F, Chilton J, MacCoss M J, Rinner O. Using iRT, a normalized retention time for more targeted measurement of peptides. Proteomics. 2012; 12:1111-1121.

Rost H L, Rosenberger G, Navarro P, Gillet L, Miladinovic S M, Schubert O T, Wolski W, Collins B C, Malmstrom J, Malmstrom L, Aebersold R. OpenSWATH enables automated, targeted analysis of data-independent acquisition MS data. Nat Biotech. 2014; 32:219-223.

Weisser H, Nahnsen S, Grossmann J, Nilse L, Quandt A, Brauer H, Sturm M, Kenar E, Kohlbacher O, Aebersold R, Malmstrom L. An automated pipeline for high-throughput label-free quantitative proteomics. J Proteome Res. 2013; 12:1628-1644.

Mallick P, Schirle M, Chen S S, Flory M R, Lee H, Martin D, Ranish J, Raught B, Schmitt R, Werner T, Kuster B, Aebersold R. Computational prediction of proteotypic peptides for quantitative proteomics. Nat Biotechnol. 2007; 25:125-131

Beasley-Green A, Burris N M, Bunk D M, Phinney K W, Multiplexed LC-MS/MS assay for urine albumin, J Proteome Res. 2014 Sep. 5; 13(9):3930-9.

SEQ ID NOs for all the peptide sequences described herein are listed in Table 20 below.

TABLE 20

| SEQ ID NO: | Sequence |
|---|---|
| 1 | ACAHW |
| 2 | AFSSL |
| 3 | DGPCG |
| 4 | DSTIQ |
| 5 | DWVSV |
| 6 | FAGNY |
| 7 | FALLM |
| 8 | FSVQM |
| 9 | FVGQG |
| 10 | GDGWH |
| 11 | GVQAT |
| 12 | INFAC |
| 13 | KACAH |
| 14 | KGVQA |
| 15 | LECGA |
| 16 | MAETC |
| 17 | NETHA |
| 18 | QDFNI |
| 19 | SGSVI |
| 20 | SLGFD |
| 21 | STEYG |
| 22 | TALQP |
| 23 | TLDEY |
| 24 | VFMYL |
| 25 | VGGTG |
| 26 | VLNLG |
| 27 | VWLPL |
| 28 | YFIIQ |
| 29 | WHCQC |
| 30 | CSGFN |
| 31 | CKPTC |
| 32 | RTLDEYWRS |
| 33 | RSTEYGEGYACDTDLRG |
| 34 | RFVGQGGARM |

TABLE 20-continued

| SEQ ID NO: | Sequence |
|---|---|
| 35 | RMAETCVPVLRC |
| 36 | KACAHWSGHCCLWDASVQVKA |
| 37 | RWHCQCKQ |
| 38 | KQDFNITDISLLEHRL |
| 39 | RLECGANDMKV |
| 40 | KSLGFDKV |
| 41 | KVFMYLSDSRC |
| 42 | RCSGFNDRD |
| 43 | RDWVSVVTPARD |
| 44 | RDGPCGTVLTRN |
| 45 | RNETHATYSNTLYLADEIIIRD |
| 46 | KINFACSYPLDMKV |
| 47 | KTALQPMVSALNIRV |
| 48 | RVGGTGMFTVRM |
| 49 | RFALLMTNCYATPSSNATDPLKY |
| 50 | KYFIIQDRC |
| 51 | RDSTIQVVENGESSQGRF |
| 52 | RFSVQMFRF |
| 53 | KCKPTCSGTRF |
| 54 | RSGSVIDQSRV |
| 55 | RVLNLGPITRK |
| 56 | KGVQATVSRA |
| 57 | RAFSSLGLLKV |
| 58 | KVWLPLLLSATLTLTFQ |
| 59 | TLDEYWR |
| 60 | DGPCGTVLTR |
| 61 | YFIIQDR |
| 62 | FVGQGGAR |
| 63 | DWVSVVTPAR |
| 64 | SGSVIDQSR |
| 65 | FSVQMFR |
| 66 | STEYGEGYACDTDLR |
| 67 | VFMYLSDSR |
| 68 | MAETCVPVLR |
| 69 | DSTIQVVENGESSQGR |
| 70 | TALQPMVSALNIR |
| 71 | YSQQQLMETSHR |
| 72 | RDWENPGVTQLNR |
| 73 | GDFQFNISR |

TABLE 20-continued

| SEQ ID NO: | Sequence |
|---|---|
| 74 | IDPNAWVER |
| 75 | DVSLLHKPTTQISDFHVATR |
| 76 | VDEDQPFPAVPK |
| 77 | DWENPGVTQLNR |
| 78 | APLDNDIGVSEATR |
| 79 | WVGYGQDSR |
| 80 | GDFQFNIS |
| 83 | QTALVELVK |
| 84 | SHCIAEVENDEMPADLPSLAADFVESK |
| 85 | LVNEVTEFAK |
| 86 | RPCFSALEVDETYVPK |
| 87 | VFDEFKPLVEEPQNLIK |
| 88 | QNCELFEQLGEYK |
| 89 | AVMDDFAAFVEK |
| 90 | RMPCAEDYLSVVLNQLCVLHEK |
| 91 | KQTALVELVK |
| 92 | VHTECCHGDLLECADDR |
| 93 | LCTVATLR |
| 94 | LVRPEVDVMCTAFHDNEETFLKK |
| 95 | ECCEKPLLEK |
| 96 | LVAASQAALGL |
| 97 | DDNPNLPR |
| 98 | FQNALLVR |
| 99 | VPQVSTPTLVEVSR |
| 100 | RHPYFYAPELLFFAK |
| 101 | AEFAEVSK |
| 102 | SLHTLFGDK |
| 103 | KVPQVSTPTLVEVSR |
| 104 | KYLYEIAR |
| 105 | TYETTLEK |
| 106 | RHPDYSVVLLR |
| 107 | HPDYSVVLLLR |
| 108 | KLVAASQAALGL |
| 109 | LVRPEVDVMCTAFHDNEETFLK |
| 110 | FKDLGEENFK |
| 111 | YLYEIAR |
| 112 | VHTECCHGDLLECADDRADLAK |
| 113 | NECFLQHKDDNPNLPR |
| 114 | AAFTECCQAADK |

TABLE 20-continued

| SEQ ID NO: | Sequence |
|---|---|
| 115 | ETYGEMADCCAK |
| 116 | QEPERNECFLQHKDDNPNLPR |
| 117 | YICENQDSISSK |
| 118 | ADDKETCFAEEGK |
| 119 | NECFLQHK |
| 120 | CCTESLVNR |
| 121 | LAKTYETTLEKCCAAADPHECYAK |
| 122 | MPCAEDYLSVVLNQLCVLHEK |
| 123 | HPYFYAPELLFFAK |
| 124 | SLHTLFGDKLCTVATLR |
| 125 | LKECCEKPLLEK |
| 126 | ALVLIAFAQYLQQCPFEDHVK |
| 127 | ADDKETCFAEEGKK |
| 128 | EFNAETFTFHADICTLSEK |
| 129 | DVFLGMFLYEYAR |
| 130 | LDELRDEGK |
| 131 | CCAAADPHECYAK |
| 132 | NYAEAKDVFLGMFLYEYAR |
| 133 | TCVADESAENCDK |
| 134 | EFNAETFTFHADICTLSEKER |
| 135 | DLGEENFK |
| 136 | VNVDAVGGEALGR |
| 137 | LLGNVLVCVLAR |
| 138 | GTFSQLSELHCDK |
| 139 | LLQDEFPGIPSPLDAAVECHR |
| 140 | SGAQATWTELPWPHEK |
| 141 | QGHNSVFLIK |
| 142 | EVGTPHGIILDSVDAAFICPGSSR |
| 143 | NFPSPVDAAFR |
| 144 | GGYTLVSGYPK |
| 145 | GECQAEGVLFFQGDR |
| 146 | VSFLSALEEYTK |
| 147 | THLAPYSDELR |
| 148 | QGLLPVLESFK |
| 149 | DYVSQFEGSALGK |
| 150 | EQLGPVTQEFWDNLEK |
| 151 | LLDNWDSVTSTFSK |
| 152 | DLATVYVDVLK |
| 153 | FLENEDR |

TABLE 20-continued

| SEQ ID NO: | Sequence |
|---|---|
| 154 | VFSNGADLSGVTEEAPLK |
| 155 | LSITGTYDLK |
| 156 | AVLTIDEK |
| 157 | LQHLENELTHDIITK |
| 158 | SASLHLPK |
| 159 | SVLGQLGITK |
| 160 | TDTSHHDQDHPTFNK |
| 161 | DTEEEDFHVDQVTTVK |
| 162 | LYHSEAFTVNFGDTEEAK |
| 163 | DGAGDVAFVK |
| 164 | ASYLDCIR |
| 165 | SVIPSDGPSVACVK |
| 166 | IECVSAETTEDCIAK |
| 167 | DSAHGFLK |
| 168 | SASDLTWDNLK |
| 169 | DDTVCLAK |
| 170 | FDEFFSEGCAPGSK |
| 171 | EFQLFSSPHGK |
| 172 | CDEWSVNSVGK |
| 173 | FYYIYNEK |
| 174 | DTWVEHWPEEDECQDEENQK |
| 175 | EPGQDLVVLPLSITTDFIPSFR |
| 176 | SSLSVPYVIVPLK |
| 177 | NTLIIYLDK |
| 178 | QLYNVEATSYALLALLQLK |
| 179 | IHWESASLLR |
| 180 | DICEEQVNSLPGSITK |
| 181 | FISLGEACK |
| 182 | VFLDCCNYITELR |
| 183 | QGALELIK |
| 184 | DSCVGSLVVK |
| 185 | GLEVTITAR |
| 186 | EYVLPSFEVIVEPTEK |
| 187 | EVVADSVWVDVK |
| 188 | VSHSEDDCLAFK |
| 189 | SGSDEVQVGQQR |
| 190 | LVAYYTLIGASGQR |
| 191 | TIYTPGSTVLYR |
| 192 | GYTQQLAFR |

TABLE 20-continued

| SEQ ID NO: | Sequence |
|---|---|
| 193 | DAPDHQELNLDVSLQLPSR |
| 194 | VELLHNPAFCSLATTK |
| 195 | ACEPGVDYVYK |
| 196 | IPIEDGSGEVVLSR |
| 197 | SNLDEDIIAEENIVSR |
| 198 | VYAYYNLEESCTR |
| 199 | VTIKPAPETEK |
| 200 | DFDFVPPVVR |
| 201 | TGLQEVEVK |
| 202 | APSTWLTAYVVK |
| 203 | VHQYFNVELIQPGAVK |
| 204 | VPVAVQGEDTVQSLTQGDGVAK |
| 205 | SGIPIVTSPYQIHFTK |
| 206 | QPSSAFAAFVK |
| 207 | ADIGCTPGSGK |
| 208 | AAVYHHFISDGVR |
| 209 | LNNLTFLYLDHNALESVPLNLPESLR |
| 210 | LDFTGNLIEDIEDGTFSK |
| 211 | LSLLEELSLAENQLLK |
| 212 | DFADIPNLR |
| 213 | EGPYSISVLYGDEEVPR |
| 214 | EATTEFSVDAR |
| 215 | FNEEHIPDSPFVVPVASPSGDAR |
| 216 | AFGPGLQGGSAGSPAR |
| 217 | VSGQGLHEGHTFEPAEFIIDTR |
| 218 | VANPSGNLTETYVQDR |
| 219 | SPFSVAVSPSLDLSK |
| 220 | FNGTHIPGSPFK |
| 221 | VGEPGHGGDPGLVSAYGAGLEGGVTGNPAEFVVNTSNAGAGALSVTIDGPSK |
| 222 | VGSAADIPINISETDLSLLTATVVPPSGR |
| 223 | ENGVYLIDVK |
| 224 | DGSCSVEYIPYEAGTYSLNVTYGGHQVPGSPFK |
| 225 | YNEQHVPGSPFTAR |
| 226 | VKETADFK |
| 227 | YGGQPVPNFPSK |
| 228 | DAGEGLLAVQITDPEGKPK |
| 229 | NGHVGISFVPK |
| 230 | GTVEPQLEAR |
| 231 | ASGPGLNTTGVPASLPVEFTIDAK |
| 232 | IANLQTDLSDGLR |
| 233 | GLVEPVDVVDNADGTQTVNYVPSR |
| 234 | EAGAGGLAIAVEGPSK |
| 235 | TGVAVNKPAEFTVDAK |
| 236 | DGSCGVAYVVQEPGDYEVSVK |
| 237 | EEGPYEVEVTYDGVPVPGSPFPLEAVAPTKPSK |
| 238 | FGGEHVPNSPFQVTALAGDQPSVQPPLR |
| 239 | VEPGLGADNSVVR |
| 240 | LYSVSYLLK |
| 241 | SPFEVYVDK |
| 242 | SADFVVEAIGDDVGTLGFSVEGPSQAK |
| 243 | AGVAPLQVK |
| 244 | AEISCTDNQDGTCSVSYLPVLPGDYSILVK |
| 245 | DAGEGGLSLAIEGPSK |
| 246 | AHVVPCFDASK |
| 247 | LPQLPITNFSR |
| 248 | AWGPGLEGGVVGK |
| 249 | YTPVQQGPVGVNVTYGGDPIPK |
| 250 | FADQHVPGSPFSVK |
| 251 | DQEFTVK |
| 252 | AEISFEDR |
| 253 | VNQPASFAVSLNGAK |
| 254 | TFSVWYVPEVTGTHK |
| 255 | CAPGVVGPAEADIDFDIIR |
| 256 | LDVQFSGLTK |
| 257 | NGQHVASSPIPVVISQSEIGDASR |
| 258 | VTAQGPGLEPSGNIANK |
| 259 | DAGYGGLSLSIEGPSK |
| 260 | WGDEHIPGSPYR |
| 261 | DVDIIDHHDNTYTVK |
| 262 | GAGTGGLGLAVEGPSEAK |
| 263 | THIQDNHDGTYTVAYVPDVTGR |

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A method of identifying signature peptides for quantifying a polypeptide in a sample, comprising:
   acquiring mass spectrometry (MS) data on multiple candidate peptides derived from the polypeptide in multiple samples,
   wherein acquiring MS data comprises operating a mass spectrometer;
   using the MS data to calculate correlation values for pairwise comparisons among the multiple candidate peptides;
   eliminating candidate peptides containing a methionine amino acid residue; and
   identifying highly correlated peptides among the multiple candidate peptides without methionine,
   wherein the highly correlated peptides have mean or median correlation values ranked in the top 80% among the multiple candidate peptides without methionine, and
   wherein the highly correlated peptides are identified as the signature peptides for quantifying the polypeptide.

2. The method of claim 1, wherein the MS data is collected by a targeted acquisition method.

3. The method of claim 1, wherein the MS data is collected by a data independent acquisition method.

4. The method of claim 1, wherein the correlation values are coefficient of determination ($r^2$) values.

5. The method of claim 1, wherein the multiple candidate peptides are derived by proteolysis or chemical cleavage of the polypeptide.

6. The method of claim 1, wherein the sample is derived from food, water, cheek swab, blood, serum, plasma, urine, saliva, semen, cells, tissue, tumor, or a combination thereof.

7. The method of claim 1, further comprising ranking the correlation values of the multiple candidate peptides.

8. The method of claim 1, wherein the highly correlated peptides have mean or median correlation values ranked in the top 70% among the multiple candidate peptides without methionine.

9. The method of claim 1, wherein the multiple candidate peptides are obtained from a data-dependent MS screen, data-independent MS data, targeted peptides data, MS spectral database, or proteotypic peptide prediction, or a combination thereof.

10. The method of claim 1, further comprising eliminating candidate peptides that satisfy one or more of the following criteria:
   i. not previously detected by MS;
   ii. not unique to the polypeptide;
   iii. absent from the polypeptide's mature form;
   iv. containing an uncleaved protease recognition site;
   v. susceptible to post-translational modification (PTM);
   vi. containing asparagine and/or cysteine residues;
   vii. sensitive to endogenous proteases;
   viii. having m/z values lower than an m/z bottom cutoff value;
   ix. having m/z values higher than an m/z top cutoff value; and
   x. having signal intensities lower than an intensity bottom cutoff value in the acquired MS data.

11. The method of claim 1, wherein the identified signature peptides have signal intensities more than 20 times the background noise intensity value in the acquired MS data.

12. The method of claim 1, wherein the highly correlated peptides have mean or median correlation values ranked in the top 60% among the multiple candidate peptides without methionine.

13. The method of claim 1, wherein the highly correlated peptides have mean or median correlation values ranked in the top 50% among the multiple candidate peptides without methionine.

14. The method of claim 1, wherein the highly correlated peptides have mean or median correlation values ranked in the top 40% among the multiple candidate peptides without methionine.

15. A method of identifying signature peptides for quantifying a polypeptide in a sample, comprising:
   acquiring mass spectrometry (MS) data on multiple candidate peptides derived from the polypeptide in multiple samples,
   wherein acquiring MS data comprises operating a mass spectrometer;
   using the MS data to calculate correlation values for pairwise comparisons among the multiple candidate peptides;
   eliminating candidate peptides containing a methionine amino acid residue;
   ranking the mean or median correlation values of the multiple candidate peptides; and
   identifying highly correlated peptides among the multiple candidate peptides without methionine,
   wherein the highly correlated peptides have mean or median correlation values ranked in the top 10 among the multiple candidate peptides without methionine, and
   wherein the highly correlated peptides are identified as the signature peptides for quantifying the polypeptide.

16. The method of claim 15, wherein the highly correlated peptides have mean or median correlation values ranked in the top 6 among the multiple candidate peptides without methionine.

17. A method of quantifying a polypeptide in a sample, comprising:
   acquiring mass spectrometry (MS) data on multiple candidate peptides derived from the polypeptide in multiple samples;
   using the MS data to calculate correlation values for pairwise comparisons among the multiple candidate peptides;
   eliminating candidate peptides containing a methionine amino acid residue;
   identifying highly correlated peptides among the multiple candidate peptides without methionine,
   wherein the highly correlated peptides have mean or median correlation values ranked in the top 80% among the multiple candidate peptides without methionine, and
   wherein the highly correlated peptides are identified as signature peptides for quantifying the polypeptide;
   cleaving the polypeptide in the sample to yield the signature peptides;
   analyzing the sample on a mass spectrometer;
   detecting MS signals of the signature peptides; and
   quantifying the polypeptide based on the detected MS signals of the signature peptides.

18. The method of claim 17, further comprising spiking the sample with an internal standard and detecting MS signals of the internal standard.

19. The method of claim 18, wherein the internal standard comprises the signature peptide labeled with a stable isotope.

20. The method of claim 18, further comprising normalizing the signature peptide's MS signals to the internal standard's MS signals.

\* \* \* \* \*